United States Patent [19]
Paoletti et al.

[11] Patent Number: 5,766,597
[45] Date of Patent: Jun. 16, 1998

[54] MALARIA RECOMBINANT POXVIRUSES

[75] Inventors: Enzo Paoletti, Delmar, N.Y.; Charles de Taisne, Lyons, France; John A. Tine, Scotia, N.Y.

[73] Assignee: Virogenetics Corporation, Troy, N.Y.

[21] Appl. No.: 257,073

[22] Filed: Jun. 9, 1994

Related U.S. Application Data

[63] Continuation-in-part of Ser. No. 105,483, Aug. 12, 1993, Pat. No. 5,494,807, Ser. No. 178,476, Jan. 7, 1994, Ser. No. 36,217, Mar. 24, 1993, Pat. No. 5,364,773, Ser. No. 102,702, Aug. 5, 1993, Pat. No. 5,453,364, and Ser. No. 75,783, Jun. 11, 1993, abandoned, which is a continuation-in-part of Ser. No. 847,951, Mar. 6, 1992, abandoned, Ser. No. 724,109, Jul. 1, 1991, abandoned, Ser. No. 847,977, Mar. 3, 1992, abandoned, and Ser. No. 852,305, Mar. 18, 1992, abandoned, which is a continuation-in-part of Ser. No. 672,183, Mar. 20, 1991, abandoned, said Ser. No. 105,483, is a continuation of Ser. No. 847,951, said Ser. No. 178,476, is a continuation of Ser. No. 724,109, said Ser. No. 36,217, is a continuation of Ser. No. 666,056, Mar. 7, 1991, abandoned, said Ser. No. 102,702, is a continuation of Ser. No. 847,977.

[51] Int. Cl.$^6$ ............... A61K 39/015; A61K 39/275; A61K 39/285; C12N 7/01
[52] U.S. Cl. ............... 424/199.1; 435/235.1; 435/320.1; 435/69.3; 424/268.1; 424/265.1; 424/272.1
[58] Field of Search ............... 435/235.1, 69.1, 435/69.3, 320.1, 172.3; 424/199.1, 272.1, 268.1, 265.1; 935/65

[56] References Cited

U.S. PATENT DOCUMENTS

| | | | |
|---|---|---|---|
| 5,185,146 | 2/1993 | Altenburger | 424/89 |
| 5,494,807 | 2/1996 | Paoletti et al. | 435/69.3 |
| 5,505,941 | 4/1996 | Paoletti | 424/93.2 |

FOREIGN PATENT DOCUMENTS

| | | | |
|---|---|---|---|
| 0324350 | 1/1989 | European Pat. Off. | C12N 15/00 |
| 8903429 | 4/1989 | WIPO | C12P 21/00 |

OTHER PUBLICATIONS

Perkus, M.E. et al. 1985. Science, vol. 229, pp. 981–984.
Pye, D. et al. 1991. Infection & Immunity, vol. 59, pp. 2403–2411.
Langford, C. et al. 1988. Vaccines 88, pp. 89–94.
Hollingdale, M.R. et al. 1990. Immunology Letters, vol. 25, pp. 71–76.
Phillips, R.S. 1992. Immunobiol., vol. 184, pp. 240–262.
Kumar, S. et al. 1988. Nature, vol. 334, pp. 258–260.
Bzik, D.J. et al. 1988. Molecular & Biochemical Parasitol., vol. 30, pp. 279–288.
Knapp, B. et al. 1989. Molecular & Biochemical Parasitol., vol. 32, pp. 73–84.
Li, W.B. et al. 1989. Molecular & Biochemical Parasitol., vol. 33, pp. 13–26.
Hill, A.V.S. et al. 1989. J. Infect. Diseas., vol. 159, pp. 625–634.

*Primary Examiner*—Mary E. Mosher
*Attorney, Agent, or Firm*—Frommer Lawrence & Haug LLP; William S. Frommer; Thomas J. Kowalski

[57] ABSTRACT

What is described is a recombinant poxvirus, such as vaccinia or canarypox virus, containing foreign DNA from Plasmodium such as coding for at least one of CSP, PfSSP2, LSA-1, LSA-1-repeatless, MSA-1, SERA, AMA-1, Pfs25, MSA-1 N-terminal p83 and MSA-1 C-terminal gp42. What is also described is a vaccine containing the recombinant poxvirus for inducing an immunological response in a host animal inoculated with the vaccine. Preferred recombinants have attenuated virulence. In certain embodiments the vaccinia has deleted or disrupted the thymidine kinase gene, the hemorrhagic region, the A type inclusion body region, the host range gene region and, the large subunit, ribonucleotide reductase; and, contains coding sequences for CSP, PfSSP2, LSA-1-repeatless, MSA-1, SERA, AMA-1 and Pfs25. That embodiment is termed NYVAC-Pf7 and is a multicomponent, multistage vaccine since it codes for and expresses sporozoite proteins, liver stage proteins, blood stage proteins and, sexual stage proteins.

19 Claims, 41 Drawing Sheets

| | | | |
|---|---|---|---|
| ATGAAGTCAT | ATATTTCCTT | GTTTTTCATA | 30 |
| M K S | Y I S L | F F I | 10 |
| TTGTGTGTTA | TATTTAACAA | AAATGTTATA | 60 |
| L C V | I F N K | N V I | 20 |
| AAATGTACAG | GAGAAAGTCA | AACAGGTAAT | 90 |
| K C [T | G E S Q | T G N] | 30 |
| ACAGGAGGAG | GTCAAGCAGG | TAATACAGGA | 120 |
| [T G G | G Q A G | N] [T G | 40 |
| GGAGGTCAAG | CAGGTAATAC | AGTAGGAGAT | 150 |
| G G Q | A G N] [T | V G D | 50 |
| CAAGCAGGTA | GTACAGGAGG | AAGTCCACAA | 180 |
| Q A G | S] [T G G | S P Q | 60 |
| GGTAGTACGG | GAGCAAGTCA | ACCCGGAAGT | 210 |
| G S] [T | G A S Q | P G S] | 70 |
| TCCGAACCAA | GCAATCCTGT | AAGTTCCGGA | 240 |
| S E P | S N P V | S S G | 80 |
| CATTCTGTAA | GTACTGTATC | AGTATCACAA | 270 |
| H S V | S T V S | V S S | 90 |
| ACTTCAACTT | CTTCAGAAAA | ACAGGATACA | 300 |
| T S T | S S E K | Q D T | 100 |
| ATTCAAGTAA | AATCAGCTTT | ATTAAAAGAT | 330 |
| I Q V | K S A L | L K D | 110 |
| TATATGGGTT | TAAAAGTTAC | TGGTCCATGT | 360 |
| Y M G | L K V T | G P C | 120 |
| AACGAAAATT | TCATAATGTT | CTTAGTTCCT | 390 |
| N E N | F I M F | L V P | 130 |
| CATATATATA | TTGATGTTGA | TACAGAAGAT | 420 |
| H I Y | I D V D | T E D | 140 |
| ACTAATATCG | AATTAAGAAC | AACATTGAAA | 450 |
| T N I | E L R T | T L K | 150 |

*FIG.2*

```
GAAACAAATA  ATGCAATATC  ATTTGAATCA        480
 E  T  N     N  A  I  S    F  E  S        160

AACAGTGGTT  CATTAGAAAA  AAAAAAATAT        510
 N  S  G     S  L  E  K    K  K  Y        170

GTAAAACTAC  CATCAAATGG  TACAACTGGT        540
 V  K  L     P  S  N  G    T  T  G        180

GAACAAAGTT  CTAGTTCAAG  TTCAAGTTCT        570
 E  Q  S     S  S  S  S    S  S  S        190

AGTTCAAATT  CTAGTTCAAG  TTCAAGTTCA        600
 S  S  N     S  S  S  S    S  S  S        200

AGTTCAAGTT  CTAGTTCAAG  TTCAAGTTCA        630
 S  S  S     S  S  S  S    S  S  S        210

AGTTCTAGTT  CAAGTTCTAG  TTCAAGTTCA        660
 S  S  S     S  S  S  S    S  S  S        220

GAAAGTCTTC  CTGCTAATGG  ACCTGATTCC        690
 E  S  L     P  A  N  G    P  D  S        230

CCTACTGTTA  AACCGCCAAG  AAATTTACAA        720
 P  T  V     K  P  P  R    N  L  Q        240

AATATATGTG  AAACTGGAAA  AAACTTCAAG        750
 N  I  C     E  T  G  K    N  F  K        250

TTGGTAGTAT  ATATTAAGGA  GAATACATTA        780
 L  V  V     Y  I  K  E    N  T  L        260

ATAATTAAAT  GGAAAGTATA  CGGAGAAACA        810
 I  I  K     W  K  V  Y    G  E  T        270

AAAGATACTA  CTGAAAATAA  CAAAGTTGAT        840
 K  D  T     T  E  N  N    K  V  D        280

GTAAGAAAGT  ATTTGATAAA  TGAAAAGGAA        870
 V  R  K     Y  L  I  N    E  K  E        290

ACCCCATTTA  CTAGTATACT  AATACATGCG        900
 T  P  F     T  S  I  L    I  H  A        300
```

*FIG. 2 (Contiued)*

| | | | |
|---|---|---|---|
| TATAAAGAAC | ATAATGGAAC | AAACTTAATA | 930 |
| Y K E | H N G T | N L I | 310 |
| GAAAGTAAAA | ACTACGCATT | AGGATCAGAC | 960 |
| E S K | N Y A L | G S D | 320 |
| ATTCCAGAAA | AATGTGATAC | CTTAGCTTCC | 990 |
| I P E | K C D T | L A S | 330 |
| AATTGCTTTT | TAAGTGGTAA | TTTTAACATT | 1020 |
| N C F | L S G N | F N I | 340 |
| GAAAAATGCT | TTCAATGTGC | TCTTTTAGTA | 1050 |
| E K C | F Q C A | L L V | 350 |
| GAAAAAGAAA | ATAAAATGA | CGTATGTTAC | 1080 |
| E K E | N K D | V C Y | 360 |
| AAATACCTAT | CTGAAGATAT | TGTAAGTAAA | 1110 |
| K Y L | S E D I | V S K | 370 |
| TTCAAAGAAA | TAAAAGCTGA | GACAGAAGAT | 1140 |
| F K E | I K A E | T E D | 380 |
| GATGATGAAG | ATGATTATAC | TGAATATAAA | 1170 |
| D D E | D D Y T | E Y K | 390 |
| TTAACAGAAT | CTATTGATAA | TATATTAGTA | 1200 |
| L T E | S I D N | I L V | 400 |
| AAAATGTTTA | AAACAAATGA | AAATAATGAT | 1230 |
| K M F | K T N E | N N D | 410 |
| AAATCAGAAT | TAATAAAATT | AGAAGAAGTA | 1260 |
| K S E | L I K L | E E V | 420 |
| GATGATAGTT | TGAAATTAGA | ATTAATGAAT | 1290 |
| D D S | L K L E | L M N | 430 |
| TACTGTAGTT | TACTTAAAGA | CGTAGATACA | 1320 |
| Y C S | L L K D | V D T | 440 |
| ACAGGTACCT | TAGATAATTA | TGGGATGGGA | 1350 |
| N T G | T L D Y | G M G | 450 |

FIG.2 (Continued)

```
AATGAAATGG  ATATATTTAA  TAACTTAAAG                    1380
 N  E  M     D  I  F     N  L  K                       460

AGATTATTAA  TTTATCATTC  AGAAGAAAAT                    1410
 R  L  L     I  Y  H  S    E  E  N                     470

ATTAATACTT  TAAAAATAA   ATTCCGTAAT                    1440
 I  N  T     L  K  N  K    F  R  N                     480

GCAGCTGTAT  GTCTTAAAA   TGTTGATGAT                    1470
 A  A  V     C  L  K  N    V  D  D                     490

TGGATTGTAA  ATAAGAGG    TTTAGTATTA                    1500
 W  I  V     N  K  R  G    L  V  L                     500

CCTGAATTAA  ATTATGATTT  AGAATATTTC                    1530
 P  E  L     N  Y  D  L    E  Y  F                     510

AATGAACATT  TATATAATGA  TAAAAATTCT                    1560
 N  E  H     L  Y  N  D    K  N  S                     520

CCAGAAGATA  AAGATAATAA  AGGAAAAGGT                    1590
 P  E  D     K  D  N  K    G  K  G                     530

GTCGTACATG  TTGATACAAC  TTTAGAAAAA                    1620
 V  V  H     V  D  T  T    L  E  K                     540

GAAGATACTT  TATCATATGA  TAACTCAGAT                    1650
 E  D  T     L  S  Y  D    N  S  D                     550

AATATGTTTT  GTAATAAAGA  ATATTGTAAC                    1680
 N  M  F     C  N  K  E    Y  C  N                     560

AGATTAAAAG  ATGAAAATAA  TTGTATATCT                    1710
 R  L  K     D  E  N  N    C  I  S                     570

AATCTTCAAG  TTGAAGATCA  AGGTAATTGT                    1740
 N  L  Q     V  E  D  Q    G  N  C                     580

GATACTTCAT  GGATTTTTGC  TTCAAAATAT                    1770
 D  T  S     W  I  F  A    S  K  Y                     590

CATTTAGAAA  CTATTAGATG  TATGAAAGGA                    1800
 H  L  E     T  I  R  C    M  K  G                     600
```

*FIG. 2 (Continued)*

| | | | |
|---|---|---|---|
| TATGAACCTA | CCAAAATTTC | TGCTCTTTAT | 1830 |
| Y E P | T K I S | A L Y | 610 |
| GTAGCTAATT | GTTATAAGG | TGAACATAAA | 1860 |
| V A N | C Y K G | E H K | 620 |
| GATAGATGTG | ATGAAGGTTC | TAGTCCAATG | 1890 |
| D R C | D E G S | S P M | 630 |
| GAATTCTTAC | AAATTATTGA | AGATTATGGA | 1920 |
| E F L | Q I I E | D Y G | 640 |
| TTCTTACCAG | CAGAATCAAA | TTATCCATAT | 1950 |
| F L P | A E S N | Y P Y | 650 |
| AACTATGTGA | AAGTTGGAGA | ACAATGTCCA | 1980 |
| N Y V | K V G E | Q C P | 660 |
| AAGGTAGAAG | ATCACTGGAT | GAATCTATGG | 2010 |
| K V E | D H W M | N L W | 670 |
| GATAATGGAA | AAATCTTACA | TAACAAAAAT | 2040 |
| D N G | K I L H | N K N | 680 |
| GAACCTAATA | GTTTAGATGG | TAAGGGATAT | 2070 |
| E P N | S L D G | K G Y | 690 |
| ACTGCATATG | AAAGTGAAAG | ATTTCATGAT | 2100 |
| T A Y | E S E R | F H D | 700 |
| AATATGGATG | CATTTGTTAA | AATTATTAAA | 2130 |
| N M D | A F V K | I I K | 710 |
| ACTGAAGTAA | TGAATAAAGG | TTCAGTTATT | 2160 |
| T E V | M N K G | S V I | 720 |
| GCATATATTA | AAGCTGAAAA | TGTTATGGGA | 2190 |
| A Y I | K A E N | V M G | 730 |
| TATGAATTTA | GTGGAAAGAA | AGTACAGAAC | 2220 |
| Y E F | S G K K | V Q N | 740 |
| TTATGTGGTG | ATGATACAGC | TGATCATGCA | 2250 |
| L C G | D D T A | D H A | 750 |

FIG.2 (Continued)

| | | | |
|---|---|---|---|
| GTTAATATTG | TTGGTTATGG | TAATTATGTG | 2280 |
| V N I | V G Y G | N Y V | 760 |
| AATAGCGAAG | GAGAAAAAAA | ATCCTATTGG | 2310 |
| N S E | G E K K | S Y W | 770 |
| ATTGTAAGAA | ACAGTTGGGG | TCCATATTGG | 2340 |
| I V R | N S W G | P Y W | 780 |
| GGAGATGAAG | GTTATTTTAA | AGTAGATATG | 2370 |
| G D E | G Y F K | V D M | 790 |
| TATGGACCAA | CTCATTGTCA | TTTTAACTTT | 2400 |
| Y G P | T H C H | F N F | 800 |
| ATTCACAGTG | TTGTTATATT | CAATGTTGAT | 2430 |
| I H S | V V I F | N V D | 810 |
| TTACCTATGA | ATAATAAAAC | AACTAAAAAA | 2460 |
| L P M | N N K T | T K K | 820 |
| GAATCAAAAA | TATATGATTA | TTATTTAAAG | 2490 |
| E S K | I Y D Y | Y L K | 830 |
| GCCTCTCCAG | AATTTTATCA | TAACCTTTAC | 2520 |
| A S P | E F Y H | N L Y | 840 |
| TTTAAGAATT | TTAATGTTGG | TAAGAAAAAT | 2550 |
| F K N | F N V G | K K N | 850 |
| TTATTCTCTG | AAAAGGAAGA | TAATGAAAAC | 2580 |
| L F S | E K E D | N E N | 860 |
| AACAAAAAAT | TAGGTAACAA | CTATATTATA | 2610 |
| N K K | L G N N | Y I I | 870 |
| TTCGGTCAAG | ATACGGCAGG | ATCAGGACAA | 2640 |
| F G Q | D T A G | S G Q | 880 |
| AGTGGAAAGG | AAAGCAATAC | TGCATTAGAA | 2670 |
| S G K | E S N T | A L E | 890 |
| TCTGCAGGAA | CTTCAAATGA | AGTCTCAGAA | 2700 |
| S A G | T S N E | V S E | 900 |

FIG. 2 (Continued)

```
CGTGTTCATG  TTTATCACAT  ATTAAAACAT                2730
  R   V   H    V   Y   H   I    L   K   H          910

ATAAAGGATG  GCAAAATAAG  AATGGGTATG                2760
  I   K   D    G   K   I   R    M   G   M          920

CGTAAATATA  TAGATACACA  AGATGTAAAT                2790
  R   K   Y    I   D   T   Q    D   V   N          930

AAGAAACATT  CTTGTACAAG  ATCCTATGCA                2820
  K   K   H    S   C   T   R    S   Y   A          940

TTTAATCCAG  AGAATTATGA  AAAATGTGTA                2850
  F   N   P    E   N   Y   E    K   C   V          950

AATTTATGTA  ATGTGAACTG  GAAAACATGC                2880
  N   L   C    N   V   N   W    K   T   C          960

GAGGAAAAAA  CATCACCAGG  ACTTTGTTTA                2910
  E   E   K    T   S   P   G    L   C   L          970

TCCAAATTGG  ATACAAATAA  CGAATGTTAT                2940
  S   K   L    D   T   N   N    E   C   Y          980

TTCTGTTATG  TATAAAATAA  TATAACAAAA                2970
  F   C   Y    V   *                                984

AAAAAAAAAA  A                                     2981
```

FIG. 2 (Continued)

| | | | |
|---|---|---|---|
| ATGATGAACA | TGAAAATTGT | TTTATTCAGT | 30 |
| M  M  N | M  K  I  V | L  F  S | 10 |
| TTATTGCTCT | TTGTCATAAG | ATGGAATATT | 60 |
| L  L  L | F  V  I  R | W  N  I | 20 |
| ATTAGTTGTA | ATAAAACGA | CAAGAACCAA | 90 |
| I  S  C | N  K  N  D | K  N  Q | 30 |
| GGTGTTGATA | TGAATGTTTT | GAATAATTAT | 120 |
| G  V  D | M  N  V  L | N  N  Y | 40 |
| GAAAATTTAT | TTAAAGTTGT | TAAATGTGAA | 150 |
| E  N  L | F  K  V  V | K  C  E | 50 |
| TATTGTAATG | AACATACTTA | TGTTAAAGGT | 180 |
| Y  C  N | E  H  T  Y | V  K  G | 60 |
| AAGAAAGCTC | CTTCAGATCC | TCAATGTGCT | 210 |
| K  K  A | P  S  D  P | Q  C  A | 70 |
| GATATAAAAG | AAGAATGCAA | AGAATTACTT | 240 |
| D  I  K | E  E  C  K | E  L  L | 80 |
| AAGGAAAAAC | AATACACAGA | TTCAGTTACA | 270 |
| K  E  K | Q  Y  T  D | S  V  T | 90 |
| ATTTAATGG | ATGGTTTTAA | ATCAGCAAAT | 300 |
| Y  L  M | D  G  F  K | S  A  N | 100 |
| AATTCAGCAA | ATAATGGTAA | AAAAAATAAC | 330 |
| N  S  A | N  N  G  K | K  N  N | 110 |
| GCTGAAGAAA | TGAAAAATTT | AGTAAATTTC | 360 |
| A  E  E | M  K  N  L | V  N  F | 120 |
| TTACAATCTC | ATAAGAAATT | AATTAAAGCA | 390 |
| L  Q  S | H  K  K  L | I  K  A | 130 |
| TTAAAAAAGA | ATATTGAAAG | TATACAAAAT | 420 |
| L  K  K | N  I  E  S | I  Q  N | 140 |
| AAGAAACACT | TAATTTATAA | AAACAAATCA | 450 |
| K  K  H | L  I  Y  K | N  K  S | 150 |

*FIG.3*

| | | | |
|---|---|---|---|
| TATAATCCAT | TATTACTTTC | TTGTGTTAAA | 480 |
| Y N P | L L L S | C V K | 160 |
| AAAATGAATA | TGTTAAAAGA | AAATGTTGAC | 510 |
| K M N | M L K E | N V D | 170 |
| TATATTCAAA | AAAATCAAAA | CTTATTTAAA | 540 |
| Y I Q | K N Q N | L F K | 180 |
| GAATTAATGA | ATCAAAAGC | TACCTACTCT | 570 |
| E L M | N Q K A | T Y S | 190 |
| TTTGTTAATA | CCAAAAAAAA | AATTATTTCT | 600 |
| F V N | T K K K | I I S | 200 |
| TTAAAATCAC | AAGGTCATAA | AAAAGAAACC | 630 |
| L K S | Q G H K | K E T | 210 |
| TCACAAAATC | AAAATGAAAA | TAACGACAAT | 660 |
| S Q N | Q N E N | N D N | 220 |
| CAAAAATATC | AAGAAGTTAA | TGATGAAGAT | 690 |
| Q K Y | Q E [V N | D E D | 230 |
| GATGTAAATG | ATGAAGAAGA | TACAAACGAT | 720 |
| D] [V N | D E E D] | [T N D | 240 |
| GACGAAGATA | CTAACGATGA | AGAAGATACA | 750 |
| D E D] | [T N D E | E D] [T | 250 |
| AACGATGACG | AAGATACAAA | TGATGACGAA | 780 |
| N D D | E D] [T N | D D E | 260 |
| GATACTAACG | ATGAAGAAGA | TACTAACGAC | 810 |
| D] [T N | D E E D] | [T N D | 270 |
| GAAGAAGATC | ATGAAAATAA | TAATGCTACA | 840 |
| E E D] | H E N N | N A T | 280 |
| GCATACGAAT | TAGGTATCGT | CCCAGTTAAC | 870 |
| A Y E | L G I V | P V N | 290 |
| GATGTGTTAA | ATGTTAATAT | GAAAAATATG | 900 |
| D V L | N V N M | K N M | 300 |

FIG. 3 (Continued)

```
ATAACAGGAA   ATAATTTTAT   GGATGTTGTT       930
 I  T  G     N  N  F  M    D  V  V         310

AAAAGTACAT   TAGCTCAATC   AGGTGGATTA       960
 K  S  T     L  A  Q  S    G  G  L         320

GGAAGTAATG   ATTTAATAAA   TTTCTTAAAT       990
 G  S  N     D  L  I  N    F  L  N         330

CAAGGTAAAG   AAATAGGAGA   AAATTTATTA      1020
 Q  G  K     E  I  G  E    N  L  L         340

AACATAACAA   AGATGAACTT   GGGAGATAAG      1050
 N  I  T     K  M  N  L    G  D  K         350

AATAATCTTG   AAAGTTTTCC   TTTAGATCAA      1080
 N  N  L     E  S  F  P    L  D  Q         360

TTAAATATGT   TAAAAGATAA   TTTAATAAAC      1110
 L  N  M     L  K  D  N    L  I  N         370

TATGAATTCA   TATTAAATAA   TTTGAAAACA      1140
 Y  E  F     I  L  N  N    L  K  T         380

AGTGTTTTAA   ATAAATTAAA   AGATTTATTA      1170
 S  V  L     N  K  L  K    D  L  L         390

TTAAGATTAT   TATACAAAGC   ATATGTATCA      1200
 L  R  L     L  Y  K  A    Y  V  S         400

TATAAGAAAA   GAAAAGCTCA   AGAAAAAGGA      1230
 Y  K  K     R  K  A  Q    E  K  G         410

TTACCAGAAC   CTACTGTTAC   TAATGAAGAA      1260
 L  P  E     P  T  V  T    N  E  E         420

TATGTTGAAG   AATTAAAGAA   AGGTATTCTA      1290
 Y  V  E     E  L  K  K    G  I  L         430

GATATGGGTA   TCAAATTATT   ATTTAGTAAA      1320
 D  M  G     I  K  L  L    F  S  K         440

GTTAAAAGCC   TATTAAAAAA   ATTAAAAAAT      1350
 V  K  S     L  L  K  K    L  K  N         450
```

*FIG.3(Continued)*

```
AAAATATTCC  CTAAGAAAAA  AGAAGATAAT    1380
 K  I  F     P  K  K  K   E  D  N     460

CAAGCAGTAG  ATACCAAAAG  TATGGAAGAA    1410
 Q  A  V     D  T  K  S   M  E  E     470

CCCAAAGTTA  AAGCACAACC  AGCTCTTAGA    1440
 P  K  V     K  A  Q  P   A  L  R     480

GGTGTTGAAC  CAACGGAAGA  TTCTAATATT    1470
 G  V  E     P  T  E  D   S  N  I     490

ATGAACAGTA  TTAATAATGT  TATGGATGAA    1500
 M  N  S     I  N  N  V   M  D  E     500

ATTGATTTCT  TTGAAAAAGA  ATTAATCGAA    1530
 I  D  F     F  E  K  E   L  I  E     510

AATAATAATA  CACCTAATGT  TGTACCACCA    1560
 N  N  N     T  P  N  V   V  P  P     520

ACTCAATCAA  AAAAAAAAAA  CAAAAATGAA    1590
 T  Q  S     K  K  K  N   K  N  E     530

ACTGTATCTG  GTATGGATGA  AAATTTTGAT    1620
 T  V  S     G  M  D  E   N  F  D     540

AATCATCCTG  AAAATTATTT  TAAAGAAGAA    1650
 N  H  P     E  N  Y  F   K  E  E     550

TATTATTATG  ATGAAAATGA  TGATATGGAA    1680
 Y  Y  Y     D  E  N  D   D  M  E     560

GTAAAAGTTA  AAAAAATAGG  TGTCACATTA    1710
 V  K  V     K  K  I  G   V  T  L     570

AAAAAATTTG  AACCACTTAA  AAATGGAAAT    1740
 K  K  F     E  P  L  K   N  G  N     580

GTTAGTGAAA  CCATTAAATT  GATTCATTTA    1770
 V  S  E     T  I  K  L   I  H  L     590

GGAAATAAAG  ATAAAAAACA  CATTGAAGCT    1800
 G  N  K     D  K  K  H   I  E  A     600
```

*FIG. 3 (Continued)*

| | | | |
|---|---|---|---|
| ATAAACAACG | ATATTCAAAT | TATTAAACAA | 1830 |
| I N N | D I Q I | I K Q | 610 |
| GAATTACAAG | CTATTTATAA | TGAACTTATG | 1860 |
| E L Q | A I Y N | E L M | 620 |
| ATTATACAA | ATGGAAACAA | AAATATTCAA | 1890 |
| N Y T | N G N K | N I Q | 630 |
| CAAATATTTC | AACAAAATAT | TCTAGAAAAT | 1920 |
| Q I F | Q Q N I | L E N | 640 |
| GATGTTCTTA | ATCAAGAAAC | GGAGGAAGAA | 1950 |
| D V L | N Q E T | E E E | 650 |
| ATGGAAAAAC | AAGTTGAAGC | AATCACCAAG | 1980 |
| M E K | Q V E A | I T K | 660 |
| CAAATAGAAG | CTGAAGTGGA | TGCCCTCGCA | 2010 |
| Q I E | A E V D | A L A | 670 |
| CCAAAAAATA | AGGAAGAAGA | AGAAAAAGAA | 2040 |
| P K N | [K E E E | E][K E] | 680 |
| AAAGAAAAG | AAAAGGAAAA | AGAAGAAAAA | 2070 |
| [K E][K | E][K E][K | E E][K | 690 |
| GAAAAGAAG | AAAAAGAAAA | AGAAAAAGAA | 2100 |
| E][K E | E][K E][K | E][K E | 700 |
| GAAAAGAAA | AAGAAAAGA | AAAAGAAGAA | 2130 |
| E][K E] | [K E][K E] | [K E E] | 710 |
| AAAGAAGAAG | AAAAAAAAGA | AAAAGAAGAA | 2160 |
| [K E E | E][K K E] | [K E E | 720 |
| GAACAAGAAG | AAGAAGAAGA | AGAAATAGTA | 2190 |
| E][Q E | E E E E | E] I V | 730 |
| CCAGAAAATT | TGACAACTGA | AGAATCAAAA | 2220 |
| P E N | L T T E | E S K | 740 |
| TAA | | | 2223 |
| * | | | |

FIG. 3 (Continued)

| | | | | |
|---|---|---|---|---|
| TTTAATGGTA | AAGAAGCATG | CAGATCAATT | 30 | |
| F N G | K E A C | R S I | 10 | |
| AACCCAGATG | AAGCTGTTGC | ATATGGTGCA | 60 | |
| N P D | E A V A | Y G A | 20 | |
| GCTGTACAAG | CAGCCATTTT | ATCTGGTGAC | 90 | |
| A V Q | A A I L | S G D | 30 | |
| CAATCAAATG | CTGTCCAAGA | TTTATTATTA | 120 | |
| Q S N | A V Q D | L L L | 40 | |
| TTAGATGTTT | GCTCCTTATC | ATTAGGTTTA | 150 | |
| L D V | C S L S | L G L | 50 | |
| GAAACTGCTG | GTGGTGTTAT | GACCAAATTA | 180 | |
| E T A | G G V M | T K L | 60 | |
| ATTGAAAGAA | ACACAACCAT | ACCTGCTAAA | 210 | |
| I E R | N T T I | P A K | 70 | |
| AAGAGTCAAA | TCTTTACTAC | TTATGCTGAT | 240 | |
| K S Q | I F T T | Y A D | 80 | |
| AACCAACCAG | GTGTCTTAAT | TCAAGTATAT | 270 | |
| N Q P | G V L I | Q V Y | 90 | |
| GAAGGTGAAA | GAGCCTTAAC | CAAAGATAAC | 300 | |
| E G E | R A L T | K D N | 100 | |
| AATTTATTAG | GAAAATTTCA | CTTAGATGGT | 330 | |
| N L L | G K F H | L D G | 110 | |
| ATTCCACCTG | CACCAAGAAA | GGTACCACAA | 360 | |
| I P P | A P R K | V P Q | 120 | |
| ATCGAAGTTA | CATTCGATAT | CGATGCTAAC | 390 | |
| I E V | T F D I | D A N | 130 | |
| GGTATCTTAA | ACGTTACGGC | TGTAGAAAAA | 420 | |
| G I L | N V T A | V E K | 140 | |
| TCCACTGGTA | AACAAAACCA | TATTACAATT | 450 | |
| S T G | K Q N H | I T I | 150 | |

FIG. 4

```
ACCAACGACA  AAGGAAGATT  ATCTCAAGAT    480
 T  N  D     K  G  R     S  Q  D      160

GAAATTGATC  GTATGGTTAA  TGATGCTGAA    510
 E  I  D     R  M  V  N  D  A  E      170

AAATACAAAG  CAGAAGATGA  AGAAAACAGA    540
 K  Y  K     A  E  D  E  E  N  R      180

AAAAGAATCG  AAGCAAGAAA  CAGCCTTGAA    570
 K  R  I     E  A  R  N  S  L  E      190

AATTACTGCT  ATGGAGTTAA  AAGCTCATTA    600
 N  Y  C     Y  G  V  K  S  S  L      200

GAAGACCAAA  AAATTAAAGA  AAAATTACAA    630
 E  D  Q     K  I  K  E  K  L  Q      210

CCAGCTGAAA  TTGAAACATG  TATGAAAACT    660
 P  A  E     I  E  T  C  M  K  T      220

ATTACAACCA  TACTTGAATG  GTTAGAAAAA    690
 I  T  T     I  L  E  W  L  E  K      230

AACCAACTTG  CTGGAAAAGA  TGAATATGAA    720
 N  Q  L     A  G  K  D  E  Y  E      240

GCCAAACAAA  AAGAAGCAGA  ATCGGTTTGT    750
 A  K  Q     K  E  A  E  S  V  C      250

GCTCCAATTA  TGTCTAAAAT  CTATCAAGAT    780
 A  P  I     M  S  K  I  Y  Q  D      260

GCTGCTGGTG  CAGCCGGTGG  TATGCCAGGA    810
 A  A  G     A  A [G  G  M  P] [G     270

GGTATGCCCG  GTGGAATGCC  AGGTGGAATG    840
 G  M  P] [G  G  M  P]  G  G  M       280

CCAGGTGGAA  TGCCAGGTGG  TATGAATTTC    870
 P] [G  G    M  P] [G  G  M  N  F     290

CCAGGAGGTA  TGCCCGGAGC  AGGAATGCCA    900
 P] [G  G    M  P] [G  A  G  M  P]    300
```

*FIG. 4 (Continued)*

```
GGAAATGCCC  CAGCTGGAAG  TGGACCAACA                  930
  G   N   A   P   A   G   S   G   P   T             310

GTTGAAGAAG  TTGATTAAAC  TAAAAAAAAA                  960
  V   E   E   V   D   *                             315

AAAAAA                                              966
```

FIG. 4 (Continued)

| | | | |
|---|---|---|---|
| ATGAGAAAAT | TATACTGCGT | ATTATTATTG | 30 |
| M R K | L Y C V | L L L | 10 |
| AGCGCTTTG | AGTTTACATA | TATGATAAAC | 60 |
| S A F | E F T Y | M I N | 20 |
| TTTGGAAGAG | GACAGAATTA | TTGGGAACAT | 90 |
| F G R | G Q N Y | W E H | 30 |
| CCATATCAAA | ATAGTGATGT | GTATCGTCCA | 120 |
| P Y Q | N S D V | Y R P | 40 |
| ATCAACGAAC | ATAGGGAACA | TCCAAAAGAA | 150 |
| I N E | H R E H | P K E | 50 |
| TACGAATATC | CATTACACCA | GGAACATACA | 180 |
| Y E Y | P L H Q | E H T | 60 |
| TACCAACAAG | AAGATTCAGG | AGAAGACGAA | 210 |
| Y Q Q | E D S G | E D E | 70 |
| AATACATTAC | AACACGCATA | TCCAATAGAC | 240 |
| N T L | Q H A Y | P I D | 80 |
| CACGAAGGTG | CCGAACCCGC | ACCACAAGAA | 270 |
| H E G | A E P A | P Q E | 90 |
| CAAAATTTAT | TTTCAAGCAT | TGAAATAGTA | 300 |
| Q N L | F S S I | E I V | 100 |
| GAAAGAAGTA | ATTATATGGG | TAATCCATGG | 330 |
| E R S | N Y M G | N P W | 110 |
| ACGGAATATA | TGGCAAAATA | TGATATTGAA | 360 |
| T E Y | M A K Y | D I E | 120 |
| GAAGTTCATG | GTTCAGGTAT | AAGAGTAGAT | 390 |
| E V H | G S G I | R V D | 130 |
| TTAGGAGAAG | ATGCTGAAGT | AGCTGGAACT | 420 |
| L G E | D A E V | A G T | 140 |
| CAATATAGAC | TTCCATCAGG | GAAATGTCCA | 450 |
| Q Y R | L P S G | K C P | 150 |

*FIG.5*

| | | | |
|---|---|---|---|
| GTATTTGGTA | AAGGTATAAT | TATTGAGAAT | 480 |
| V  F  G | K  G  I  I | I  E  N | 160 |
| TCAAATACTA | CTTTTTTAAC | ACCGGTAGCT | 510 |
| S  N  T | T  F  L  T | P  V  A | 170 |
| ACGGAAATC | AATATTTAAA | AGATGGAGGT | 540 |
| T  G  N | Q  Y  L  K | D  G  G | 180 |
| TTTGCTTTTC | CTCCAACAGA | ACCTCTTATG | 570 |
| F  A  F | P  P  T  E | P  L  M | 190 |
| TCACCAATGA | CATTAGATGA | AATGAGACAT | 600 |
| S  P  M | T  L  D  E | M  R  H | 200 |
| TTTTATAAAG | ATAATAAATA | TGTAAAAAAT | 630 |
| F  Y  K | D  N  K  Y | V  K  N | 210 |
| TTAGATGAAT | TGACTTTATG | TTCAAGACAT | 660 |
| L  D  E | L  T  L  C | S  R  H | 220 |
| GCAGGAAATA | TGATTCCAGA | TAATGATAAA | 690 |
| A  G  N | M  I  P  D | N  D  K | 230 |
| AATTCAAATT | ATAAATATCC | AGCTGTTTAT | 720 |
| N  S  N | Y  K  Y  P | A  V  Y | 240 |
| GATGACAAAG | ATAAAAGTG | TCATATATTA | 750 |
| D  D  K | D  K  K  C | H  I  L | 250 |
| TATATTGCAG | CTCAAGAAAA | TAATGGTCCT | 780 |
| Y  I  A | A  Q  E  N | N  G  P | 260 |
| AGATATTGTA | ATAAAGACGA | AAGTAAAAGA | 810 |
| R  Y  C | N  K  D  E | S  K  R | 270 |
| AACAGCATGT | TTTGTTTTAG | ACCAGCAAAA | 840 |
| N  S  M | F  C  F  R | P  A  K | 280 |
| GATATATCAT | TTCAAAACTA | TACATATTTA | 870 |
| D  I  S | F  Q  N  Y | T  Y  L | 290 |
| AGTAAGAATG | TAGTTGATAA | CTGGGAAAAA | 900 |
| S  K  N | V  V  D  N | W  E  K | 300 |

*FIG. 5 (Continued)*

| | | | |
|---|---|---|---|
| GTTTGCCCTA | GAAAGAATTT | ACAGAATGCA | 930 |
| V C P | R K N L | Q N A | 310 |
| AAATTCGGAT | TATGGGTCGA | TGGAAATTGT | 960 |
| K F G | L W V D | G N C | 320 |
| GAAGATATAC | CACATGTAAA | TGAATTTCCA | 990 |
| E D I | P H V N | E F P | 330 |
| GCAATTGATC | TTTTTGAATG | TAATAAATTA | 1020 |
| A I D | L F E C | N K L | 340 |
| GTTTTTGAAT | TGAGTGCTTC | GGATCAACCT | 1050 |
| V F E | L S A S | D Q P | 350 |
| AAACAATATG | AACAACATTT | AACAGATTAT | 1080 |
| K Q Y | E Q H L | T D Y | 360 |
| GAAAAAATTA | AAGAAGGTTT | CAAAAATAAG | 1110 |
| E K I | K E G F | K N K | 370 |
| AACGCTAGTA | TGATCAAAAG | TGCTTTTCTT | 1140 |
| N A S | M I K S | A F L | 380 |
| CCCACTGGTG | CTTTTAAAGC | AGATAGATAT | 1170 |
| P T G | A F K A | D R Y | 390 |
| AAAAGTCATG | GTAAGGGTTA | TAATTGGGGA | 1200 |
| K S H | G K G Y | N W G | 400 |
| AATTATAACA | CAGAAACACA | AAAATGTGAA | 1230 |
| N Y N | T E T Q | K C E | 410 |
| ATTTTTAATG | TCAAACCAAC | ATGTTTAATT | 1260 |
| I F N | V K P T | C L I | 420 |
| AACAATTCAT | CATACATTGC | TACTACTGCT | 1290 |
| N N S | S Y I A | T T A | 430 |
| TTGTCCCATC | CCATCGAAGT | TGAAAACAAT | 1320 |
| L S H | P I E V | E N N | 440 |
| TTTCCATGTT | CATTATATAA | AGATGAAATA | 1350 |
| F P C | S L Y K | D E I | 450 |

*FIG.5 (Continued)*

```
ATGAAAGAAA  TCGAAAGAGA  ATCAAAACGA    1380
 M  K  E     I  E  R  E   S  K  R      460

ATTAAATTAA  ATGATAATGA  TGATGAAGGG    1410
 I  K  L     N  D  N  D   D  E  G      470

AATAAAAAAA  TTATGCTCCA  AGAATTTTA     1440
 N  K  K     I  M  L  Q   E  F  L      480

ATTTCAGATG  ATAAAGACAG  TTTAAAACGC    1470
 I  S  D     D  K  D  S   L  K  R      490

CCATGTGACC  CTGAAATGGT  AAGTAATAGT    1500
 P  C  D     P  E  M  V   S  N  S      500

ACATGTCGTT  TCTTTGTATG  TAAATGTGTA    1530
 T  C  R     F  F  V  C   K  C  V      510

GAAAGAAGGG  CAGAAGTAAC  ATCAAATAAT    1560
 E  R  R     A  E  V  T   S  N  N      520

GAAGTTGTAG  TTAAAGAAGA  ATATAAAGAT    1590
 E  V  V     V  K  E  E   Y  K  D      530

GAATATGCAG  ATATTCCTGA  ACATAAACCA    1620
 E  Y  A     D  I  P  E   H  K  P      540

ACTTATGATA  AAATGAAAAT  TATAATTGCA    1650
 T  Y  D     K  M  K  I   I  I  A      550

TCATCAGCTC  GTGTCGCTGT  ATTAGCAACT    1680
 S  S  A     R  V  A  V   L  A  T      560

ATTTTAATGG  TTTATCTTTA  TAAAAGAAAA    1710
 I  L  M     V  Y  L  Y   K  R  K      570

GGAAATGCTG  AAAAATATGA  TAAAATGGAT    1740
 G  N  A     E  K  Y  D   K  M  D      580

GAACCACAAG  ATTATGGGAA  ATCAAATTCA    1770
 E  P  Q     D  Y  G  K   S  N  S      590

AGAAATGATG  AAATGTTAGA  TCCTGAGGCA    1800
 R  N  D     E  M  L  D   P  E  A      600
```

FIG. 5 (Continued)

```
TCTTTTTGGG  GGGAAGAAAA  AAGAGCATCA           1830
  S  F  W     G  E  E  K    R  A  S           610

CATACAACAC  CAGTTCTGAT  GGAAAAACCA           1860
  H  T  T    P  V  L  M    E  K  P            620

TACTATTAAT  TTTTATGGAT  CC                   1882
  Y  Y  *                                     622
```

*FIG. 5 (Continued)*

| | |
|---|---|
| ATGAAGATCA TATTCTTTCT ATGTTCATTT | 30 |
| CTTTTCTTTA TTATAAATAC ACAATGTGTA | 60 |
| ACACATGAAA GTTATCAAGA ACTTGTCAAA | 90 |
| AAACTAGAAG CTTTAGAAGA TGCAGTATTG | 120 |
| ACAGGTTATG GTTTATTTCA TAAGGAAAAA | 150 |
| ATGATCTTAA ATGAAGAAGA AATTACTACA | 180 |
| AAAGGTGCAA GTGCTCAAAG TGGTACAAGT | 210 |
| GGTACAAGTG GTACAAGTGG TACAAGTGGT | 240 |
| ACAAGTGGTA CAAGTGGTAC AAGTGCTCAA | 270 |
| AGTGGTACAA GTGGTACAAG TGCTCAAAGT | 300 |
| GGTACAAGTG GTACAAGTGC TCAAAGTGGT | 330 |
| ACAAGTGGTA CAAGTGGTAC AAGTGGTACA | 360 |
| AGTCCATCAT CTCGTTCAAA CACTTTACCT | 390 |
| CGTTCAAATA CTTCATCTGG TGCAAGCCCT | 420 |
| CCAGCTGATG CAAGCGATTC AGATGCTAAA | 450 |
| TCTTACGCTG ATTTAAAACA CAGAGTACGA | 480 |
| AATTACTTGT TCACTATTAA AGAACTCAAA | 510 |
| TATCCCGAAC TCTTTGATTT AACCAATCAT | 540 |
| ATGTTAACTT TGTGTGATAA TATTCATGGT | 570 |
| TTCAAATATT TAATTGATGG ATATGAAGAA | 600 |
| ATTAATGAAT TATTATATAA ATTAAACTTT | 630 |
| TATTTTGATT TATTAAGAGC AAAATTAAAT | 660 |

*FIG.6*

| | |
|---|---|
| GATGTATGTG CTAATGATTA TTGTCAAATA | 690 |
| CCTTTCAATC TTAAAATTCG TGCAAATGAA | 720 |
| TTAGACGTAC TTAAAAAACT TGTGTTCGGA | 750 |
| TATAGAAAAC CATTAGACAA TATTAAAGAT | 780 |
| AATGTAGGAA AAATGGAAGA TTACATTAAA | 810 |
| AAAATAAAA CAACCATAGC AAATATAAAT | 840 |
| GAATTAATTG AAGGAAGTAA GAAAACAATT | 870 |
| GATCAAAATA AGAATGCAGA TAATGAAGAA | 900 |
| GGAAAAAAAA AATTATACCA AGCTCAATAT | 930 |
| GATCTTTCTA TTTACAATAA ACAATTAGAA | 960 |
| GAAGCACATA ATTTAATAAG CGTTTTAGAA | 990 |
| AAACGTATTG ACACTTTAAA AAAAAATGAA | 1020 |
| AACATTAAGG AATTACTTGA TAAGATAAAT | 1050 |
| GAAATTAAAA ATCCCCCACC GGCCAATTCT | 1080 |
| GGAAATACAC CAAATACTCT CCTTGATAAG | 1110 |
| AACAAAAAAA TCGAGGAACA CGAAGAAAAA | 1140 |
| ATAAAGAAA TTGCCAAAAC TATTAAATTT | 1170 |
| AACATTGATA GTTTATTTAC TGATCCACTT | 1200 |
| GAATTAGAAT ATTATTTAAG AGAAAAAAAT | 1230 |
| AAAAAAGTTG ATGTAACACC TAAATCACAA | 1260 |
| GATCCTACGA AATCTGTTCA AATACCAAAA | 1290 |
| GTTCCTTATC CAAATGGTAT TGTATATCCT | 1320 |

FIG.6 (Continued)

```
TTACCACTCA CTGATATTCA TAATTCATTA      1350

GCTGCAGATA ATGATAAAAA TTCATATGGT      1380

GATTTAATGA ATCCTGATAC TAAAGAAAAA      1410

ATTAATGAAA AAATTATTAC AGATAATAAG      1440

GAAAGAAAAA TATTCATTAA TAACATTAAA      1470

AAACAAATTG ATTTAGAAGA AAAAAAATT       1500

AATCACACAA AAGAACAAAA TAAAAAATTA      1530

CTTGAAGATT ATGAAAGTC AAAAAAGGAT       1560

TATGAAGAAT TACTTGAAAA ATTTTATGAA      1590

ATGAAATTTA ATAATAATTT TGACAAAGAT      1620

GTCGTAGATA AAATATTCAG TGCAAGATAT      1650

ACATATAATG TTGAAAAACA AAGATATAAT      1680

AATAAATTTT CATCCTCTAA TAATTCTGTA      1710

TATAATGTTC AAAAATTAAA AAAGGCTCTT      1740

TCATATCTTG AAGATTATTC TTTAAGAAAA      1770

GGAATTTCTG AAAAGATTT TAATCATTAT       1800

TATACTTTGA AAACTGGCCT CGAAGCTGAT      1830

ATAAAAAAAT TAACAGAAGA AATAAAGAGT      1860

AGTGAAAACA AAATTCTAGA AAAAAATTTT      1890

AAAGGACTAA CACATTCAGC AAATGCTTCC      1920

TTAGAAGTAT ATGATATTGT AAAATTACAA      1950

GTACAAAAAG TTTTATTAAT TAAAAAAATA      1980
```

FIG.6 (Continued)

| | |
|---|---|
| GAAGACTTAA GAAAGATAGA ATTATTTTTA | 2010 |
| AAAAATGCAC AACTAAAAGA TAGTATTCAT | 2040 |
| GTACCAAATA TTTATAAACC ACAAAATAAA | 2070 |
| CCAGAACCAT ATTATTTAAT TGTATTAAAA | 2100 |
| AAAGAAGTAG ATAAATTAAA AGAATTTATA | 2130 |
| CCAAAAGTAA AAGACATGTT AAAGAAAGAA | 2160 |
| CAAGCTGTCT TATCAAGTAT TACACAACCT | 2190 |
| TTAGTTGCAG CAAGCGAAAC AACTGAAGAT | 2220 |
| GGGGGTCACT CCACACACAC ATTATCCCAA | 2250 |
| TCAGGAGAAA CAGAAGTAAC AGAAGAAACA | 2280 |
| GAAGAAACAG AAGAAACAGT AGGACACACA | 2310 |
| ACAACGGTAA CAATAACATT ACCACCAAAA | 2340 |
| GAAGTAAAAG TTGTTGAAAA TTCAATAGAA | 2370 |
| CATAAGAGTA ATGACAATTC ACAAGCCTTG | 2400 |
| ACAAAAACAG TTTATCTAAA GAAATTAGAT | 2430 |
| GAATTTTTAA CTAAATCATA TATATGTCAT | 2460 |
| AAATATATTT TAGTATCAAA CTCTAGTATG | 2490 |
| GACCAAAAAT TATTAGAGGT ATATAATCTT | 2520 |
| ACTCCAGAAG AAGAAAATGA ATTAAAATCA | 2550 |
| TGTGATCCAT TAGATTTATT ATTTAATATT | 2580 |
| CAAAATAACA TACCTGCTAT GTATTCATTA | 2610 |
| TATGATAGTA TGAACAATGA TTTACAACAT | 2640 |

*FIG.6 (Continued)*

```
CTCTTTTTTG AATTATATCA AAAGGAAATG      2670
ATTTATTATT TACATAAACT AAAAGAGGAA      2700
AATCACATCA AAAATTATT AGAGGAGCAA       2730
AAACAAATAA CTGGAACATC ATCTACATCC      2760
AGTCCTGGAA ATACAACCGT AAATACTGCT      2790
CAATCCGCAA CTCACAGTAA TTCCCAAAAC      2820
CAACAATCAA ATGCATCCTC TACCAATACC      2850
CAAAATGGTG TAGCTGTATC ATCTGGTCCT      2880
GCTGTAGTTG AAGAAAGTCA TGATCCCTTA      2910
ACAGTATTGT CTATTAGTAA CGATTTGAAA      2940
GGTATTGTTA GTCTCTTAAA TCTTGGAAAT      2970
AAAACTAAAG TACCTAATCC ATTAACCATT      3000
TCTACAACAG AGATGGAAAA ATTTTATGAG      3030
AATATTTTAA AAAATAATGA TACCTATTTT      3060
AATGATGATA TCAAACAATT CGTAAAATCT      3090
AATTCAAAAG TAATTACAGG TTTGACCGAA      3120
ACACAAAAAA ATGCATTAAA TGATGAAATT      3150
AAAAAATTAA AAGATACTTT ACAGTTATCA      3180
TTTGATTTAT ATAATAAATA TAAATTAAAA      3210
TTAGATAGAT TATTTAATAA GAAAAAGAA       3240
CTTGGCCAAG ACAAATGCA AATTAAAAAA       3270
CTTACTTTAT TAAAAGAACA ATTAGAATCA      3300
```

FIG.6 (Continued)

| | |
|---|---|
| AAATTGAATT CACTTAATAA CCCACATAAT | 3330 |
| GTATTACAAA ACTTTTCTGT TTTCTTTAAC | 3360 |
| AAAAAAAAG AAGCTGAAAT AGCAGAAACT | 3390 |
| GAAAACACAT TAGAAAACAC AAAAATATTA | 3420 |
| TTGAAACATT ATAAGGACT TGTTAAATAT | 3450 |
| TATAATGGTG AATCATCTCC ATTAAAAACT | 3480 |
| TTAAGTGAAG TATCAATTCA AACAGAAGAT | 3510 |
| AATTATGCCA ATTTAGAAAA ATTTAGAGTA | 3540 |
| TTAAGTAAAA TAGATGGAAA ACTCAATGAT | 3570 |
| AATTTACATT TAGGAAAGAA AAAATTATCT | 3600 |
| TTCTTATCAA GTGGATTACA TCAGTTAATT | 3630 |
| ACTGAATTAA AAGAAGTAAT AAAAAATAAA | 3660 |
| AATTATACAG GTAATTCTCC AAGTGAAAAT | 3690 |
| AATAAGAAAG TTAACGAAGC TTTAAAATCT | 3720 |
| TACGAAAATT TTCTCCCAGA AGCAAAAGTT | 3750 |
| ACAACAGTTG TAACTCCACC TCAACCAGAT | 3780 |
| GTAACTCCAT CTCCATTATC TGTAAGGGTA | 3810 |
| AGTGGTAGTT CAGGATCCAC AAAAGAAGAA | 3840 |
| ACACAAATAC CAACTTCAGG CTCTTTATTA | 3870 |
| ACAGAATTAC AACAAGTAGT ACAATTACAA | 3900 |
| AATTATGACG AAGAAGATGA TTCCTTAGTT | 3930 |
| GTATTACCCA TTTTTGGAGA ATCCGAAGAT | 3960 |

*FIG.6 (Continued)*

```
AATGACGAAT ATTTAGATCA AGTAGTAACT              3990

GGAGAAGCAA TATCTGTCAC AATGGATAAT              4020

ATCCTCTCAG GATTTGAAAA TGAATATGAT              4050

GTTATATATT TAAAACCTTT AGCTGGAGTA              4080

TATAGAAGCT TAAAAAAACA AATTGAAAA               4110

AACATTTTA CATTTAATTT AAATTTGAAC               4140

GATATCTTAA ATTCACGTCT TAAGAAACGA              4170

AAATATTTCT TAGATGTATT AGAATCTGAT              4200

TTAATGCAAT TTAAACATAT ATCCTCAAAT              4230

GAATACATTA TTGAAGATTC ATTTAATTA               4260

TTGAATTCAG AACAAAAAAA CACACTTTTA              4290

AAAGTTACA AATATATAAA AGAATCAGTA               4320

GAAATGATA TTAAATTTGC ACAGGAAGGT               4350

ATAAGTTATT ATGAAAGGT TTTAGCGAAA               4380

TATAAGGATG ATTTAGAATC AATTAAAAAA              4410

GTTATCAAAG AAGAAAGGA GAAGTTCCCA               4440

TCATCACCAC CAACAACACC TCCGTCACCA              4470

GTAAAAACAG ACGAACAAAA GAAGGAAAGT              4500

AAGTTCCTTC CATTTTTAAC AAACATTGAG              4530

ACCTTATACA ATAACTTAGT TAATAAAATT              4560

GACGATTACT TAATTAACTT AAAGGCAAAG              4590

ATTAACGATT GTAATGTTGA AAAAGATGAA              4620
```

FIG. 6 (Continued)

```
GCACATGTTA AAATAACTAA ACTTAGTGAT        4650

TTAAAAGCAA TTGATGACAA AATAGATCTT        4680

TTTAAAAACC ATAACGACTT CGAAGCAATT        4710

AAAAAATTGA TAAATGATGA TACGAAAAAA        4740

GATATGCTTG GCAAATTACT TAGTACAGGA        4770

TTAGTTCAAA ATTTTCCTAA TACAATAATA        4800

TCAAAATTAA TTGAAGGAAA ATTCCAAGAT        4830

ATGTTAAACA TTTCACAACA CCAATGCGTA        4860

AAAAAACAAT GTCCAGAAAA TTCTGGATGT        4890

TTCAGACATT TAGATGAAAG AGAAGAATGT        4920

AAATGTTTAT TAAATTACAA ACAAGAAGGT        4950

GATAAATGTG TTGAAAATCC AAATCCTACT        4980

TGTAACGAAA ATAATGGTGG ATGTGATGCA        5010

GATGCCAAAT GTACCGAAGA AGATTCAGGT        5040

AGCAACGGAA AGAAAATCAC ATGTGAATGT        5070

ACTAAACCTG ATTCTTATCC ACTTTTCGAT        5100

GGTATTTTCT GCAGTTCCTC TAACTTCTTA        5130

GGAATATCAT TCTTATTAAT ACTCATGTTA        5160

ATATTATACA GTTTCATTTA A                 5181
```

FIG. 6 (Continued)

```
ATGATGAGAA AATTAGCTAT TTTATCTGTT          30
TCTTCCTTCC TATTTGTTGA GGCCTTATTC          60
CAGGAATACC AGTGCTATGG AAGTTCGTCA          90
AACACAAGGG TTCTAAATGA ATTAAATTAT         120
GATAATGCAG GCACTAATTT ATATAATGAA         150
TTAGAAATGA ATTATTATGG GAAACAGGAA         180
AATTGGTATA GTCTTAAAAA AAATAGTAGA         210
TCACTTGGAG AAAATGATGA TGGAAATAAC         240
GAAGACAACG AGAAATTAAG GAAACCAAAA         270
CATAAAAAAT TAAAGCAACC AGCGGATGGT         300
AATCCTGATC CAAATGCAAA CCCAAATGTA         330
GATCCCAATG CCAACCCAAA TGTAGATCCA         360
AATGCAAACC CAAATGTAGA TCCAAATGCA         390
AACCCAAATG CAAACCCAAA TGCAAACCCA         420
AATGCAAACC CAAATGCAAA CCCAAATGCA         450
AACCCAAATG CAAACCCAAA TGCAAACCCA         480
AATGCAAACC CAAATGCAAA CCCAAATGCA         510
AACCCAAATG CAAACCCAAA TGCAAACCCA         540
AACGCAAACC CCAATGCAAA TCCTAATGCA         570
AACCCCAATG CAAATCCTAA TGCAAATCCT         600
AATGCCAATC CAAATGCAAA TCCAAATGCA         630
AACCCAAACG CAAACCCCAA TGCAAATCCT         660
```

FIG. 7

```
AATGCCAATC  CAAATGCAAA  TCCAAATGCA           690

AACCCAAATG  CAAACCCAAA  TGCAAACCCC           720

AATGCAAATC  CTAATAAAAA  CAATCAAGGT           750

AATGGACAAG   GTCACAATAT  GCCAAATGAC          780

CCAAACCGAA  ATGTAGATGA  AAATGCTAAT           810

GCCAACAGTG  CTGTAAAAAA  TAATAATAAC           840

GAAGAACCAA   GTGATAAGCA  CATAAAAGAA          870

TATTTAAACA  AAATACAAAA  TTCTCTTTCA           900

ACTGAATGGT  CCCCATGTAG  TGTAACTTGT           930

GGAAATGGTA  TTCAAGTTAG  AATAAAGCCT           960

GGCTCTGCTA  ATAAACCTAA  AGACGAATTA           990

GATTATGCAA  ATGATATTGA  AAAAAAAATT          1020

TGTAAAATGG  AAAAATGTTC  CAGTGTGTTT          1050

AATGTCGTAA  ATAGTTCAAT  AGGATTAATA          1080

ATGGTATTAT  TCTTCTTGTT  CCTTAATTAG          1110
```

FIG. 7 (Continued)

```
ATGAGAAAAT TATACTGCGT ATTATTATTG    30
AGCGCCTTTG AGTTTACATA TATGATAAAC    60
TTTGGAAGAG GACAGAATTA TTGGGAACAT    90
CCATATCAAA ATAGTGATGT GTATCGTCCA   120
ATCAACGAAC ATAGGGAACA TCCAAAAGAA   150
TACGAATATC CATTACACCA GGAACATACA   180
TACCAACAAG AAGATTCAGG AGAAGACGAA   210
AATACATTAC AACACGCATA TCCAATAGAC   240
CACGAAGGTG CCGAACCCGC ACCACAAGAA   270
CAAAATTTAT TTTCAAGCAT TGAAATAGTA   300
GAAAGAAGTA ATTATATGGG TAATCCATGG   330
ACGGAATATA TGGCAAAATA TGATATTGAA   360
GAAGTTCATG GTTCAGGTAT AAGAGTAGAT   390
TTAGGAGAAG ATGCTGAAGT AGCTGGAACT   420
CAATATAGAC TTCCATCAGG GAAATGTCCA   450
GTATTTGGTA AAGGTATAAT TATTGAGAAT   480
TCAAATACTA CTTTTTTAAC ACCGGTAGCT   510
ACGGGAAATC AATATTTAAA AGATGGAGGT   540
TTTGCTTTTC CTCCAACAGA ACCTCTTATG   570
TCACCAATGA CATTAGATGA AATGAGACAT   600
TTTTATAAAG ATAATAAATA TGTAAAAAAT   630
TTAGATGAAT TGACTTTATG TTCAAGACAT   660
```

*FIG.8*

```
GCAGGAAATA TGATTCCAGA TAATGATAAA      690
AATTCAAATT ATAAATATCC AGCTGTTTAT      720
GATGACAAAG ATAAAAGTG TCATATATTA       750
TATATTGCAG CTCAAGAAAA TAATGGTCCT      780
AGATATTGTA ATAAAGACGA AAGTAAAAGA      810
AACAGCATGT TTTGTTTTAG ACCAGCAAAA      840
GATATATCAT TTCAAAACTA TACATATTTA      870
AGTAAGAATG TAGTTGATAA CTGGGAAAAA      900
GTTTGCCCTA GAAAGAATTT ACAGAATGCA      930
AAATTCGGAT TATGGGTCGA TGGAAATTGT      960
GAAGATATAC CACATGTAAA TGAATTTCCA      990
GCAATTGATC TTTTGAATG TAATAAATTA      1020
GTTTTTGAAT TGAGTGCTTC GGATCAACCT      1050
AAACAATATG AACAACATTT AACAGATTAT      1080
GAAAAAATTA AAGAAGGTTT CAAAAATAAG      1110
AACGCTAGTA TGATCAAAAG TGCTTTTCTT      1140
CCCACTGGTG CTTTTAAAGC AGATAGATAT      1170
AAAAGTCATG GTAAGGGTTA TAATTGGGGA      1200
AATTATAACA CAGAAACACA AAAATGTGAA      1230
ATTTTTAATG TCAAACCAAC ATGTTTAATT      1260
AACAATTCAT CATACATTGC TACTACTGCT      1290
TTGTCCCATC CCATCGAAGT TGAAAACAAT      1320
```

*FIG.8 (Continued)*

| | |
|---|---|
| TTTCCATGTT CATTATATAA AGATGAAATA | 1350 |
| ATGAAAGAAA TCGAAAGAGA ATCAAAACGA | 1380 |
| ATTAAATTAA ATGATAATGA TGATGAAGGG | 1410 |
| AATAAAAAAA TTATAGCTCC AAGAATTTTT | 1440 |
| ATTTCAGATG ATAAGACAG TTTAAAATGC | 1470 |
| CCATGTGACC CTGAAATGGT AAGTAATAGT | 1500 |
| ACATGTCGTT TCTTTGTATG TAAATGTGTA | 1530 |
| GAAAGAAGGG CAGAAGTAAC ATCAAATAAT | 1560 |
| GAAGTTGTAG TTAAAGAAGA ATATAAAGAT | 1590 |
| GAATATGCAG ATATTCCTGA ACATAAACCA | 1620 |
| ACTTATGATA AAATGAAAAT TATAATTGCA | 1650 |
| TCATCAGCTC GTGTCGCTGT ATTAGCAACT | 1680 |
| ATTTTAATGG TTTATCTTTA TAAAAGAAAA | 1710 |
| GGAAATGCTG AAAAATATGA TAAAATGGAT | 1740 |
| GAACCACAAG ATTATGGAA ATCAAATTCA | 1770 |
| AGAAATGATG AAATGTTAGA TCCTGAGGCA | 1800 |
| TCTTTTTGGG GGGAAGAAAA AAGAGCATCA | 1830 |
| CATACAACAC CAGTTCTGAT GGAAAAACCA | 1860 |
| TACTATTAAT TTTTATGGAT CC | 1882 |

FIG. 8 (Continued)

```
ATGAATAAAC TTTACAGTTT GTTTCTTTTC        30
CTTTTCATTC AACTTAGCAT AAAATATAAT        60
AATGCGAAAG TTACCGTGGA TACTGTATGC        90
AAAAGAGGAT TTTTAATTCA GATGAGTGGT       120
CATTTGGAAT GTAAATGTGA AAATGATTTG       150
GTGTTAGTAA ATGAAGAAAC ATGTGAAGAA       180
AAAGTTCTGA AATGTGACGA AAAGACTGTA       210
AATAAACCAT GTGGAGATTT TTCCAAATGT       240
ATTAAAATAG ATGGAAATCC CGTTTCATAC       270
GCTTGTAAAT GTAATCTTGG ATATGATATG       300
GTAAATAATG TTTGTATACC AAATGAATGT       330
AAGAATGTAA CTTGTGGTAA CGGTAAATGT       360
ATATTAGATA CAAGCAATCC TGTTAAAACT       390
GGAGTTTGCT CATGTAATAT AGGCAAAGTT       420
CCCAATGTAC AAGATCAAAA TAAATGTTCA       450
AAAGATGGAG AAACCAAATG CTCATTAAAA       480
TGCTTAAAAG AAAATGAAAC CTGTAAAGCT       510
GTTGATGGAA TTTATAAATG TGATTGTAAA       540
GATGGATTTA TAATAGATAA TGAAAGCTCT       570
ATATGTACTG CTTTTCAGC ATATAATATT       600
TTAAATCTAA GCATTATGTT TATACTATTT       630
TCAGTATGCT TTTTTATAAT GTAA            654
```

FIG. 9

| | |
|---|---|
| ATGAATCATC TTGGGAATGT TAAATATTTA | 30 |
| GTCATTGTGT TTTTGATTTT CTTTGATTTG | 60 |
| TTTCTAGTTA ATGGTAGAGA TGTGCAAAAC | 90 |
| AATATAGTGG ATGAAATAAA ATATCGTGAA | 120 |
| GAAGTATGTA ATGATGAGGT AGATCTTTAC | 150 |
| CTTCTAATGG ATTGTTCTGG AAGTATACGT | 180 |
| CGTCATAATT GGGTGAACCA TGCAGTACCT | 210 |
| CTAGCTATGA AATTGATACA ACAATTAAAT | 240 |
| CTTAATGATA ATGCAATTCA CTTATATGCT | 270 |
| AGTGTTTTTT CAAACAATGC AAGAGAAATT | 300 |
| ATTAGATTAC ATAGTGATGC ATCTAAAAAC | 330 |
| AAAGAGAAGG CTTTAATTAT TATAAAGTCA | 360 |
| CTCTTAAGTA CAAATCTTCC ATATGGTAAA | 390 |
| ACAAACTTAA CTGATGCACT GTTACAAGTA | 420 |
| AGAAAACATT TAAATGACCG AATCAATAGA | 450 |
| GAGAATGCTA ATCAATTAGT TGTTATATTA | 480 |
| ACAGATGGAA TTCCAGATAG TATTCAAGAT | 510 |
| TCATTAAAAG AATCAAGAAA ATTAAGTGAT | 540 |
| CGTGGTGTTA AAATAGCTGT TTTTGGTATT | 570 |
| GGACAAGGTA TTAATGTAGC TTTCAACAGA | 600 |
| TTTCTTGTAG GTTGTCATCC ATCAGATGGT | 630 |
| AAATGTAACT TGTATGCTGA TTCTGCATGG | 660 |

FIG.10

```
GAAAATGTAA AAAATGTTAT CGGACCCTTT        690

ATGAAGGCTG TTTGTGTTGA AGTAGAAAAA        720

ACAGCAAGTT GTGGTGTTTG GGACGAATGG        750

TCTCCATGTA GTGTAACTTG TGGTAAAGGT        780

ACCAGGTCAA GAAAAGAGA AATCTTACAC         810

GAAGGATGTA CAAGTGAATT ACAAGAACAA        840

TGTGAAGAAG AAAGATGTCT TCCAAAACGG        870

GAACCATTAG ATGTTCCAGA TGAACCCGAA        900

GATGATCAAC CTAGACCAAG AGGAGATAAT        930

TTTGCTGTCG AAAAACCAAA CGAAAATATA        960

ATAGATAATA ATCCACAAGA ACCTTCACCA        990

AATCCAGAAG AAGGAAAGGG TGAAAATCCA       1020

AACGGATTTG ATTTAGATGA AAATCCAGAA       1050

AATCCACCAA ATCCACCAAA TCCACCAAAT       1080

CCACCAAATC CACCAAATCC ACCAAATCCA       1110

GATATTCCTG AACAAGAACC AAATATACCT       1140

GAAGATTCAG AAAAAGAAGT ACCTTCTGAT       1170

GTTCCAAAAA ATCCAGAAGA CGATCGAGAA       1200

GAAAACTTTG ATATTCCAAA GAAACCCGAA       1230

AATAAGCACG ATAATCAAAA TAATTTACCA       1260

AATGATAAAA GTGATAGATA TATTCCATAT       1290

TCACCATTAT CTCCAAAAGT TTTGGATAAT       1320
```

FIG. 10 (Continued)

| | |
|---|---|
| GAAAGGAAAC AAAGTGACCC CCAAAGTCAA | 1350 |
| GATAATAATG GAAATAGGCA CGTACCTAAT | 1380 |
| AGTGAAGATA GAGAAACACG TCCACATGGT | 1410 |
| AGAAATAATG AAAATAGATC ATACAATAGA | 1440 |
| AAACATAACA ATACTCCAAA ACATCCTGAA | 1470 |
| AGGGAAGAAC ATGAAAGCC AGATAATAAT | 1500 |
| AAAAAAAAG CAGGATCAGA TAATAAATAT | 1530 |
| AAAATTGCAG GTGGAATAGC TGGAGGATTA | 1560 |
| GCTTTACTCG CATGTGCTGG ACTTGCTTAT | 1590 |
| AAATTCGTAG TACCAGGAGC AGCAACACCC | 1620 |
| TATGCCGGAG AACCTGCACC TTTTGATGAA | 1650 |
| ACATTAGGTG AAGAAGATAA AGATTTGGAC | 1680 |
| GAACCTGAAC AATTCAGATT ACCTGAAGAA | 1710 |
| AACGAGTGGA ATTAA | 1725 |

*FIG. 10 (Continued)*

| | |
|---|---|
| ATGAAACATA TTTTGTACAT ATCATTTTAC | 30 |
| TTTATCCTTG TTAATTTATT GATATTTCAT | 60 |
| ATAAATGGAA AGATAATAAA GAATTCTGAA | 90 |
| AAAGATGAAA TCATAAAATC TAACTTGAGA | 120 |
| AGTGGTTCTT CAAATTCTAG GAATCGAATA | 150 |
| AATGAGGAAA AGCACGAGAA GAAACACGTT | 180 |
| TTATCTCATA ATTCATATGA GAAAACTAAA | 210 |
| AATAATGAAA ATAATAAATT TTTCGATAAG | 240 |
| GATAAAGAGT TAACGATGTC TAATGTAAAA | 270 |
| AATGTGTCAC AAACAAATTT CAAAAGTCTT | 300 |
| TTAAGAAATC TTGGTGTTTC AGAGAATATA | 330 |
| TTCCTTAAAG AAAATAAATT AAATAAGGAA | 360 |
| GGGAAATTAA TTGAACACAT AATAAATGAT | 390 |
| GATGACGATA AAAAAAAATA TATTAAAGGG | 420 |
| CAAGACGAAA ACAGACAAGA AGATCTTGAA | 450 |
| GAAAAAGCGC GCGCATCTAA AGAAACGAGG | 480 |
| AAGGCTGATA CGAAAAAAAA TTTAGAAAGA | 510 |
| AAAAAGGAAC ATGGAGATGT ATTAGCAGAG | 540 |
| GATTTATATG GTCGTTTAGA AATACCAGCT | 570 |
| ATAGAACTTC CATCAGAAAA TGAACGTGGA | 600 |
| TATTATATAC CACATCAATC TTCTTTACCT | 630 |
| CAGGACAACA GAGGGAATAG TAGAGATTCC | 660 |

*FIG. II*

| | |
|---|---|
| AAGGAAATAT CTATAATAGA AAAAACAAAT | 690 |
| AGAGAATCTA TTACAACAAA TGTTGAAGGA | 720 |
| CGAAGGGATA TACATAAAGG ACATCTTGAA | 750 |
| GAAAGAAAG ATGGTTCAAT AAAACCAGAA | 780 |
| CAAAAGAAG ATAAATCTGC TGACATACAA | 810 |
| AATCATACAT TAGAGACAGT AAATATTTCT | 840 |
| GATGTTAATG ATTTTCAAAT AAGTAAGTAT | 870 |
| GAGGATGAAA TAAGTGCTGA ATATGACGAT | 900 |
| TCATTAATAG ATGAAGAAGA AGATGATGAA | 930 |
| GACTTAGACG AATTTAAGCC TATTGTGCAA | 960 |
| TATGACAATT TCCAAGATGA AGAAAACATA | 990 |
| GGAATTTATA AAGAACTAGA AGATTTGATA | 1020 |
| GAGAAAATG AAAATTTAGA TGATTTAGAT | 1050 |
| GAAGGAATAG AAAAATCATC AGAAGAATTA | 1080 |
| TCTGAAGAAA AAATAAAAAA AGGAAAGAAA | 1110 |
| TATGAAAAAA CAAAGGATAA TAATTTTAAA | 1140 |
| CCAAATGATA AAAGTTTGTA TGATGAGCAT | 1170 |
| ATTAAAAAAT ATAAAAATGA TAAGCAGGTT | 1200 |
| AATAAGGAAA AGGAAAAATT CATAAAATCA | 1230 |
| TTGTTTCATA TATTTGACGG AGACAATGAA | 1260 |
| ATTTTACAGA TCGTGGATGA GTTATCTGAA | 1290 |
| GATATAACTA AATATTTTAT GAAACTATAA | 1320 |

FIG.II (Continued)

SEQUENCE LISTING ( 1 ) GENERAL INFORMATION:

( i i i ) NUMBER OF SEQUENCES: 143

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

TTAGTTAATT AGGCGGCCGC                                                         20

( 2 ) INFORMATION FOR SEQ ID NO:2:

( i ) SEQUENCE CHARACTERISTICS:
( A ) LENGTH: 2981 base pairs
( B ) TYPE: nucleic acid
( C ) STRANDEDNESS: single
( D ) TOPOLOGY: linear ( x i ) SEQUENCE DESCRIPTION: SEQ ID NO:2:

ATGAAGTCAT ATATTTCCTT GTTTTTCATA TTGTGTGTTA TATTTAACAA AAATGTTATA         60

AAATGTACAG GAGAAAGTCA AACAGGTAAT ACAGGAGGAG GTCAAGCAGG TAATACAGGA         120

GGAGGTCAAG CAGGTAATAC AGTAGGAGAT CAAGCAGGTA GTACAGGAGG AAGTCCACAA         180

GGTAGTACGG GAGCAAGTCA ACCCGGAAGT TCCGAACCAA GCAATCCTGT AAGTTCCGGA         240

CATTCTGTAA GTACTGTATC AGTATCACAA ACTTCAACTT CTTCAGAAAA ACAGGATACA         300

ATTCAAGTAA AATCAGCTTT ATTAAAAGAT TATATGGGTT TAAAAGTTAC TGGTCCATGT         360

AACGAAAATT TCATAATGTT CTTAGTTCCT CATATATATA TTGATGTTGA TACAGAAGAT         420

| | | | | | |
|---|---|---|---|---|---|
| ACTAATATCG | AATTAAGAAC | AACATTGAAA | GAAACAAATA | ATGCAATATC | ATTTGAATCA | 480 |
| AACAGTGGTT | CATTAGAAAA | AAAAAAATAT | GTAAAACTAC | CATCAAATGG | TACAACTGGT | 540 |
| GAACAAAGTT | CTAGTTCAAG | TTCAAGTTCT | AGTTCAAATT | CTAGTTCAAG | TTCAAGTTCA | 600 |
| AGTTCAAGTT | CTAGTTCAAG | TTCAAGTTCA | AGTTCTAGTT | CAAGTTCTAG | TTCAAGTTCA | 660 |
| GAAAGTCTTC | CTGCTAATGG | ACCTGATTCC | CCTACTGTTA | AACCGCCAAG | AAATTTACAA | 720 |
| AATATATGTG | AAACTGGAAA | AAACTTCAAG | TTGGTAGTAT | ATATTAAGGA | GAATACATTA | 780 |
| ATAATTAAAT | GGAAAGTATA | CGGAGAAACA | AAAGATACTA | CTGAAAATAA | CAAAGTTGAT | 840 |
| GTAAGAAAGT | ATTTGATAAA | TGAAAAGGAA | ACCCCATTTA | CTAGTATACT | AATACATGCG | 900 |
| TATAAAGAAC | ATAATGGAAC | AAACTTAATA | GAAAGTAAAA | ACTACGCATT | AGGATCAGAC | 960 |
| ATTCCAGAAA | AATGTGATAC | CTTAGCTTCC | AATTGCTTTT | TAAGTGGTAA | TTTTAACATT | 1020 |
| GAAAAATGCT | TTCAATGTGC | TCTTTTAGTA | GAAAAGAAA | ATAAAAATGA | CGTATGTTAC | 1080 |
| AAATACCTAT | CTGAAGATAT | TGTAAGTAAA | TTCAAAGAAA | TAAAAGCTGA | GACAGAAGAT | 1140 |
| GATGATGAAG | ATGATTATAC | TGAATATAAA | TTAACAGAAT | CTATTGATAA | TATATTAGTA | 1200 |
| AAAATGTTTA | AAACAAATGA | AAATAATGAT | AAATCAGAAT | TAATAAAATT | AGAAGAAGTA | 1260 |
| GATGATAGTT | TGAAATTAGA | ATTAATGAAT | TACTGTAGTT | TACTTAAAGA | CGTAGATACA | 1320 |
| ACAGGTACCT | TAGATAATTA | TGGGATGGGA | AATGAAATGG | ATATATTTAA | TAACTTAAAG | 1380 |
| AGATTATTAA | TTTATCATTC | AGAAGAAAAT | ATTAATACTT | TAAAAAATAA | ATTCCGTAAT | 1440 |
| GCAGCTGTAT | GTCTTAAAAA | TGTTGATGAT | TGGATTGTAA | ATAAGAGAGG | TTTAGTATTA | 1500 |
| CCTGAATTAA | ATTATGATTT | AGAATATTTC | AATGAACATT | TATATAATGA | TAAAAATTCT | 1560 |
| CCAGAAGATA | AAGATAATAA | AGGAAAAGGT | GTCGTACATG | TTGATACAAC | TTTAGAAAAA | 1620 |
| GAAGATACTT | TATCATATGA | TAACTCAGAT | AATATGTTTT | GTAATAAAGA | ATATTGTAAC | 1680 |
| AGATTAAAAG | ATGAAAATAA | TTGTATATCT | AATCTTCAAG | TTGAAGATCA | AGGTAATTGT | 1740 |
| GATACTTCAT | GGATTTTGC | TTCAAAATAT | CATTAGAAA | CTATTAGATG | TATGAAAGGA | 1800 |
| TATGAACCTA | CCAAAATTTC | TGCTCTTTAT | GTAGCTAATT | GTTATAAAGG | TGAACATAAA | 1860 |
| GATAGATGTG | ATGAAGGTTC | TAGTCCAATG | GAATTCTTAC | AAATTATTGA | AGATTATGGA | 1920 |
| TTCTTACCAG | CAGAATCAAA | TTATCCATAT | AACTATGTGA | AGTTGGAGA | ACAATGTCCA | 1980 |
| AAGGTAGAAG | ATCACTGGAT | GAATCTATGG | GATAATGGAA | AAATCTTACA | TAACAAAAAT | 2040 |
| GAACCTAATA | GTTTAGATGG | TAAGGGATAT | ACTGCATATG | AAAGTGAAAG | ATTTCATGAT | 2100 |
| AATATGGATG | CATTTGTTAA | AATTATTAAA | ACTGAAGTAA | TGAATAAAGG | TTCAGTTATT | 2160 |
| GCATATATTA | AAGCTGAAAA | TGTTATGGGA | TATGAATTTA | GTGGAAAGAA | AGTACAGAAC | 2220 |
| TTATGTGGTG | ATGATACAGC | TGATCATGCA | GTTAATATTG | TTGGTTATGG | TAATTATGTG | 2280 |
| AATAGCGAAG | GAGAAAAAA | ATCCTATTGG | ATTGTAAGAA | ACAGTTGGGG | TCCATATTGG | 2340 |
| GGAGATGAAG | GTTATTTTAA | AGTAGATATG | TATGGACCAA | CTCATTGTCA | TTTTAACTTT | 2400 |
| ATTCACAGTG | TTGTTATATT | CAATGTTGAT | TTACCTATGA | ATAATAAAAC | AACTAAAAAA | 2460 |
| GAATCAAAAA | TATATGATTA | TTATTTAAAG | GCCTCTCCAG | AATTTTATCA | TAACCTTTAC | 2520 |
| TTTAAGAATT | TTAATGTTGG | TAAGAAAAAT | TTATTCTCTG | AAAAGGAAGA | TAATGAAAAC | 2580 |
| AACAAAAAAT | TAGGTAACAA | CTATATTATA | TTCGGTCAAG | ATACGGCAGG | ATCAGGACAA | 2640 |
| AGTGGAAAGG | AAAGCAATAC | TGCATTAGAA | TCTGCAGGAA | CTTCAAATGA | AGTCTCAGAA | 2700 |
| CGTGTTCATG | TTTATCACAT | ATTAAAACAT | ATAAAGGATG | GCAAAATAAG | AATGGGTATG | 2760 |
| CGTAAATATA | TAGATACACA | AGATGTAAAT | AAGAAACATT | CTTGTACAAG | ATCCTATGCA | 2820 |

```
TTTAATCCAG AGAATTATGA AAAATGTGTA AATTTATGTA ATGTGAACTG GAAAACATGC      2880

GAGGAAAAAA CATCACCAGG ACTTTGTTTA TCCAAATTGG ATACAAATAA CGAATGTTAT      2940

TTCTGTTATG TATAAAATAA TATAACAAAA AAAAAAAAA A                          2981
```

( 2 ) INFORMATION FOR SEQ ID NO:3:

( i ) SEQUENCE CHARACTERISTICS:
    ( A ) LENGTH: 984 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:3:

```
Met Lys Ser Tyr Ile Ser Leu Phe Phe Ile Leu Cys Val Ile Phe Asn
 1               5                  10                  15

Lys Asn Val Ile Lys Cys Thr Gly Glu Ser Gln Thr Gly Asn Thr Gly
             20                  25                  30

Gly Gly Gln Ala Gly Asn Thr Gly Gly Gly Gln Ala Gly Asn Thr Val
         35                  40                  45

Gly Asp Gln Ala Gly Ser Thr Gly Gly Ser Pro Gln Gly Ser Thr Gly
     50                  55                  60

Ala Ser Gln Pro Gly Ser Ser Glu Pro Ser Asn Pro Val Ser Ser Gly
65                  70                  75                  80

His Ser Val Ser Thr Val Ser Val Ser Ser Thr Ser Thr Ser Ser Glu
                 85                  90                  95

Lys Gln Asp Thr Ile Gln Val Lys Ser Ala Leu Leu Lys Asp Tyr Met
            100                 105                 110

Gly Leu Lys Val Thr Gly Pro Cys Asn Glu Asn Phe Ile Met Phe Leu
        115                 120                 125

Val Pro His Ile Tyr Ile Asp Val Asp Thr Glu Asp Thr Asn Ile Glu
    130                 135                 140

Leu Arg Thr Thr Leu Lys Glu Thr Asn Asn Ala Ile Ser Phe Glu Ser
145                 150                 155                 160

Asn Ser Gly Ser Leu Glu Lys Lys Lys Tyr Val Lys Leu Pro Ser Asn
                165                 170                 175

Gly Thr Thr Gly Glu Gln Ser Ser Ser Ser Ser Ser Ser Ser Ser Ser
            180                 185                 190

Asn Ser Ser Ser Ser Ser Ser Ser Ser Ser Ser Ser Ser Ser Ser Ser
        195                 200                 205

Ser Ser Ser Ser Ser Ser Ser Ser Ser Ser Ser Ser Glu Ser Leu Pro
    210                 215                 220

Ala Asn Gly Pro Asp Ser Pro Thr Val Lys Pro Pro Arg Asn Leu Gln
225                 230                 235                 240

Asn Ile Cys Glu Thr Gly Lys Asn Phe Lys Leu Val Val Tyr Ile Lys
                245                 250                 255

Glu Asn Thr Leu Ile Ile Lys Trp Lys Val Tyr Gly Glu Thr Lys Asp
            260                 265                 270

Thr Thr Glu Asn Asn Lys Val Asp Val Arg Lys Tyr Leu Ile Asn Glu
        275                 280                 285

Lys Glu Thr Pro Phe Thr Ser Ile Leu Ile His Ala Tyr Lys Glu His
    290                 295                 300

Asn Gly Thr Asn Leu Ile Glu Ser Lys Asn Tyr Ala Leu Gly Ser Asp
305                 310                 315                 320
```

| Ile | Pro | Glu | Lys | Cys | Asp | Thr | Leu | Ala | Ser | Asn | Cys | Phe | Leu | Ser | Gly |
|  |  |  |  | 325 |  |  |  |  | 330 |  |  |  |  | 335 |  |
| Asn | Phe | Asn | Ile | Glu | Lys | Cys | Phe | Gln | Cys | Ala | Leu | Leu | Val | Glu | Lys |
|  |  |  | 340 |  |  |  |  | 345 |  |  |  |  | 350 |  |  |
| Glu | Asn | Lys | Asn | Asp | Val | Cys | Tyr | Lys | Tyr | Leu | Ser | Glu | Asp | Ile | Val |
|  |  | 355 |  |  |  |  | 360 |  |  |  |  | 365 |  |  |  |
| Ser | Lys | Phe | Lys | Glu | Ile | Lys | Ala | Glu | Thr | Glu | Asp | Asp | Glu | Asp |
|  | 370 |  |  |  |  | 375 |  |  |  |  | 380 |  |  |  |
| Asp | Tyr | Thr | Glu | Tyr | Lys | Leu | Thr | Glu | Ser | Ile | Asp | Asn | Ile | Leu | Val |
| 385 |  |  |  |  | 390 |  |  |  |  | 395 |  |  |  |  | 400 |
| Lys | Met | Phe | Lys | Thr | Asn | Glu | Asn | Asn | Asp | Lys | Ser | Glu | Leu | Ile | Lys |
|  |  |  |  | 405 |  |  |  |  | 410 |  |  |  |  | 415 |  |
| Leu | Glu | Glu | Val | Asp | Asp | Ser | Leu | Lys | Leu | Glu | Leu | Met | Asn | Tyr | Cys |
|  |  |  |  | 420 |  |  |  |  | 425 |  |  |  |  | 430 |  |
| Ser | Leu | Leu | Lys | Asp | Val | Asp | Thr | Thr | Gly | Thr | Leu | Asp | Asn | Tyr | Gly |
|  |  |  | 435 |  |  |  |  | 440 |  |  |  |  | 445 |  |  |
| Met | Gly | Asn | Glu | Met | Asp | Ile | Phe | Asn | Asn | Leu | Lys | Arg | Leu | Leu | Ile |
|  | 450 |  |  |  |  | 455 |  |  |  |  | 460 |  |  |  |  |
| Tyr | His | Ser | Glu | Glu | Asn | Ile | Asn | Thr | Leu | Lys | Asn | Lys | Phe | Arg | Asn |
| 465 |  |  |  |  | 470 |  |  |  |  | 475 |  |  |  |  | 480 |
| Ala | Ala | Val | Cys | Leu | Lys | Asn | Val | Asp | Asp | Trp | Ile | Val | Asn | Lys | Arg |
|  |  |  |  | 485 |  |  |  |  | 490 |  |  |  |  | 495 |  |
| Gly | Leu | Val | Leu | Pro | Glu | Leu | Asn | Tyr | Asp | Leu | Glu | Tyr | Phe | Asn | Glu |
|  |  |  |  | 500 |  |  |  |  | 505 |  |  |  |  | 510 |  |
| His | Leu | Tyr | Asn | Asp | Lys | Asn | Ser | Pro | Glu | Asp | Lys | Asp | Asn | Lys | Gly |
|  |  | 515 |  |  |  |  | 520 |  |  |  |  | 525 |  |  |  |
| Lys | Gly | Val | Val | His | Val | Asp | Thr | Thr | Leu | Glu | Lys | Glu | Asp | Thr | Leu |
|  | 530 |  |  |  |  | 535 |  |  |  |  | 540 |  |  |  |  |
| Ser | Tyr | Asp | Asn | Ser | Asp | Asn | Met | Phe | Cys | Asn | Lys | Glu | Tyr | Cys | Asn |
| 545 |  |  |  |  | 550 |  |  |  |  | 555 |  |  |  |  | 560 |
| Arg | Leu | Lys | Asp | Glu | Asn | Asn | Cys | Ile | Ser | Asn | Leu | Gln | Val | Glu | Asp |
|  |  |  |  | 565 |  |  |  |  | 570 |  |  |  |  | 575 |  |
| Gln | Gly | Asn | Cys | Asp | Thr | Ser | Trp | Ile | Phe | Ala | Ser | Lys | Tyr | His | Leu |
|  |  |  | 580 |  |  |  |  | 585 |  |  |  |  | 590 |  |  |
| Glu | Thr | Ile | Arg | Cys | Met | Lys | Gly | Tyr | Glu | Pro | Thr | Lys | Ile | Ser | Ala |
|  |  | 595 |  |  |  |  | 600 |  |  |  |  | 605 |  |  |  |
| Leu | Tyr | Val | Ala | Asn | Cys | Tyr | Lys | Gly | Glu | His | Lys | Asp | Arg | Cys | Asp |
|  | 610 |  |  |  |  | 615 |  |  |  |  | 620 |  |  |  |  |
| Glu | Gly | Ser | Ser | Pro | Met | Glu | Phe | Leu | Gln | Ile | Ile | Glu | Asp | Tyr | Gly |
| 625 |  |  |  |  | 630 |  |  |  |  | 635 |  |  |  |  | 640 |
| Phe | Leu | Pro | Ala | Glu | Ser | Asn | Tyr | Pro | Tyr | Asn | Tyr | Val | Lys | Val | Gly |
|  |  |  |  | 645 |  |  |  |  | 650 |  |  |  |  | 655 |  |
| Glu | Gln | Cys | Pro | Lys | Val | Glu | Asp | His | Trp | Met | Asn | Leu | Trp | Asp | Asn |
|  |  |  | 660 |  |  |  |  | 665 |  |  |  |  | 670 |  |  |
| Gly | Lys | Ile | Leu | His | Asn | Lys | Asn | Glu | Pro | Asn | Ser | Leu | Asp | Gly | Lys |
|  |  | 675 |  |  |  |  | 680 |  |  |  |  | 685 |  |  |  |
| Gly | Tyr | Thr | Ala | Tyr | Glu | Ser | Glu | Arg | Phe | His | Asp | Asn | Met | Asp | Ala |
|  | 690 |  |  |  |  | 695 |  |  |  |  | 700 |  |  |  |  |
| Phe | Val | Lys | Ile | Ile | Lys | Thr | Glu | Val | Met | Asn | Lys | Gly | Ser | Val | Ile |
| 705 |  |  |  |  | 710 |  |  |  |  | 715 |  |  |  |  | 720 |
| Ala | Tyr | Ile | Lys | Ala | Glu | Asn | Val | Met | Gly | Tyr | Glu | Phe | Ser | Gly | Lys |
|  |  |  |  | 725 |  |  |  |  | 730 |  |  |  |  | 735 |  |
| Lys | Val | Gln | Asn | Leu | Cys | Gly | Asp | Asp | Thr | Ala | Asp | His | Ala | Val | Asn |

|  |  |  |  |  |  |  |  |  |  |  |  |  |  |
|---|---|---|---|---|---|---|---|---|---|---|---|---|---|
| | | | | | 740 | | | 745 | | | | 750 | |
| Ile | Val | Gly 755 | Tyr | Gly | Asn | Tyr | Val 760 | Asn | Ser | Glu | Gly | Glu 765 | Lys Lys Ser |
| Tyr | Trp 770 | Ile | Val | Arg | Asn | Ser 775 | Trp | Gly | Pro | Tyr | Trp 780 | Gly | Asp Glu Gly |
| Tyr 785 | Phe | Lys | Val | Asp | Met 790 | Tyr | Gly | Pro | Thr | His 795 | Cys | His | Phe Asn Phe 800 |
| Ile | His | Ser | Val | Val 805 | Ile | Phe | Asn | Val | Asp 810 | Leu | Pro | Met | Asn Asn Lys 815 |
| Thr | Thr | Lys | Lys 820 | Glu | Ser | Lys | Ile | Tyr 825 | Asp | Tyr | Tyr | Leu | Lys Ala Ser 830 |
| Pro | Glu | Phe 835 | Tyr | His | Asn | Leu | Tyr 840 | Phe | Lys | Asn | Phe | Asn 845 | Val Gly Lys |
| Lys | Asn 850 | Leu | Phe | Ser | Glu | Lys 855 | Glu | Asp | Asn | Glu | Asn 860 | Asn | Lys Lys Leu |
| Gly 865 | Asn | Asn | Tyr | Ile | Ile 870 | Phe | Gly | Gln | Asp | Thr 875 | Ala | Gly | Ser Gly Gln 880 |
| Ser | Gly | Lys | Glu | Ser 885 | Asn | Thr | Ala | Leu | Glu 890 | Ser | Ala | Gly | Thr | Ser 895 | Asn |
| Glu | Val | Ser | Glu 900 | Arg | Val | His | Val | Tyr 905 | His | Ile | Leu | Lys | His 910 | Ile Lys |
| Asp | Gly | Lys 915 | Ile | Arg | Met | Gly | Met 920 | Arg | Lys | Tyr | Ile | Asp 925 | Thr Gln Asp |
| Val | Asn 930 | Lys | Lys | His | Ser | Cys 935 | Thr | Arg | Ser | Tyr | Ala 940 | Phe | Asn Pro Glu |
| Asn 945 | Tyr | Glu | Lys | Cys | Val 950 | Asn | Leu | Cys | Asn | Val 955 | Asn | Trp | Lys Thr Cys 960 |
| Glu | Glu | Lys | Thr | Ser 965 | Pro | Gly | Leu | Cys | Leu 970 | Ser | Lys | Leu | Asp Thr Asn 975 |
| Asn | Glu | Cys | Tyr 980 | Phe | Cys | Tyr | Val | | | | | | |

( 2 ) INFORMATION FOR SEQ ID NO:4:

( i ) SEQUENCE CHARACTERISTICS:
    ( A ) LENGTH: 2223 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

| | | | | | |
|---|---|---|---|---|---|
| ATGATGAACA | TGAAAATTGT | TTTATTCAGT | TTATTGCTCT | TTGTCATAAG | ATGGAATATT | 60 |
| ATTAGTTGTA | ATAAAAACGA | CAAGAACCAA | GGTGTTGATA | TGAATGTTTT | GAATAATTAT | 120 |
| GAAAATTTAT | TTAAAGTTGT | TAAATGTGAA | TATTGTAATG | AACATACTTA | TGTTAAAGGT | 180 |
| AAGAAAGCTC | CTTCAGATCC | TCAATGTGCT | GATATAAAAG | AAGAATGCAA | AGAATTACTT | 240 |
| AAGGAAAAAC | AATACACAGA | TTCAGTTACA | TATTTAATGG | ATGGTTTTAA | ATCAGCAAAT | 300 |
| AATTCAGCAA | ATAATGGTAA | AAAAAATAAC | GCTGAAGAAA | TGAAAAATTT | AGTAAATTTC | 360 |
| TTACAATCTC | ATAAGAAATT | AATTAAAGCA | TTAAAAAGA | ATATTGAAAG | TATACAAAAT | 420 |
| AAGAAACACT | TAATTTATAA | AAACAAATCA | TATAATCCAT | TATTACTTTC | TTGTGTTAAA | 480 |
| AAAATGAATA | TGTTAAAAGA | AAATGTTGAC | TATATTCAAA | AAAATCAAAA | CTTATTTAAA | 540 |
| GAATTAATGA | ATCAAAAAGC | TACCTACTCT | TTTGTTAATA | CCAAAAAAAA | AATTATTTCT | 600 |
| TTAAAATCAC | AAGGTCATAA | AAAAGAAACC | TCACAAAATC | AAAATGAAAA | TAACGACAAT | 660 |

| | | | | |
|---|---|---|---|---|
| CAAAAATATC | AAGAAGTTAA | TGATGAAGAT | GATGTAAATG | ATGAAGAAGA TACAAACGAT | 720 |
| GACGAAGATA | CTAACGATGA | AGAAGATACA | AACGATGACG | AAGATACAAA TGATGACGAA | 780 |
| GATACTAACG | ATGAAGAAGA | TACTAACGAC | GAAGAAGATC | ATGAAAATAA TAATGCTACA | 840 |
| GCATACGAAT | TAGGTATCGT | CCCAGTTAAC | GATGTGTTAA | ATGTTAATAT GAAAAATATG | 900 |
| ATAACAGGAA | ATAATTTTAT | GGATGTTGTT | AAAAGTACAT | TAGCTCAATC AGGTGGATTA | 960 |
| GGAAGTAATG | ATTTAATAAA | TTTCTTAAAT | CAAGGTAAAG | AAATAGGAGA AAATTTATTA | 1020 |
| AACATAACAA | AGATGAACTT | GGGAGATAAG | AATAATCTTG | AAAGTTTTCC TTTAGATCAA | 1080 |
| TTAAATATGT | TAAAAGATAA | TTTAATAAAC | TATGAATTCA | TATTAAATAA TTTGAAAACA | 1140 |
| AGTGTTTTAA | ATAAATTAAA | AGATTATTA | TTAAGATTAT | TATACAAAGC ATATGTATCA | 1200 |
| TATAAGAAAA | GAAAAGCTCA | AGAAAAGGA | TTACCAGAAC | CTACTGTTAC TAATGAAGAA | 1260 |
| TATGTTGAAG | AATTAAAGAA | AGGTATTCTA | GATATGGGTA | TCAAATTATT ATTTAGTAAA | 1320 |
| GTTAAAAGCC | TATTAAAAAA | ATTAAAAAAT | AAAATATTCC | CTAAGAAAAA AGAAGATAAT | 1380 |
| CAAGCAGTAG | ATACCAAAAG | TATGGAAGAA | CCCAAAGTTA | AAGCACAACC AGCTCTTAGA | 1440 |
| GGTGTTGAAC | CAACGGAAGA | TTCTAATATT | ATGAACAGTA | TTAATAATGT TATGGATGAA | 1500 |
| ATTGATTTCT | TTGAAAAAGA | ATTAATCGAA | AATAATAATA | CACCTAATGT TGTACCACCA | 1560 |
| ACTCAATCAA | AAAAAAAAAA | CAAAAATGAA | ACTGTATCTG | GTATGGATGA AAATTTTGAT | 1620 |
| AATCATCCTG | AAAATTATTT | TAAAGAAGAA | TATTATTATG | ATGAAAATGA TGATATGGAA | 1680 |
| GTAAAAGTTA | AAAAAATAGG | TGTCACATTA | AAAAAATTTG | AACCACTTAA AAATGGAAAT | 1740 |
| GTTAGTGAAA | CCATTAAATT | GATTCATTTA | GGAAATAAAG | ATAAAAAACA CATTGAAGCT | 1800 |
| ATAAACAACG | ATATTCAAAT | TATTAAACAA | GAATTACAAG | CTATTTATAA TGAACTTATG | 1860 |
| AATTATACAA | ATGGAAACAA | AAATATTCAA | CAAATATTTC | AACAAAATAT TCTAGAAAAT | 1920 |
| GATGTTCTTA | ATCAAGAAAC | GGAGGAAGAA | ATGGAAAAAC | AAGTTGAAGC AATCACCAAG | 1980 |
| CAAATAGAAG | CTGAAGTGGA | TGCCCTCGCA | CCAAAAAATA | AGGAAGAAGA AGAAAAAGAA | 2040 |
| AAAGAAAAAG | AAAAGGAAAA | AGAAGAAAAA | GAAAAAGAAG | AAAAAGAAAA AGAAAAAGAA | 2100 |
| GAAAAAGAAA | AAGAAAAAGA | AAAAGAAGAA | AAGAAGAAG | AAAAAAAAGA AAAAGAAGAA | 2160 |
| GAACAAGAAG | AAGAAGAAGA | AGAAATAGTA | CCAGAAAATT | TGACAACTGA AGAATCAAAA | 2220 |
| TAA | | | | | 2223 |

( 2 ) INFORMATION FOR SEQ ID NO:5:

( i ) SEQUENCE CHARACTERISTICS:
        ( A ) LENGTH: 740 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

```
Met Met Asn Met Lys Ile Val Leu Phe Ser Leu Leu Leu Phe Val Ile
 1               5                  10                  15

Arg Trp Asn Ile Ile Ser Cys Asn Lys Asn Asp Lys Asn Gln Gly Val
            20                  25                  30

Asp Met Asn Val Leu Asn Asn Tyr Glu Asn Leu Phe Lys Val Val Lys
        35                  40                  45

Cys Glu Tyr Cys Asn Glu His Thr Tyr Val Lys Gly Lys Lys Ala Pro
    50                  55                  60
```

-continued

```
Ser  Asp  Pro  Gln  Cys  Ala  Asp  Ile  Lys  Glu  Glu  Cys  Lys  Glu  Leu  Leu
65                  70                       75                            80

Lys  Glu  Lys  Gln  Tyr  Thr  Asp  Ser  Val  Thr  Tyr  Leu  Met  Asp  Gly  Phe
                    85                       90                       95

Lys  Ser  Ala  Asn  Asn  Ser  Ala  Asn  Asn  Gly  Lys  Lys  Asn  Asn  Ala  Glu
               100                      105                     110

Glu  Met  Lys  Asn  Leu  Val  Asn  Phe  Leu  Gln  Ser  His  Lys  Lys  Leu  Ile
          115                      120                     125

Lys  Ala  Leu  Lys  Lys  Asn  Ile  Glu  Ser  Ile  Gln  Asn  Lys  Lys  His  Leu
          130                 135                     140

Ile  Tyr  Lys  Asn  Lys  Ser  Tyr  Asn  Pro  Leu  Leu  Leu  Ser  Cys  Val  Lys
145                      150                     155                          160

Lys  Met  Asn  Met  Leu  Lys  Glu  Asn  Val  Asp  Tyr  Ile  Gln  Lys  Asn  Gln
                    165                      170                     175

Asn  Leu  Phe  Lys  Glu  Leu  Met  Asn  Gln  Lys  Ala  Thr  Tyr  Ser  Phe  Val
               180                      185                     190

Asn  Thr  Lys  Lys  Lys  Ile  Ile  Ser  Leu  Lys  Ser  Gln  Gly  His  Lys  Lys
          195                      200                     205

Glu  Thr  Ser  Gln  Asn  Gln  Asn  Glu  Asn  Asn  Asp  Asn  Gln  Lys  Tyr  Gln
          210                      215                     220

Glu  Val  Asn  Asp  Glu  Asp  Asp  Val  Asn  Asp  Glu  Glu  Asp  Thr  Asn  Asp
225                      230                      235                         240

Asp  Glu  Asp  Thr  Asn  Asp  Glu  Glu  Asp  Thr  Asn  Asp  Asp  Glu  Asp  Thr
                    245                      250                     255

Asn  Asp  Asp  Glu  Asp  Thr  Asn  Asp  Glu  Glu  Asp  Thr  Asn  Asp  Glu  Glu
               260                      265                     270

Asp  His  Glu  Asn  Asn  Asn  Ala  Thr  Ala  Tyr  Glu  Leu  Gly  Ile  Val  Pro
          275                      280                     285

Val  Asn  Asp  Val  Leu  Asn  Val  Asn  Met  Lys  Asn  Met  Ile  Thr  Gly  Asn
     290                      295                     300

Asn  Phe  Met  Asp  Val  Val  Lys  Ser  Thr  Leu  Ala  Gln  Ser  Gly  Gly  Leu
305                      310                      315                         320

Gly  Ser  Asn  Asp  Leu  Ile  Asn  Phe  Leu  Asn  Gln  Gly  Lys  Glu  Ile  Gly
                    325                      330                     335

Glu  Asn  Leu  Leu  Asn  Ile  Thr  Lys  Met  Asn  Leu  Gly  Asp  Lys  Asn  Asn
               340                      345                     350

Leu  Glu  Ser  Phe  Pro  Leu  Asp  Gln  Leu  Asn  Met  Leu  Lys  Asp  Asn  Leu
          355                      360                     365

Ile  Asn  Tyr  Glu  Phe  Ile  Leu  Asn  Asn  Leu  Lys  Thr  Ser  Val  Leu  Asn
     370                      375                     380

Lys  Leu  Lys  Asp  Leu  Leu  Leu  Arg  Leu  Leu  Tyr  Lys  Ala  Tyr  Val  Ser
385                      390                      395                         400

Tyr  Lys  Lys  Arg  Lys  Ala  Gln  Glu  Lys  Gly  Leu  Pro  Glu  Pro  Thr  Val
                    405                      410                     415

Thr  Asn  Glu  Glu  Tyr  Val  Glu  Glu  Leu  Lys  Lys  Gly  Ile  Leu  Asp  Met
               420                      425                     430

Gly  Ile  Lys  Leu  Leu  Phe  Ser  Lys  Val  Lys  Ser  Leu  Leu  Lys  Lys  Leu
          435                      440                     445

Lys  Asn  Lys  Ile  Phe  Pro  Lys  Lys  Glu  Asp  Asn  Gln  Ala  Val  Asp
     450                      455                     460

Thr  Lys  Ser  Met  Glu  Glu  Pro  Lys  Val  Lys  Ala  Gln  Pro  Ala  Leu  Arg
465                      470                      475                         480

Gly  Val  Glu  Pro  Thr  Glu  Asp  Ser  Asn  Ile  Met  Asn  Ser  Ile  Asn  Asn
```

|       |       |       |       | 485   |       |       |       | 490   |       |       |       | 495   |       |       |
|-------|-------|-------|-------|-------|-------|-------|-------|-------|-------|-------|-------|-------|-------|-------|
| Val   | Met   | Asp   | Glu   | Ile   | Asp   | Phe   | Phe   | Glu   | Lys   | Glu   | Leu   | Ile   | Glu   | Asn   | Asn |

Val Met Asp Glu Ile Asp Phe Phe Glu Lys Glu Leu Ile Glu Asn Asn
                500                     505                510
Asn Thr Pro Asn Val Val Pro Pro Thr Gln Ser Lys Lys Asn Lys
        515                 520                 525
Asn Glu Thr Val Ser Gly Met Asp Glu Asn Phe Asp Asn His Pro Glu
    530                 535                 540
Asn Tyr Phe Lys Glu Glu Tyr Tyr Tyr Asp Glu Asn Asp Asp Met Glu
545                 550                 555                     560
Val Lys Val Lys Lys Ile Gly Val Thr Leu Lys Lys Phe Glu Pro Leu
                565                 570                     575
Lys Asn Gly Asn Val Ser Glu Thr Ile Lys Leu Ile His Leu Gly Asn
            580                 585                 590
Lys Asp Lys Lys His Ile Glu Ala Ile Asn Asn Asp Ile Gln Ile Ile
        595                 600                 605
Lys Gln Glu Leu Gln Ala Ile Tyr Asn Glu Leu Met Asn Tyr Thr Asn
    610                 615                 620
Gly Asn Lys Asn Ile Gln Gln Ile Phe Gln Gln Asn Ile Leu Glu Asn
625                 630                 635                     640
Asp Val Leu Asn Gln Glu Thr Glu Glu Glu Met Glu Lys Gln Val Glu
                645                 650                     655
Ala Ile Thr Lys Gln Ile Glu Ala Glu Val Asp Ala Leu Ala Pro Lys
            660                 665                 670
Asn Lys Glu Glu Glu Glu Lys Glu Lys Glu Lys Glu Lys Glu Lys Glu
        675                 680                 685
Glu Lys Glu Lys Glu Glu Lys Glu Lys Glu Lys Glu Glu Lys Glu Lys
    690                 695                 700
Glu Lys Glu Lys Glu Glu Lys Glu Glu Glu Lys Lys Glu Lys Glu Glu
705                 710                 715                     720
Glu Gln Glu Glu Glu Glu Glu Glu Ile Val Pro Glu Asn Leu Thr Thr
                725                 730                 735
Glu Glu Ser Lys
            740

( 2 ) INFORMATION FOR SEQ ID NO:6:

( i ) SEQUENCE CHARACTERISTICS:
( A ) LENGTH: 966 base pairs
( B ) TYPE: nucleic acid
( C ) STRANDEDNESS: single
( D ) TOPOLOGY: linear ( x i ) SEQUENCE DESCRIPTION: SEQ ID NO:6:

```
TTTAATGGTA AAGAAGCATG CAGATCAATT AACCCAGATG AAGCTGTTGC ATATGGTGCA        60
GCTGTACAAG CAGCCATTTT ATCTGGTGAC CAATCAAATG CTGTCCAAGA TTTATTATTA       120
TTAGATGTTT GCTCCTTATC ATTAGGTTTA GAAACTGCTG GTGGTGTTAT GACCAAATTA       180
ATTGAAAGAA ACACAACCAT ACCTGCTAAA AAGAGTCAAA TCTTTACTAC TTATGCTGAT       240
AACCAACCAG GTGTCTTAAT TCAAGTATAT GAAGGTGAAA GAGCCTTAAC CAAAGATAAC       300
AATTTATTAG GAAAATTTCA CTTAGATGGT ATTCCACCTG CACCAAGAAA GGTACCACAA       360
ATCGAAGTTA CATTCGATAT CGATGCTAAC GGTATCTTAA ACGTTACGGC TGTAGAAAAA       420
TCCACTGGTA AACAAAACCA TATTACAATT ACCAACGACA AAGGAAGATT ATCTCAAGAT       480
GAAATTGATC GTATGGTTAA TGATGCTGAA AAATACAAAG CAGAAGATGA AGAAAACAGA       540
AAAAGAATCG AAGCAAGAAA CAGCCTTGAA AATTACTGCT ATGGAGTTAA AAGCTCATTA       600
```

```
GAAGACCAAA AAATTAAAGA AAAATTACAA CCAGCTGAAA TTGAAACATG TATGAAAACT        660

ATTACAACCA TACTTGAATG GTTAGAAAAA AACCAACTTG CTGGAAAAGA TGAATATGAA        720

GCCAAACAAA AAGAAGCAGA ATCGGTTTGT GCTCCAATTA TGTCTAAAAT CTATCAAGAT        780

GCTGCTGGTG CAGCCGGTGG TATGCCAGGA GGTATGCCCG GTGGAATGCC AGGTGGAATG        840

CCAGGTGGAA TGCCAGGTGG TATGAATTTC CCAGGAGGTA TGCCCGGAGC AGGAATGCCA        900

GGAAATGCCC CAGCTGGAAG TGGACCAACA GTTGAAGAAG TTGATTAAAC TAAAAAAAAA        960

AAAAAA                                                                  966
```

(2) INFORMATION FOR SEQ ID NO:7:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:7:

```
Phe Asn Gly Lys Glu Ala Cys Arg Ser Ile Asn Pro Asp Glu Ala Val
  1               5                  10                  15

Ala Tyr Gly Ala Ala Val Gln Ala Ala Ile Leu Ser Gly Asp Gln Ser
             20                  25                  30

Asn Ala Val Gln Asp Leu Leu Leu Leu Asp Val Cys Ser Leu Ser Leu
         35                  40                  45

Gly Leu Glu Thr Ala Gly Gly Val Met Thr Lys Leu Ile Glu Arg Asn
     50                  55                  60

Thr Thr Ile Pro Ala Lys Lys Ser Gln Ile Phe Thr Thr Tyr Ala Asp
 65                  70                  75                  80

Asn Gln Pro Gly Val Leu Ile Gln Val Tyr Glu Gly Glu Arg Ala Leu
                 85                  90                  95

Thr Lys Asp Asn Asn Leu Leu Gly Lys Phe His Leu Asp Gly Ile Pro
            100                 105                 110

Pro Ala Pro Arg Lys Val Pro Gln Ile Glu Val Thr Phe Asp Ile Asp
        115                 120                 125

Ala Asn Gly Ile Leu Asn Val Thr Ala Val Glu Lys Ser Thr Gly Lys
    130                 135                 140

Gln Asn His Ile Thr Ile Thr Asn Asp Lys Gly Arg Leu Ser Gln Asp
145                 150                 155                 160

Glu Ile Asp Arg Met Val Asn Asp Ala Glu Lys Tyr Lys Ala Glu Asp
                165                 170                 175

Glu Glu Asn Arg Lys Arg Ile Glu Ala Arg Asn Ser Leu Glu Asn Tyr
            180                 185                 190

Cys Tyr Gly Val Lys Ser Ser Leu Glu Asp Gln Lys Ile Lys Glu Lys
        195                 200                 205

Leu Gln Pro Ala Glu Ile Glu Thr Cys Met Lys Thr Ile Thr Thr Ile
    210                 215                 220

Leu Glu Trp Leu Glu Lys Asn Gln Leu Ala Gly Lys Asp Glu Tyr Glu
225                 230                 235                 240

Ala Lys Gln Lys Glu Ala Glu Ser Val Cys Ala Pro Ile Met Ser Lys
                245                 250                 255

Ile Tyr Gln Asp Ala Ala Gly Ala Ala Gly Gly Met Pro Gly Gly Met
            260                 265                 270
```

|  | Pro | Gly | Gly<br>275 | Met | Pro | Gly | Gly | Met<br>280 | Pro | Gly | Gly | Met<br>285 | Pro | Gly | Gly | Met |
| --- | --- | --- | --- | --- | --- | --- | --- | --- | --- | --- | --- | --- | --- | --- | --- | --- |
|  | Asn | Phe<br>290 | Pro | Gly | Gly | Met | Pro<br>295 | Gly | Ala | Gly | Met | Pro<br>300 | Gly | Asn | Ala | Pro |
|  | Ala<br>305 | Gly | Ser | Gly | Pro | Thr<br>310 | Val | Glu | Glu | Val | Asp<br>315 | | | | | |

( 2 ) INFORMATION FOR SEQ ID NO:8:

( i ) SEQUENCE CHARACTERISTICS:
        ( A ) LENGTH: 1884 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
ATGAGAAAAT TATACTGCGT ATTATTATTG AGCGCCTTTG AGTTTACATA TATGATAAAC      60
TTTGGAAGAG GACAGAATTA TTGGGAACAT CCATATCAAA ATAGTGATGT GTATCGTCCA     120
ATCAACGAAC ATAGGGAACA TCCAAAAGAA TACGAATATC CATTACACCA GGAACATACA     180
TACCAACAAG AAGATTCAGG AGAAGACGAA ATACATTAC AACACGCATA TCCAATAGAC      240
CACGAAGGTG CCGAACCCGC ACCACAAGAA CAAAATTTAT TTCAAGCAT TGAAATAGTA      300
GAAAGAAGTA ATTATATGGG TAATCCATGG ACGGAATATA TGGCAAAATA TGATATTGAA     360
GAAGTTCATG GTTCAGGTAT AAGAGTAGAT TTAGGAGAAG ATGCTGAAGT AGCTGGAACT     420
CAATATAGAC TTCCATCAGG GAAATGTCCA GTATTTGGTA AAGGTATAAT TATTGAGAAT     480
TCAAATACTA CTTTTTTAAC ACCGGTAGCT ACGGGAAATC AATATTTAAA AGATGGAGGT     540
TTTGCTTTTC CTCCAACAGA ACCTCTTATG TCACCAATGA CATTAGATGA AATGAGACAT     600
TTTTATAAAG ATAATAAATA TGTAAAAAAT TTAGATGAAT TGACTTTATG TTCAAGACAT     660
GCAGGAAATA TGATTCCAGA TAATGATAAA AATTCAAATT ATAAATATCC AGCTGTTTAT     720
GATGACAAAG ATAAAAAGTG TCATATATTA TATATTGCAG CTCAAGAAAA TAATGGTCCT     780
AGATATTGTA ATAAAGACGA AAGTAAAAGA AACAGCATGT TTTGTTTTAG ACCAGCAAAA     840
GATATATCAT TTCAAAACTA TACATATTTA AGTAAGAATG TAGTTGATAA CTGGGAAAAA     900
GTTTGCCCTA GAAAGAATTT ACAGAATGCA AAATTCGGAT TATGGGTCGA TGGAAATTGT     960
GAAGATATAC CACATGTAAA TGAATTTCCA GCAATTGATC TTTTTGAATG TAATAAATTA    1020
GTTTTTGAAT TGAGTGCTTC GGATCAACCT AAACAATATG AACAACATTT AACAGATTAT    1080
GAAAAAATTA AGAAGGTTT CAAAAATAAG AACGCTAGTA TGATCAAAAG TCGACGGATC      1140
AAAAGTGCTT TTCTTCCCAC TGGTGCTTTT AAAGCAGATA GATATAAAAG TCATGGTAAG    1200
GGTTATAATT GGGGAAATTA TAACACAGAA ACACAAAAAT GTGAAATTTT TAATGTCAAA    1260
CCAACATGTT TAATTAACAA TTCATCATAC ATTGCTACTA CTGCTTTGTC CCATCCCATC    1320
GAAGTTGAAA ACAATTTTCC ATGTTCATTA TATAAAGATG AAATAATGAA AGAAATCGAA    1380
AGAGAATCAA AACGAATTAA ATTAAATGAT AATGATGATG AAGGGAATAA AAAAATTATG    1440
CTCCAAGAAT TTTTAATTTC AGATGATAAA GACAGTTTAA AACGCCCATG TGACCCTGAA    1500
ATGGTAAGTA ATAGTACATG TCGTTTCTTT GTATGTAAAT GTGTAGAAAG AAGGGCAGAA    1560
GTAACATCAA ATAATGAAGT TGTAGTTAAA GAAGAATATA AAGATGAATA TGCAGATATT    1620
CCTGAACATA AACCAACTTA TGATAAAATG AAAATTATAA TTGCATCATC AGCTGCTGTC    1680
GCTGTATTAG CAACTATTTT AATGGTTTAT CTTTATAAAA GAAAGGAAA TGCTGAAAAA     1740
TATGATAAAA TGGATGAACC ACAAGATTAT GGGAAATCAA ATTCAAGAAA TGATGAAATG    1800
```

```
TTAGATCCTG AGGCATCTTT TTGGGGGGAA GAAAAAAGAG CATCACATAC AACACCAGTT    1860

CTGATGGAAA AACCATACTA TTAA                                          1884
```

(2) INFORMATION FOR SEQ ID NO:9:

(i) SEQUENCE CHARACTERISTICS:
        (A) LENGTH: 628 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:9:

```
Met Arg Lys Leu Tyr Cys Val Leu Leu Leu Ser Ala Phe Glu Phe Thr
 1               5                  10                  15

Tyr Met Ile Asn Phe Gly Arg Gly Gln Asn Tyr Trp Glu His Pro Tyr
             20                  25                  30

Gln Asn Ser Asp Val Tyr Arg Pro Ile Asn Glu His Arg Glu His Pro
         35                  40                  45

Lys Glu Tyr Glu Tyr Pro Leu His Gln Glu His Thr Tyr Gln Gln Glu
     50                  55                  60

Asp Ser Gly Glu Asp Glu Asn Thr Leu Gln His Ala Tyr Pro Ile Asp
 65                  70                  75                  80

His Glu Gly Ala Glu Pro Ala Pro Gln Glu Gln Asn Leu Phe Ser Ser
                 85                  90                  95

Ile Glu Ile Val Glu Arg Ser Asn Tyr Met Gly Asn Pro Trp Thr Glu
             100                 105                 110

Tyr Met Ala Lys Tyr Asp Ile Glu Glu Val His Gly Ser Gly Ile Arg
         115                 120                 125

Val Asp Leu Gly Glu Asp Ala Glu Val Ala Gly Thr Gln Tyr Arg Leu
    130                 135                 140

Pro Ser Gly Lys Cys Pro Val Phe Gly Lys Gly Ile Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
    210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
    290                 295                 300

Lys Asn Leu Gln Asn Ala Lys Phe Gly Leu Trp Val Asp Gly Asn Cys
305                 310                 315                 320
```

|   |   |   |   |   |   |   |   |   |   |   |   |   |   |   |
|---|---|---|---|---|---|---|---|---|---|---|---|---|---|---|
| Glu | Asp | Ile | Pro | His<br>325 | Val | Asn | Glu | Phe<br>330 | Pro | Ala | Ile | Asp | Leu<br>335 | Phe | Glu |
| Cys | Asn | Lys | Leu<br>340 | Val | Phe | Glu | Leu | Ser<br>345 | Ala | Ser | Asp | Gln<br>350 | Pro | Lys | Gln |
| Tyr | Glu | Gln<br>355 | His | Leu | Thr | Asp | Tyr<br>360 | Glu | Lys | Ile | Lys | Glu<br>365 | Gly | Phe | Lys |
| Asn | Lys<br>370 | Asn | Ala | Ser | Met | Ile<br>375 | Lys | Ser | Arg | Arg | Ile<br>380 | Lys | Ser | Ala | Phe |
| Leu<br>385 | Pro | Thr | Gly | Ala | Phe<br>390 | Lys | Ala | Asp | Arg | Tyr<br>395 | Lys | Ser | His | Gly | Lys<br>400 |
| Gly | Tyr | Asn | Trp | Gly<br>405 | Asn | Tyr | Asn | Thr | Glu<br>410 | Thr | Gln | Lys | Cys | Glu<br>415 | Ile |
| Phe | Asn | Val | Lys<br>420 | Pro | Thr | Cys | Leu | Ile<br>425 | Asn | Asn | Ser | Ser | Tyr<br>430 | Ile | Ala |
| Thr | Thr | Ala<br>435 | Leu | Ser | His | Pro | Ile<br>440 | Glu | Val | Glu | Asn | Asn<br>445 | Phe | Pro | Cys |
| Ser | Leu<br>450 | Tyr | Lys | Asp | Glu | Ile<br>455 | Met | Lys | Glu | Ile | Glu<br>460 | Arg | Glu | Ser | Lys |
| Arg<br>465 | Ile | Lys | Leu | Asn | Asp<br>470 | Asn | Asp | Glu | Gly<br>475 | Asn | Lys | Lys | Ile<br>480 | Met |
| Leu | Gln | Glu | Phe | Leu<br>485 | Ile | Ser | Asp | Asp | Lys<br>490 | Asp | Ser | Leu | Lys | Arg<br>495 | Pro |
| Cys | Asp | Pro | Glu<br>500 | Met | Val | Ser | Asn | Ser<br>505 | Thr | Cys | Arg | Phe | Phe<br>510 | Val | Cys |
| Lys | Cys | Val<br>515 | Glu | Arg | Arg | Ala | Glu<br>520 | Val | Thr | Ser | Asn | Asn<br>525 | Glu | Val | Val |
| Val | Lys<br>530 | Glu | Glu | Tyr | Lys | Asp<br>535 | Glu | Tyr | Ala | Asp | Ile<br>540 | Pro | Glu | His | Lys |
| Pro<br>545 | Thr | Tyr | Asp | Lys | Met<br>550 | Lys | Ile | Ile | Ile | Ala<br>555 | Ser | Ser | Ala | Ala | Val<br>560 |
| Ala | Val | Leu | Ala | Thr<br>565 | Ile | Leu | Met | Val | Tyr<br>570 | Leu | Tyr | Lys | Arg | Lys<br>575 | Gly |
| Asn | Ala | Glu | Lys<br>580 | Tyr | Asp | Lys | Met | Asp<br>585 | Glu | Pro | Gln | Asp | Tyr<br>590 | Gly | Lys |
| Ser | Asn | Ser<br>595 | Arg | Asn | Asp | Glu | Met<br>600 | Leu | Asp | Pro | Glu | Ala<br>605 | Ser | Phe | Trp |
| Gly | Glu | Glu | Lys | Arg<br>610 | Ala | Ser | His<br>615 | Thr | Thr | Pro | Val<br>620 | Leu | Met | Glu | Lys |
| Pro<br>625 | Tyr | Tyr | Asn |   |   |   |   |   |   |   |   |   |   |   |   |

( 2 ) INFORMATION FOR SEQ ID NO:10:

( i ) SEQUENCE CHARACTERISTICS:
        ( A ) LENGTH: 5181 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | | | | | |
|---|---|---|---|---|---|
| ATGAAGATCA | TATTCTTTCT | ATGTTCATTT | CTTTTCTTTA | TTATAAATAC | ACAATGTGTA | 60 |
| ACACATGAAA | GTTATCAAGA | ACTTGTCAAA | AAACTAGAAG | CTTTAGAAGA | TGCAGTATTG | 120 |
| ACAGGTTATG | GTTTATTTCA | TAAGGAAAAA | ATGATCTTAA | ATGAAGAAGA | AATTACTACA | 180 |
| AAAGGTGCAA | GTGCTCAAAG | TGGTACAAGT | GGTACAAGTG | GTACAAGTGG | TACAAGTGGT | 240 |
| ACAAGTGGTA | CAAGTGGTAC | AAGTGCTCAA | AGTGGTACAA | GTGGTACAAG | TGCTCAAAGT | 300 |

-continued

```
GGTACAAGTG GTACAAGTGC TCAAAGTGGT ACAAGTGGTA CAAGTGGTAC AAGTGGTACA      360
AGTCCATCAT CTCGTTCAAA CACTTTACCT CGTTCAAATA CTTCATCTGG TGCAAGCCCT      420
CCAGCTGATG CAAGCGATTC AGATGCTAAA TCTTACGCTG ATTTAAAACA CAGAGTACGA      480
AATTACTTGT TCACTATTAA AGAACTCAAA TATCCCGAAC TCTTTGATTT AACCAATCAT      540
ATGTTAACTT TGTGTGATAA TATTCATGGT TTCAAATATT TAATTGATGG ATATGAAGAA      600
ATTAATGAAT TATTATATAA ATTAAACTTT TATTTTGATT TATTAAGAGC AAAATTAAAT      660
GATGTATGTG CTAATGATTA TTGTCAAATA CCTTTCAATC TTAAAATTCG TGCAAATGAA      720
TTAGACGTAC TTAAAAAACT TGTGTTCGGA TATAGAAAAC CATTAGACAA TATTAAAGAT      780
AATGTAGGAA AAATGGAAGA TTACATTAAA AAAAATAAAA CAACCATAGC AAATATAAAT      840
GAATTAATTG AAGGAAGTAA GAAAACAATT GATCAAAATA AGAATGCAGA TAATGAAGAA      900
GGAAAAAAAA AATTATACCA AGCTCAATAT GATCTTTCTA TTTACAATAA ACAATTAGAA      960
GAAGCACATA ATTTAATAAG CGTTTTAGAA AAACGTATTG ACACTTTAAA AAAAAATGAA     1020
AACATTAAGG AATTACTTGA TAAGATAAAT GAAATTAAAA ATCCCCCACC GGCCAATTCT     1080
GGAAATACAC CAAATACTCT CCTTGATAAG AACAAAAAAA TCGAGGAACA CGAAGAAAAA     1140
ATAAAGAAA TTGCCAAAAC TATTAAATTT AACATTGATA GTTTATTTAC TGATCCACTT     1200
GAATTAGAAT ATTATTTAAG AGAAAAAAAT AAAAAAGTTG ATGTAACACC TAAATCACAA     1260
GATCCTACGA AATCTGTTCA AATACCAAAA GTTCCTTATC CAAATGGTAT TGTATATCCT     1320
TTACCACTCA CTGATATTCA TAATTCATTA GCTGCAGATA ATGATAAAAA TTCATATGGT     1380
GATTTAATGA ATCCTGATAC TAAAGAAAAA ATTAATGAAA AAATTATTAC AGATAATAAG     1440
GAAAGAAAAA TATTCATTAA TAACATTAAA AAACAAATTG ATTAGAAGA AAAAAAAATT     1500
AATCACACAA AAGAACAAAA TAAAAAATTA CTTGAAGATT ATGAAAAGTC AAAAAAGGAT     1560
TATGAAGAAT TACTTGAAAA ATTTTATGAA ATGAAATTTA ATAATAATTT TGACAAAGAT     1620
GTCGTAGATA AAATATTCAG TGCAAGATAT ACATATAATG TTGAAAAACA AAGATATAAT     1680
AATAAATTTT CATCCTCTAA TAATTCTGTA TATAATGTTC AAAAATTAAA AAAGGCTCTT     1740
TCATATCTTG AAGATTATTC TTTAAGAAAA GGAATTTCTG AAAAAGATTT TAATCATTAT     1800
TATACTTTGA AAACTGGCCT CGAAGCTGAT ATAAAAAAAT TAACAGAAGA AATAAAGAGT     1860
AGTGAAAACA AAATTCTAGA AAAAAATTTT AAAGGACTAA CACATTCAGC AAATGCTTCC     1920
TTAGAAGTAT ATGATATTGT AAAATTACAA GTACAAAAAG TTTTATTAAT TAAAAAAATA     1980
GAAGACTTAA GAAAGATAGA ATTATTTTTA AAAAATGCAC AACTAAAAGA TAGTATTCAT     2040
GTACCAAATA TTTATAAACC ACAAAATAAA CCAGAACCAT ATTATTTAAT TGTATTAAAA     2100
AAAGAAGTAG ATAAATTAAA AGAATTTATA CCAAAAGTAA AAGACATGTT AAAGAAAGAA     2160
CAAGCTGTCT TATCAAGTAT TACACAACCT TTAGTTGCAG CAAGCGAAAC AACTGAAGAT     2220
GGGGGTCACT CCACACACAC ATTATCCCAA TCAGGAGAAA CAGAAGTAAC AGAAGAAACA     2280
GAAGAAACAG AAGAAACAGT AGGACACACA ACAACGGTAA CAATAACATT ACCACCAAAA     2340
GAAGTAAAAG TTGTTGAAAA TTCAATAGAA CATAAGAGTA ATGACAATTC ACAAGCCTTG     2400
ACAAAAACAG TTTATCTAAA GAAATTAGAT GAATTTTTAA CTAAATCATA TATATGTCAT     2460
AAATATATTT TAGTATCAAA CTCTAGTATG GACCAAAAAT TATTAGAGGT ATATAATCTT     2520
ACTCCAGAAG AAGAAAATGA ATTAAAATCA TGTGATCCAT TAGATTTATT ATTTAATATT     2580
CAAAATAACA TACCTGCTAT GTATTCATTA TATGATAGTA TGAACAATGA TTTACAACAT     2640
CTCTTTTTTG AATTATATCA AAAGGAAATG ATTTATTATT TACATAAACT AAAAGAGGAA     2700
```

| | | | | | |
|---|---|---|---|---|---|
|AATCACATCA|AAAAATTATT|AGAGGAGCAA|AAACAAATAA|CTGGAACATC|ATCTACATCC 2760|
|AGTCCTGGAA|ATACAACCGT|AAATACTGCT|CAATCCGCAA|CTCACAGTAA|TTCCCAAAAC 2820|
|CAACAATCAA|ATGCATCCTC|TACCAATACC|CAAAATGGTG|TAGCTGTATC|ATCTGGTCCT 2880|
|GCTGTAGTTG|AAGAAAGTCA|TGATCCCTTA|ACAGTATTGT|CTATTAGTAA|CGATTGAAA 2940|
|GGTATTGTTA|GTCTCTTAAA|TCTTGGAAAT|AAAACTAAAG|TACCTAATCC|ATTAACCATT 3000|
|TCTACAACAG|AGATGGAAAA|ATTTTATGAG|AATATTTTAA|AAATAATGA|TACCTATTTT 3060|
|AATGATGATA|TCAAACAATT|CGTAAAATCT|AATTCAAAAG|TAATTACAGG|TTTGACCGAA 3120|
|ACACAAAAAA|ATGCATTAAA|TGATGAAATT|AAAAAATTAA|AAGATACTTT|ACAGTATCA 3180|
|TTTGATTTAT|ATAATAAATA|TAAATTAAAA|TTAGATAGAT|TATTTAATAA|GAAAAAGAA 3240|
|CTTGGCCAAG|ACAAATGCA|AATTAAAAAA|CTTACTTTAT|TAAAGAACA|ATTAGAATCA 3300|
|AAATTGAATT|CACTTAATAA|CCCACATAAT|GTATTACAAA|ACTTTCTGT|TTTCTTTAAC 3360|
|AAAAAAAAG|AAGCTGAAAT|AGCAGAAACT|GAAACACAT|TAGAAACAC|AAAAATATTA 3420|
|TTGAAACATT|ATAAAGGACT|TGTTAAATAT|TATAATGGTG|AATCATCTCC|ATTAAAAACT 3480|
|TTAAGTGAAG|TATCAATTCA|AACAGAAGAT|AATTATGCCA|ATTTAGAAAA|ATTTAGAGTA 3540|
|TTAAGTAAAA|TAGATGGAAA|ACTCAATGAT|AATTTACATT|TAGGAAAGAA|AAAATTATCT 3600|
|TTCTTATCAA|GTGGATTACA|TCATTTAATT|ACTGAATTAA|AAGAAGTAAT|AAAAAATAAA 3660|
|AATTATACAG|GTAATTCTCC|AAGTGAAAAT|AATAAGAAAG|TTAACGAAGC|TTTAAAATCT 3720|
|TACGAAAATT|TTCTCCCAGA|AGCAAAAGTT|ACAACAGTTG|TAACTCCACC|TCAACCAGAT 3780|
|GTAACTCCAT|CTCCATTATC|TGTAAGGGTA|AGTGGTAGTT|CAGGATCCAC|AAAAGAAGAA 3840|
|ACACAAATAC|CAACTTCAGG|CTCTTTATTA|ACAGAATTAC|AACAAGTAGT|ACAATTACAA 3900|
|AATTATGACG|AAGAAGATGA|TTCCTTAGTT|GTATTACCCA|TTTTTGGAGA|ATCCGAAGAT 3960|
|AATGACGAAT|ATTTAGATCA|AGTAGTAACT|GGAGAAGCAA|TATCTGTCAC|AATGGATAAT 4020|
|ATCCTCTCAG|GATTTGAAAA|TGAATATGAT|GTTATATATT|TAAAACCTTT|AGCTGGAGTA 4080|
|TATAGAAGCT|TAAAAAAACA|AATTGAAAAA|AACATTTTTA|CATTTAATTT|AAATTTGAAC 4140|
|GATATCTTAA|ATTCACGTCT|TAAGAAACGA|AAATATTTCT|TAGATGTATT|AGAATCTGAT 4200|
|TTAATGCAAT|TTAAACATAT|ATCCTCAAAT|GAATACATTA|TTGAAGATTC|ATTTAAATTA 4260|
|TTGAATTCAG|AACAAAAAAA|CACACTTTTA|AAAAGTTACA|AATATATAAA|AGAATCAGTA 4320|
|GAAAATGATA|TTAAATTTGC|ACAGGAAGGT|ATAAGTTATT|ATGAAAAGGT|TTTAGCGAAA 4380|
|TATAAGGATG|ATTTAGAATC|AATTAAAAAA|GTTATCAAAG|AAGAAAAGGA|GAAGTTCCCA 4440|
|TCATCACCAC|CAACAACACC|TCCGTCACCA|GCAAAAACAG|ACGAACAAAA|GAAGGAAAGT 4500|
|AAGTTCCTTC|CATTTTTAAC|AAACATTGAG|ACCTTATACA|ATAACTTAGT|TAATAAAATT 4560|
|GACGATTACT|TAATTAACTT|AAAGGCAAAG|ATTAACGATT|GTAATGTTGA|AAAAGATGAA 4620|
|GCACATGTTA|AAATAACTAA|ACTTAGTGAT|TTAAAAGCAA|TTGATGACAA|AATAGATCTT 4680|
|TTTAAAAACC|ATAACGACTT|CGAAGCAATT|AAAAAATTGA|TAAATGATGA|TACGAAAAAA 4740|
|GATATGCTTG|GCAAATTACT|TAGTACAGGA|TTAGTTCAAA|ATTTTCCTAA|TACAATAATA 4800|
|TCAAAATTAA|TTGAAGGAAA|ATTCCAAGAT|ATGTTAAACA|TTTCACAACA|CCAATGCGTA 4860|
|AAAAAACAAT|GTCCAGAAAA|TTCTGGATGT|TTCAGACATT|TAGATGAAAG|AGAAGAATGT 4920|
|AAATGTTTAT|TAAATTACAA|ACAAGAAGGT|GATAAATGTG|TTGAAAATCC|AAATCCTACT 4980|
|TGTAACGAAA|ATAATGGTGG|ATGTGATGCA|GATGCCAAAT|GTACCGAAGA|AGATTCAGGT 5040|
|AGCAACGGAA|AGAAAATCAC|ATGTGAATGT|ACTAAACCTG|ATTCTTATCC|ACTTTTCGAT 5100|

```
GGTATTTTCT GCAGTTCCTC TAACTTCTTA GGAATATCAT TCTTATTAAT ACTCATGTTA      5 1 6 0

ATATTATACA GTTTCATTTA A                                                5 1 8 1
```

( 2 ) INFORMATION FOR SEQ ID NO:11:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
ATGATGAGAA AATTAGCTAT TTTATCTGTT TCTTCCTTCC TATTTGTTGA GGCCTTATTC        6 0

CAGGAATACC AGTGCTATGG AAGTTCGTCA AACACAAGGG TTCTAAATGA ATTAAATTAT      1 2 0

GATAATGCAG GCACTAATTT ATATAATGAA TTAGAAATGA ATTATTATGG AAACAGGAA       1 8 0

AATTGGTATA GTCTTAAAAA AAATAGTAGA TCACTTGGAG AAAATGATGA TGGAAATAAC      2 4 0

GAAGACAACG AGAAATTAAG GAAACCAAAA CATAAAAAAT TAAAGCAACC AGCGGATGGT      3 0 0

AATCCTGATC CAAATGCAAA CCCAAATGTA GATCCCAATG CCAACCCAAA TGTAGATCCA      3 6 0

AATGCAAACC CAAATGTAGA TCCAAATGCA AACCCAAATG CAAACCCAAA TGCAAACCCA      4 2 0

AATGCAAACC CAAATGCAAA CCCAAATGCA AACCCAAATG CAAACCCAAA TGCAAACCCA      4 8 0

AATGCAAACC CAAATGCAAA CCCAAATGCA AACCCAAATG CAAACCCAAA TGCAAACCCA      5 4 0

AACGCAAACC CCAATGCAAA TCCTAATGCA AACCCCAATG CAAATCCTAA TGCAAATCCT      6 0 0

AATGCCAATC CAAATGCAAA TCCAAATGCA AACCCAAACG CAAACCCCAA TGCAAATCCT      6 6 0

AATGCCAATC CAAATGCAAA TCCAAATGCA AACCCAAATG CAAACCCAAA TGCAAACCCC      7 2 0

AATGCAAATC CTAATAAAAA CAATCAAGGT AATGGACAAG GTCACAATAT GCCAAATGAC      7 8 0

CCAAACCGAA ATGTAGATGA AAATGCTAAT GCCAACAGTG CTGTAAAAAA TAATAATAAC      8 4 0

GAAGAACCAA GTGATAAGCA CATAAAAGAA TATTTAAACA AAATACAAAA TTCTCTTTCA      9 0 0

ACTGAATGGT CCCCATGTAG TGTAACTTGT GGAAATGGTA TTCAAGTTAG AATAAAGCCT      9 6 0

GGCTCTGCTA ATAAACCTAA AGACGAATTA GATTATGCAA ATGATATTGA AAAAAAAATT     1 0 2 0

TGTAAAATGG AAAAATGTTC CAGTGTGTTT AATGTCGTAA ATAGTTCAAT AGGATTAATA     1 0 8 0

ATGGTATTAT TCTTCTTGTT CCTTAATTAG                                      1 1 1 0
```

( 2 ) INFORMATION FOR SEQ ID NO:12:

( i ) SEQUENCE CHARACTERISTICS:
        ( A ) LENGTH: 1882 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
ATGAGAAAAT TATACTGCGT ATTATTATTG AGCGCCTTTG AGTTACATA TATGATAAAC         6 0

TTTGGAAGAG GACAGAATTA TTGGGAACAT CCATATCAAA ATAGTGATGT GTATCGTCCA      1 2 0

ATCAACGAAC ATAGGGAACA TCCAAAAGAA TACGAATATC CATTACACCA GGAACATACA      1 8 0

TACCAACAAG AAGATTCAGG AGAAGACGAA AATACATTAC AACACGCATA TCCAATAGAC      2 4 0

CACGAAGGTG CCGAACCCGC ACCACAAGAA CAAAATTTAT TTTCAAGCAT TGAAATAGTA      3 0 0

GAAAGAAGTA ATTATATGGG TAATCCATGG ACGGAATATA TGGCAAAATA TGATATTGAA      3 6 0

GAAGTTCATG GTTCAGGTAT AAGAGTAGAT TTAGGAGAAG ATGCTGAAGT AGCTGGAACT      4 2 0

CAATATAGAC TTCCATCAGG GAAATGTCCA GTATTGGTA AAGGTATAAT TATTGAGAAT      4 8 0
```

```
TCAAATACTA CTTTTTTAAC ACCGGTAGCT ACGGGAAATC AATATTTAAA AGATGGAGGT      540
TTTGCTTTTC CTCCAACAGA ACCTCTTATG TCACCAATGA CATTAGATGA AATGAGACAT      600
TTTTATAAAG ATAATAAATA TGTAAAAAAT TTAGATGAAT TGACTTTATG TTCAAGACAT      660
GCAGGAAATA TGATTCCAGA TAATGATAAA AATTCAAATT ATAAATATCC AGCTGTTTAT      720
GATGACAAAG ATAAAAGTG  TCATATATTA TATATTGCAG CTCAAGAAAA TAATGGTCCT      780
AGATATTGTA ATAAAGACGA AAGTAAAAGA AACAGCATGT TTTGTTTTAG ACCAGCAAAA      840
GATATATCAT TTCAAAACTA TACATATTTA AGTAAGAATG TAGTTGATAA CTGGGAAAAA      900
GTTGCCCTA  GAAAGAATTT ACAGAATGCA AAATTCGGAT TATGGGTCGA TGGAAATTGT      960
GAAGATATAC CACATGTAAA TGAATTTCCA GCAATTGATC TTTTTGAATG TAATAAATTA     1020
GTTTTTGAAT TGAGTGCTTC GGATCAACCT AAACAATATG AACAACATTT AACAGATTAT     1080
GAAAAAATTA AGAAGGTTT  CAAAAATAAG AACGCTAGTA TGATCAAAAG TGCTTTTCTT     1140
CCCACTGGTG CTTTTAAAGC AGATAGATAT AAAAGTCATG GTAAGGGTTA TAATTGGGGA     1200
AATTATAACA CAGAAACACA AAAATGTGAA ATTTTAATG  TCAAACCAAC ATGTTTAATT     1260
AACAATTCAT CATACATTGC TACTACTGCT TTGTCCCATC CCATCGAAGT TGAAAACAAT     1320
TTTCCATGTT CATTATATAA AGATGAAATA ATGAAGAAA  TCGAAGAGA  ATCAAAACGA     1380
ATTAAATTAA ATGATAATGA TGATGAAGGG AATAAAAAAA TTATAGCTCC AAGAATTTTT     1440
ATTTCAGATG ATAAAGACAG TTTAAAATGC CCATGTGACC CTGAAATGGT AAGTAATAGT     1500
ACATGTCGTT TCTTTGTATG TAAATGTGTA GAAAGAAGGG CAGAAGTAAC ATCAAATAAT     1560
GAAGTTGTAG TTAAAGAAGA ATATAAAGAT GAATATGCAG ATATTCCTGA ACATAAACCA     1620
ACTTATGATA AAATGAAAAT TATAATTGCA TCATCAGCTC GTGTCGCTGT ATTAGCAACT     1680
ATTTTAATGG TTTATCTTTA TAAAAGAAAA GGAAATGCTG AAAAATATGA TAAAATGGAT     1740
GAACCACAAG ATTATGGGAA ATCAAATTCA AGAAATGATG AAATGTTAGA TCCTGAGGCA     1800
TCTTTTTGGG GGGAAGAAAA AAGAGCATCA CATACAACAC CAGTTCTGAT GGAAAAACCA     1860
TACTATTAAT TTTTATGGAT CC                                              1882
```

( 2 ) INFORMATION FOR SEQ ID NO:13:

( i ) SEQUENCE CHARACTERISTICS:
        ( A ) LENGTH: 654 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
ATGAATAAAC TTTACAGTTT GTTTCTTTTC CTTTTCATTC AACTTAGCAT AAAATATAAT       60
AATGCGAAAG TTACCGTGGA TACTGTATGC AAAAGAGGAT TTTAATTCA  GATGAGTGGT      120
CATTGGAAT  GTAAATGTGA AAATGATTTG GTGTTAGTAA ATGAAGAAAC ATGTGAAGAA      180
AAAGTTCTGA ATGTGACGA  AAAGACTGTA ATAAACCAT  GTGGAGATTT TTCCAAATGT      240
ATTAAAATAG ATGGAAATCC CGTTTCATAC GCTTGTAAAT GTAATCTTGG ATATGATATG      300
GTAAATAATG TTTGTATACC AAATGAATGT AAGAATGTAA CTTGTGGTAA CGGTAAATGT      360
ATATTAGATA CAAGCAATCC TGTTAAAACT GGAGTTTGCT CATGTAATAT AGGCAAAGTT      420
CCCAATGTAC AAGATCAAAA TAAATGTTCA AAAGATGGAG AAACCAAATG CTCATTAAAA      480
TGCTTAAAAG AAAATGAAAC CTGTAAAGCT GTTGATGGAA TTTATAAATG TGATTGTAAA      540
GATGGATTTA TAATAGATAA TGAAAGCTCT ATATGTACTG CTTTTCAGC  ATATAATATT      600
```

TTAAATCTAA GCATTATGTT TATACTATTT TCAGTATGCT TTTTATAAT GTAA        654

( 2 ) INFORMATION FOR SEQ ID NO:14:

( i ) SEQUENCE CHARACTERISTICS:
        ( A ) LENGTH: 1725 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

ATGAATCATC TTGGGAATGT TAAATATTTA GTCATTGTGT TTTTGATTTT CTTTGATTTG    60
TTTCTAGTTA ATGGTAGAGA TGTGCAAAAC AATATAGTGG ATGAAATAAA ATATCGTGAA   120
GAAGTATGTA ATGATGAGGT AGATCTTTAC CTTCTAATGG ATTGTTCTGG AAGTATACGT   180
CGTCATAATT GGGTGAACCA TGCAGTACCT CTAGCTATGA AATTGATACA ACAATTAAAT   240
CTTAATGATA ATGCAATTCA CTTATATGCT AGTGTTTTTT CAAACAATGC AAGAGAAATT   300
ATTAGATTAC ATAGTGATGC ATCTAAAAAC AAAGAGAAGG CTTTAATTAT TATAAAGTCA   360
CTCTTAAGTA CAAATCTTCC ATATGGTAAA ACAAACTTAA CTGATGCACT GTTACAAGTA   420
AGAAAACATT TAAATGACCG AATCAATAGA GAGAATGCTA ATCAATTAGT TGTTATATTA   480
ACAGATGGAA TTCCAGATAG TATTCAAGAT TCATTAAAAG AATCAAGAAA ATTAAGTGAT   540
CGTGGTGTTA AAATAGCTGT TTTTGGTATT GGACAAGGTA TTAATGTAGC TTTCAACAGA   600
TTTCTTGTAG GTTGTCATCC ATCAGATGGT AAATGTAACT TGTATGCTGA TTCTGCATGG   660
GAAAATGTAA AAAATGTTAT CGGACCCTTT ATGAAGGCTG TTTGTGTTGA AGTAGAAAAA   720
ACAGCAAGTT GTGGTGTTTG GGACGAATGG TCTCCATGTA GTGTAACTTG TGGTAAAGGT   780
ACCAGGTCAA GAAAAAGAGA AATCTTACAC GAAGGATGTA CAAGTGAATT ACAAGAACAA   840
TGTGAAGAAG AAAGATGTCT TCCAAAACGG GAACCATTAG ATGTTCCAGA TGAACCCGAA   900
GATGATCAAC CTAGACCAAG AGGAGATAAT TTTGCTGTCG AAAAACCAAA CGAAAATATA   960
ATAGATAATA ATCCACAAGA ACCTTCACCA AATCCAGAAG AAGGAAAGGG TGAAAATCCA  1020
AACGGATTTG ATTTAGATGA AAATCCAGAA AATCCACCAA ATCCACCAAA TCCACCAAAT  1080
CCACCAAATC CACCAAATCC ACCAAATCCA GATATTCCTG AACAAGAACC AAATATACCT  1140
GAAGATTCAG AAAAAGAAGT ACCTTCTGAT GTTCCAAAAA ATCCAGAAGA CGATCGAGAA  1200
GAAAACTTTG ATATTCCAAA GAAACCCGAA AATAAGCACG ATAATCAAAA TAATTTACCA  1260
AATGATAAAA GTGATAGATA TATTCCATAT TCACCATTAT CTCCAAAAGT TTTGGATAAT  1320
GAAAGGAAAC AAAGTGACCC CCAAAGTCAA GATAATAATG GAAATAGGCA CGTACCTAAT  1380
AGTGAAGATA GAGAAACACG TCCACATGGT AGAAATAATG AAAATAGATC ATACAATAGA  1440
AAACATAACA ATACTCCAAA ACATCCTGAA AGGGAAGAAC ATGAAAAGCC AGATAATAAT  1500
AAAAAAAAAG CAGGATCAGA TAATAAATAT AAAATTGCAG GTGGAATAGC TGGAGGATTA  1560
GCTTTACTCG CATGTGCTGG ACTTGCTTAT AAATTCGTAG TACCAGGAGC AGCAACACCC  1620
TATGCCGGAG AACCTGCACC TTTTGATGAA ACATTAGGTG AAGAAGATAA AGATTTGGAC  1680
GAACCTGAAC AATTCAGATT ACCTGAAGAA AACGAGTGGA ATTAA                 1725

( 2 ) INFORMATION FOR SEQ ID NO:15:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATGAAACATA TTTTGTACAT ATCATTTTAC TTTATCCTTG TTAATTTATT GATATTTCAT        60
ATAAATGGAA AGATAATAAA GAATTCTGAA AAAGATGAAA TCATAAAATC TAACTTGAGA       120
AGTGGTTCTT CAAATTCTAG GAATCGAATA AATGAGGAAA AGCACGAGAA GAAACACGTT       180
TTATCTCATA ATTCATATGA GAAAACTAAA AATAATGAAA ATAATAAATT TTTCGATAAG       240
GATAAAGAGT TAACGATGTC TAATGTAAAA AATGTGTCAC AAACAAATTT CAAAAGTCTT       300
TTAAGAAATC TTGGTGTTTC AGAGAATATA TTCCTTAAAG AAAATAAATT AAATAAGGAA       360
GGGAAATTAA TTGAACACAT AATAAATGAT GATGACGATA AAAAAAAATA TATTAAAGGG       420
CAAGACGAAA ACAGACAAGA AGATCTTGAA GAAAAAGCGC GCGCATCTAA AGAAACGAGG       480
AAGGCTGATA CGAAAAAAAA TTTAGAAAGA AAAAAGGAAC ATGGAGATGT ATTAGCAGAG       540
GATTTATATG GTCGTTTAGA AATACCAGCT ATAGAACTTC CATCAGAAAA TGAACGTGGA       600
TATTATATAC CACATCAATC TTCTTTACCT CAGGACAACA GAGGGAATAG TAGAGATTCC       660
AAGGAAATAT CTATAATAGA AAAACAAAT AGAGAATCTA TTACAACAAA TGTTGAAGGA        720
CGAAGGGATA TACATAAAGG ACATCTTGAA GAAAAGAAAG ATGGTTCAAT AAAACCAGAA       780
CAAAAAGAAG ATAAATCTGC TGACATACAA AATCATACAT TAGAGACAGT AAATATTTCT       840
GATGTTAATG ATTTTCAAAT AAGTAAGTAT GAGGATGAAA TAAGTGCTGA ATATGACGAT       900
TCATTAATAG ATGAAGAAGA AGATGATGAA GACTTAGACG AATTTAAGCC TATTGTGCAA       960
TATGACAATT TCCAAGATGA AGAAACATA GGAATTTATA AGAACTAGA AGATTTGATA       1020
GAGAAAAATG AAAATTTAGA TGATTAGAT GAAGGAATAG AAAAATCATC AGAAGAATTA      1080
TCTGAAGAAA AAATAAAAAA AGGAAAGAAA TATGAAAAAA CAAAGGATAA TAATTTTAAA      1140
CCAAATGATA AAAGTTTGTA TGATGAGCAT ATTAAAAAAT ATAAAAATGA TAAGCAGGTT      1200
AATAAGGAAA AGGAAAAATT CATAAAATCA TTGTTTCATA TATTTGACGG AGACAATGAA      1260
ATTTTACAGA TCGTGGATGA GTTATCTGAA GATATAACTA AATATTTTAT GAAACTATAA      1320
```

( 2 ) INFORMATION FOR SEQ ID NO:16:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
TATGAGTAAC TTAACTCTTT TGTTAATTAA AAGTATATTC AAAAAATAAG TTATATAAAT        60
AGATCTGAAT TCGTT                                                        75
```

( 2 ) INFORMATION FOR SEQ ID NO:17:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
AACGAATTCA GATCTATTTA TATAACTTAT TTTTGAATA TACTTTTAAT TAACAAAAGA        60
GTTAAGTTAC TCA                                                          73
```

( 2 ) INFORMATION FOR SEQ ID NO:18:

( i ) SEQUENCE CHARACTERISTICS:
: ( A ) LENGTH: 39 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:18:

CCCCCCGAAT TCGTCGACGA TTGTTCATGA TGGCAAGAT                              39

( 2 ) INFORMATION FOR SEQ ID NO:19:

( i ) SEQUENCE CHARACTERISTICS:
: ( A ) LENGTH: 68 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:19:

CCCGGGGAT CCCTCGAGGG TACCAAGCTT AATTAATTAA ATATTAGTAT AAAAAGTGAT        60

TTATTTTT                                                                68

( 2 ) INFORMATION FOR SEQ ID NO:20:

( i ) SEQUENCE CHARACTERISTICS:
: ( A ) LENGTH: 77 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:20:

AAGCTTGGTA CCCTCGAGGG ATCCCCGGG TAGCTAGCTA ATTTTCTTT TACGTATTAT         60

ATATGTAATA AACGTTC                                                      77

( 2 ) INFORMATION FOR SEQ ID NO:21:

( i ) SEQUENCE CHARACTERISTICS:
: ( A ) LENGTH: 39 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:21:

TTTTTCTGC AGGTAAGTAT TTTTAAAACT TCTAACACC                               39

( 2 ) INFORMATION FOR SEQ ID NO:22:

( i ) SEQUENCE CHARACTERISTICS:
: ( A ) LENGTH: 66 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:22:

AGAAAAATCA GTTAGCTAAG ATCTCCCGGG CTCGAGGGTA CCGGATCCTG ATTAGTTAAT       60

TTTTGT                                                                  66

( 2 ) INFORMATION FOR SEQ ID NO:23:

( i ) SEQUENCE CHARACTERISTICS:
: ( A ) LENGTH: 70 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:23:

```
GATCACAAAA ATTAACTAAT CAGGATCCGG TACCCTCGAG CCCGGGAGAT CTTAGCTAAC    60

TGATTTTTCT                                                          70
```

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GGTCGACGGA TCCT                                                     14
```

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GATCAGGATC CGTCGACCTG CA                                            22
```

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
GGGCTGAAGC TTGCTGGCCG CTCATTAGAC AAGCGAATGA GGGAC                   45
```

( 2 ) INFORMATION FOR SEQ ID NO:27:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
AGATCTCCCG GGCTCGAGTA ATTAATTAAT TTTTATTACA CCAGAAAAGA CGGCTTGAGA    60

TC                                                                  62
```

( 2 ) INFORMATION FOR SEQ ID NO:28:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

```
TATCTCGAAT TCCCGCGGCT TTAAATGGAC GGAACTCTTT TCCCC                   45
```

( 2 ) INFORMATION FOR SEQ ID NO:29:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

TATCTCGAAT TCCCGCGGCT TTAAATGGAC GGAACTCTTT TCCCC    45

( 2 ) INFORMATION FOR SEQ ID NO:30:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GATCTTTTGT TAACAAAAAC TAATCAGCTA TCGCGAATCG ATTCCCGGGG GATCCGGTAC    60

CC    62

( 2 ) INFORMATION FOR SEQ ID NO:31:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TCGAGGGTAC CGGATCCCCC GGGAATCGAT TCGCGATAGC TGATTAGTTT TTGTTAACAA    60

AA    62

( 2 ) INFORMATION FOR SEQ ID NO:32:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCCCCCAAGC TTACATCATG CAGTGGTTAA AC    32

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

GATTAAACCT AAATAATTGT    20

( 2 ) INFORMATION FOR SEQ ID NO:34:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

ACAATTATTT AGGTTAACTG CA    22

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single ( D ) TOPOLOGY: linear ( x i ) SEQUENCE DESCRIPTION: SEQ ID NO:35:

GTTAACCTAA ATAATTGT    18

( 2 ) INFORMATION FOR SEQ ID NO:36:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

ATAAAAATTA GCTACTCAGG TACCCTGCAG TCGCGAGGAT CCGAATTCCC CGGGCTCGAG    60

TGATTAATTA GTTTTTAT    78

( 2 ) INFORMATION FOR SEQ ID NO:37:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

ATAAAAACTA ATTAATCACT CGAGCCCGGG GAATTCGGAT CCTCGCGACT GCAGGGTACC    60

TGAGTAGCTA ATTTTTAT    78

( 2 ) INFORMATION FOR SEQ ID NO:38:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

ATCATCGAAT TCTGAATGTT AAATGTTATA CTTG    34

( 2 ) INFORMATION FOR SEQ ID NO:39:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGGGGTACCT TTGAGAGTAC CACTTCAG    28

( 2 ) INFORMATION FOR SEQ ID NO:40:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGGTCTAGAG CGGCCGCTTA TAAAGATCTA AAATGCATAA TTTC    44

( 2 ) INFORMATION FOR SEQ ID NO:41:

( i ) SEQUENCE CHARACTERISTICS:
        ( A ) LENGTH: 35 base pairs (B) TYPE: nucleic acid
(C) STRANDEDNESS: single
(D) TOPOLOGY: linear (xi) SEQUENCE DESCRIPTION: SEQ ID NO:41:

ATCATCCTGC AGGTATTCTA AACTAGGAAT AGATG     35

(2) INFORMATION FOR SEQ ID NO:42:

(i) SEQUENCE CHARACTERISTICS:
(A) LENGTH: 82 base pairs
(B) TYPE: nucleic acid
(C) STRANDEDNESS: single
(D) TOPOLOGY: linear (xi) SEQUENCE DESCRIPTION: SEQ ID NO:42:

GTACGTGACT AATTAGCTAT AAAAGGATC CGGTACCCTC GAGTCTAGAA TCGATCCCGG     60

GTTTTTATGA CTAGTTAATC AC     82

(2) INFORMATION FOR SEQ ID NO:43:

(i) SEQUENCE CHARACTERISTICS:
(A) LENGTH: 82 base pairs
(B) TYPE: nucleic acid
(C) STRANDEDNESS: single
(D) TOPOLOGY: linear (xi) SEQUENCE DESCRIPTION: SEQ ID NO:43:

GGCCGTGATT AACTAGTCAT AAAAACCCGG GATCGATTCT AGACTCGAGG GTACCGGATC     60

CTTTTTATAG CTAATTAGTC AC     82

(2) INFORMATION FOR SEQ ID NO:44:

(i) SEQUENCE CHARACTERISTICS:
(A) LENGTH: 70 base pairs
(B) TYPE: nucleic acid
(C) STRANDEDNESS: single
(D) TOPOLOGY: linear (xi) SEQUENCE DESCRIPTION: SEQ ID NO:44:

GATCTTAATT AATTAGTCAT CAGGCAGGGC GAGAACGAGA CTATCTGCTC GTTAATTAAT     60

TAGGTCGACG     70

(2) INFORMATION FOR SEQ ID NO:45:

(i) SEQUENCE CHARACTERISTICS:
(A) LENGTH: 70 base pairs
(B) TYPE: nucleic acid
(C) STRANDEDNESS: single
(D) TOPOLOGY: linear (xi) SEQUENCE DESCRIPTION: SEQ ID NO:45:

GATCCGTCGA CCTAATTAAT TAACGAGCAG ATAGTCTCGT TCTCGCCCTG CCTGATGACT     60

AATTAATTAA     70

(2) INFORMATION FOR SEQ ID NO:46:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:46:

GTACATAAGC TTTTTGCATG     20

(2) INFORMATION FOR SEQ ID NO:47:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
TATGAATTCC  TCGAGGGATC  CAGGCCTTTT  TTATTGACTA  GTTAATCAGT  CTAATATACG    60
TACTAAATAC                                                                70
```

(2) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
CTAATTTCGA  ATGTCCGACG                                                    20
```

(2) INFORMATION FOR SEQ ID NO:49:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

```
TTAGAATTCT  CGCGACCCGG  GTTTTTATAG  CTAATTAGTA  CTTATTACAA  ATACTATAAT    60
ATTTAG                                                                    66
```

(2) INFORMATION FOR SEQ ID NO:50:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

```
ATCATCGAAT  TCTGAATGTT  AAATGTTATA  CTTG                                  34
```

(2) INFORMATION FOR SEQ ID NO:51:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

```
GGGGGTACCT  TTGAGAGTAC  CACTTCAG                                          28
```

(2) INFORMATION FOR SEQ ID NO:52:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

```
GGGTCTAGAG CGGCCGCTTA TAAAGATCTA AAATGCATAA TTTC                              44
```

( 2 ) INFORMATION FOR SEQ ID NO:53:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

```
ATCATCCTGC AGGTATTCTA AACTAGGAAT AGATG                                       35
```

( 2 ) INFORMATION FOR SEQ ID NO:54:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

```
TCGGGATCCG GGTTAATTAA TTAGTCATCA GGCAGGGCG                                   39
```

( 2 ) INFORMATION FOR SEQ ID NO:55:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
TAGCTCGAGG GTACCTACGA TACAAACTTA ACGGATATCG                                  40
```

( 2 ) INFORMATION FOR SEQ ID NO:56:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
AATTGCGGCC GC                                                                12
```

( 2 ) INFORMATION FOR SEQ ID NO:57:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

```
CAGTTGGTAC CACTGGTATT TTATTTCAG                                              29
```

( 2 ) INFORMATION FOR SEQ ID NO:58:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

```
TATCTGAATT CCTGCAGCCC GGGTTTTTAT AGCTAATTAG TCAAATGTGA GTTAATATTA            60
```

G                                                                                                        61

( 2 ) INFORMATION FOR SEQ ID NO:59:

( i ) SEQUENCE CHARACTERISTICS:
  ( A ) LENGTH: 66 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:59:

TCGCTGAATT CGATATCAAG CTTATCGATT TTATGACTA GTTAATCAAA TAAAAAGCAT   60

ACAAGC   66

( 2 ) INFORMATION FOR SEQ ID NO:60:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:60:

TTATCGAGCT CTGTAACATC AGTATCTAAC   30

( 2 ) INFORMATION FOR SEQ ID NO:61:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:61:

TCCGGTACCG CGGCCGCAGA TATTTGTTAG CTTCTGC   37

( 2 ) INFORMATION FOR SEQ ID NO:62:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:62:

TCGCTCGAGT AGGATACCTA CCTACTACCT ACG   33

( 2 ) INFORMATION FOR SEQ ID NO:63:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:63:

TCGCTCGAGC TTTCTTGACA ATAACATAG   29

( 2 ) INFORMATION FOR SEQ ID NO:64:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:64:

TAGGAGCTCT TTATACTACT GGGTTACAAC 30

( 2 ) INFORMATION FOR SEQ ID NO:65:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:65:

AATTCCTCGA GGGATCC 17

( 2 ) INFORMATION FOR SEQ ID NO:66:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:66:

CGGGATCCCT CGAGG 15

( 2 ) INFORMATION FOR SEQ ID NO:67:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:67:

CCGGTTAATT AATTAGTTAT TAGACAAGGT GAAAACGAAA CTATTTGTAG CTTAATTAAT 60

TAGGTCACC 69

( 2 ) INFORMATION FOR SEQ ID NO:68:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:68:

CCGGGGTCGA CCTAATTAAT TAAGCTACAA ATAGTTTCGT TTTCACCTTG TCTAATAACT 60

AATTAATTAA 70

( 2 ) INFORMATION FOR SEQ ID NO:69:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:69:

TAATTAACTA GCTACCCGGG 20

( 2 ) INFORMATION FOR SEQ ID NO:70:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:70:

GTACATTAAT TGATCGATGG GCCCTTAA 28

( 2 ) INFORMATION FOR SEQ ID NO:71:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AGCTTCCCGG GTAAGTAATA CGTCAAGGAG AAAACGAAAC GATCTGTAGT TAGCGGCCGC 60

CTAATTAACT AAT 73

( 2 ) INFORMATION FOR SEQ ID NO:72:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

AGGGCCCATT CATTATGCAG TTCCTCTTTT GCTTGCTAG ACATCAATCG CCGGCGGATT 60

AATTGATTA 69

( 2 ) INFORMATION FOR SEQ ID NO:73:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

CGATTACTAT GAAGGATCCG TT 22

( 2 ) INFORMATION FOR SEQ ID NO:74:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

TAATGATACT TCCTAGGCAA 20

( 2 ) INFORMATION FOR SEQ ID NO:75:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

CGATTACTAG ATCTGAGCTC CCCGGGCTCG AGGGATCCGT T 41

( 2 ) INFORMATION FOR SEQ ID NO:76:

( i ) SEQUENCE CHARACTERISTICS:
        ( A ) LENGTH: 39 base pairs
        ( B ) TYPE: nucleic acid -continued ( C ) STRANDEDNESS: single
          ( D ) TOPOLOGY: linear ( x i ) SEQUENCE DESCRIPTION: SEQ ID NO:76:

TAATGATCTA GACTCGAGGG GCCCGAGCTC CCTAGGCAA                                     39

( 2 ) INFORMATION FOR SEQ ID NO:77:

( i ) SEQUENCE CHARACTERISTICS:
          ( A ) LENGTH: 16 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:77:

GATCCGAATT CTAGCT                                                              16

( 2 ) INFORMATION FOR SEQ ID NO:78:

( i ) SEQUENCE CHARACTERISTICS:
          ( A ) LENGTH: 12 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:78:

GCTTAAGATC GA                                                                  12

( 2 ) INFORMATION FOR SEQ ID NO:79:

( i ) SEQUENCE CHARACTERISTICS:
          ( A ) LENGTH: 75 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:79:

TATGAGTAAC TTAACTCTTT TGTTAATTAA AAGTATATTC AAAAAATAAG TTATATAAAT              60

AGATCTGAAT TCGTT                                                               75

( 2 ) INFORMATION FOR SEQ ID NO:80:

( i ) SEQUENCE CHARACTERISTICS:
          ( A ) LENGTH: 73 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:80:

ACTCATTGAA TTGAGAAAAC AATTAATTTT CATATAAGTT TTTTATTCAA TATATTTATC              60

TAGACTTAAG CAA                                                                 73

( 2 ) INFORMATION FOR SEQ ID NO:81:

( i ) SEQUENCE CHARACTERISTICS:
          ( A ) LENGTH: 49 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:81:

AAAATGGGCG TGGATTGTTA ACTTTATATA ACTTATTTTT TGAATATAC                          49

( 2 ) INFORMATION FOR SEQ ID NO:82:

( i ) SEQUENCE CHARACTERISTICS:

(A) LENGTH: 67 base pairs
(B) TYPE: nucleic acid
(C) STRANDEDNESS: single
(D) TOPOLOGY: linear (xi) SEQUENCE DESCRIPTION: SEQ ID NO:82:

ACACGAATGA TTTCTAAAG TATTTGGAAA GTTTATAGG TAGTTGATAG AACAAAATAC 60

ATAATTT 67

(2) INFORMATION FOR SEQ ID NO:83:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:83:

TGTGCTTACT AAAAGATTTC ATAAACCTTT CAAAATATCC ATCAACTATC T 51

(2) INFORMATION FOR SEQ ID NO:84:

(i) SEQUENCE CHARACTERISTICS:
(A) LENGTH: 46 base pairs
(B) TYPE: nucleic acid
(C) STRANDEDNESS: single
(D) TOPOLOGY: linear (xi) SEQUENCE DESCRIPTION: SEQ ID NO:84:

TGTAAAAATA AATCACTTTT TATACTAAGA TCTCCCGGGC TGCAGC 46

(2) INFORMATION FOR SEQ ID NO:85:

(i) SEQUENCE CHARACTERISTICS:
(A) LENGTH: 66 base pairs
(B) TYPE: nucleic acid
(C) STRANDEDNESS: single
(D) TOPOLOGY: linear (xi) SEQUENCE DESCRIPTION: SEQ ID NO:85:

TGTTTTATGT ATTAAAACAT TTTATTTAG TGAAAAATAT GATTCTAGAG GGCCCGACGT 60

CGCCGG 66

(2) INFORMATION FOR SEQ ID NO:86:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:86:

TTTCTGTATA TTTGCACCAA TTTAGATCTT ACTCAAAATA TGTAACAATA 50

(2) INFORMATION FOR SEQ ID NO:87:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:87:

TGTCATTTAA CACTATACTC ATATTAATAA AAATAATATT TATT 44

(2) INFORMATION FOR SEQ ID NO:88:

( i ) SEQUENCE CHARACTERISTICS:
  ( A ) LENGTH: 72 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:88:

GATCCTGAGT ACTTTGTAAT ATAATGATAT ATATTTCAC TTTATCTCAT TTGAGAATAA  60

AAAGATCTTA GG  72

( 2 ) INFORMATION FOR SEQ ID NO:89:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:89:

GACTCATGAA ACATTATATT ACTATATATA AAAGTGAAAT AGAGTAAACT CTTATTTTC  60

TAGAATCCTT AA  72

( 2 ) INFORMATION FOR SEQ ID NO:90:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:90:

GATCCAGATC TCCCGGGAAA AAAATTATTT AACTTTCAT TAATAGGGAT TTGACGTATG  60

TAGCGTACTA GG  72

( 2 ) INFORMATION FOR SEQ ID NO:91:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:91:

GTCTAGAGGG CCCTTTTTTT AATAAATTGA AAAGTAATTA TCCCTAAACT GCATACTACG  60

CATGATCCTT AA  72

( 2 ) INFORMATION FOR SEQ ID NO:92:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:92:

GTCTCAGAAC GTGTTCATGT  20

( 2 ) INFORMATION FOR SEQ ID NO:93:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear (x i) SEQUENCE DESCRIPTION: SEQ ID NO:93:

CACGGATCCA TGAAGTCATA TATTTCCTT　　　　　　　　　　　　　　　　　　　　　　　29

(2) INFORMATION FOR SEQ ID NO:94:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (x i) SEQUENCE DESCRIPTION: SEQ ID NO:94:

GTGAAGCTTA ATCCATAATC TTCAATAATT　　　　　　　　　　　　　　　　　　　　　　　30

(2) INFORMATION FOR SEQ ID NO:95:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (x i) SEQUENCE DESCRIPTION: SEQ ID NO:95:

GTGAAGCTTT TATACATAAC AGAAATAACA　　　　　　　　　　　　　　　　　　　　　　　30

(2) INFORMATION FOR SEQ ID NO:96:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:96:

CACGGATCCA TGATGAACAT GAAAATTGTT TTATTC　　　　　　　　　　　　　　　　　　　36

(2) INFORMATION FOR SEQ ID NO:97:

(i) SEQUENCE CHARACTERISTICS:
  (A) LENGTH: 33 base pairs
  (B) TYPE: nucleic acid
  (C) STRANDEDNESS: single
  (D) TOPOLOGY: linear (x i) SEQUENCE DESCRIPTION: SEQ ID NO:97:

GTGCTCGAGT TATTTGATT CTTCAGTTGT CAA　　　　　　　　　　　　　　　　　　　　33

(2) INFORMATION FOR SEQ ID NO:98:

(i) SEQUENCE CHARACTERISTICS:
  (A) LENGTH: 35 base pairs
  (B) TYPE: nucleic acid
  (C) STRANDEDNESS: single
  (D) TOPOLOGY: linear (x i) SEQUENCE DESCRIPTION: SEQ ID NO:98:

GTGCTCGAGG TTTAATTATT TTGATTCTTC AGTTG　　　　　　　　　　　　　　　　　　　35

(2) INFORMATION FOR SEQ ID NO:99:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (x i) SEQUENCE DESCRIPTION: SEQ ID NO:99:

CCAGGAGGTA TGCCCGGAGC AGG	23

( 2 ) INFORMATION FOR SEQ ID NO:100:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:100:

TAATCATGAG AAAATTATAC TGCG	24

( 2 ) INFORMATION FOR SEQ ID NO:101:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:101:

Met Arg Lys Leu Cys Val
1               5

( 2 ) INFORMATION FOR SEQ ID NO:102:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:102:

TGAGGATCCA TAAAAATTAA TAGTATGGTT TTTCCATC	38

( 2 ) INFORMATION FOR SEQ ID NO:103:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:103:

TAGAATCTGC AGGAACTTCA A	21

( 2 ) INFORMATION FOR SEQ ID NO:104:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:104:

CTACACGAGC TCCCGGGCTC GAGATAAAAA TTATACATAA CAGAAATAAC ATTC	54

( 2 ) INFORMATION FOR SEQ ID NO:105:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:105:

CTAGAGAAGC TTCCCGGGAT CCTCAAAATT GAAAATATAT AATTACAATA TAAAATGAAG  60

TCATATATTT CCTTGT  76

( 2 ) INFORMATION FOR SEQ ID NO:106:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

ACTTCCGGGT TGACTTGCT  19

( 2 ) INFORMATION FOR SEQ ID NO:107:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

GGCTATCCAT CAAATGGTAC AACTGGTGAA CAAGAAAGTC TTCCTGCTAA TGGACCTGAT  60

TCCCC  65

( 2 ) INFORMATION FOR SEQ ID NO:108:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

TAGTATACTA GTAAATGGGG T  21

( 2 ) INFORMATION FOR SEQ ID NO:109:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

GCATTAGAAT CTGCAGGAAC  20

( 2 ) INFORMATION FOR SEQ ID NO:110:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

TTGTCAGTAC TGCAGGAGCT CTACATAACA GAAATAACAT TCG  43

( 2 ) INFORMATION FOR SEQ ID NO:111:

( i ) SEQUENCE CHARACTERISTICS:
        ( A ) LENGTH: 26 base pairs
        ( B ) TYPE: nucleic acid -continued ( C ) STRANDEDNESS: single
( D ) TOPOLOGY: linear ( x i ) SEQUENCE DESCRIPTION: SEQ ID NO:111:

TAATCATGAA TAAACTTTAC AGTTTG 26

( 2 ) INFORMATION FOR SEQ ID NO:112:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( x i ) SEQUENCE DESCRIPTION: SEQ ID NO:112:

GGATCCTCGA GCTGCAGATC TATAAAATT ACATTATAAA AAAGCATAC 49

( 2 ) INFORMATION FOR SEQ ID NO:113:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:113:

TAATCATGAA TATTCGAAAG TTC 23

( 2 ) INFORMATION FOR SEQ ID NO:114:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:114:

GCGAATTCAT AAAAATTAAG AATCATCTCC TTC 33

( 2 ) INFORMATION FOR SEQ ID NO:115:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:115:

GAAAGCTTCT TTATTCTATA C 21

( 2 ) INFORMATION FOR SEQ ID NO:116:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:116:

CCTCAACAAA TAGGAAGGAA G 21

( 2 ) INFORMATION FOR SEQ ID NO:117:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( x i ) SEQUENCE DESCRIPTION: SEQ ID NO:117:

GATTATCGCG ATATCCGTTA AGTTTGTATC GTAATGCAGG AATACCAGTG CTATGGAAGT    60

TCGTCAAAC    69

( 2 ) INFORMATION FOR SEQ ID NO:118:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

GTTTGACGAA CTTCCATAGC ACTGGTATTC CTGCATTACG ATACAAACTT AACGGATATC    60

GCGATAATC    69

( 2 ) INFORMATION FOR SEQ ID NO:119:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:119:

AAAGAATATG ATCTTCATTA CGATACAAAC TTAACGGATA TCCCTATAGT GAGTCGTA    58

( 2 ) INFORMATION FOR SEQ ID NO:120:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

GTGTATTTAT AATAAAGAAA AGAAATGAAC ATAGAAAGAA TATGATC    47

( 2 ) INFORMATION FOR SEQ ID NO:121:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

GTTCCTCTAA CTTCTTAGGA ATATCATTCT TATTAATACT CATGTTAATA TTATACAGTT    60

TCATTTAATT TTTATC    76

( 2 ) INFORMATION FOR SEQ ID NO:122:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:122:

TCGAGATAAA AATTAAATGA AACTGTATAA TATTAACATG AGTATTAATA AGAATGATAT    60

TCCTAAGAAG TTAGAGGAAC TGCA    84

( 2 ) INFORMATION FOR SEQ ID NO:123:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:123:

CTAGGTCGAC TCCGTCCATG GATTAC 26

( 2 ) INFORMATION FOR SEQ ID NO:124:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:124:

GATATCCTTA AGTCTTATTA ATATGAAACA TATTTGTAC ATATCATTTT ACTTTATCCT 60

TGTTAATTTA TTGATATTTC ATATAAATGG AAAGATAATA AAGAATTCTG ACAG 114

( 2 ) INFORMATION FOR SEQ ID NO:125:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:125:

CTGTCAGAAT TCTTTATTAT CTTTCCATTT ATATGAAATA TCAATAAATT AACAAGGATA 60

AAGTAAAATG ATATGTACAA AATATGTTTC ATATTAATAA GACTTAAGGA TATC 114

( 2 ) INFORMATION FOR SEQ ID NO:126:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

GCACGAGAAG AAACACG 17

( 2 ) INFORMATION FOR SEQ ID NO:127:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

CGTTATATCT CAAGATCTTC TTGTCTG 27

( 2 ) INFORMATION FOR SEQ ID NO:128:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

CCTTAAAGAA AATAAATTAA ATAAGGAAGG GAAATTAATT GAACAC 46

( 2 ) INFORMATION FOR SEQ ID NO:129:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

```
TTATGTATAT CCCTTCGTCC                                                  20
```

( 2 ) INFORMATION FOR SEQ ID NO:130:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

```
AGAGATTCCA AGGAAATATC TATAATAGAA AAACAAATA GAGAATCTAT TACAACAAAT      60

GTTGAAGGAC G                                                          71
```

( 2 ) INFORMATION FOR SEQ ID NO:131:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

```
TGTGAGCGGA TAACAATT                                                   18
```

( 2 ) INFORMATION FOR SEQ ID NO:132:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

```
GATAAGGTAC CATAAAAATT ATAGTTTCAT AAAATATTTA G                         41
```

( 2 ) INFORMATION FOR SEQ ID NO:133:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

```
GTAAAACGAC GGCCAGT                                                    17
```

( 2 ) INFORMATION FOR SEQ ID NO:134:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

```
GATAAGGTAC CATAAAAATT ATAGTTTCAT AAAATATTTA G                         41
```

( 2 ) INFORMATION FOR SEQ ID NO:135:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

```
AACTGGCCTC GAAGCTG                                                              17
```

( 2 ) INFORMATION FOR SEQ ID NO:136:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

```
GTGTTAAAGG GTTAGTCCTT GGTTCCAGCT GACG                                           34
```

( 2 ) INFORMATION FOR SEQ ID NO:137:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

```
CAATCAGGAA CCAAGGCAAT ATCTGTCACA                                                30
```

( 2 ) INFORMATION FOR SEQ ID NO:138:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

```
CAAGTAATTT TTATC                                                                15
```

( 2 ) INFORMATION FOR SEQ ID NO:139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

```
TCGAGATAAA AATTA                                                                15
```

( 2 ) INFORMATION FOR SEQ ID NO:140:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

```
TATGGGATCC TCAAAATTGA AAATATATAA TTACAATATA AATGAAGAT CATATTCTTT                60
CTATGTTC                                                                        68
```

( 2 ) INFORMATION FOR SEQ ID NO:141:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:141:

TGTGGGATCC TCGAGATAAA AATTAAATGA AACTGTA         37

( 2 ) INFORMATION FOR SEQ ID NO:142:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( v ) FRAGMENT TYPE: internal ( x i ) SEQUENCE DESCRIPTION: SEQ ID NO:142:

```
Glu Gln Gln Ser Asp Leu Glu Gln Glu Arg Leu Ala Lys Glu Lys Leu
1               5                   10                  15
Gln
```

( 2 ) INFORMATION FOR SEQ ID NO:143:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( v ) FRAGMENT TYPE: internal ( x i ) SEQUENCE DESCRIPTION: SEQ ID NO:143:

```
Glu Gln Gln Ser Asp Leu Glu Arg Thr Lys Ala Ser Lys Glu Thr Leu
1               5                   10                  15
Gln
```

MALARIA RECOMBINANT POXVIRUSES

CROSS-REFERENCE TO RELATED APPLICATIONS

This application is a continuation-in-part of application Ser. No. 08/075,783, filed Jun. 11, 1993, abandoned, which in turn is a continuation-in-part of application Ser. No. 07/852,305, filed Mar. 18, 1992, abandoned, which in turn is a continuation-in-part of application Ser. No. 07/672,183, filed Mar. 20, 1991, abandoned, incorporated herein by reference. Application Ser. No. 08/075,783 is also a continuation-in-part of application Ser. No. 07/847,951, filed Mar. 6, 1992, abandoned, 07/724,109, filed Jul. 1, 1991, abandoned, and 07/847,977, filed Mar. 3, 1992, abandoned. Reference is also made to application Ser. No. 08/105,483, U.S. Pat. No. 5,494,807, filed Aug. 12, 1993 as a continuation of application Ser. No. 07/847,951, filed Mar. 6, 1992, entitled "Genetically Engineered Vaccine Strain", abandoned, application Ser. No. 08/178,476, filed Jan. 7, 1994, as a continuation of application Ser. No. 07/724,109 filed Jul. 1, 1991, abandoned, and application Ser. No. 08/036,217, U.S. Pat. No. 5,364,773 filed Mar. 24, 1993 as a continuation of application Ser. No. 07/666,056, filed Mar. 7, 1991, abandoned, each of which is also incorporated herein by reference, and this application is also a continuation-in-part of each of those applications. In addition, reference is also made to copending application Ser. No. 08/102,702, U.S. Pat. No. 5,453,364 filed Aug. 5, 1993 as a continuation of application Ser. No. 07/847,977, filed Mar. 3, 1992, abandoned and this application is additionally a continuation-in-part thereof.

FIELD OF THE INVENTION

The present invention relates to a modified poxvirus and to methods of making and using the same. More in particular, the invention relates to recombinant poxvirus, which virus expresses gene products of a Plasmodium gene, and to vaccines which provide protective immunity against Plasmodium infections.

Several publications are referenced in this application within parentheses. Full citation to these references is found at the end of the specification immediately preceding the claims. These references relate to the field to which this invention pertains; and, each of these references are hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. Nos. 5,110,587, 4,769,330, 4,772,848 and 4,603,112, the disclosures of which are hereby incorporated herein by reference. In this regard reference is also made to U.S. Pat. No. 5,174,993, also incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell and Helinski, 1969; Sambrook et al., 1989).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipoxvirus, fowlpox, has been engineered as a recombinant virus expressing the rabies G gene (Taylor et al., 1988a; Taylor et al., 1988b). This recombinant virus is also described in PCT Publication No. WO 89/03429. On inoculation of the recombinant into a number of non-avian species an immune response to rabies is elicited which in mice, cats and dogs is protective against a lethal rabies challenge.

Immunization with vaccinia can induce very rare complications involving the skin or central nervous system. The frequency of the more serious CNS complications appeared to correlate with the vaccinia strain used for immunization during the smallpox irradication program. A great deal of work has recently been applied to develop attenuated vaccinia vaccine strains. Laboratory studies have demonstrated that the deletion of certain vaccinia genes reduces the virulence of resulting recombinants in animal models (Buller et al., 1985; Buller et al., 1988; Child et al., 1990; Flexner et al., 1987; Shida et al., 1988; Kotwal et al., 1989). Thus, a highly attenuated strain of vaccinia virus that retains the capacity to induce strong immune responses, is desired for use as a human vaccine vector (Tartaglia et al., 1992).

Malaria today still remains one of the world's major health problems. It is estimated that 200–300 million malaria cases occur annually while 1–2 million people, mostly children, die of malaria each year. Malaria in humans is caused by one of four species of the genus Plasmodium—*P. falciparum, P. vivax, P. malariae,* and *P. ovale*. Clinically, *P. falciparum* is the most important human Plasmodium parasite because this species is responsible for most malaria fatalities.

Plasmodium infections begin when sporozoites are injected into the bloodstream by the bite of an infected female Anopheles mosquito. The liver stage of infection begins when the sporozoites disappear from the blood stream and invade hepatocytes. Over a 5–7 day period, merozoites develop asexually within the infected liver cells and are subsequently released into the blood stream where they invade erythrocytes, initiating the blood stage of infection. Parasites in infected erythrocytes develop asexually through ring, trophozoite, and schizont stages. The rupture of schizonts releases merozoites which can then infect more red blood cells. This self-perpetuating cycle of blood stage infection causes the clinical symptoms of malaria.

Some merozoites that infect red blood cells differentiate into male and female gametocytes. These gametocytes, which allow sexual reproduction, are subsequently ingested by Anopheles mosquitoes during a blood meal. After ingestion, gametes emerge from the gametocytes in the mosquito midgut, the female gamete is fertilized by the male gamete, and the resultant zygotes invade the gut wall where they undergo asexual division and eventually produce sporozoites which lodge in the mosquito salivary gland. The transmission cycle is completed when the infected mosquito takes other blood meals and injects the sporozoites into the human blood stream.

Immunity to Plasmodium does develop naturally although repeated infections over many years are required. This may be a result of the antigenic diversity exhibited by some Plasmodium proteins among different parasite isolates. As a consequence, previously infected "semi-immune" adults rarely display clinical symptoms while children under the age of 5 are most susceptible to severe clinical disease. The developed immunity is not long lasting and will decline without reinfection. Immunity to Plasmodium is also species and stage specific, i.e. one may be immune to *P. falciparum* but not *P. vivax* and immunity to sporozoites will not protect against merozoites.

Malaria control measures have so far relied on drug treatment to control and prevent infections and pesticide use to control mosquito populations. The development of an effective malaria vaccine has become imperative due to the emergence and spread of drug resistant parasites in recent years. Most current efforts at developing a malaria vaccine are targeted to three stages in the parasite life cycle—the infection of liver cells by sporozoites, the perpetuation of the blood stage by merozoites, and the transmission to mosquitos by gametocytes. In most cases, purified parasite proteins have been utilized as subunit vaccines with variable and generally disappointing results.

It is evident that to successfully immunize humans against *P. falciparum*-induced malaria, a vaccine must be derived that stimulates a more effective level of immunity than occurs with a single natural infection.

The complex life cycle of *P. falciparum* provides four targets for vaccine intervention to prevent the development and spread of malaria—the sporozoite, the liver stage, the blood stage, and the sexual stage (Miller et al., 1986). Vaccine-induced immunity to sporozoites could prevent the infection of hepatocytes, which would prevent the further development of disease. However, protection against sporozoites and not other parasite stages would require a sterile immunity because liver infection by even a few sporozoites might be sufficient to bypass the induced anti-sporozoite immunity and begin the infectious cycle, thus causing disease. Immunity to the liver stage could prevent blood stage infection by eliminating parasitized hepatocytes before the release of merozoites. Also, because many antigens are expressed during both the liver and blood stages, immunity which was directed against the liver stage might also act on blood stage parasites. Likewise, immunity induced to blood stage antigens could act to prevent or reduce completion of exoerythrocytic development. Intervention at the blood stage might also hinder parasite transmission to mosquitoes by reducing or preventing the formation of gametocytes. Finally, immunity to sexual stage antigens could function to prevent transmission of parasites to, or their development within, mosquitoes. Most current malaria vaccination strategies have focused on the production of subunit vaccines based on individual proteins or synthetic peptides representing specific epitopes of such proteins. Such vaccines may be ineffective due to the variability of particular parasite antigens and/or to genetic nonresponsiveness of vaccinees to the particular vaccinating antigen. The few multicomponent vaccine candidates thus far developed also consist of proteins (or portions of proteins) derived from only a single stage. However, the simultaneous induction of immunity to each of these stages may achieve a more effective level of protection than can be attained by immunizing against one antigen or one stage and any nonresponsiveness to one component may be offset by responses to other components.

SERA, the serine repeat antigen, is a *Plasmodium falciparum* protein expressed during the blood and liver stages of infection (Szarfman et al., 1988). In the blood stage, SERA is found in the parasitophorous vacuole and surrounding membranes of trophozoites and schizonts (Chulay et al., 1987; Coppel et al., 1988; Delplace et al., 1987; Knapp et al., 1989). The SERA precursor protein has a molecular weight of 126 kD [also described as 140 kD (Perrin et al., 1984), 113 kD (Chulay et al., 1987), and 105 kD (Banyal and Inselburg, 1985)] and is processed at the time of schizont rupture into 50, 47, and 18 kD fragments (Delplace et al., 1987; Delplace et al., 1988). The 47 and 18 kD fragments are associated by disulfide bonds to form a 73 kD complex.

Complete SERA genes have been obtained from genomic DNA of the FCR3 and FCBR strains and complete or partial cDNA clones obtained from 5 strains (Bzik et al., 1988; Coppel et al., 1988; Horii et al., 1988; Knapp et al., 1989; Li et al., 1989; Weber et al., 1987). The SERA gene is encoded in four exons separated by three intervening sequences (Knapp et al., 1989; Li et al., 1989). The coding sequence is characterized by two repeat structures; one a series of glycine-rich octamers near the initiation codon and the second a polyserine repeat from which the protein derives its name. The predicted amino acid sequence does not contain a hydrophobic transmembrane region. SERA mRNA is 3.6–4.1 Kb long and appears to be quite abundant in late trophozoites and schizonts (Bzik et al., 1988; Knapp et al., 1989).

Although the data are limited, it appears that SERA is well conserved among strains of *P. falciparum*. Comparison of the various genomic and cDNA clones indicates that the majority of the SERA coding sequence is invariant in the strains studied. Most nucleotide differences among these strains occur within or around the polyserine repeat and also within the octapeptide repeats (Bzik et al., 1988; Horii et al., 1988; Knapp et al., 1989; Li et al., 1989). The genomic organization of SERA is conserved in 12 strains as studied by Southern analysis (Coppel et al., 1988; Horii et al., 1988; Knapp et al., 1989). Immunoprecipitation analysis of ten geographically diverse *P. falciparum* isolates indicated that the sizes of SERA and its processed fragments are well conserved. Some variation was observed with the 47 kD fragment, which varied in size from 47–50 kD (Bhatia et al., 1987). This fragment contains the polyserine repeats. Thus, the size variation in the 47 kD fragment is probably due to differences in the polyserine repeats, perhaps different numbers of serine residues.

Interestingly, two SERA alleles have been described in the FCR3 strain—allele I and allele II—whose differences primarily occur within both repeat regions (Li et al., 1989). Southern analysis indicates that the Honduras I strain contains a SERA gene corresponding only to FCR3 allele I (Li et al., 1989) whereas the nucleotide sequence of the SERA gene from the FCBR strain is identical to FCR3 allele II (Knapp et al., 1989; Li et al., 1989).

The functional role of SERA during the parasite life cycle is not known. Recently, homology searches of protein databases have revealed that SERA has significant similarity at and around two active sites found in cysteine proteinases and may therefore be a cysteine proteinase (Higgins et al., 1989). However, it has since been pointed out that although SERA has a cysteine proteinase conformation, it may actually be a serine proteinase due to the presence of a serine at the putative catalytic site (Eakin et al., 1989; Mottram et al., 1989). Although this has yet to be confirmed experimentally, it may indicate an important role for SERA in the parasite life cycle because it is known that proteases are necessary for the cleavage of some proteins during the blood stage and also that protease inhibitors interrupt the development of the parasite (Debrabant and Delplace, 1989).

ABRA, the acidic basic repeat antigen, is also expressed during both the blood and liver stages of *P. falciparum* infection (Szarfman et al., 1988). In infected erythrocytes, ABRA is expressed during the late trophozoite and schizont stages and is found in the parasitophorous vacuole (Chulay et al., 1987; Stahl et al., 1986). ABRA has a molecular weight of 100–102 kD and is released from rupturing schizonts (Chulay et al., 1987; Stahl et al., 1986; Weber et al., 1988).

A complete genomic ABRA gene from the CAMP strain and partial ABRA cDNAs from the FCR3 and FC27 strains have been obtained (Stahl et al., 1986; Weber et al., 1988). The ABRA coding sequence does not contain introns and is characterized by two repeat structures. The first consists of eight hexapeptide repeats near the center of the coding sequence and the second consists of a series of tandem dipeptide and tripeptide repeats, mostly of the amino acid sequences KE and KEE (Stahl et al., 1986; Weber et al., 1988).

Based on limited data, ABRA appears to be well conserved among *P. falciparum* strains. The partial cDNA clones from the FCR3 and FC27 strains are almost identical to the CAMP strain genomic ABRA gene. The FCR3 clone differs at four positions and the FC27 clone contains some rearrangements within the carboxy-terminal repeat region as compared to the CAMP ABRA gene (Stahl et al., 1986; Weber et al., 1988). The general genomic organization of ABRA as detected by Southern analysis is conserved in six *P. falciparum* isolates (Stahl et al., 1986). Additionally, immunoprecipitation analysis indicates that the size of ABRA from seven geographically diverse isolates is conserved (Chulay et al., 1987; Stahl et al., 1986).

Pfhsp70 is a *Plasmodium falciparum* protein that shares significant similarity with members of the mammalian 70 kD heat shock protein family (Ardeshir et al., 1987; Bianco et al., 1986; Newport et al., 1988). Pfhsp70 is expressed during the liver (Renia et al., 1990) and throughout the blood stages of infection (Ardeshir et al., 1987; Bianco et al., 1986), but not by sporozoites (Bianco et al., 1986; Renia et al., 1990). Experiments with *P. falciparum*-infected human hepatocyte cultures suggest that Pfhsp70 is expressed on the hepatocyte surface during the liver stage (Renia et al., 1990). The localization of Pfhsp70 during the blood stage remains controversial, with exclusively cytoplasmic and merozoite surface locations both reported (Ardeshir et al., 1987; Bianco et al., 1986). Pfhsp70 has a molecular weight of 75 kD (Ardeshir et al., 1987; Bianco et al., 1986; Kumar et al., 1988a), although a molecular weight of 72 kD has also been reported (Dubois et al., 1984; Jendoubi and Pereira da Silva, 1987).

A complete genomic Pfhsp70 gene from the FCR3 strain and partial Pfhsp70 cDNAs from the FC27, Honduras 1, and 7G8 strains have been obtained (Ardeshir et al., 1987; Bianco et al., 1986; Kumar et al., 1988a; Yang et al., 1987). The partial cDNAs encode approximately 40% of the carboxy-terminal coding sequence and each initiates at the same nucleotide relative to the complete gene (Ardeshir et al., 1987; Bianco et al., 1986; Kumar et al., 1988a). The carboxy-terminal portion of the coding sequence is characterized by a series of 7–8 tandem repeats, mostly of sequence GGMP (Ardeshir et al., 1987; Bianco et al., 1986; Kumar et al., 1988a; Yang et al., 1987). Pfhsp70 mRNA is 2.8 Kb in size (Kumar et al., 1988a).

Based on limited data, Pfhsp70 appears to be well conserved among *P. falciparum* strains and isolates. The partial cDNAs from the FC27 and Honduras 1 strains are identical in the coding region and differ from the 7G8 partial cDNA at only a few nucleotides. The FCR3 genomic gene is very similar to the cDNAs in its carboxy-terminus, with the only differences being the presence of an additional GGMP repeat and a few nucleotide substitutions. The general genomic organization of the carboxy-terminal region of Pfhsp70 as detected by Southern analysis is conserved in 14 *P. falciparum* strains (Ardeshir et al., 1987; Kumar et al., 1990). Also, immunoprecipitation analysis indicates that the size of Pfhsp70 from 20 geographically diverse isolates is conserved (Ardeshir et al., 1987; Jendoubi and Pereira da Silva, 1987). Some variation of tryptic peptide maps among three strains has been detected, however (Jendoubi and Pereira da Silva, 1987).

The function of Pfhsp70 in the parasite life cycle is not known. However, the induction of Pfhsp70 expression at the two-nuclei stage after sporozoite infection of liver cells has led to the suggestion that this heat shock-like protein may play a role in parasite differentiation (Renia et al., 1990).

AMA-1 is a late-stage schizont protein originally isolated from *Plasmodium knowlesi* infected erythrocytes as a 66 kD protein (PK66). PK66 is processed to 44/42 kD components at the time of merozoite release and these maturation products are associated with the merozoite surface. When isolated in native form, PK66 induced inhibitory antibodies and protected rhesus monkeys against a blood-stage challenge (Deans et al., 1988). The *Plasmodium falciparum* equivalent of PK66 has been isolated by using human antimalarial antibodies (Peterson et al., 1988) or rabbit anti-PK66 polyclonal serum (Thomas et al., 1990), and has also been called PF83.

In *Plasmodium knowlesi*, AMA-1 is synthesized late in schizogony and is distributed at the apex of the merozoites developing within the segmenting schizont. At schizont rupture, AMA-1 is processed to a 44/42 kD doublet (Waters et al., 1990). During the invasion of erythrocytes, the 44/42 kD doublet is not carried into the erythrocytes, but remains associated with the invasion interface.

In *Plasmodium falciparum*, AMA-1 is located at the apex of the segmented schizont, although a merozoite surface localization cannot be excluded (Peterson et al., 1988). AMA-1 is probably first located in the apical complex and then exported to the merozoite surface. During erythrocyte invasion, AMA-1 is lost: it cannot be found in the newly infected erythrocyte.

AMA-1 is highly conserved among different isolates of *Plasmodium falciparum*: Camp, FCR3, 7G8 Thai TN, FC27 (Thomas et al., 1990). The AMA-1 gene is 1863 bp long, no introns have been reported, and it codes for a 623 amino acid protein (Peterson et al., 1989) without repetitive sequences. This protein has a structure expected for an integral membrane protein: it contains two hydrophobic stretches, one near the N-terminus which may act a signal peptide, and a second located 55 amino acids from the C-terminus (Peterson et al., 1989; Thomas et al., 1990).

AMA-1 is considered a strong vaccine candidate because of it's genetic conservation, surface location on the merozoite, and possible role in erythrocyte invasion as well as studies with the analogous protein from *P. knowlesi*, Pk66. Immunization of rhesus monkeys with purified Pk66 induces protection against blood stage challenge (Deans et al., 1988). Additionally, serum from protected monkeys inhibits parasite invasion in vitro (Deans et al., 1988).

Pfs25 is a *P. falciparum* protein expressed during the sexual stages of parasite development. This 25 kD membrane protein is localized on the surface of zygotes and ookinetes (Vermeulen et al., 1985) and as a consequence is probably only expressed in the mosquito midgut and not in the human host (Carter et al., 1988; Kaslow et al., 1989).

The Pfs25 gene from the 3D7 clone of *P. falciparum* strain NF54 consists of an uninterrupted open reading frame of 654 bp encoding a protein with a predicted molecular weight of 24.1 kD (Kaslow et al., 1988). The predicted amino acid sequence includes a hydrophobic signal peptide at the N-terminus and a short hydrophobic anchor sequence at the C-terminus, consistent with the surface localization of Pfs25. In addition to four potential N-glycosylation sites, the Pfs25 coding sequence contains an organization of predicted cysteine residues that suggests the presence of four tandemly repeated EGF-like domains (Kaslow et al., 1988). Pfs25 is very highly conserved, with only one single-base substitution detected among 8 geographically diverse isolates (Kaslow et al., 1989).

Antibodies to Pfs25 have not been detected in humans from endemic areas, probably because this protein is not expressed in the human host (Carter et al., 1988). Immunizations of H-2 congenic mouse strains generated anti-Pfs25 antibodies in all strains tested, indicating that this protein is a good immunogen (Good et al., 1988).

Pfs25 is considered a potential vaccine candidate based on the ability of anti-Pfs25 mAbs to block transmission of the parasite from the vertebrate host to mosquitoes (Kaslow et al., 1989). Immunization of mice with a vaccinia recombinant producing surface-expressed Pfs25 also generates transmission blocking antibodies after three inoculations and the generation of such antibodies by vaccinia recombinants is not restricted to particular MHC haplotypes (Kaslow et al., 1991).

Pfs16 is a *P. falciparum* protein expressed by the sporozoite as well as the sexual stages of the parasite developmental cycle. This 16 kD protein is found on the membrane of intracellular gametocytes and possibly the parasitophorous vacuole membrane, on the outer membrane of extracellular macrogametes, and on the surface of sporozoites (Moelans et al., 1991a). The Pfs16 gene is 544 bp in length and the coding sequence is characterized by a putative N-terminal signal sequence, a hydrophobic anchor sequence, and a highly hydrophilic C-terminus.

Pfs16 is highly conserved among *P. falciparum* isolates. Of eight strains studied, variation was only found in two isolates which contained two and three amino acid substitutions, respectively (Moelans et al., 1991b).

Pfs16 is considered as a vaccine candidate for several reasons. First, the expression of Pfs16 by both sporozoites and sexual stages make this protein attractive for inclusion in a multi-stage vaccine because immunity to it may protect against infection by sporozoites and transmission by sexual stages. Of note is that in preliminary studies with four Pfs16-specific mAbs, no in vitro inhibition of sporozoite invasion was detected (Targett, 1990). Second, sera from adults living in highly endemic regions has been shown to recognize the Pfs16 protein, indicating that it is immunogenic in humans (Moelans et al., 1991a). Third, polyvalent rabbit sera raised against gametes and gametocytes recognizes Pfs16 and has high transmission blocking activity. Preliminary studies with two Pfs16-specific mAbs indicate that one of the antibodies has transmission blocking activity (Moelans et al., 1991a).

The *P. falciparum* circumsporozoite (CS) protein ("CSP") is a 60 kD membrane protein that is uniformly distributed over the sporozoite surface (Nussenzweig et al., 1984). CS is not expressed at any other stage of the parasite life cycle.

The CS gene consists of an uninterrupted open reading frame of approximately 1200 bp. CS is characterized by a central region consisting of the repeated sequence NANP with a few variant NVDP repeats, flanked by nonrepetitive regions that contain charged residues (Dame et al., 1984). The repetitive NANP sequences are conserved, although the number of repeats can vary among different isolates. Variation in non-repetitive regions is seen near the amino-terminus due to insertions or deletions, while the carboxy-terminal domain contains only base pair substitutions (Caspers et al., 1989). Of the 412 amino acids of CS, only thirteen positions segregated in three distinct polymorphic regions are known to be variant (Caspers et al., 1989). Three regions found in the non-repetitive domains are relatively well conserved among species of Plasmodia, region I in the N-terminal domain and regions II and III in the C-terminal domain (Lockyer and Holder, 1989).

Both humoral and cell-mediated immune responses to CS appear to play a role in the induction of anti-sporozoite immunity. In terms of humoral responses, it has been shown that naturally protected humans contain antibodies to the CS protein and these antibodies increase with age and parallel acquired immunity (Nussenzweig and Nussenzweig, 1989). However, CS and sporozoite-specific antibody levels in naturally infected adults do not correlate with protection from further infection (Hoffman et al., 1987), suggesting that other factors such as cell mediated immunity may be important in natural immunity. However, several studies have shown that humans can be protected by immunization with irradiated sporozoites (Clyde, 1975; Rieckmann, 1974) and that protection was correlated with antibodies against the CS protein (Nussenzweig et al., 1985). Human vaccine trials with CS-based peptide subunits have demonstrated the ability of such constructs to induce CS-specific antibody responses and to completely protect some vaccinees (Herrington et al., 1987; Ballou et al., 1987).

Cell mediated responses to the CS protein have also been studied. Several T cell epitopes have been identified in the P. falciparum CS protein in man (Good et al., 1987). Interestingly, most human T cell epitopes occur in polymorphic regions of CS suggesting that parasite mutations and selection have occurred in response to immune pressure from T cells. However, one human T helper epitope, CS.T3, is located in a conserved region of the CS protein and is recognized by human T cells in association with many different human MHC class II molecules (Sinigagla et al., 1988). Also, sporozoites are able to induce cytotoxic T cells specific for a CD8$^+$ CTL epitope on the CS protein (Kumar et al., 1988b), suggesting that such cells may be important for the induction of immunity to P. falciparum.

The P. falciparum sporozoite surface protein 2 (PfSSP2) is a 90 Kd protein which is expressed on the surface of sporozoites and also within the sporozoite micronemes (Rogers et al., 1992). PfSSP2 is expressed by infected hepatocytes early after invasion by sporozoites (up to 48 hours) but not at later times (Rogers et al., 1992). PfSSP2 is identical to the previously described thrombospondin related anonymous protein (TRAP), which was characterized as a blood stage protein (Robson et al., 1988). Although devoid of repetitive amino acid sequences, PfSSP2 does contain a sequence with similarity to region II of CSP (Rogers et al., 1992; Robson et al., 1988).

Several lines of evidence suggest the importance of PfSSP2 in the induction of protective immunity to malaria. PfSSP2-specific antibodies have been demonstrated to inhibit sporozoite invasion and development in hepatocytes in vitro (Rogers et al., 1992). Also, humans immunized with irradiated sporozoites and protected from subsequent sporozoite challenge develop both antibody and T cell proliferative responses to PfSSP2. Recent challenge studies in the P. yoelii rodent malaria model system have provided provocative evidence for the role of SSP2 in protective immunity to sporozoites (Khusmith et al., 1991). Stable mastocytoma cell lines were derived by transformation with a fragment encoding 497 amino acids of P. yoelii SSP2. When mice were immunized with one of these cell lines and challenged with 200 P. yoelii sporozoites, ~50–60% of the mice were protected. Similar results were obtained when a cell line transfected with the P. yoelii CSP gene was used for immunization. However, when a combination of the two cell lines was used for immunization, 100% protection of the mice from challenge with sporozoites was achieved. Both humoral and CTL responses to SSP2 and CSP were induced and protection was dependent on CD8$^+$ T-cells (Khusmith et al., 1991). These results strongly support the evaluation of PfSSP2 for inclusion in a multicomponent vaccine against P. falciparum.

The P. falciparum liver stage specific antigen (LSA-1) is a 230 Kd acidic protein that has been localized as flocculent material within the parasitophorous vacuole of P. falciparum exoerythrocytic parasites (Guerin-Marchand et al., 1987; Hollindale et al., 1990). The LSA-1 gene from the NF54 strain consists of a 5,730 bp uninterrupted open reading frame. The gene contains a central repetitive region of 86 repeats flanked by non-repetitive regions containing putative T-cell epitopes (Zhu et al., 1991). The repeats consist of 17 amino acids, which are defined as major, EQQSDLEQERLAKEKLQ (84 copies) (SEQ ID NO:142), and minor EQQSDLERTKASKETLQ (2 copies) (SEQ ID NO:143). The gene contains a putative secretory signal but has no apparent hydrophobic anchor region, suggesting that it is secreted.

LSA-1 is under strong consideration as a vaccine candidate because it has recently been demonstrated that individuals who carry the HLA-B53 allele, which is associated with resistance to severe malaria, develop HLA-B53-restricted LSA-1-specific CTL responses (Hill et al., 1992). The CTL epitope has been localized to the C-terminal non-repetitive region of LSA-1 (Hill et al., 1992). Also, the analogous liver stage antigen from P. berghei, LSA-2, has been identified with cross-reactive antibodies raised against peptides derived from the repeats of P. falciparum LSA-1. Mice immunized with these peptides are protected against P. berghei sporozoite challenge (Hollingdale et al., 1990).

The merozoite surface antigen 1 (MSA-1) is expressed during both the blood and liver stages of P. falciparum infection (Holder, 1988; Szarfman et al., 1988). MSA-1 is the major antigen found on the surface of mature intracellular merozoites (Holder, 1988). The full length MSA-1 precursor protein has a molecular weight of 195 Kd, is glycosylated (Howard et al., 1984), and is attached to the merozoite membrane via a C-terminal phosphatidyl inositol linkage (Haldar et al., 1985). At about the time of schizont rupture, the MSA-1 precursor is proteolytically processed into major products of 83, 42, and 19 Kd that are associated with the surface of free merozoites (Lyon et al., 1987; Holder, 1988). When merozoites invade erythrocytes, only the 19 Kd fragment is carried into the cell (Holder, 1988; Blackman et al., 1990).

Complete MSA-1 genes have been isolated from several different P. falciparum isolates. MSA-1 is encoded by a long uninterrupted open reading frame. A repeat region is found near the 5' end of the coding sequence that consists of degenerate tandem tripeptides of sequence SXX, where X is any amino acid (Holder, 1988). Comparison of genes from different isolates indicate that there is strain variability of MSA-1. The coding sequence can be divided into 17 distinct blocks that exhibit varying degrees of similarity among different strains (Tanabe et al., 1987). Some blocks are highly conserved, some are semi-conserved, and some show little conservation. The variability observed among strains is not widely polymorphic but appears to be of two types. Thus, the polymorphism of MSA-1 can be considered as dimorphic, with an allele consisting of conserved blocks as well as variable blocks from one of the two allotypes (Tanabe et al., 1987). Two minor regions, including the tripeptide repeats, do not follow this dimorphic rule (Peterson et al., 1988).

Several studies have examined the immunological recognition of MSA-1 by individuals from malaria endemic areas. In terms of humoral responses, it appears that a majority of infected individuals produce antibodies to MSA-1 (Reese et al., 1981; Perrin et al., 1981; Perrin and Dayal, 1982; Holder and Freeman, 1982; Hall et al., 1984; Rzepczyk et al., 1989). Studies utilizing conserved and dimorphic fragments of MSA-1 from each of the two allotypes (represented by the K1 and MAD20 strains) suggest that although conserved regions are recognized by 50–60% of adults (Gentz et al., 1988; Sinigaglia et al., 1988b), the responses to dimorphic regions were very significant (some fragments were recognized by 85% of adults) and correlated with the frequency of the particular allotype in the local parasite population (Fruh et al., 1991). Thus, humans make antibodies directed against the antigenic variants of MSA-1 that are present during infection. Interestingly, adults generate antibody responses to some particular dimorphic regions more frequently than children (Fruh et al., 1991), indicating that the quality of the antibody response against MSA-1 evolves during repeated *P. falciparum* infections. Also, antibody responses against many regions of MSA-1 are short-lived, especially in children and infants (Muller et al., 1989; Fruh et al., 1991).

The recognition of MSA-1 by T-cells from immune individuals has been readily demonstrated (Sinigaglia et al., 1988b; Crisanti et al., 1988; Rzepczyk et al., 1989; Simitsek et al., 1990). Six different MSA-1 T-cell epitopes have thus far been identified by studies with human T-cell clones: four are located in close proximity within a conserved block (Sinigaglia et al., 1988b; Crisanti et al., 1988; Rzepczyk et al., 1989) and two are found in highly variable regions (Rzepczyk et al., 1989). Interestingly, lymphocytes from some non-immune individuals also respond to both constant and variable MSA-1 epitopes (Sinigaglia et al., 1988b; Rzepczyk et al., 1989; Simitsek et al., 1990). The recognition of two of the constant region epitopes in the context of particular human class II MHC molecules has been described (Crisanti et al., 1988).

Although its functional role in the parasite life cycle is not known, several lines of evidence suggest the importance of MSA-1 in the induction of protective immunity to *P. falciparum*. Most important, numerous studies have demonstrated that immunization with purified MSA-1 or subfragments of MSA-1 can completely or partially protect Aotus monkeys from challenge with blood stage parasites (Perrin et al., 1984; Hall et al., 1984; Cheung et al., 1986; Siddiqui et al., 1986; Siddiqui et al., 1987; Patarroyo et al., 1987a; Patarroyo et al., 1987b; Patarroyo et al., 1988; Holder et al., 1988; Ettinger et al., 1991). MSA-1, and MSA-1-specific antibodies, are also found in immune complexes that form in vitro when schizonts rupture in the presence of immune serum (Lyon et al., 1986; Lyon et al., 1989). Finally, the expression of MSA-1 at both the liver and blood stages suggests that immunity to this protein could act at both stages to limit infection.

It can be appreciated that provision of a malaria recombinant poxvirus, and of vaccines which provide protective immunity against Plasmodium infections, or which stimulate an immunological response in a host to Plasmodium immunogens would be a highly desirable advance over the current state of technology. It can be further appreciated that provision of an attenuated malaria recombinant poxvirus, and of vaccines which provide protective immunity against Plasmodium infections, or which generate an immunological response in a host to Plasmodium immunogens, e.g., such an attenuated recombinant poxvirus which contains genes coding for and expresses a plurality of antigens such as from various stages of malaria or of the Plasmodium life cycle, e.g., CSP, PfSSP2, LSA-1, MSA-1, SERA, AMA-1 and Pfs25 proteins, would be a highly desirable advance over the current state of technology. Likewise, such malaria recombinant poxviruses are also highly desirable for the production of Plasmodium immunogens in vitro.

OBJECTS OF THE INVENTION

It is therefore an object of this invention to provide recombinant poxviruses, which viruses express gene products of Plasmodium, and to provide a method of making such recombinant poxviruses.

It is an additional object of this invention to provide for the cloning and expression of Plasmodium coding sequences or antigens, particularly SERA, ABRA, Pfhsp70, AMA-1, Pfs25, Pfs16, CSP, PfSSP2, LSA-1 repeatless, MSA-1 and AMA-1 and combinations thereof, in a poxvirus vector, particularly vaccinia virus and avipox virus such as fowlpox or canarypox virus, e.g., CSP, PfSSP2, LSA-1-repeatless, MSA-1, SERA, AMA-1 and Pfs25 in an attenuated vaccinia vector such as a vector having open reading frames for virulence deleted or disrupted.

It is another object of this invention to provide a vaccine which is capable of eliciting malaria antibodies and protective immunity against Plasmodium infection. It is a further object of the invention to provide malaria recombinant poxvirus useful for the production of Plasmodium immunogens, in vivo or in vitro; and, the recombinant immunogens.

These and other objects and advantages of the present invention will become more readily apparent after consideration of the following.

STATEMENT OF THE INVENTION

In one aspect, the present invention relates to a recombinant poxvirus containing therein a DNA sequence from Plasmodium in a nonessential region of the poxvirus genome. The poxvirus is advantageously a vaccinia virus or an avipox virus, such as fowlpox virus or canarypox virus.

According to the present invention, the recombinant poxvirus expresses gene products of the foreign Plasmodium gene. In particular, the foreign DNA codes for a SERA, ABRA, Pfhsp70, AMA-1, Pfs25, Pfs16, PfSSP2, LSA-1, LSA-1-repeatless, MSA-1, CSP, MSA-1 N-terminal p83 or MSA-1 C-terminal gp42 gene. Advantageously, a plurality of Plasmodium genes are co-expressed in the host by the recombinant poxvirus, e.g., CSP, PfSSP2, LSA-1-repeatless, MSA-1, SERA, AMA-1 and Pfs25; and, preferably the recombinant poxvirus has attenuated virulence. For instance, the invention includes vaccinia recombinants expressing the CSP, PfSSP2, LSA1-repeatless, MSA-1, SERA, AMA-1, Pfs25, ABRA, Pfhsp70, or Pfs16 *P. falciparum* antigens, a NYVAC recombinant that expresses seven *P. falciparum* antigens (NYVAC-Pf7), and ALVAC recombinants expressing some of these *P. falciparum* antigens, as well as NYVAC single recombinants expressing the CSP, PfSSP2, LSA1-repeatless, SERA, or MSA-1 N-terminal p83 and C-terminal gp42 processing fragments; a NYVAC-based COPAK recombinant expressing PfSSP2; vaccinia WR-host range single recombinants expressing CSP, PfSSP2, LSA1-repeatless, MSA-1, SERA, or AMA-1; ALVAC single recombinants expressing PfSSP2, LSA1-repeatless, MSA-1, or MSA-1 N-terminal p83 and C-terminal gp42 processing fragments; an ALVAC recombinant expressing the seven *P. falciparum* antigens CSP, PfSSP2, LSA-1-repeatless, MSA-1, SERA, AMA-1, and Pfs25. The invention is also directed to the methods of using the malaria recombinant poxvirus for the production of Plasmodium gene products, either in vivo or in vitro as well as to the recombinant gene products.

In another aspect, the present invention relates to a vaccine for inducing an immunological response in a host animal inoculated with the vaccine, said vaccine including a carrier and a recombinant poxvirus containing, in a nonessential region thereof, DNA from Plasmodium, as well as to methods for inducing such an immunological response in an animal by inoculating the animal with a malaria recombinant poxvirus. Advantageously, the DNA codes for and expresses a SERA, ABRA, Pfhsp70, AMA-1, Pfs25, Pfs16, PfSSP2, LSA-1, LSA-1-repeatless, MSA-1, CSP, MSA-1 N-terminal p83 or MSA-1 C-terminal gp42 Plasmodium gene or a combination thereof. A plurality of Plasmodium genes advantageously are co-expressed in the host, e.g., CSP, PfSSP2, LSA-1-repeatless, MSA-1, SERA, AMA-1, and Pfs25; and preferably the recombinant poxvirus has attenuated virulence. The poxvirus used in the recombinant, the vaccine and method according to the present invention is advantageously a vaccinia virus or an avipox virus, such as fowlpox virus or canarypox virus, e.g., NYVAC, ALVAC or TROVAC recombinants.

BRIEF DESCRIPTION OF THE DRAWINGS

A better understanding of the present invention will be had by referring to the accompanying drawings, in which:

FIG. 2 shows the nucleotide (SEQ ID NO:2) and predicted amino acid (SEQ ID NO:3) sequence of the SERA cDNA in p126.15;

FIG. 3 shows the nucleotide (SEQ ID NO:4) and predicted amino acid (SEQ ID NO:5) sequence of the ABRA cDNA in pABRA-8;

FIG. 4 shows the nucleotide (SEQ ID NO:6) and predicted amino acid (SEQ ID NO:7) sequence of the Pfhsp70 partial cDNA in pHSP70.2;

FIG. 5 shows the nucleotide (SEQ ID NO:8) and predicted amino acid (SEQ ID NO:9) sequence of the 3D7 strain AMA-1 gene;

FIG. 6 shows the nucleotide sequence of the MSA-1 gene in p486195 (SEQ ID NO:10);

FIG. 7 shows the nucleotide sequence of the CSP gene in pIBI25-CS (SEQ ID NO:11);

FIG. 8 shows the nucleotide sequence of the AMA-1 gene in pHA.AMA-1 (SEQ ID NO:12);

FIG. 9 shows the nucleotide sequence of the Pfs25 gene in pPfs25.1 (SEQ ID NO:13);

FIG. 10 shows the nucleotide sequence of the PfSSP2 gene in pVAC-SSP2 (SEQ ID NO:14);

FIG. 11 shows the nucleotide sequence of the LSA-1-repeatless gene in pLSARPLS.I4L.1 (SEQ ID NO:15)

DETAILED DESCRIPTION OF THE INVENTION

Figure 1:
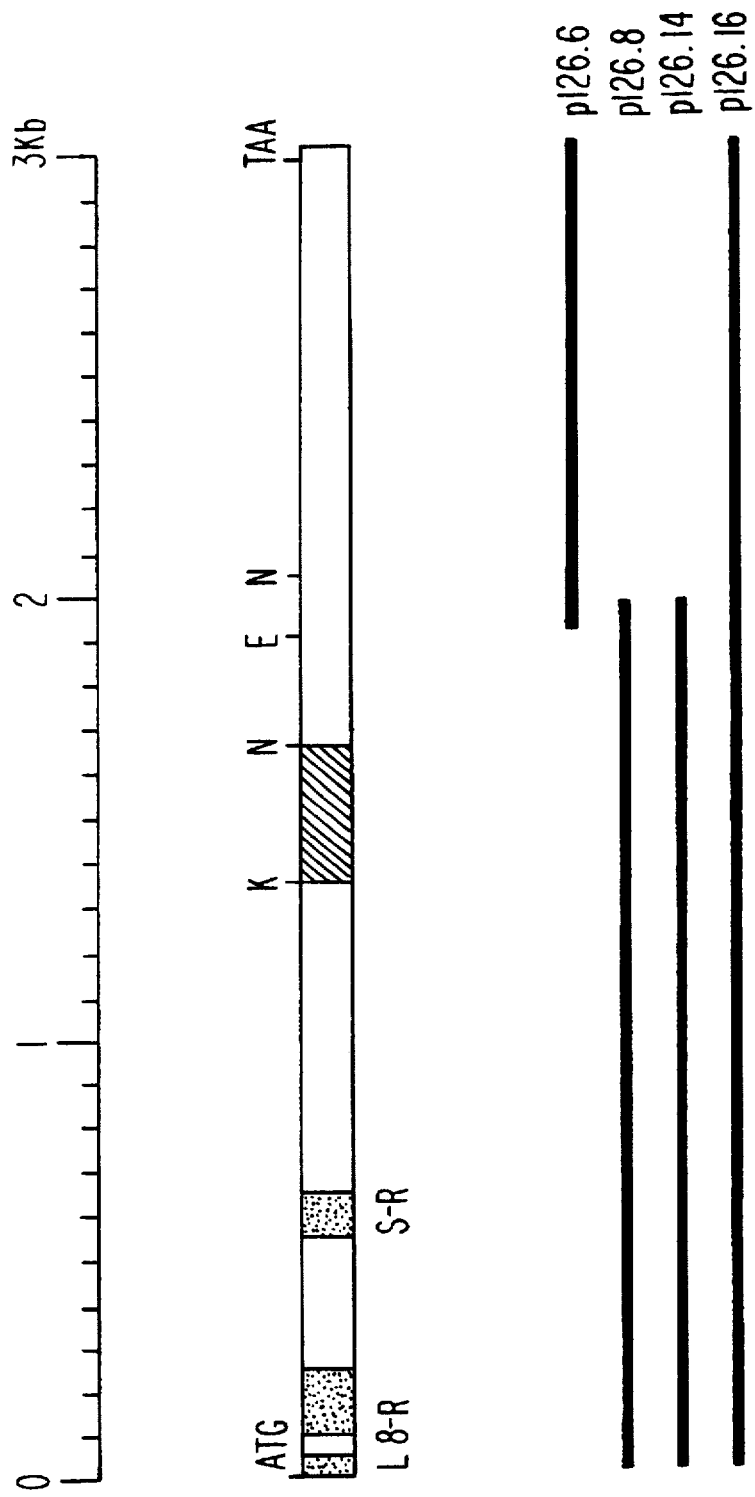
FIG. 1 schematically shows the SERA coding sequence.

The invention is directed to recombinant poxviruses containing therein a DNA sequence from Plasmodium in a nonessential region of the poxvirus genome. The recombinant poxviruses express gene products of the foreign Plasmodium gene. For example, P. falciparum genes were expressed in live recombinant poxviruses. This expression makes these recombinants useful for vaccines, for stimulating an immunological response to the gene products, or for the in vitro production of the gene products, e.g., for subsequent use of the products as immunogens. The SERA, ABRA, Pfhsp70, and AMA-1 P. falciparum blood stage genes were isolated, characterized and inserted into poxvirus, e.g., vaccinia, canarypox, virus recombinants, as well as the Pfs25, Pfs16, PfSSP2, LSA-1, LSA-1-repeatless, MSA-1, MSA-1 N-terminal p83, MSA-1 C-terminal gp42 and CSP P. falciparum genes. Preferably the recombinant poxvirus expresses a plurality of Plasmodium genes, e.g., CSP, PfSSP2, LSA-1-repeatless, MSA-1, SERA, AMA-1, and Pfs25; and, the poxvirus has attenuated virulence such as a vaccinia having attenuated virulence, e.g., a NYVAC recombinant such as NYVAC-Pf7, described below.

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically (nu$^+$/nu$^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

ALVAC, TROVAC and NYVAC were deposited under the terms of the Budapest Treaty with the American Type Culture Collection (ATCC), 12301 Parklawn Drive, Rockville, Md., 20852, U.S.A. NYVAC under ATCC accession number Vr-2559 on Mar. 6, 1997; TYOVAC under ATCC accession number VR-2553 on Feb. 6, 1997 and, ALVAC under ATCC accession number VR-2547 on Nov. 14, 1996.

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

After infecting cells in vitro with an inventive recombinant, the expression products are collected and the collected malarial expression products can then be employed in a vaccine, antigenic or immunological composition which also contains a suitable carrier.

Alternatively, the viral vector system, especially the preferred poxvirus vector system, can be employed in a vaccine, antigenic or immunological composition which also contains a suitable carrier. The recombinant poxvirus in the composition expresses the malarial products in vivo after administration or inoculation.

The antigenic, immunological or vaccine composition of the invention either containing products expressed or containing a recombinant poxvirus is administered in the same fashion as typical malarial antigenic immunological or vaccine compositions. One skilled in the medical arts can determine dosage from this disclosure without undue experimentation, taking into consideration such factors as the age, weight, and general health of the particular individual.

Additionally, the inventive recombinant poxvirus and the expression products therefrom stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of particular malarial antigen(s) and therefrom the presence or absence of malaria or, to determine whether an immune response to malaria or malarial antigen(s) has simply been stimulated.

Monoclonal antibodies are immunogiobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

The invention is illustrated by the non-limiting examples (below), which are not to be considered a limitation of this invention as many apparent variations of which are possible without departing from the spirit or scope thereof. In the examples herein, the following methods and materials are employed.

EXAMPLES

Enzymes, Bacteria, and Plasmids. Restriction enzymes and other DNA modifying enzymes were obtained from Boehringer Mannheim (Indianapolis, Ind.), New England Biolabs (Beverly, Mass.), and BRL Life Technologies Inc. (Gaithersburg, Mass.) and used according to manufacturers recommendations, unless otherwise noted. Standard molecular cloning procedures were followed (Sambrook et al., 1989).

The E. coli strains XL-1 Blue and SURE were obtained from Stratagene (La Jolla, Calif.) and strain NM522 from IBI (New Haven, Conn.). Plasmid vector pUC19 was obtained from New England Biolabs (Beverly, Mass.).

Cell Lines and Virus Strains. Vaccinia recombinants containing Plasmodium blood stage genes were generated with the Copenhagen vaccinia strain, or NYVAC (vP866) (Tartaglia et al., 1992) vaccinia strain (having attenuated virulence), or the vP668 vaccinia recombinant or, vP1170—a WR L-variant vaccinia virus (Panicali et al., 1981) from which the K1L ORF has been deleted and replaced by a 42K entomopox virus promoter/E. coli gpt gene expression cassette, as rescuing virus. Canarypox recombinants containing P. falciparum genes were generated with the ALVAC strain (having attenuated virulence) as rescuing virus (Tartaglia et al., 1992). All poxvirus stocks were produced in either Vero (ATCC CCL81) or MRC5 (ATCC CCL71) cells in Eagles MEM medium supplemented with 5–10% newborn calf serum (Flow Laboratories, McLean, Va.), or in primary chick embryo fibroblast (CEF) cells, or RK13 cells in Eagles MEM medium supplemented with 5–10% newborn calf serum (Flow Laboratories, McLean, Va.).

Polymerase Chain Reaction (PCR). The GeneAmp DNA amplification kit (Perkin Elmer Cetus, Norwalk, Conn.) was used for PCR (Saiki et al., 1988) according to the manufacturers specifications with custom synthesized oligonucleotides as primers. Reactions were processed in a Thermal Cycler (Perkin Elmer Cetus) with standard conditions (Saiki et al., 1988).

Construction of P. Falciparum FCR3 Strain Blood Stage cDNA Library. Total RNA from human erythrocytes infected with P. falciparum FCR3 strain was obtained from Dr. P. Delplace (INSERM-U42, 369 rue Jules-Guesde, 59650 Villeneuve-D'Ascq, France). Poly-$A^+$ RNA was isolated from this sample by use of oligo(dT) cellulose (Stratagene, La Jolla, Calif.) as described by Aviv and Leder (Aviv and Leder, 1972) and modified by Kingston (Kingston, 1987). Briefly, total RNA was mixed with oligo (dT) cellulose in Binding buffer (0.5M NaCl, 0.01M Tris-Cl, pH 7.5) and incubated for 30 minutes at room temperature. Poly-$A^+$ RNA/oligo(dT) cellulose complexes were pelleted by centrifugation and washed 3 times with Binding buffer. Purified poly-$A^+$ RNA was eluted from the oligo(dT) cellulose in Elution buffer (0.01M Tris-Cl, pH 7.5). A second elution with DEPC-treated $dH_2O$ was performed, the eluates were pooled, and the poly-$A^+$ RNA recovered by ethanol precipitation.

The purified poly-$A^+$ RNA was used as a template for the synthesis of first strand cDNA by reverse transcriptase in a reaction primed with oligo(dT) (Klickstein and Neve, 1987; Watson and Jackson, 1985). For this reaction, 12 ug poly-A$^+$ RNA was incubated with 105 units AMV reverse transcriptase (Life Sciences) in 100 mM Tris-Cl pH 8.3, 30 mM KCl, 6 mM MgCl$_2$, 25 mM DTT, 80 units RNasin, 1 mM each dNTP, and 24 ug/ml oligo(dT)$_{12-18}$ as primer for 2 hours at 42° C. After organic extractions, double stranded cDNA was obtained by use of DNA polymerase I and RNase H with first strand cDNA as template (Klickstein and Neve, 1987; Watson and Jackson, 1985). The first strand cDNA was incubated with 25 units DNA polymerase I and 1 unit RNase H in 20 mM Tris-Cl pH 6, 5 mM MgCl$_2$, 10 mM (NH$_4$)$_2$SO$_4$, 100 mM KCl, 500 ug/ml BSA, 25 mM DTT, and 0.1 mM each dNTP at 12° C. for one hour followed by one hour at room temperature to synthesize second strand cDNA. The double stranded cDNA was recovered by organic extractions and ethanol precipitation.

The double-stranded blood stage cDNA was then sequentially treated with T4 DNA polymerase to create blunt ends and EcoRI methylase to protect internal EcoRI sites. EcoRI linkers were then added followed by digestion with EcoRI and size selection on a 5–25% sucrose gradient. Fractions containing long cDNAs (1–10 Kb) were pooled and ligated into EcoRI cleaved Lambda ZAPII vector (Stratagene, La Jolla, Calif.). The resulting phage were packaged and used to infect the XL-1 Blue *E. coli* strain (Stratagene, La Jolla, Calif.). The phage were then harvested from these cells and amplified by one additional cycle of infection of XL-1 Blue to produce a high titer FCR3 strain blood stage cDNA library.

Screen of cDNA Library for Plasmodium Blood Stage cDNA Clones. The FCR3 strain cDNA library was screened by plaque hybridization with $^{32}$P end-labelled oligonucleotides derived from published sequences of blood stage genes to detect cDNA. The cDNA library was plaqued on lawns of XL-1 Blue (Stratagene, La Jolla, Calif.) in 150 mm dishes at a density of 100,000 plaques per dish. Plaques were transferred to nitrocellulose filters which were then soaked in 1.5M NaCl/0.5M NaOH for 2 minutes, 1.5M NaCl/0.5M Tris-Cl pH 8 for 5 minutes, 0.2M Tris-Cl pH 7.5/2× SSC for one minute, and baked for 2 hours in an 80° C. vacuum oven. Filters were prehybridized in 6× SSC, 5× Denhardts, 20 mM NaH$_2$PO$_4$, 500 ug/ml salmon sperm DNA for two hours at 42° C. Hybridizations were performed in 0.4% SDS, 6× SSC, 20 mM NaH$_2$PO$_4$, 500 ug/ml salmon sperm DNA for 18 hours at 42° C. after the addition of $^{32}$P-labelled oligonucleotides. After hybridization, filters were rinsed 3 times with 6× SSC, 0.1% SDS, washed for 10 minutes at room temperature, and washed for 5 minutes at 58° C. Filters were then exposed to X-ray film at −70° C.

Plaques hybridizing with oligonucleotide probes were cored from plates and resuspended in SM buffer (100 mM NaCl, 8 mM MgSO$_4$, 50 mM Tris-Cl pH 7.5, 0.01% gelatin) containing 4% chloroform. Dilutions of such phage stocks were used to infect XL-1 Blue, plaques were transferred to nitrocellulose, and the filters were hybridized with $^{32}$P-labelled oligonucleotides. Well isolated positive plaques were selected and subjected to two additional rounds of purification as just described.

Isolation of Plasmodium cDNA-containing Plasmids From Positive Phage Clones. Plasmodium cDNAs in the pBluescript plasmid vector were obtained by an in vivo excision protocol developed for use with the lambda ZAPII vector (Stratagene, La Jolla, Calif.). Briefly, purified recombinant lambda phage stocks were incubated with XL-1 Blue cells and R408 filamentous helper phage for 15 minutes at 37° C. After the addition of 2× YT media (1% NaCl, 1% yeast extract, 1.6% Bacto-tryptone), incubation was continued for 3 hours at 37° C. followed by 20 minutes at 70° C. After centrifugation, filamentous phage particles containing pBluescript phagemid (with cDNA insert) were recovered in the supernatant. Dilutions of the recovered filamentous phage stock were mixed with XL-1 Blue and plated to obtain colonies containing pBluescript plasmids with Plasmodium CDNA inserts.

DNA Sequence Analysis of Plasmodium Genes. Plasmodium genes were obtained in pBluescript or cloned into other plasmid vectors. DNA sequencing was performed with the Sequenase modified T7 polymerase (U.S. Biochemicals, Cleveland, Ohio). Sequencing reactions were performed on alkali denatured double stranded plasmid templates (Hattori and Sakaki, 1986) with the T3 and T7 primers or custom synthesized oligodeoxyribonucleotides. Sequence data were analyzed with the IBI Pustell Sequence Analysis Package, Version 2.02 (International Biotechnologies, New Haven, Conn.).

Generation of SERA cDNA by PCR. By use of the polymerase chain reaction (PCR), the 5' portion of the coding sequence of SERA was amplified with specific oligonucleotide primers and first strand cDNA as template (Saiki et al., 1988; Frohman et al., 1988). SERA-specific first strand cDNA was synthesized by reverse transcriptase using the reaction conditions described above and specific oligonucleotides as primers. RNA was subsequently eliminated by treatment with RNase A prior to PCR. The Gene-Amp DNA amplification kit (Perkin Elmer Cetus, Norwalk, Conn.) was used for PCR. Briefly, first strand cDNA in 50 mM KCl, 10 mM Tris-Cl pH 8.3, 1.5 mM MgCl$_2$, 0.01% gelatin was mixed with 200 uM each dNTP, 1 uM of each primer, and 2.5 units Taq polymerase. Reactions were processed in a Thermal Cycler (Perkin Elmer Cetus) with 1 cycle of denaturation, annealing, and extension at 94° C. for 2 minutes, 43° C. for 3 minutes, and 72° C. for 40 minutes; 40 cycles at 94° C. for 1 minute, 43° C. for 2 minutes, and 72° C. for 4 minutes followed by a final extension at 72° C. for 20 minutes.

The inclusion of restriction sites in primers used for PCR allowed the cloning of amplified SERA cDNA into plasmid vectors. Clones containing cDNAs derived from two independent PCRs were obtained for each SERA cDNA that was amplified in order to control for Taq polymerase errors.

Generation of Vaccinia Recombinants Containing P. Falciparum Genes. *P. falciparum* genes were cloned such that they are placed under the control of poxvirus promoters for expression by vaccinia vectors. The promoters utilized are the vaccinia early/late H6 promotor (Perkus et al., 1989), the Pi or C10LW early promotor from vaccinia WR (Wachsman et al., 1989), the vaccinia I3L early intermediate promotor (Perkus et al., 1985; Schmitt and Stunnenburg 1988), and the entomopoxvirus 42K early promotor (Gettig et al., unpublished).

*P. falciparum* genes must then be cloned into vaccinia donor plasmids in preparation for insertion into vaccinia virus. The pCOPCS-5H and pCOPCS-6H donor plasmids have been previously described (Perkus et al., 1991).

Donor plasmids contain segments of vaccinia DNA which flank a series of restriction sites which can be used for the cloning of foreign genes. These flanking arms direct the insertion of the cloned foreign genes to defined positions on the genome. In NYVAC embodiments, four sites on the NYVAC genome for the insertion of *P. falciparum* genes were employed: ATI, TK, HA, and I4L (ORFs A26L, J2R, A56R, and I4L, respectively; Goebel et al., 1990). These ORFs had been precisely deleted from the genome of NYVAC (Tartaglia et al., 1992) to create the insertion sites. The donor plasmids that direct insertion to these sites are described below.

Plasmid pSD494 directs the insertion of foreign genes to the ATI site and was derived as follows. pSD414 contains the SalIB fragment of the vaccinia genome (within which the ATI site is located) cloned into pUC8. To remove unwanted DNA sequences to the left of the A26L region, pSD414 was cut with XbaI (pos. 137,079) and with HindIII at the pUC/vaccinia DNA junction, and then blunt ended with the Klenow fragment of *E. coli* DNA polymerase and ligated, resulting in plasmid pSD483. To remove unwanted DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 Kb vector fragment was isolated and ligated with the annealed synthetic oligonucleotide pair ATI3 (SEQ ID NO:16) (5'-TAT GAG TAA CTT AAC TCT TTT GTT AAT TAA AAG TAT ATT CAA AAA ATA AGT TAT ATA AAT AGA TCT GAA TTC GTT-3') and ATI4 (SEQ ID NO:17) (5'-AAC GAA TTC AGA TCT ATT TAT ATA ACT TAT TTT TTG AAT ATA CTT TTA ATT AAC AAA AGA GTT AAG TTA CTC A-3') which reconstructed the region upstream from A26L and replaced the A26L ORF with a short polylinker region containing the restriction sites BglII, EcoRI, and HpaI. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction followed by blunt ending with Klenow fragment and ligation. The resulting plasmid was designated pSD489. The 1.8 Kb ClaI (pos. 137,198)/EcoRV (pos. 139,048) fragment from pSD489 containing the A26L ORF was replaced with the corresponding 0.7 Kb polylinker-containing ClaI/EcoRV fragment from pSD485, generating pSD492. The BglII and EcoRI sites in the polylinker region of pSD492 are unique. To expand the restriction sites present in the polylinker region, a BglII/EcoRI fragment from pSD482 was ligated with BglII/EcoRI-digested pSD492 to generate pSD494. This insertion expands the polylinker to include BglII, SmaI, HindIII, BamHI, XhoI, EcoRI, and HpaI sites.

The pSD544 insertion vector (the HA site) was derived as follows. pSD456 is a subclone of Copenhagen vaccinia DNA containing the HA gene (A56R; Goebel et al., 1990) and surrounding regions. pSD456 was used as template in polymerase chain reactions for synthesis of left and right vaccinia arms flanking the A56R ORF. The left arm was synthesized using synthetic oligodeoxynucleotides MPSYN279 (SEQ ID NO:18) (5'-CCCCCC-GAATTCGTCGACGATTGTTCATGATGGCAAGAT-3') and MPSYN280 (SEQ ID NO:19) (5'-CCCGGGGGATCCCTCGAGGGTACCAAGCTTA-ATTAATTAAATATTAGTATAAAAAGTGATTTATTTTT-3') as primers. The right arm was synthesized using MPSYN281 (SEQ ID NO:20) (5'-AAGCTTGGTACCCTCGAGGGATC-CCCCGGGTAGCTAGCTAA TTTTTCTTTTACGTATTATATATGTAATAAACGTTC-3') and MPSYN312 (SEQ ID NO:21) (5'-TTTTT-TCTGCAGGTAAGTATTTTTAAAACTTCTAACACC-3') as primers. Gel-purified PCR fragments for the left and right arms were combined in a further PCR reaction. The resulting product was cut with EcoRI/HindIII. The resulting 0.9 kb fragment was gel-purified and ligated into pUC8 cut with EcoRI/HindIII, resulting in plasmid pSD544.

Plasmid pSD550 (the I4L site) was derived as follows. Plasmid pSD548 (Tartaglia et al., 1992) is a vaccinia vector plasmid in which the I4L ORF (Goebel et al., 1990) is replaced by a cloning region consisting of BglII and SmaI sites. To expand the multicloning region, pSD548 was cut with BglII and SmaI and ligated with annealed complementary synthetic oligonucleotides 539A (SEQ ID NO:22) (5'-AGAAAAATCAGTTAGCTAAGATCTC-CCGGGCTCGAGGGTACCGGATCCTGATTAG TTAATTTTTGT-3') and 539B (SEQ ID NO:23) (5'-GATCACAAAAATTAA CTAATCAGGATCCGGTACCCTCGAGCCCGGGAGA-TCTTAGCTAACTGATTTTTCT-3'). In the resulting plasmid, pSD550, the multicloning region contains BglII, SmaI, XhoI, KpnI and BamHI restriction sites.

Plasmid pSD542 (the TK site) was derived as follows. To modify the polylinker region, plasmid pSD513 (Tartaglia et al., 1992) was cut with PstI/BamHI and ligated with annealed synthetic oligonucleotides MPSYN288 (SEQ ID NO:24) (5'-GGTCGACGGATCCT-3') and MPSYN289 (SEQ ID NO:25) (5'-GATCAGGATCCGTCGACCTGCA-3') resulting in plasmid pSD542.

Plasmid pSD553 is a vaccinia deletion/insertion plasmid of the COPAK series. It contains the vaccinia K1L host range gene (Gillard et al., 1986) within flanking Copenhagen vaccinia arms, replacing the ATI region (orfs A25L, A26L; Goebel et al., 1990). pSD553 was constructed as follows. Left and right vaccinia flanking arms were constructed by polymerase chain reaction using pSD414, a pUC8-based clone of vaccinia SalI B (Goebel et al., 1990) as template. The left arm was synthesized using synthetic deoxyoligonucleotides MPSYN267 (SEQ ID NO:26) (5'-GGGCTGAAGCTTGCTGGCCGCTCATTAGACAAG-CGAATGAGGGAC-3') and MPSYN268 (SEQ ID NO:27) (5'-AGATCTCCCGGGCTCGAGTAATTAATTAA TTTTTATTACACCAGAAAAGACGGCTTGAGATC-3') as primers. The right arm was synthesized using synthetic deoxyoligonucleotides MPSYN269 (SEQ ID NO:28) (5'-TAATTACTCGAGCCCGGGAGATCTAATTTAA TTTAATTTATATAACTCATTTTTTGAATATAC T-3') and MPSYN270 (SEQ ID NO:29) (5'-TATCTCGAATTCCCGCGGCTTTAAATGGACGGA-ACTCTTTTCCCC-3') as primers. The two PCR-derived DNA fragments coontaining the left and right arms were combined in a further PCR reaction. The resulting product was cut with EcoRI/HindIII and a 0.9 kb fragment isolated. The 0.9 kb fragment was ligated with pUC8 cut with EcoRI/HindIII, resulting in plasmid pSD541. The polylinker region located at the vaccinia deletion locus was expanded as follows. pSD541 was cut with BglII/XhoI and ligated with annealed complementary synthetic deoxyoligonucleotides MPSYN333 (SEQ ID NO:30) (5'-GATCTTTTGTTAACAAAAACTAATCAG-CTATCGCGAATCGATTCCCGGGGGATCCGGTACCC-3') and MPSYN334 (SEQ ID NO:31) (5'-TCGAGGGTACCGGATCCCCC GGGAATCGATT-CGCGATAGCTGATTAGTTTTTGTTAACAAAA-3') generating plasmid pSD552. The K1L host range gene was isolated as a 1 kb BclII(partial)/HpaI fragment from plasmid pSD552 (Perkus et al., 1990). pSD552 was cut with BglII/HpaI and ligated with the K1L containing fragment, generating pSD553.

Plasmid pMPI3H contains the vaccinia I3L early/intermediate promoter element (Schmitt and Stunnenberg, 1988) in a pUC8 background. The promoter element was synthesized by polymerase chain reaction (PCR) using pMPVC1, a subclone of vaccinia HindIII I, as template and synthetic oligonucleotides MPSYN283 (SEQ ID NO:32) (5'-CCCCCCAAGCTTACATCATGCAGTGGTTAAAC-3') and MPSYN287 (SEQ ID NO:33) (5'-GATTAAACCTAAATAATTGT-3'). DNA from this reaction was cut with HindIII and RsaI and a 0.1 kb fragment containing the promoter element was purified. A linker region was assembled by annealing complementary synthetic oligonucleotides MPSYN398 (SEQ ID NO:34) (5'-ACAATTATTTAGGTTAACTGCA-3') and MPSYN399 (SEQ ID NO:35) (5'-GTTAACCTAAATAATTGT-3'). The PCR-derived promoter element and the polylinker region were ligated with vector plasmid pUC8 which had been cut with HindIII and PstI. The resulting plasmid, pMPI3H, contains the I3L promoter region from positions −100 through −6 relative to the initiation codon, followed by a polylinker region containing HpaI, PstI, SalI, BamHI, SmaI and EcoRI sites. Cleavage with HpaI produces blunt ended DNA linearized at position −6 in the promoter.

DSD541. Plasmid pSD541 is a vaccinia insertion plasmid. It is deleted for vaccinia sequences nt. 317,812 through 138,976, encompassing the A25L and A26L ORFs (Goebel et al., 1990a,b). The deletion junction consists of a polylinker region containing XhoI, SmaI and BglII restriction sites, flanked on both sides by stop codons and early vaccinia transcriptional terminators (Yuen and Moss, 1987). pSD541 was constructed by polymerase chain reaction (PCR) using cloned vaccinia SalI E plasmid pSD414 as template. Synthetic oligonucleotides MPSYN267 (SEQ ID NO:26) (5'-GGG CTC AAG CTT GCG GCC GCT CAT TAG ACA AGC GAA TGA GGG AC-3') and MPSYN268 (SEQ ID NO:27) (5'-AGA TCT CCC GGG CTC GAG TAA TTA ATT AAT TTT TAT TAC ACC AGA AAA GAC GGC TTG AGA TC-3') were used as primers to generate the left vaccinia arm, and synthetic oligonucleotides MPSYN269 (SEQ ID NO:28) (5'-TAA TTA CTC GAG CCC GGG AGA TCT AAT TTA ATT TAA TTT ATA TAA CTC ATT TTT TGA ATA TAC T-3') and MPSYN270 (SEQ ID NO:29) (5'-TAT CTC GAA TTC CCG CGG CTT TAA ATG GAC GGA ACT CTT TTC CCC-3') were used as primers to generate the right vaccinia arm. PCR products consisting of the left and right vaccinia arms were combined, and subjected to PCR amplification. The PCR product was digested with EcoRI and HindIII and electrophoresed on an agarose gel. The 0.8 kb fragment was isolated and ligated into pUC8 cut with EcoRI/HindIII, resulting in plasmid pSD541.

WR-host range vaccinia recombinants are generated by inserting expression cassettes into the K1L site of vP1170. This recombinant has been deleted of the K1L open reading frame and contains a 42K promoter/Ecogpt gene expression cassette in its place. Insertion into the K1L site is via the pSD157K1LINS insertion vector, which contains vaccinia flanking arms directing insertion to the K1L site plus the K1L gene. The construction of this vector is described below.

pSD157K1LINS. Preexisting plasmid pHM-1 is WR vaccinia HindIII M cloned in pBR322. Preexisting plasmid pHK is WR vaccinia HindIII K cloned in pBR322.

Plasmid pHK was cut with HindIII/BglII and a 1.2 kb fragment isolated and cloned into pBS-SK+ (Stratagene) cut with BamHI/HindIII. The resulting plasmid was designated pBS-HKARM (#784). pBS-HKARM was digested with Asp718 in the polylinker region, blunt ended with Klenow fragment of E. coli DNA polymerase, and digested with HindIII at the pBS/vaccinia junction. The resulting 4.1 kb vector fragment was used as described below. pHM-1 was cut with NruI/HindIII and a 2.0 kb fragment isolated. This fragment was ligated with the vector fragment from pBS-KARM, resulting in plasmid pMPWRMK (#791). pMPWRMK was cut with HpaI and ligated with annealed synthetic oligonucleotides MPSYN527 (SEQ ID NO:36) (5'-ATA AAA ATT AGC TAC TCA GGT ACC CTG CAG TCG CGA GGA TCC GAA TTC CCC GGG CTC GAG TGA TTA ATT AGT TTT TAT-3') and MPSYN528 (SEQ ID NO:37) (5'-ATA AAA ACT AAT TAA TCA CTC GAG CCC GGG GAA TTC GGA TCC TCG CGA CTG CAG GGT ACC TGA GTA GCT AAT TTT TAT-3'). The resulting plasmid is pSD157K1LINS.

In ALVAC embodiments, four sites on the A1VAC genome for the insertion of P. falciparum genes have been employed: C3, C5, C6, and C7. The insertion plasmids which target these sites have been derived such that insertion removes the targeted ORF from the resulting recombinant, replacing it with the foreign expression cassette.

pVQC5LSP6. The pVQC5LSP6 ALVAC C5 insertion vector, which contains 1535 bp upstream of C5, a polylinker containing KpnI, SmaI, XbaI, and NotI sites, and 404 bp of canarypox DNA (31 bp of C5 coding sequence and 373 bp of downstream sequence) was derived in the following manner. A genomic library of canarypox DNA was constructed in the cosmid vector puK102, probed with pRW764.5 and a clone containing a 29 kb insert identified (pHCOS1). A 3.3 kb ClaI fragment from pHCOS1 containing the C5 region was identified. Sequence analysis of the ClaI fragment was used to extend the sequence in from nucleotides 1-1372. The C5 insertion vector was constructed as follows.

The 1535 bp upstream sequence was generated by PCR amplification using oligonucleotides C5A (SEQ ID NO:39) (5'-ATC ATC GAA TTC TGA ATG TTA AAT GTT ATA CTT G-3') and C5B (SEQ ID NO:39) (5'-GGG GGT ACC TTT GAG AGT ACC ACT TCA G-3') and purified genomic canarypox DNA as template. This fragment was digested with EcoRI (within oligo C5A) and cloned into EcoRI/SmaI digested pUC8 generating pC5LAB. The 404 bp arm was generated by PCR amplification using oligonucleotides C5C (SEQ ID NO:40) (5'-GGG TCT AGA GCG GCC GCT TAT AAA GAT CTA AAA TGC ATA ATT TC-3') and C5DA (SEQ ID NO:41) (5'-ATC ATC CTG CAG GTA TTC TAA ACT AGG AAT AGA TG-3'). This fragment was digested with PstI (within oligo C5DA) and cloned into SmaI/PstI digested pC5LAB generating pC5L.

pC5L was digested within the polylinker with Asp718 and NotI, treated with alkaline phosphatase and ligated to kinased and annealed oligonucleotides CP26 (SEQ ID NO:42) (5'-GTA CGT GAC TAA TTA GCT ATA AAA AGG ATC CGG TAC CCT CGA GTC TAG AAT CGA TCC CGG GTT TTT ATG ACT AGT TAA TCA C-3') and CP27 (SEQ ID NO:43) (5'-GGC CGT GAT TAA CTA GTC ATA AAA ACC CGG GAT CGA TTC TAG ACT CGA GGG TAC CGG ATC CTT TTT ATA GCT AAT TAG TCA C-3') (containing a disabled Asp718 site, translation stop codons in six reading frames, vaccinia early transcription termination signal, BamHI, KpnI, XhoI, XbaI, ClaI, and SmaI restriction sites, vaccinia early transcription termination signal, translation stop codons in six reading frames, and a disabled NotI site) generating plasmid pC5LSP.

pC5LSP was digested with BamHI and ligated to annealed oligonucleotides CP32 (SEQ ID NO:44) (5'-GAT CTT AAT TAA TTA GTC ATC AGG CAG GGC GAG AAC GAG ACT ATC TGC TCG TTA ATT AAT TAG GTC GAC G-3') and CP33 (SEQ ID NO:45) (5'-GAT CCG TCG ACC TAA TTA ATT AAC GAG CAG ATA GTC TCG TTC TCG CCC TGC CTG ATG ACT AAT TAA TTA A-3') to generate pVQC5LSP6.

PC7. The pC7 ALVAC C7 insertion vector, which contains 2,085 bp of ALVAC DNA upstream of the C7 ORF (thymidine kinase—TK), a polylinker containing SmaI, NruI, EcoRI, XhoI and StuI restriction sites, and 812 bp of ALVAC DNA downstream of the C7 ORF, was derived in the following manner.

A 5.7 kb BalII fragment containing the ALVAC TK gene locus was identified by hybridization with a fowlpox virus TK gene probe, cloned to generate pCPtk, and sequenced. Analysis of this sequence revealed the complete ALVAC TK ORF.

To construct a de-ORFed insertion plasmid, a 3450 bp PstI/NsiI fragment from pCPtk was first cloned into the blunt-ended Asp718/XbaI sites of pBS-SK+to generate pEU1. To delete the TK ORF and replace it with a polylinker containing cloning sites, two PCR fragments were amplified from pCPtk with the oligonucleotide primer pairs RG578 (SEQ ID NO:46) (5'-GTA CAT AAG CTT TTT GCA TG-3')/RG581 (SEQ ID NO:47) (5'-TAT GAA TTC CTC GAG GGA TCC AGG CCT TTT TTA TTG ACT AGT TAA TCA GTC TAA TAT ACG TAC TAA ATA C-3') and RG579 (SEQ ID NO:48) (5'-CTA ATT TCG AAT GTC CGA CG-3') /RG580 (SEQ ID NO:49) ((5'-TTA GAA TTC TCG CGA CCC GGG TTT TTA TAG CTA ATT AGT ACT TAT TAC AAA TAC TAT AAT ATT TAG-3'). These fragments were purified, digested with HindIII/EcoRI and BstBI/EcoRI, respectively, and a three-way ligation performed with HindIII/BstBI-digested pEU1. The resulting plasmid was designated pC7 and confirmed by sequence analysis.

The pNVQH6C5SP18 ALVAC C5 insertion vector, which contains 1535 bp upstream of C5, a polylinker containing KpnI, SmaI, XbaI, and NotI sites, and 404 bp of canarypox DNA (31 bp of C5 coding sequence and 373 bp of downstream sequence) was derived in the following manner. A genomic library of canarypox DNA was constructed in the cosmid vector puK102, probed with pRW764.5 and a clone containing a 29 kb insert identified (pHCOS1). A 3.3 kb ClaI fragment from pHCOS1 containing the C5 region was identified. Sequence analysis of the ClaI fragment was used to extend the sequence in from nucleotides 1-1372. The C5 insertion vector was constructed as follows. The 1535 bp upstream sequence was generated by PCR amplification using oligonucleotides C5A (SEQ ID NO:50) (5'-ATCATCGAATTCTGAATGTTAAATGTTATACTTG-3') and C5B (SEQ ID NO:51) (5'-GGGGGTACCTTTGAGAGTACCACTTCAG-3') and purified genomic canarypox DNA as template. This fragment was digested with EcoRI (within oligo C5A) and cloned into EcoRI/SmaI digested pUC8 generating pC5LAB. The 404 bp arm was generated by PCR amplification using oligonucleotides C5C (SEQ ID NO:52) (5'-GGGTCTAGAGCGGCCGCTTATAAAGATCTAAAAT-GCATAATTTC-3') and C5DA (SEQ ID NO:53) (5'-ATCATCCTGCAGGTATTCTAAACTAGGAATAGATG-3'). This fragment was digested with PstI (within oligo C5DA) and cloned into SmaI/PstI digested pC5LAB generating pC5L. pC5L was digested within the polylinker with Asp718 and NotI, treated with alkaline phosphatase and ligated to kinased and annealed oligonucleotides CP26 (SEQ ID NO:42) (5'-GTACGTGACTAATTAGCTATAAAAAG-GATCCGGTACCCTCGAGTCTAGAATCGATCCC GGGTTTTTATGACTAGTTAATCAC-3') and CP27 (SEQ ID NO:43) (5'-GGCCGTGATTAACTAGTCATAAAAAC-CCGGGATCGATTCTAGACTCGAGGGTACCGGA TCCTTTTTATAGCTAATTAGTCAC-3') (containing a disabled Asp718 site, translation stop codons in six reading frames, vaccinia early transcription termination signal (Yuen and Moss, 1987), BamHI, KpnI, XhoI, XbaI, ClaI, and SmaI restriction sites, vaccinia early transcription termination signal, translation stop codons in six reading frames, and a disabled NotI site, generating plasmid pC5LSP. The early/late H6 vaccinia virus promoter (Perkus et al., 1989) was derived by PCR from a plasmid containing the promoter using oligonucleotides CP30 (SEQ ID NO:54) (5'-TCGGGATCCGGGTTAATTAATTAGTCATCAGGCA-GGGCG-3') and CP31 (SEQ ID NO:55) (5'-TAGCTCGA-GGGTACCTACGATACAAACTTAACGGATATCG-3'). The PCR product was digested with BamHI and XhoI (sites created at the 5' and 3' termini by the PCR) and ligated to similarly digested pC5LSP generating pVQH6C5LSP. pVQH6C5LSP was digested with EcoRI, treated with alkaline phosphatase, ligated to self-annealed oligonucleotide CP29 (SEQ ID NO:56) (5'-AATTGCGGCCGC-3'), digested with NotI and linear purified followed by self-ligation. This procedure introduced a NotI site to pVQH6C5LSP, generating pNVQH6C5SP18.

The pNC5LSP-5 plasmid, another ALVAC C5 insertion vector, was derived as follows. Plasmid pC5LSP was digested with EcoRI, treated with alkaline phosphatase, ligated to self-annealed oligonucleotide CP29 (SEQ ID NO:41), digested with NotI and linear purified followed by self-ligation. This procedure introduced a NotI site to pC5LSP, generating pNC5LSP-5.

Insertion plasmid VQCP3L was derived as follows. An 8.5 kb canarypox BglII fragment was cloned in the BamHI site of PBS-SK plasmid vector to form pWW5. Nucleotide sequence analysis revealed a reading frame designated C3. In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:57) (5'-CAGTTGGTACCACTGGTATTTTATTTCAG-3') and RG278 (SEQ ID NO:58) (5'-TATCTGAATTCCTGCAGCCCGGGTTTT-TATAGCTAATTAGTCAAATGTGAGTTAA TATTAG-3'). Primers for the 3' sequences were RG279 (SEQ ID NO:59) (5'TCGCTGAATTCGATATCAAGCTTATCGATTTTTAT-GACTAGTTAATCAAA TAAAAAGCATACAAGC-3') and RG280 (SEQ ID NO:60) (5'-TTATCGAGCTCTGTAACATCAGTATCTAAC-3'). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into AsP718/SacI digested pBS-SK plasmid vector. The resultant plasmid was designated as pC3L. A 908 bp fragment of canarypox DNA, immediately upstream of the C3 locus was obtained by digestion of plasmid pWW5 with NsiI and SspI. A 604 bp fragment of canarypox and DNA was derived by PCR using plasmid pWW5 as template and oligonucleotides CP16 (SEQ ID NO:61) (5'-TCCGGTACCGCG-GCCGCAGATATTTGTTAGCTTCTGC-3') and CP17 (SEQ ID NO:62) (5'-TCGCTCGAGTAGGATACCTACCTACTACCTACG-3'). The 604 bp fragment was digested with Asp718 and XhoI (sites present at the 5' ends of oligonucleotides CP16 and CP17, respectively) and cloned into Asp718-XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI, and ligated to the 908 bp NsiI-SspI fragment generating SPCPLAX which contains 1444 bp of canarypox DNA upstream of the C3 locus. A 2178 bp BglII-StyI fragment of canarypox DNA was isolated from plasmids pXX4 (which contains a 6.5 kb NsiI fragment of canarypox DNA cloned into the PstI site of pBS-SK). A 279 bp fragment of canarypox DNA was isolated by PCR using plasmid pXX4 as template and oligonucleotides CP19 (SEQ ID NO:63) (5'-TCGCTCGAGCTTTCTTGACAATAACATAG-3') and CP20 (SEQ ID NO:64) (5'-TAGGAGCTCTTTATACTACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA. To add additional unique sites to the polylinker, pC3I was digested within the polylinker region with EcoRI and ClaI, treated with alkaline phosphatase and ligated to kinased and annealed oligonucleotides CP12 (SEQ ID NO:65) (5'-AATTCCTCGAGGGATCC-3') and CP13 (SEQ ID NO:66) (5'-CGGGATCCCTCGAGG-3') (containing an EcoRI sticky end, XhoI site, BamHI site and a sticky end compatible with ClaI) generating plasmid SPCP3S. SPCP3S was digested within the canarypox sequences downstream of the C3 locus with StyI and SacI (pBS-SK) and ligated to a 261 bp BglII-SacI fragment from SPC3RA and the 2178 bp BglII-StyI fragment from pXX4 generating plasmid CPRAL containing 2572 bp of canarypox DNA downstream of the C3 locus. SPCP3S was digested within the canarypox sequences upstream of the C3 locus with Asp718 (in PBS-SK) and AccI and ligated to a 1436 bp Asp718-AccI fragment from SPCPLAX generating plasmid CPLAL containing 1457 bp of canarypox DNA upstream of the C3 locus. The derived plasmid was designated as SPCP3L. VQCPCP3L was derived from pSPCP3L by digestion with XmaI, phosphatase treating the linearized plasmid, and ligation to annealed, kinased oligonucleotides CP23 (SEQ ID NO:67) (5'-CCGGTTAATTAATTAGTTATTAGACAAGGTGAAAA CGAAACTATTTGTAGCTTAATTAATTAGGTCACC-3') and CP24 (SEQ ID NO:68) (5'-CCGGGGTCGACCTAATTAATTAAGCTA-CAAATAGTTTCGTTTTCACCTT GTCTAATAACTAATTAATTAA-3').

The ALVAC C6 insertion vector pC6L contains a 1615 bp SacI/KpnI fragment containing the C6 region of ALVAC inserted in the pBS.SK vector (Stratagene, La Jolla, Calif.). A polylinker region has been introduced approximately at position 400 of the C6 sequence which contains translational stops in six reading frames, early transcriptional termination signals in both directions, and a series of restriction enzyme sites for cloning (SmaI, PstI, XhoI, and EcoRI).

Transfection of insertion vectors into tissue culture cells infected with rescuing poxvirus (e.g., Copenhagen vaccinia virus, NYVAC, ALVAC, TROVAC, vP1170) and the identification of recombinants by in situ hybridization was as previously described (Piccini et al., 1987).

Development of ALVAC

The parental canarypox virus (Rentschler strain) is a vaccine strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988b). It is an attenuated vaccine strain useful in vaccination of day old chickens. The parental virus strain Duvette was obtained in France as a fowlpox scale from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

Development of NYVAC

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L—K1L) vP804; and (6) large subunit, ribonucleotide reductase (I4L) vP866 (NYVAC).

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Panicali et al., 1982; Perkus et al., 1989).

Construction of Plasmid DSD460 For Deletion of Thymidine Kinase Gene (J2R). Plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SSDI site.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:69/70)

```
                          SmaI
MPSYN43   5'      TAATTAACTAGCTACCCGGG      3'
MPSYN44   3' GTACATTAATTGATCGATGGGCCCTTAA   5'
             NlaIII                    EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:71/72)

```
          HindIII    SmaI
MPSYN45   5'  AGCTTCCCGGGTAAGTAATACGTCAAGGAGAAAACGAA
MPSYN46   3'       AGGGCCCATTCATTATGCAGTTCCTCTTTTGCTT NotI                    SspI
    ACGATCTGTAGTTAGCGGCCGCCTAATTAACTAAT   3'  MPSYN45
    TGCTAGACATCAATCGCCGGCGGATTAATTGATTA   5'  MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 as template and the complementary 20 mer oligonucleotide MPSYN47 SEQ ID NO:1 (5' TTAGT-TAATTAGGCGGCCGC 3') as primer. Recombinant virus vP410 was identified by plaque hybridization.

Construction of Plasmid pSD486 for Deletion of Hemorrhagic Region (B13R+B14R). Plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:73/74)

```
            ClaI         BamHI  HpaI
SD22mer  5' CGATTACTATGAAGGATCCGTT   3'
SD20mer  3'     TAATGATACTTCCTAGGCAA 5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:75/76)

```
            ClaI          SacI         XhoI         HpaI
SD42mer  5' CGATTACTAGATCTGAGCTCCCCGGGCTCGAGGGATCCGTT   3'
SD40mer  3'     TAATGATCTAGACTCGAGGGGCCCGAGCTCCCTAGGCAA 5'
                BglII          SmaI         BamHI
``` generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6 (SEQ ID NO:77/78)

```
        BamHI    EcoRI    HpaI
HEM5  5' GATCCGAATTCTAGCT    3'
HEM6  3'         GCTTAAGATCGA 5'
``` generating plasmid pSD486. pSD486 was used as donor plasmid for recombination with recombinant vaccinia virus vP533, generating vP553, which was isolated as a clear plaque in the presence of X-gal.

Construction of Plasmid yMP494Δ for deletion of ATI Region (A26L). Plasmid pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:79/80)

(pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the *E. coli* Beta-galactosidase gene (Shapira et al., 1983) under the control of the vaccinia 11 kDa promoter (Bertholet et al., 1985; Perkus et al., 1990) was inserted into the BalI site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:81) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Construction of Plasmid pSD467 for Deletion of Hemagalutinin Gene (A56R). Vaccinia SalI G restriction fragment (pos. 160,744–173,351) crosses the HindIII A/B junction (pos. 162,539). pSD419 contains vaccinia SalI G cloned into pUC8. Vaccinia sequences derived from HindIII B were removed by digestion of pSD419 with HindIII within vac-

```
       NdeI
ATI3 5' TATGAGTAACTTAACTCTTTTGTTAATTAAAAGTATATTCAAAAAATAAGT
ATI4 3'     ACTCATTGAATTGAGAAAACAATTAATTTTCATATAAGTTTTTTATTCA

BglII    EcoRI    HpaI
       TATATAAATAGATCTGAATTCGTT    3' ATI3
       ATATATTTATCTAGACTTAAGCAA    5' ATI4
``` reconstructing the region upstream from A26L and replacing the A26L ORF with a short polylinker region containing the restriction sites BglII, EcoRI and HpaI, as indicated above. The resulting plasmid was designated pSD485. Since the BhII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV cinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with Ea I (pos. 162,054) near the end of the gene. The 3.6 kb RsaI/EagI vector fragment from pSD456 was isolated and ligated with annealed synthetic oligonucleotides MPSYN59, MPSYN62, MPSYN60, and MPSYN61 (SEQ ID NO:82/83/84/85)

```
                    RsaI
MPSYN59  5' ACACGAATGATTTTCTAAAGTATTTGGAAAGTTTTATAGGT-
MPSYN62  3' TGTGCTTACTAAAAGATTTCATAAACCTTTCAAAATATCCA-

MPSYN59     AGTTGATAGAACAAAATACATAATTT 3'
MPSYN62     TCAACTATCT 5'

MPSYN60  5'                       TGTAAAAATAAATCACTTTTTATA-
MPSYN61  3' TGTTTTATGTATTAAAACATTTTTATTTAGTGAAAAATAT-
```

```
               -continued
          BglII   SmaI    PstI    EagI
MPSYN60   CTAAGATCTCCCGGGCTGCAGC              3'
MPSYN61   GATTCTAGAGGGCCCGACGTCGCCGG          5'
``` reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053].

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BalII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Construction of Plasmid DMPCSK1Δ for Deletion of Open Reading Frames [C7L-K1L]l. The following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L-K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide (SEQ ID NO:86)

```
                       BglII
MPSYN82  5' TTTCTGTATATTTGCACCAATTTAGATCTT-
            ACTCAAAATATGTAACAATA    3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L-K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide (SEQ ID NO:87) MPSYN233 5'-TGTCATTTAACACTATACTCATATTAA-TAAAAATAATATTTATT-3'. The resulting plasmid, pMPCSK1Δ, is deleted for vaccinia sequences positions 18,805–29,108, encompassing 12 vaccinia open reading frames [C7L-K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Construction of Plasmid DSD548 for deletion of Large Subunit, Ribonucleotide Reductase (I4L). Plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below.

To construct a vector plasmid to accept the left vaccinia flanking arm, pUC8 was cut with BamHI/EcoRI and ligated with annealed synthetic oligonucleotides 518A1/518A2 (SEQ ID NO:88/89)

```
              BamHI    RsaI
518A1    5'   GATCCTGAGTACTTTGTAATATAATGATATATATTTTCACTTTATCTCAT
518A2    3'         GACTCATGAAACATTATATTACTATATATAAAAGTGAAATAGAGTA

BglII      EcoRI
         TTGAGAATAAAAAGATCTTAGG              3'   518A1
         AACTCTTATTTTTCTAGAATCCTTAA          5'   518A2
``` forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:90/91)

```
              BamHI  BglII     SmaI
518B1    5'   GATCCAGATCTCCCGGGAAAAAAATTATTTAACTTTTCATTAATAG-
518B2    3'         GTCTAGAGGGCCCTTTTTTTAATAAATTGAAAAGTAATTATC-

RsaI     EcoRI
         GGATTTGACGTATGTAGCGTACTAGG           3'   518B1
         CCTAAACTGCATACTACGCATGATCCTTAA       5'   518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of the I4L coding sequences.

The right vaccinia flanking arm was isolated as a 0.6 kb EcoRI/BolII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC".

Serological reagents. The CSP repeat-specific mAb Pf2A10 was provided by Dr. R. Wirtz (WRAIR, Washington, D.C.). Mouse anti-PfSSP2 serum and the PfSSP2-specific mAb 88:10:161 were provided by Dr. W. Rogers (Naval Medical Research Institute (NMRI), Washington D.C.). Rabbit anti-LSA-1 serum was provided by Dr. D. Lanar (WRAIR, Washington, D.C.). Rabbit anti-gp195 (MSA-1) serum and the MSA-1-specific mAb CE2.1 were provided by Dr. S. Chang (University of Hawaii, Honolulu, Hi.). The MSA-1 specific mAb 3D3 was provided by Dr. J. Lyon (WRAIR, Washington, D.C.). Rabbit anti-p126 (SERA) serum and the SERA-specific mAb 23D5 were provided by Dr. P. Delplace (INSERM-U42, Villeneuve-D'Ascq, France). A pool of antimalaria human immunoglobulins from African donors with high antimalaria titers was used for the detection of AMA-1 (also detects MSP-1, SERA, and CSP) and was provided by Dr. M. Hommel (Liverpool School of Tropical Medicine, Liverpool, England). The Pfs25-specific mAb 4B7 was provided by Dr. D. Kaslow (NIAID, NIH).

Immunoprecipitation analysis of noxvirus-expressed P. falciparum antigens. Immunoprecipitations were performed essentially as described previously (Taylor et al. 1990). Briefly, HeLa or CEF cell monolayers were infected with vaccinia recombinants (or mock infected) at an moi of 10 PFU/cell. At one hour post infection, the inoculum was removed and replaced by methionine-free medium supplemented with $^{35}$S-methionine. At 8 hours post infection, cells were lysed under non-denaturing conditions by the addition of buffer A (Stephenson et al. 1979) and immunoprecipitation performed using appropriate serological reagents and protein A-Sepharose CL-4B (Pharmacia, Piscataway, N.J.) as described (Taylor et al. 1990). Immunoprecipitates were solubilized in Laemmli disrupting solution (Laemmli, 1970) prior to analysis by denaturing polyacrylamide gel electrophoresis and autoradiography.

Endoglycosidase Digestions of Vaccinia-expressed P. Falciparum Antigens. After immunoprecipitation, peptides from recombinant-infected Vero cells and culture supernatants were digested with endoglycosidase H (endo H) and glycopeptidase F (PNGase F) as described (Mason, 1989). The digested glycoproteins were subsequently analyzed by denaturing polyacrylamide gel electrophoresis.

Expression analysis by flow cytometry. Hela cells were infected with NYVAC-Pf7 (vP1209), NYVAC or appropriate control recombinants at a multiplicity of 5 pfu/cell for 16 hours. Unfixed infected cells were then stained by indirect methods using appropriate serological reagents. 10,000 live stained cells were evaluated for surface fluorescence with a FACScan flow cytometer (Becton Dickinson). Fluorescence was measured using logarithmic amplification after gating on forward-angle vs 900 light scatter to exclude dead cells and debris. Antibodies used for evaluation were: mAb Pf2A10 for CSP, rabbit anti-PfSSP2 for PfSSP2, rabbit anti-gp195 for MSA-1, a pooled human anti-malarial serum used to detect AMA-1, and mAb 4B7 for Pfs25. The control recombinants were the NYVAC parent, vP1190C (NYVAC-CSP), vP1189 (NYVAC-PfSSP2), vP924 (NYVAC-MSA1), vP1018 (NYVAC-AMA1), vP1085 (NYVAC-Pfs25).

Expression analysis by plaque immunoassay. Test and control recombinants were plated on CEF monolayers under agarose at dilutions calculated to result in about 50–80 plaques per 60 mm dish. After four days incubation at 37° C., the infected monolayers were processed by plaque immunoassay for detection of internal expression of malarial genes using the following sera: mAb Pf2A10 for CSP, mAb 88:10:161 for PfSSP2, mAb 3D3 for MSA-1, mAb 23D5 for SERA, mAb 4B7 for Pfs25. Briefly, agarose overlays were removed from the dishes, which were then washed with cold PBS. Monolayers were fixed with cold methanol and permeabilized with saponin in PBS (PBS-S). Dilutions of the primary antibodies were added to the appropriate plates, incubated at 37° C. for 30 minutes with gentle agitation, and washed extensively with PBS-S. Horseradish proxidase-conjugated rabbit anti-mouse serum was incubated with the monolayers for 30 minutes at 37° C. with gentle agitation, and washed extensively with PBS-S. Positive plaques were then visualized by adding HRP substrate and incubating for 5–30 minutes at room temperature. The reactions were then stopped by addition of water to each dish, which was subsequently aspirated and the dishes allowed to dry. Positive and negative plaques were then counted for test and control samples. In addition to NYVAC-Pf7 (vP1209), the following controls were evaluated: vP866 (NYVAC parent), vP1190C (NYVAC-CSP), vP1189 (NYVAC-PfSSP2), vP924 (NYVAC-MSA-1), vP1187 (NYVAC-SERA), vP1085 (NYVAC-Pfs25).

EXAMPLE 1

GENERATION OF SERA-CONTAINING VACCINIA VIRUS RECOMBINANT

Several lines of evidence suggest the importance of SERA in protective immunity to *P. falciparum*. Most importantly, immunization with purified SERA protein partially protects Saimiri monkeys from both heterologous and homologous challenge with blood stage parasites (Delplace et al., 1988; Perrin et al., 1984). Additionally, SERA-specific antisera and mAbs have been shown to inhibit parasite invasion and growth in vitro (Banyal and Inselburg, 1985; Delplace et al., 1985; Delplace et al., 1987; Perrin et al., 1984). SERA, and anti-SERA antibodies, are also found in immune complexes that form in vitro when schizonts rupture in the presence of immune serum (Chulay et al., 1987; Lyon et al., 1989). Because SERA is expressed during both the liver and blood stages of *P. falciparum* infection (Szarfman et al., 1988), it can be envisioned that vaccine-induced anti-SERA immunity may limit the spread of blood stage infection by acting on infected liver cells. These results have generated an interest in SERA as a potential vaccine candidate.

To this end, cDNA encoding SERA from the FCR3 *P. falciparum* strain was isolated and a vaccinia virus recombinant containing the SERA coding sequence was generated. The full length SERA precursor protein was expressed in cells infected with this recombinant and released into the culture medium.

Overlapping cDNA clones spanning the SERA coding sequence were isolated from the FCR3 strain of *Plasmodium falciparum*.

Referring now to FIG. 1, a schematic representation of the SERA coding sequence is shown below the scale. Dotted boxes represent the leader peptide (L), octamer repeat region (8-R), and serine repeat region (S-R). The shaded box delineates a KpnI/NdeI restriction fragment. The location of SERA cDNA clones is shown in relation to the coding sequence. The star (*) indicates the position of a point mutation in clone p126.8.

The p126.6 cDNA was isolated from the blood stage cDNA Lambda ZAPII cDNA library by hybridization to a SERA-specific oligonucleotide JAT2 (SEQ ID NO:92) (5'-GTCTCAGAACGTGTTCATGT-3'), which was derived from the 3' end of the SERA coding sequence (Bzik et al., 1988; Knapp et al., 1989). Clones derived from the 5' end of the SERA coding sequence were obtained by PCR with primers JAT15 (SEQ ID NO:93) (5'-CACGGATCCATGAAGTCATATATTTCCTT-3') and JAT16 (SEQ ID NO:94) (5'-GTGAAGCTTAATCCATAATCTTCAATAATT-3') and SERA first strand cDNA template (obtained with oligonucleotide primer JAT17 (SEQ ID NO:95) (5'-GTGAAGCTTTTATACATAACAGAAATAACA-3') and were cloned into pUC19. These 1923 bp cDNAs extend from the initiation codon to a point 31 bp 3' of the internal EcoRI site (position 1892). One such cDNA, p126.8, was found by DNA sequence analysis to contain a Taq polymerase error at nucleotide 1357. This error, an A to G substitution, resides within a 315 bp KonI/NdeI restriction fragment (FIG. 1). A second SERA 5' cDNA, p126.9, has no mutations within this KpnI/NdeI fragment. An unmutated 5' SERA CDNA was generated by replacing the 315 bp KpnI/NdeI fragment in p126.8 with the analogous fragment from p126.9 to generate p126.14. Full length SERA cDNA was generated by ligating the p126.14 5' cDNA as an XmaI/EcoRI fragment into a partial EcoRI/XmaI digested p126.6 vector fragment to generate p126.15 (FIG. 1).

The complete nucleotide sequence of the p126.15 SERA cDNA insert, as well as the predicted amino acid sequence, is shown in FIG. 2. This cDNA contains a 2955 bp open reading frame encoding 984 amino acids that is identical to the SERA allele II gene in the FCR3 strain and the FCBR SERA gene (Knapp et al., 1989; Li et al., 1989). The leader peptide is underlined, the octapeptide repeat region is underlined in bold and enclosed in brackets and the serine repeat region is highlighted in bold in FIG. 2.

A vaccinia donor plasmid was constructed by isolating SERA cDNA from p126.15 as a 3 Kb XmaI/EcoRV fragment and ligating the XmaI end into an XmaI/BalII digested pCOPCS-5H vector fragment. DNA polymerase I Klenow fragment was used to fill in the pCOPCS-5H BglII site which was subsequently ligated to the EcoRV end to generate p126.16. In this insertion plasmid, SERA is under the control of the early/late vaccinia H6 promoter (Rosel et al., 1986) and the insertion of this CDNA is directed to the site of a C7L-K1L deletion.

The p126.16 insertion vector was used as a donor plasmid to insert SERA into vaccinia virus by recombination. A SERA-containing recombinant was isolated, plaque purified, and amplified and the resultant virus designated vP870.

Immunoprecipitation analysis was performed on Vero cells infected at an moi of 10 PFU/cell and pulsed with $^{35}$S-methionine. Immunoprecipitated proteins were resolved by 10% SDS-PAGE and bands visualized by autoradiography. Expression of SERA by vP870 in Vero cells can be detected by immunoprecipitation with SERA-specific rabbit antiserum. At 8 hours post-infection, the anti-SERA reagent detects a high molecular weight SERA protein in the culture medium indicating that it is released from infected cells. This result is consistent with the absence of a putative hydrophobic transmembrane domain within the SERA coding sequence (Bzik et al., 1988; Knapp et al., 1989; Li et al., 1989). Smaller SERA-specific peptides remain cell-associated at this timepoint.

EXAMPLE 2

GENERATION OF ABRA-CONTAINING VACCINIA VIRUS RECOMBINANT

The functional role of ABRA in the parasite life cycle is unknown. Despite this, several studies suggest the importance of ABRA as a vaccine candidate. First, an ABRA-specific mAb inhibits the release of merozoites from rupturing schizonts and results in immune complex formation, thus preventing the spread of infection in vitro (Chulay et al., 1987). ABRA, and anti-ABRA antibodies, are also found in such immune complexes formed in vitro when schizonts rupture in the presence of immune serum (Chulay et al., 1987). Because ABRA is expressed during both the liver and blood stages of *P. falciparum* infection (Szarfman et al., 1988), it can be envisioned that vaccine-induced anti-ABRA immunity may limit the spread of blood stage infection by acting on infected liver cells. Finally, the apparent conservation of ABRA (Chulay et al., 1987; Stahl et al., 1986; Weber et al., 1988) suggests that immunity to this protein might confer protection against numerous isolates.

To this end, cDNA encoding ABRA from the FCR3 *P. falciparum* strain was isolated and a vaccinia virus recombinant containing the ABRA coding sequence was generated.

Full length ABRA cDNA was generated by PCR with ABRA-specific primers JAT32 (SEQ ID NO:96) (5'-CACGGATCCATGATGAACATGAAAATTGTTTTATTC-3') and JAT34 (SEQ ID NO:98) (5'-GTGCTCGAGTTATTTTTGATTCTTCAGTTGTCAA-3') and ABRA first strand cDNA template (obtained with primer JAT33 (SEQ ID NO:98) (5'-GTGCTCGAGGTTTAATTATTTTGATTCTTCAGTTG-3'). The amplified ABRA CDNA was flanked by BamHI and XhoI restriction sites due to their inclusion in primers JAT32 and JAT34, respectively. This allowed the cloning of ABRA as a BamHI/XhoI fragment into the vaccinia donor plasmid pCOPAK-H6. Clones containing ABRA cDNA derived from two independent PCRs were obtained to control for Tag polymerase errors. Two such clones are pABRA-2 and pABRA-4.

Complete nucleotide sequence analysis of pABRA-2 and pABRA-4 revealed one amino acid-altering Taa polymerase error each in pABRA-2 (at position 1580, an A insertion) and pABRA-4 (at position 140, a C for T substitution). Additionally, pABRA-4 contains a deletion of an A residue within a poly-A stretch beginning at position 583 of the insert. This deletion has been previously reported for a partial FCR3 strain ABRA cDNA clone (Weber et al., 1988).

A composite ABRA cDNA consisting of segments from the pABRA-2 and pABRA-4 inserts was derived in order to correct the deletion and polymerase errors. A 2460 bp NdeI fragment was isolated from pABRA-2 which extended from the internal ABRA NdeI site at position 1191, through the 5' end of the ABRA insert, to an NdeI site in the right flanking arm of pCOPAK H6. This fragment was inserted into pABRA-4, from which the 2460 bp NdeI fragment had been removed, to generate pABRA-8.

The complete nucleotide sequence of the pABRA-8 composite cDNA, as well as the predicted amino acid sequence, is shown in FIG. 3. This cDNA contains a 2223 bp open reading frame encoding 740 amino acids. The nucleotide and predicted amino acid sequences of the ABRA cDNA in pABRA-8 are shown. The leader peptide is underlined, the hexapeptide repeat region is underlined in bold and enclosed in brackets and the dipeptide/tripeptide repeat region is highlighted in bold and enclosed in brackets in FIG. 3.

The ABRA cDNA in the pABRA-8 insertion vector, which contains pCOPAK vector sequences, is under the control of the vaccinia H6 promoter (Rosel et al., 1986) and its insertion is directed to the ATI site.

The pABRA-8 insertion vector was used as a donor plasmid to insert ABRA into vaccinia virus by recombination. An ABRA-containing recombinant was isolated, plaque purified, and amplified and the resultant virus designated vP947.

EXAMPLE 3

GENERATION OF Pfhsp70-CONTAINING VACCINIA VIRUS RECOMBINANT

Several studies suggest the importance of Pfhsp70 as a potential vaccine candidate. First, immunization of Saimiri monkeys with a protein fraction containing Pfhsp70 results in partial protection from homologous challenge with blood stage parasites (Dubois et al., 1984). This protection correlates with the development of antibodies against Pfhsp70, as well as a 90 kD parasite protein, in vaccinated monkeys (Dubois et al., 1984; Jendoubi and Pereira da Silva, 1987). Also, Pfhsp70 expressed on the surface of infected mouse hepatocytes is a target for antibody-dependent cell-mediated cytotoxic mechanisms carried out by both spleen cells and nonparenchymal liver cells (Renia et al., 1990). Thus, it can be envisioned that anti-Pfhsp70 antibodies induced by vaccination could act to limit Plasmodium infection by acting at the liver stage via this mechanism. Additionally, in studies of humans exposed to *P. falciparum*, both specific antibodies and lymphocyte responsiveness to Pfhsp70 have been detected which indicates that this protein is an immune target during natural Plasmodium infections (Kumar et al., 1990). Finally, although the similarity among *P. falciparum* and other mammalian heat shock proteins raises the possibility of autoimmune complications (Mattei et al., 1989), results with vaccinated monkeys indicate that their humoral immune responses are preferentially directed against non-conserved regions of Pfhsp70 (Blisnick et al., 1988).

A partial cDNA encoding the carboxy terminus of Pfhsp70 from the FCR3 *P. falciparum* strain was isolated and a vaccinia recombinant that expresses this cDNA was generated.

Partial Pfhsp70 cDNA clones were isolated from the lambda ZAPII blood stage cDNA library by hybridization to the Pfhsp70 -specific oligonucleotide HSP3 (SEQ ID NO:99) (5'-CCAGGAGGTATGCCCGGAGCAGG-3'), which is derived from the 3' end of the Pfhsp70 coding sequence (Ardeshir et al., 1987; Bianco et al., 1986). One clone, designated pHSP70.2, contains the 3' 966 bp of Pfhsp70 as compared to the full length Pfhsp70 coding sequence (Yang et al., 1987). Other partial Pfhsp70 cDNAs that were obtained are identical to pHSP70.2.

The nucleotide sequence of the partial Pfhsp70 cDNA in plasmid pHSP70.2 is shown along with the predicted amino acid sequence in FIG. 4. The GGMP repeats are underlined in bold and enclosed in brackets in FIG. 4.

This cDNA contains a 948 bp open reading frame encoding 315 amino acids that is almost identical to the analogous region of the complete FCR3 strain Pfhsp70 gene published previously (Yang et al., 1987). Two single nucleotide substitutions are found in the partial clone (nucleotide position 828-G for C, position 844-G for A) that result in amino acid substitutions (Met for Ile and Gly for Ser, respectively). The partial cDNA is also almost identical to two published partial Pfhsp70 cDNAs from the FC27 and Honduras 1 strains (Ardeshir et al., 1987; Bianco et al., 1986) with two exceptions. The pHSP70.2 insert contains an extra copy of a four amino acid repeat unit at the 3'end of the coding sequence and an ATT to GAA substitution starting at nucleotide 712 of the insert.

To generate a Pfhsp70-containing vaccinia insertion vector, the Pfhsp70 partial cDNA was first placed under the control of the vaccinia H6 promoter. pHSP70.2 was digested with EcoRI, the restriction site filled in with DNA polymerase I Klenow fragment, and further digested with XhoI to liberate the Pfhsp70 cDNA. This fragment was ligated into plasmid pHES3 which was previously digested with BamHI, treated with Klenow fragment, and digested with XhoI. The resulting plasmid, pHSP70.3, contained the Pfhsp70 partial cDNA coupled to the H6 promoter and inserted in frame to an ATG initiation codon provided by the pHES3 vector. This construction introduced four amino acids between the initiator Met and the first amino acid of Pfhsp70-Gly (G), Asp (D), Gln (Q), Phe (F).

A vaccinia insertion vector was next constructed with the pCOPAK plasmid such that the H6 promoted partial Pfhsp70 cDNA could be inserted into vaccinia at the ATI site (replacing open reading frames A25L and A26L, see reference Goebel et al., 1990). First, an approximately 1 Kb NruI/XhoI fragment was isolated from pHSP70.3. This fragment, which contains the 3' 24 bp of the H6 promoter and the Pfhsp70 cDNA, was ligated to pCOPAK-H6-0 digested with NruI and XhoI, which contains the remainder of H6. The resulting plasmid, pHSP70.4, contains the full length H6 promoter linked to the Pfhsp70 partial cDNA in the pCOPAK insertion vector.

The pHSP70.4 insertion vector was used as a donor plasmid to insert the partial Pfhsp70 cDNA into vaccinia virus by recombination. A Pfhsp70-containing recombinant was isolated, plaque purified, and amplified and the resultant virus designated vP905.

Immunoprecipitation analysis was performed on Vero cells infected at an moi of 10 PFU/cell and pulsed with $^{35}$S-methionine. At 8 hours post infection, cell lysates were harvested and immunoprecipitated with human antimalaria immunoglobulins. Immunoprecipitated proteins were resolved by 10% SDS-PAGE and bands visualized by autoradiography. The antimalaria human immunoglobulins specifically immunoprecipitate a peptide of approximately 32 kD from lysates of vP905-infected Vero cells. The size of this peptide is consistent with the size of the partial Pfhsp70 cDNA contained in vP905.

EXAMPLE 4

ISOLATION OF AMA-1 GENE

The complete AMA-1 gene from the *Plasmodium falciparum* 3D7 clone was isolated and its nucleotide sequence was determined.

The complete AMA-1 gene was generated by PCR with two AMA-1 specific oligonucleotides and 3D7 genomic DNA as template. The AMA-1 specific sequences of the two oligonucleotides were derived from the PF83 Camp sequence (Thomas et al., 1990). The exact composition of the two oligonucleotides was as follows:

```
CO14   (SEQ ID NO:100):  TAATCATGAGAAAATTATACTGCG
       (SEQ ID NO:100):       M  R  K  L  C  V

CO15   (SEQ ID NO:101):  TGAGGATCCATAAAAATTAATAGTATGGTTTTTCCATC
                              BamHI                Stop
```

The PCR reaction was processed in a Thermal Cycler (Perkin Elmer Cetus, Norwalk, Conn.) with 40 cycles at 94° C. for 1 minute, 42° C. for 1.5 minutes, and 72° C. for 3 minutes, and a final extension step at 72° C. for 5 minutes. The PCR product was purified, digested with BamHI and cloned into the HpaI/BamHI plasmid pMPI3H.

The complete nucleotide sequence was determined using customized oligonucleotides. Two independent clones were sequenced and when differences were found a third clone was sequenced. The complete nucleotide and corresponding amino acid sequences are presented FIG. 5.

EXAMPLE 5

MALARIA RECOMBINANT POXVIRUS VACCINES

Recombinant poxviruses containing, in a nonessential region thereof, DNA from Plasmodium provide advantages as vaccines for inducing an immunological response in a host animal. One can readily appreciate that a variety of foreign genes from Plasmodium can be utilized in the recombinant poxvirus vectors. Moreover, one can readily appreciate that the recombinant poxviruses can contain DNA coding for and expressing two or more Plasmodium genes. Furthermore, one can readily appreciate that additional poxviruses beyond those cited in this application, for example avipox and canarypox viruses, can be utilized as malaria recombinant poxvirus vaccine vectors.

Recombinant vaccines coding for and expressing Plasmodium antigens having demonstrated protection in primate model systems, expression during blood and liver stages, in vitro neutralization of parasite growth and/or infectivity by specific serological reagents would be advantageous candidates for inducing an immunological response in a host animal. Conservation of amino acid sequences of the antigens of interest among isolates and strains may also be advantageously taken into account.

EXAMPLE 6

MODIFICATIONS OF SERA GENE

SERA. We have previously derived a SERA-containing vaccinia recombinant designated vP870 (Example 1). This recombinant contains full length SERA cDNA from the FCR3 isolate regulated by the vaccinia H6 promotor and inserted at the site of a C6L-K1L deletion. Immunoprecipitation studies have demonstrated that a SERA peptide of 136 kD is secreted from vP870-infected Vero cells. A series of intracellular SERA peptides of 135, 122, and 110 kD are also expressed in such cells. We have also further characterized the expression of SERA by vP870 (see Examples 7 and 8, below).

In addition to expressing SERA promoted by H6, we have also generated modified SERA constructs promoted by the entomopox 42K promotor, which are described here.

Linkage with 42K entomopox promotor and modification of 3' end. The 3' end of the SERA cDNA was modified to place a vaccinia early transcription termination signal ($T_5NT$) and a series of restriction sites (XhoI, SmaI, SacI) immediately after the TAA termination codon. This was accomplished by PCR with oligonucleotides JAT51 (SEQ ID NO:103) (5'-TAGAATCTGCAGGAACTTCAA-3'), JAT52 (SEQ ID NO:104) (5'-CTACACGAGCTCCCGGG-CTCGAGATAAAAATTATACATAACAGAAATAACATTC-3'), and plasmid p126.16 (Example 1) as template. The resulting ~300 bp amplified fragment was cloned as a PstI/SacI fragment into p126.16 digested with PstI and SacI to generate p126.17.

The 5' end of the SERA CDNA in p126.17 was modified to place several restriction sites (HindIII, SmaI, BamHI) and the 42K entomopox promotor before the ATG initiation codon. This was accomplished by PCR with oligonucleotides JAT53 (SEQ ID NO:105) (5'-CTAGAGAAGCTTCCCGGGATCCTCAAAA-TTGAAAATATATAATTACAATATAAAATGAAGTC ATATATTTCCTTGT-3'), JAT54 (SEQ ID NO:106) (5'-ACTTCCGGGTTGACTTGCT-3'), and plasmid p126.16 as template. The resulting ~250 bp amplified fragment was cloned as a HindIII/HindII fragment into p126.17 digested with HindIII and HindII to generate p126.18. This plasmid contains a cassette consisting of the SERA cDNA controlled by the 42K entomopox promotor, with a vaccinia early transcription termination signal, and flanked by restriction sites at the 5' (HindIII, SmaI, BamHI) and 3' (XhoI, SmaI, SacI) ends.

Generation of a donor plasmid for insertion of SERA at the ATI site. The 42K promotor/SERA cassette was isolated from p126.18 as a BamHI/XhoI fragment and cloned into a BamHI/XhoI digested pSD553 vector fragment. The resulting plasmid, designated p126.ATI, targets the insertion of 42K/SERA into the ATI site.

Construction of an ATI donor plasmid containing serine-repeatless SERA cDNA. A SERA cDNA lacking the serine repeat region was derived by replacing a 354 bp SpeI/PflMI fragment of SERA, which contains the repeats, with an analogous PCR generated fragment from which the serine repeats have been precisely deleted. This deleted fragment was derived by PCR with primers JPW14126 (SEQ ID NO:107) (5'-GGCTATCCATCAAATGGTACAACTGGT-GAACAAGAAAGTCTTCCTGCTAATGGAC CTGATTCCCC-3'), JPW15126 (SEQ ID NO:108) (5'-TAGTATACTAGTAAATGGGGT-3'), and plasmid p126.ATI as template. The resulting fragment was digested with SpeI/PflMI and cloned into an SpeI/PflMI digested p126.ATI vector fragment to generate p126.RPLS. This donor plasmid directs the insertion of the 42K/SERA serine-repeatless cassette at the ATI site.

Construction of a SERA CDNA containing a transmembrane anchor. A hybrid SERA gene was generated which contains the SERA coding sequence linked to the transmembrane anchor sequence of Epstein-Barr virus gp340. A 2780 bp SmaI/PstI 42K/truncated SERA fragment (lacking the 3' 279 bp of the coding sequence), a 130 bp PstI/BglII EBV gp340 transmembrane anchor fragment, and a SmaI/BamHI digested vector fragment were ligated to generate pINT126/ anchor. This plasmid contains the gp340 transmembrane domain linked to the truncated SERA sequence. The full length SERA coding sequence was then regenerated by inserting a PCR-generated 3' SERA fragment between the truncated SERA sequence and the gp340 anchor. The 3' fragment was amplified with primers PstI26 (SEQ ID NO:109) (5'-GCATTAGAATCTGCAGGAAC-3'), SacI26 (SEQ ID NO:110) (5'-TTGTCAGTACTGCAGGAGCT-CTACATAACAGAAATAACATTCG-3'), and plasmid p126.18 as template. This primer pair replaces the TAA termination codon with SacI and PstI sites, which add the amino acids Glu and Leu between the end of the SERA coding sequence and the gp340 transmembrane domain. The amplified fragment was then digested with PstI and cloned into PstI-digested pINT126/anchor to generate p126/anchor-1. This plasmid contains, under the control of the entomopox 42K promotor, the full length SERA coding sequence linked to the EBV gp340 transmembrane domain and targets insertion to the ATI site.

Generation of SERA-containing vaccinia recombinants. The SERA-containing donor plasmids described above were used to insert the various forms of SERA into the ATI site of NYVAC (+KIL) by recombination. The p126.ATI donor plasmid was used to generate vP1039 (42K/SERA), p126.RPLS to generate vP1040 (42K/SERA, serine-repeatless), and p126/anchor-1 to generate vP1023 (42K/ SERA+EBV gp340 anchor).

EXAMPLE 7

EXPRESSION OF SERA BY VACCINIA RECONBINANTS

Glycosylation and biosynthesis of vP870-expressed SERA. The expression of intracellular SERA peptides of 135, 122, and 110 kD and a 136 kD secreted SERA peptide by vP870 (H6/SERA) has been described previously. We have performed additional studies to further characterize SERA expression by vP870. Pulse-chase studies suggest that the smaller MW intracellular polypeptides are biosynthetic intermediates of SERA because the size of these smaller peptides increases during chase, eventually resulting in secretion. It has been implied that SERA expressed by parasites is not glycosylated, although this has not been rigorously examined. Both secreted and intracellular vP870-expressed SERA peptides are glycosylated, as determined by endoglycosidase digestion. However, the nature of N-linked sugars differs in that intracellular SERA contains only simple N-linked oligosaccharides whereas the N-linked carbohydrates on secreted SERA have been converted to complex form.

SERA expression by vP1039, vP1040, and vP1023. The expression of SERA by vP1039 (42K/SERA) is equivalent to that of vP870 (H6/SERA) as detected by immunoprecipitation with SERA-specific rabbit antiserum. vP1040 (42K/ SERA, serine-repeatless) expresses secreted and intracellular SERA peptides of 126 and 124 kD, respectively. vP1023 (42K/SERA+anchor) expresses intracellular SERA peptides equivalent to those expressed by vP870 but no secreted SERA is produced, consistent with the inclusion of the gp340 transmembrane domain in this construct.

EXAMPLE 8

IMMUNOGENICITY OF VACCINIA-EXPRESBED SERA

Rabbits were immunized with vP870 (H6/SERA) and their sera had been analyzed. Rabbit anti-vP870 sera reacts with parasitized erythrocytes by immunofluorescence analysis in a manner that is indistinguishable from anti-SERA reagents. The rabbit sera also immunoprecipitates authentic 126 kD SERA precursor and reacts with the authentic SERA precursor and processed SERA fragments of 73 kD and 50 kD by Western analysis. These studies indicate that when expressed by vaccinia virus. SERA can stimulate humoral immunity in rabbits that is reactive with SERA derived from blood stage parasites and further that the glycosylation of SERA does not impair the immune response to this protein.

EXAMPLE 9

GENERATION OF A DONOR PLASMID FOR INSERTION OF AMA-1 AT THE HA SITE

The complete AMA-1 gene from the NF54/3D7 clone was isolated by PCR. The amplified PCR fragment was cloned into vector pMPI3H, which placed AMA-1 under the control of the vaccinia I3L promotor, to generate p731AMA-1. The complete AMA-1 nucleotide sequence was determined, and has been presented previously (see Example 4).

The I3L/AMA-1 cassette was isolated from p731AMA-1 as a 2,000 bp HindIII/RamHI fragment and cloned into a HindIII/RamHI-digested pSD544 vector fragment. The resulting plasmid, designated p544AMA-1, targets the insertion of I3L/AMA-1 into the HA site.

EXAMPLE 10

GENERATION OF AN AMA-1-CONTAINING VACCINIA RECOMBINANT

The p544AMA-1 donor plasmid was used to insert I3L/AMA-1 into the HA site of NYVAC by recombination. The resulting vaccinia recombinant was designated vP1018.

EXAMPLE 11

EXPRESSION OF AMA-1 BY VP1018

The expression of AMA-1 on the surface of vP1018-infected cells was demonstrated by immunofluorescence analysis with a pool of human anti-malarial Igs. This reagent also immunoprecipitated a cell associated protein of approximately 83 kD from vP1018-infected MRC-5 cells. Interestingly, an AMA-1 peptide of ~90 kD was released from infected cells.

EXAMPLE 12

GENERATION OF AN ABRA-CONTAINING VACCINIA RECOMBINANT

An ABRA-containing vaccinia recombinant designated vP947 (see Example 2) contains vaccinia H6-promoted ABRA cDNA from the FCR3 isolate inserted at the ATI site of NYVAC (+K1L).

The pABRA-8 donor plasmid (see Example 2) was used to insert H6/ABRA into the ATI site of NYVAC (+K1L) by recombination. The resulting vaccinia recombinant was designated vP1052.

EXAMPLE 13

EXPRESSION OF ABRA BY vP947 AND vP1052

The expression of ABRA in vP947 and vP1052-infected cells was demonstrated by immunofluorescence with the ABRA-specific mAb 3D5 (provided by WRAIR). However, no product was detected by immunoprecipitation with this antibody. Analysis of transient expression from the pABRA-8 donor plasmid in NYVAC-infected cells suggests that ABRA is being expressed by the donor plasmid as detected by immunofluorescence analysis and immunoprecipitation with mAb 3D5.

EXAMPLE 14

AMPLIFICATION AND CLONING OF Pfs25

The Pfs25 gene from NF54/3D7 in plasmid pNF4.13 (Kaslow et al., 1988) was amplified by PCR with the Pfs25-specific primers JAT61 (SEQ ID NO:111) (5'-TAATCATGAATAAACTTTACAGTTTG-3'), JAT62 (SEQ ID NO:112) (5'-GGATCCTCGAGCTGCAGATCTATAAA-AATTACATTATAAAAAGCATAC-3'), and plasmid pNF4.13 as template. The ~650 bp amplified fragment, with a 5' blunt end, was digested with PstI and cloned into a HpaI/PstI-digested pMPI3H vector fragment. The resulting plasmid, pPfs25.1, contains the Pfs25 coding sequence linked to the vaccinia I3L promotor. Sequence analysis was performed to ensure that no Taq polymerase errors were introduced during amplification.

EXAMPLE 15

GENERATION OF A DONOR PLASMID FOR INSERTION OF Pfs25 AT THE I4L SITE

The I3L/Pfs25 cassette was isolated from pPfs25.1 as a 750 bp blunt/BClII fragment and cloned into a SmaI/BpIII-digested pSD550 vector fragment. The resulting donor plasmid, pPfs25.2, targets insertion of I3L/Pfs25 into the I4L site.

EXAMPLE 16

GENERATION OF A Pfs25-CONTAINING VACCINIA RECOMBINANT

The pPfs25.2 donor plasmid was used to insert I3L/Pfs25 into the I4L site of NYVAC by recombination. The resulting vaccinia recombinant was designated vP1085.

EXAMPLE 17

EXPRESSION OF Pfs25 BY vP1085

The expression of Pfs25 on the surface of vP1085-infected cells was demonstrated by immunofluorescence analysis with the Pfs25-specific mAb 4B7. This surface expression is consistent with the presence of a hydrophobic transmembrane domain in Pfs25. Two Pfs25 peptides of 25 and 28 kD were expressed in vP1085-infected cells as detected by immunoprecipitation with 4B7.

EXAMPLE 18

AMPLIFICATION AND CLONING Of Pfs16

The complete Pfs16 gene was generated by PCR using *P. falciparum* NF54 clone 3D7 genomic DNA as template and the Pfs16 specific oligonucleotides C040 (SEQ ID NO:113) (5'-TAATCATGAATATTCGAAAGTTC-3') and C041 (SEQ ID NO:114) (5'-GCGAATTCATAAAAATTAAGAATCATCTCCTTC-3'), which were derived from the NF54 sequence (Moelans et al., 1991a), as primers. The ~500 bp amplified fragment, with a 5' blunt end, was digested with EcoRI and cloned into a HpaI/EcoRI-digested pMPI3H vector fragment. The resulting plasmid, pPfs16.1, contains the Pfs16 coding sequence linked to the vaccinia I3L promotor. The amplified NF54/3D7 Pfs16 sequence is identical to the published NF54 sequence (Moelans et al., 1991a).

EXAMPLE 19

GENERATION OF A DONOR PLASMID FOR INSERTION OF Pfs16 AT THE TK SITE

The I3L/Pfs16 cassette was isolated from pPfs16.1 as a 600 bp blunt-ended fragment (HindIII/EcoRI digestion followed by Klenow fill-in) and cloned into a HincII-digested pSD542 vector fragment. The resulting donor plasmid, pPfs16.2, targets insertion of I3L/Pfs16 into the TK site.

EXAMPLE 20

GENERATION OF A Pfs16-CONTAINING VACCINIA RECOMBINANT

The pPfs16.2 donor plasmid was used to insert I3L/Pfs16 into the TK site of NYVAC by recombination. Purified recombinants were isolated and designated H3xx1, H3xx2, H3xx3, and H3xx4.

EXAMPLE 21

EXPRESSION ANALYSIS OF Pfs16-CONTAINING RECOMBINANTS

The pool of human anti-malarial Igs did not detect Pfs16 expression in H3xx4-infected cells by immunofluorescence analysis. Pfs16 expression was also not detected with this serum by immunoprecipitation analysis of cells infected with H3xx1, H3xx2, H3xx3, and H3xx4. Although this human serum contains antibodies reactive with vaccinia-expressed MSA-1, SERA, and AMA-1, it may not contain antibodies to Pfs16.

EXAMPLE 22

CLONING OF THE CS GENE

A CS construct derived from the 3D7 clone of the NF54 *P. falciparum* isolate (provided by Dr. D. Lanar, WRAIR) differs from the published CS sequence of NF54 (Caspers et al., 1989) in that nine repeat units have been deleted (repeats #20–28) and a base change from C to T at position 1199 results in an amino acid change from Ser to Phe. In the plasmid containing this construct, pCOPCS-6H-CS, CS is linked to the vaccinia H6 promotor.

Modification of a vaccinia early transcription termination signal. This CS sequence contained a vaccinia early transcription termination signal ($T_5NT$) located near the 5' end of the coding sequence. PCR was used to modify this termination signal without altering the amino acid sequence. A fragment of ~160 bp was amplified with pCOPCS-6H-CS as template and primers H6.5 (SEQ ID NO:115) (5'-GAAAGCTTCTTTATTCTATAC-3') and CS.5 (SEQ ID NO:116) (5'-CCTCAACAAATAGGAAGGAAG-3'). This fragment extends from the 5' end of the H6 promotor (and introduces a HindIII site for cloning) to a HaeIII site located 3' of the transcriptional termination signal and has an altered nucleotide sequence which eliminates that signal without changing the amino acid sequence. After digestion with HindIII, this HindIII/HaeIII fragment was ligated with a 1,058 bp HaeIII/KpnI fragment containing the remainder of the CS coding sequence and a HindIII/KpnI-digested pIBI25 (International Biotechnologies, Inc., New Haven, Conn.) vector fragment. The resulting plasmid, designated pIBI25-CS, contains the full length CS gene linked to the H6 promotor.

Generation of a donor plasmid for insertion of CS into vaccinia. A 1,100 bp NruI/KpnI fragment was isolated from pIBI25-CS which contained the 3' end of the H6 promotor linked to the CS coding sequence. This fragment was cloned into an NruI/KpnI-digested pCOPCS-5H vector fragment. The resulting donor plasmid, pCOPCS-CS, contains the regenerated H6 promotor linked to CS and targets insertion to the site of a C7L-K1L deletion.

EXAMPLE 23

MODIFICATION OF THE CS CODING SEQUENCE

Derivation of a leader-minus CS construct. A CS construct lacking the N-terminal leader sequence was derived to determine if the expected alteration of intracellular transport would affect the induction of immunological responses to CS. Prior to removal of the leader sequence, the H6/CS cassette was subcloned from p542MLF-CS (H6/CS cassette cloned as a BamHI/gIII fragment in the BamHI site of pSD542) as a PstI/SalI fragment into pIBI24 (International Biotechnologies, Inc., New Haven, Conn.) to generate pMLF-CS.24. The leader sequence was then deleted by removing an ~110 bp NruI/BstXI fragment from pMLF-CS.24, within which the leader sequence is located, and replacing this fragment with an analogous NruI/BstXI fragment that contains a precise deletion of the leader sequence. This "deleted" fragment was derived by annealing oligonucleotides NruMLFCS (SEQ ID NO:117) (5'-GATTATCGCGATATCCGTTAAGTTTG-TATCGTAATGCAGGAATACCAGTGCTATGGAAGTTCGTCAAAC-3') and NruMFCSR (SEQ ID NO:118) (5'-GTTTGACGAACTTCCATAGCACTGGTAT-TCCTGCATTACGATACAAACTTAACGGATATCGCGATAATC-3') followed by digestion with NruI and BstXI. The resulting plasmid, pMLFCS.2.24, contains a leader-minus CS gene linked to H6.

Generation of a donor plasmid for insertion of leader-minus CS into vaccinia. A 1,040 bp NruI/KpnI fragment was isolated from pMLFCS.2.24 which contained the 3' end of the H6 promotor linked to the leader-minus CS coding sequence. This fragment was cloned into an NruI/KpnI-digested pCOPCS-5H vector fragment. The resulting donor plasmid, pMLF-CS.3, contains the regenerated H6 promotor linked to leader-minus CS and targets insertion to the site of a C7L–K1L deletion.

EXAMPLE 24

GENERATION OF CS-CONTAINING VACCINIA RECOMBINANTS

The CS-containing donor plasmids described above were used to insert CS at the site of a C7L–K1L deletion in vP668 by recombination. The pCOPCS-CS donor plasmid was used to generate vP868 (H6/CS) and pMLF-CS.3 to generate vP1056 (H6/leader-minus CS).

EXAMPLE 25

EXPRESSION OF CS BY vPB68 AND vP1056

The expression of CS by vP868 was demonstrated by both immunofluorescence and immunoprecipitation. CS was expressed on the surface of vP868-infected Vero cells as determined by immunofluorescence analysis with rabbit anti-CS repeat and anti-repeatless CS serum. The anti-repeatless sera detects two CS proteins of 60 and 56 kD by immunoprecipitation of vP868-infected Vero cell lysates. The expression of a doublet is consistent with the results of others who have expressed CS from vaccinia (Cheng et al., 1986). A doublet was also detected by immunoprecipitation of vP1056-infected cell lysates. However, the molecular weights of these peptides are slightly smaller than those expressed by vP868 (58.5 and 54.5 kD versus 60 and 56 kD, respectively).

EXAMPLE 26

IMMUNOGENICITY OF VACCINIA-EXPRESSED CS

To study the immunogenicity of vaccinia-expressed CS, two rabbits were immunized intradermally with $10^8$ PFU of vP868 and boosted with the same dose at 3, 6, and 9 weeks post-inoculation. ELISA titers to CS peptides derived from NF54/3D7 that correspond to the repeat region and unique sequences in the flanking nonrepetitive regions were determined. Immunization of rabbits with vP868 induces antibodies to both the repeats and the flanking regions, although the response was not as strong to the flanking regions as to the repeats.

Primary T cell responses were studied by injecting vP868 into mice and analyzing in vitro proliferation with a peptide corresponding to amino acids 368–390 of CS. A significant T cell proliferative response was detected with spleen cells harvested 7 days after inoculation.

Studies performed with T-cells from humans immunized with irradiated sporozoites and protected from sporozoite challenge demonstrated that cells infected with vP868 can stimulate CS-specific cytotoxic T-cells in vitro and also can serve as targets for such CTLs.

EXAMPLE 27

VACCINIA RECOMBINANTS CONTAINING MULTIPLE P. FALCIPARUM GENES CS AND SERA Generation of CS/SERA-containing TK donor plasmid.

To generate a donor plasmid containing both CS and SERA, the 42K/SERA cassette was isolated from p126.18 (see above) as a 3,000 bp BamHI/XhoI fragment and cloned into a BamHI/XhoI-digested p542MLF-CS (see above) vector fragment. The resulting donor plasmid, p126/CS-TK2, contains 42K/SERA and H6/CS (promoters positioned "head-to-head," with opposite transcriptional orientations) and directs insertion to the vaccinia TK site.

Generation of CS/SERA double recombinant. The p126/CS-TK2 donor plasmid was used to insert 42K/SERA and H6/CS at the TK site of NYVAC by recombination. The resulting vaccinia recombinant was designated vP1007.

Expression of CS and SERA by vP1007. The expression of both SERA and CS in vP1007-infected cells was demonstrated by immunoprecipitation with SERA-specific rabbit serum and anti-repeatless CS serum, respectively, and was equivalent to that observed with the appropriate single recombinants.

Immunization of rabbits with vP1007. Two rabbits were immunized subcutaneously with $10^8$ PFU of vP1007 and boosted with the same dose at 3, 6, and 9 weeks post-inoculation. Serum was collected prior to immunization and every week thereafter beginning at week 2 through week 12.

EXAMPLE 28

ALVAC RECOMBINANTS CONTAINING P. FALCIPARUM GENES CS, Pfs25, SERA, Pfs16, and AMA-1

Construction of a donor plasmid for insertion of CS at the C5 site. A 1,100 bp NruI/KpnI fragment was isolated from pCOPCS-CS which contained the 3' end of the H6 promotor linked to the CS coding sequence. This fragment was cloned into an NruI/KpnI-digested pNVQH6C5SP-18 vector fragment. The resulting donor plasmid, pMLF-CS.4, contains the regenerated H6 promotor linked to CS and targets insertion to the C5 site.

Generation of a CS-containing ALVAC recombinant. The pMLF-CS.4 donor plasmid was used to insert H6/CS into the C5 site of ALVAC (canarypox CPpp having attenuated virulence) by recombination. The isolation and purification of the ALVAC recombinant (vCP182) shows that it contains the gene. Expression of CSP by vCP182 was demonstrated by immunoprecipitation.

Construction of a donor plasmid for insertion of Pfs25 at the C5 site. An I3L/Pfs25 cassette was isolated from pPfs25.1 as a 750 bp BamHI/BglII fragment and cloned into a BamHI-digested pNC5LSP-5 vector fragment. The resulting donor plasmid, pPfs25.3, targets insertion of I3L/Pfs25 into the C5 site.

Generation of a Pfs25-containing ALVAC recombinant. The pPfs25.3 donor plasmid was used to insert I3L/Pfs25 into the C5 site of ALVAC by recombination. The isolation and purification of the ALVAC recombinant (vCP179) shows that it contains the gene. Expression of Pfs25 by vCP179 was demonstrated by immunoprecipitation.

Construction of a donor plasmid for insertion of SERA at the C3 site. A 42K/SERA cassette was isolated from p126.ATI as a BamHI/XhoI fragment and cloned into a BamHI/XhoI-digested pVQCP3L vector fragment. The resulting donor plasmid, p126.C3, targets insertion of 42K/SERA into the C3 site.

Generation of a SERA-containing ALVAC recombinant. The p126.C3 donor plasmid was used to insert 42K/SERA into the C3 site of ALVAC by recombination. The isolation and purification of the ALVAC recombinant (vCP185) shows that it contains the gene. Expression of a secreted SERA protein by vCP185 was demonstrated by immunoprecipitation.

Construction of a donor plasmid for insertion of Pfs16 at the C3 site. An I3L/Pfs16 cassette was isolated from pPfs16.2 as a XhoI/BamHI fragment and cloned into a XhoI/BamHI-digested pVQCP3L vector fragment. The resulting donor plasmid, pPfs16.C3, targets insertion of I3L/Pfs16 at the C3 site.

Generation of Pfs16-containing ALVAC recombinant. The pPfs16.C3 donor plasmid is used to insert I3L/Pfs16 into the C3 site of ALVAC by recombination. The isolation and purification of the ALVAC recombinant (vCP196) shows that it contains the gene.

Construction of a donor plasmid for insertion of AMA-1 at the C6 site. An I3L/AMA-1 cassette was isolated from p731AMA-1 as a 2,000 bp blunt-ended fragment (HindIII digestion followed by Klenow fill-in and SmaI digestion) and cloned into a SmaI-digested pC6L vector fragment. The resulting plasmid, designated pC6AMA-1, targets the insertion of I3L/AMA-1 at the C6 site.

Generation of AMA-1-containing ALVAC recombinant. The pC6AMA-1 donor plasmid is used to insert I3L/AMA-1 into the C6 site of ALVAC by recombination. The isolation and purification of the ALVAC recombinant (vCP198) shows that it contains the gene. Expression of AMA-1 by vCP198 was demonstrated by immunoprecipitation.

EXAMPLE 29

INSERTION OF THE MSA-1 GENE INTO NYVAC TO GENERATE vP924

Cloning of the MSA-1 gene. Four plasmids whose inserts comprise the complete coding sequence of the MSA-1 gene from the *P. falciparum* Uganda Palo-Alto (FUP) isolate were provided by Dr. S. Chang (University of Hawaii). The MSA-1 open reading frame is 5181 nucleotides long and codes for a 1726 amino acid protein (In all descriptions of manipulations of *P. falciparum* genes, the adenine residue of the initiation codon is designated as nucleotide 1 and the first methionine residue as amino acid 1). These four clones have been described and characterized previously (Chang et al., 1988). Plasmid 3-1 contains an MSA-1 insert which extends from an EcoRI site in the 5' noncoding region of MSA-1 to an EcoRI site at position 3306. Plasmid 10-1 contains an MSA-1 insert extending from the EcoRI site at position 3306 to a second EcoRI site at position 4263. Plasmid 18-1a contains an MSA-1 insert extending from the EcoRI site at position 4263 to a PstI site at position 5113. Plasmid 18-1b contains an MSA-1 insert extending from a BglII site at position 4674 to a BglII site in the 3' noncoding region MSA-1 and overlaps the 18-1a insert.

In addition to generating the full length coding sequence, several modifications of the MSA-1 gene were performed to optimize its expression by vaccinia virus. At the 5' end, the coding sequence has been linked to the vaccinia H6 promotor and two vaccinia early transcriptional termination sequences ($T_5NT$; Yuen and Moss, 1987) located between positions 16 and 40 have been modified without altering the amino acid sequence. At the 3' end, an early transcriptional termination sequence has been added immediately after the stop codon.

Modification of the 5' end. The 5' end of the MSA-1 gene was linked to the H6 promotor and the early transcriptional termination sequences modified as follows. A 520 base pair DraI/PvuII fragment, which extends from a DraI site in the 5' noncoding region to the PvuII site at position 424, was isolated from plasmid 3-1 and cloned into a SmaI-digested pIBI24 vector fragment. The resulting plasmid was designated p24Dra/PvuII. The MSA-1 gene was adapted for expression under the control of the vaccinia H6 promoter by in vitro mutagenesis (Kunkel et al., 1987) using the oligonucleotide MAL51 (SEQ ID NO:119) (5'-AAA GAA TAT GAT CTT CAT TAC GAT ACA AAC TTA ACG GAT ATC CCT ATA GTG AGT CGT A-3') and p24Dra/PvuII. Simultaneously, a second mutagenesis was conducted to remove the two vaccinia early transcription termination signals contained between position 16 and 40 with the oligonucleotide MAL50 (SEQ ID NO:120) (5'-GTG TAT TTA TAA TAA AGA AAA GAA ATG AAC ATA GAA AGA ATA TGA TC-3'). The resulting plasmid was called pMal50+51.

The 510 base pair EcoRV/BamHI fragment of pMal50+51 was isolated and cloned into an EcoRV/BalII-digested pSP131Not vector fragment (pSP131Not was derived from pSP131 (Taylor et al., 1991) by modifying the HindIII site to a NotI site). The resulting plasmid, designated pSP131.5', contains the complete H6 promoter linked to the first 424 nucleotides (PvuII site) of the MSA-1 gene.

Modification of the 3' end. A fragment generated by annealing the complementary oligonucleotide pair MAL30 (SEQ ID NO:121) (5'-GTT CCT CTA ACT TCT TAG GAA TAT CAT TCT TAT TAA TAC TCA TGT TAA TAT TAT ACA GTT TCA TTT AAT TTT TAT C-3') and MAL31 (SEQ ID NO:122) (5'-TCG AGA TAA AAA TTA AAT GAA ACT GTA TAA TAT TAA CAT GAG TAT TAA TAA GAA TGA TAT TCC TAA GAA GTT AGA GGA ACT GCA-3') was used to modify the 3' end of the MSA-1 coding sequence. This fragment extends from a PstI site at position 5113 through the 3' end of the coding sequence, inserts an early transcriptional termination signal ($T_5AT$) after the translational termination codon, and ends with a XhoI site. The MAL30/MAL31 fragment was ligated to a PstI/XhoI-digested pIBI24 vector fragment to generate p24(30+31).

Reconstruction of the complete MSA-1 gene. After modifying the 5' and 3' ends of the MSA-1 coding sequence, a full length MSA-1 gene was derived from the incomplete plasmid clones. The 850 base pair EcoRI/PstI fragment from plasmid 18-1a was ligated into an EcoRI/PstI-digested p24 (30+31) vector fragment. The resulting plasmid was designated p195Eco/Xho and contains an MSA-1 insert extending from the EcoRI site at position 4263 through the 3' end of the coding sequence.

A 3208 base pair HindIII/EcoRI fragment from plasmid 3-1, which extends from the HindIII site at position 98 to the EcoRI site at position 3306, was ligated into a HindIII/EcoRI-digested pIBI24 vector fragment. The resulting plasmid was designated p24Hind/Eco. A 3910 base pair HindIII/NciI fragment from p24Hind/Eco was ligated to a HindIII/MluI-digested pIBI24 (EcoRI⁻) vector fragment (the EcoRI site was removed by digestion of pIBI24 with EcoRI, treatment with DNA polymerase Klenow fragment, and re-ligation). The resulting plasmid was designated p195Hind/Eco and contains the 3208 base pair HindIII/EcoRI fragment derived from plasmid 3-1.

The 820 base pair EcoRI/XhoI fragment from p195Eco/Xho was ligated to an EcoRI/XhoI-digested p195Hind/Eco vector fragment. The resulting plasmid, was designated p195HEX, contains an MSA-1 fragment extending from position 98 through 3306 linked by an EcoRI site to a fragment extending from position 4263 through the 3' end of the coding sequence.

To link this construct to the H6 promotor and the remaining 5' MSA-1 sequences, a 4145 base pair HindIII/AccI fragment from p195HEX was ligated to a HindIII/NarI-digested pSP131.5' vector fragment. The resulting plasmid, designated pSP131HEX, contains the H6 promotor linked to MSA-1 sequences comprising nucleotides 1 through 3306 and 4263 through the 3' end of the coding sequence. The 4350 base pair NotI/XhoI fragment from pSP131HEX was ligated into an EcoRV/XhoI-digested pSD486 vector fragment (Tartaglia et al., 1992). The resulting plasmid was designated p486195E.

Finally, the 957 base pair EcoRI fragment from plasmid 10-1 that contains nucleotides 3306 through 4263 of MSA-1 was ligated to an EcoRI-digested p486195E vector fragment. The resulting plasmid, designated p486195, contains the complete MSA-1 gene under the control of the H6 promotor. The nucleotide sequence of the MSA-1 gene in p486195 is shown in FIG. 6.

Subcloning of the MSA-1 gene into an ATI donor plasmid. The H6/MSA-1 gene cassette was isolated as a 5210 base pair NruI/XhoI fragment from p486195 and cloned into an NruI/XhoI-digested pMP494H-P vector fragment (pMP494H-P was derived from pSD494 by insertion of the vaccinia H6 promoter). The resulting plasmid, designated pATI.H6.195, targets the insertion of H6/MSA-1 into the ATI site.

Insertion of the MSA-1 gene into the ATI site of NYVAC. The pATI.H6.195 donor plasmid was used to insert the MSA-1 gene, under the control of the H6 promotor, into the ATI site of NYVAC by recombination. The resulting NYVAC recombinant was designated vP924. Restriction analysis was performed on vP924 genomic DNA to confirm the insertion of MSA-1 at the ATI site.

Evaluation of MSA-1 expression by vP924. The expression of MSA-1 on the surface of vP924-infected MRC-5 cells has been demonstrated by immunofluorescence analysis with mAb CE2.1. This reagent, as well as rabbit anti-gp185 serum, also immunoprecipitates a cell associated MSA-1 peptide of ~220 Kd from vP924-infected MRC-5 cells. MSA-1 expressed by vP924 is not processed into the smaller molecular weight fragments which are found in parasites.

EXAMPLE 30

INSERTION OF THE CSP AND SERA GENES INTO vP924 TO GENERATE vP967

Cloning of the CSP gene: pCOPCS-CS was prepared as per Example 22.

Cloning of the SERA gene. Isolation and characterization of SERA cDNA: p126.15 was prepared as described in Example 1.

Subcloning of SERA cDNA: p126.16 was prepared as per Example 1.

Linkage with 42K entomopox promotor and modification of 3' end: p126.17 was prepared as per Example 6.

Subcloning of the CSP and SERA genes into a TK donor plasmid.

Insertion of CSP gene into the TK donor plasmid pSD542. Plasmid pSD542-EBV340, which contains the EBV gp340 gene linked to the H6 promotor in pSD542, was digested with BglII/NotI/NruI to generate a BglII/NotI pSD542 fragment, a BglII/NruI EBV340 gene fragment, and a NruI/NotI H6 promotor fragment. The H6 promotor fragment and the pSD542 fragment were used to set up a three way ligation with a BglII/NruI CSP gene fragment derived from the digestion of the pCOPCS-CS plasmid. The resultant intermediate plasmid contained the CSP gene in the incorrect orientation. To correct this, the plasmid was digested with BamHI/BglII and ligated into the original pSD542 which had been opened with BamHI. The final plasmid, p542MLF-CS, contains the CSP gene under the control of the H6 promotor, utilizing the transcriptional stop signal within the pSD542 plasmid.

Insertion of the SERA gene into p542MLF-CS: Plasmid p126/CS-TK2 was prepared as per Example 27 and directs insertion to the NYVAC TK site.

Insertion of the CSP and SERA genes into the TK site of vP924. The p126/CS-TK2 donor plasmid was used to insert the CSP and SERA genes, under the control of the H6 and 42K promotors, respectively, into the TK site of vP924 by recombination. The resulting vaccinia recombinant was designated vP967. Restriction analysis was performed on vP967 genomic DNA to confirm the insertion of the CSP and SERA genes at the TK site.

Evaluation of CSP, SERA, and MSA-1 expression by vP967. The expression of MSA-1 and CSP on the surface of vP967-infected MRC-5 cells was demonstrated by immunofluorescence analysis with mAb CE2.1 and rabbit anti-repeatless CSP serum, respectively. MSA-1 was also detected by immunoprecipitation with rabbit anti-gp195 serum. The rabbit anti-repeatless CSP serum detected two cell associated CS proteins of 60 and 56 Kd by immunoprecipitation of vP967-infected MRC-5 cell lysates. The rabbit anti-p126 serum detected three intracellular SERA peptides of ~135, 122, and 110 Kd and a secreted SERA peptide of 137 Kd by immunoprecipitation. The 110 and 122 Kd peptides are biosynthetic intermediates of the 135 Kd intracellular SERA peptide. SERA expressed by vP967 is not processed into the smaller molecular weight fragments that are found in parasites.

EXAMPLE 31

INSERTION OF THE AMA-1 GENE INTO vP967 TO GENERATE vP1108

Cloning of the AMA-1 gene. Isolation and characterization of the AMA-1 gene: Plasmid p731AMA-1 was prepared as per Examples 4 and 9. The nucleotide sequence of the AMA-1 gene is presented in FIG. 8 and, the plasmid containing this sequence was designated p731AMA-1.

Subcloning of the AMA-1 gene into an HA donor plasmid. I3L/AMA-1 and p544AMA-1 were prepared as per Example 9.

Insertion of the AMA-1 gene into the HA site of vP967. The p544AMA-1 donor plasmid was used to insert I3L/AMA-1 into the HA site of vP967 by in vivo recombination. The resulting vaccinia recombinant was designated vP1108. Restriction analysis was performed on vP1108 genomic DNA to confirm the insertion of the AMA-1 gene at the HA site.

Evaluation of AMA-1, CSP, SERA, and MSA-1 expression by vP1008. AMA-1 is expressed on the surface of MRC-5 cells infected with a NYVAC/AMA-1 single recombinant as detected by immunofluorescence assay with the pooled human anti-malaria immunoglobulins. This reagent immunoprecipitates a cell associated AMA-1 protein of ~83 Kd from vP1008-infected MRC-5 cells and a secreted AMA-1 peptide of ~90 Kd. The expression of MSA-1, SERA, and CSP in vP1108-infected cells was detected by immunoprecipitation with rabbit anti-g195 serum, rabbit anti-p126 serum, and rabbit anti-repeatless CSP serum, respectively.

EXAMPLE 32

INSERTION OF THE Pfs25 GENE INTO vP1108 TO GENERATE vP1127

Cloning of the Pfs25 gene: pPfs25.1 was prepared as per Example 14. The nucleotide sequence of the Pfs25 gene in pPfs25.1 is shown in FIG. 9.

Subcloning of the Pfs25 gene into an I4L donor plasmid. Plasmid pPfs25.2 was prepared as per Example 16.

Insertion of the Pfs25 gene into the I4L site of vP1108. The pPfs25.2 donor plasmid was used to insert I3L/Pfs25 into the I4L site of vP1108 by recombination. The resulting vaccinia recombinant was designated vP1127. Restriction analysis was performed on vP1127 genomic DNA to confirm the insertion of the Pfs25 gene at the I4L site.

Evaluation of Pfs25, AMA-1, CSP, SERA, and MSA-1 expression by vP1127. The expression of Pfs25 on the surface of vP1127-infected MRC-5 cells has been demonstrated by immunofluorescence analysis with the Pfs25- specific mAb 4B7. Two Pfs25 peptides are expressed in vP1127-infected MRC-5 cells as detected by immunoprecipitation with 4B7—a major peptide of 25 Kd and a minor peptide of 29 Kd. The expression of MSA-1, SERA, and AMA-1 by vP1127 was detected by immunoprecipitation with the pooled human anti-malaria serum and expression of CSP was detected with the rabbit anti-repeatless CSP serum.

EXAMPLE 33

INSERTION OF THE PfSSP2 GENE INTO vP1127 TO GENERATE vP1154E

Cloning of the PfSSP2 gene. Plasmid pVAC-SSP2 was provided by Dr. D. Lanar (WRAIR). This plasmid contains the PfSSP2 gene from the *P. falciparum* NF54/3D7 clone linked to the entomopox 42K promotor and flanked at the 3' end by a vaccinia early transcription termination signal ($T_5AT$). The nucleotide sequence of the PfSSP2 gene in pVAC-SSP2 is shown in FIG. 10.

Subcloning of the PfSSP2 gene into an AMA-1/HA donor plasmid. After the insertion of AMA-1 into vP967 to generate vP1108, it was found that the donor plasmid p544AMA-1 contained a previously undetected insertion mutation within the putative leader sequence of the AMA-1 gene. This mutation, a 7 amino acid duplication of the 5' end of the leader sequence plus one additional amino acid, is present in the previously generated multiple recombinants vP1108 and vP1127. Because the mutation is found within the leader sequence of AMA-1, and thus should be removed during biosynthesis, it should not affect expression dramatically. In fact, the above mentioned recombinants each express AMA-1. However, to eliminate the possibility of unanticipated complications due to the presence of the mutation, a corrected AMA-1 sequence was generated in an HA donor plasmid. The PfSSP2 gene was then subcloned into this donor plasmid, which was used to insert PfSSP2, and replace the mutated AMA-1 gene with the corrected AMA-1 gene, in vP1127.

Correction of the AMA-1 gene in p544AMA-1. This was accomplished by modifying the p544AMA-1 donor plasmid by generating a PCR fragment containing the corrected AMA-1 sequence from NF54/3D7 genomic DNA and substituting this corrected fragment for the mutated fragment in p544.AMA-1. A fragment of ~325 base pair was amplified by PCR with NF54/3D7 genomic DNA as template and primers C014 (SEQ ID NO:100) and JAT 76 (SEQ ID NO:123) (5'-CTA GGT CGA CTC CGT CCA TGG ATT AC-3'). This fragment includes the 3' five nucleotides of the I3L promotor linked to the AMA-1 ATG initiation codon at the 5' end and extends through a StyI site to nucleotide 335 of the AMA-1 coding sequence (and introduces a SalI site for cloning at the 3' end of the fragment). After digestion with SAl, this blunt/SalI fragment was ligated with a HpaI/SalI-digested pMPI3H vector fragment to generate pI3L/5AMA, which contains the unmutated 5'325 base pair of the AMA-1 gene linked to the regenerated I3L promotor. The AMA-1 mutation in p544.AMA-1 was then corrected by ligating a HindIII/StyI I3L/5' AMA-1 fragment from pI3L/5AMA with a HindIII/StyI-digested p544.AMA-1 vector fragment. The resulting plasmid, designated pHA.AMA-1, contains the "corrected" AMA-1 coding sequence.

Insertion of PfSSP2 into pHA.AMA-1. A 42K promotor/PfSSP2 gene cassette was isolated from pVAC-SSP2 after digestion with BamHI. The BamHI sites were then filled-in with Klenow enzyme and the cassette blunt-end ligated into a pHA.AMA-1 vector fragment that had been digested with HindIII, filled-in with Klenow enzyme, and CIAP-treated. The resulting plasmid, pHA.SSP/AMA, contains 42K/PfSSP2 and I3L/AMA-1 in a head-to-head orientation (transcription is in opposite directions) and targets these genes for insertion at the HA site. This plasmid can thus be used to both insert the PfSSP2 gene into vP1127 and to replace the mutated AMA-1 gene of vP1127 with the corrected AMA-1 sequence.

Insertion of the PfSSP2 gene into the HA site of vP1127. The pHA.SSP/AMA donor plasmid was used to insert 42K/PfSSP2 and the corrected I3L/AMA-1 cassette into the HA site of vP1127 by in vivo recombination. The resulting vaccinia recombinant was designated vP1154E. Restriction analysis was performed on vPi154E genomic DNA to confirm the insertion of the PfSSP2 and AMA-1 genes at the HA site. DNA sequence analysis of the insertion site confirmed that the mutated AMA-1 gene in vP1127 had been replaced by the corrected AMA-1 gene in vP1154E.

Evaluation of PfSSP2, Pfs25, AMA-1, CSP, SERA, and MSA-1 expression by vP1154E. The expression of PfSSP2 on the surface of vP1154E-infected cells was demonstrated by immunofluorescence analysis with the mouse anti-PfSSP2 serum. This reagent also immunoprecipitates a cell associated PfSSP2 peptide of ~107 Kd and a secreted PfSSP2 peptide of ~91 Kd. The expression of MSA-1, SERA, and AMA-1 by vP1154E was detected by immunoprecipitation with the pooled human anti-malaria serum while CSP and Pfs25 were detected with mAbs Pf2A10 and 4B7, respectively.

EXAMPLE 34

INSERTION OF THE LSA1-REPEATLESS GENE INTO vP1154E TO GENERATE NYVAC-Pf7

A leader-minus, repeat-minus LSA-1 construct derived by PCR from the *P. falciparum* NF54/3D7 clone linked to the vaccinia C10LW promotor was provided by Dr. D. Lanar (WRAIR). The coding sequence of this clone, which was called LSA7.1, was intended to be identical to that shown in FIG. 11 (except the leader peptide encoded by nucleotides 4–69 was not to be included). However, DNA sequence analysis of LSA7.1 by our laboratory revealed that this construct contained a series of mutations introduced by the Taq polymerase used in its generation. These mutations were as follows: 1) 2-nucleotide deletion in C1OLW promotor at positions −2 and −1; 2) 1-nucleotide deletion at position 351; 3) G for C substitution at position 660; 4) T for A substitution at position 684 (Lys to Arg amino acid change); 5) C for T substitution at position 868 (Tyr to His amino acid change). The LSA7.1 construct was subsequently modified to correct these mutations and insert the leader sequence. This LSA1-repeatless gene was included in the multicomponent NYVAC recombinant because attempts to insert the full length LSA-1 gene into poxvirus recombinants have resulted in deletions that appear to occur within the LSA-1 repeat region. The identification of a CTL epitope within the non-repetitive region of LSA-1 (Hill et al., 1992) suggests that this repeatless construct will be an effective immunogen.

Cloning of the LSA1-repeatless gene; Modification of 5' end of LSA-7.1. To correct the 2 nucleotide promotor deletion and insert the leader sequence into pLSA7.1 (the leader sequence is comprised of nucleotides 4–69 of the LSA1-repeatless gene sequence shown in FIG. 7), two complementary oligonucleotides were annealed to create a 114 base pair fragment which includes an AflII site at the 3' end of the C10LW promotor and extends through an EcoRI site located in the 5' end of the pLSA7.1 gene at position 81. The fragment generated by annealing the oligonucleotide pair LSASIG1 (SEQ ID NO:124) (5'-GAT ATC CTT AAG TCT TAT TAA TAT GAA ACA TAT TTT GTA CAT ATC ATT TTA CTT TAT CCT TGT TAA TTT ATT GAT ATT TCA TAT AAA TGG AAA GAT AAT AAA GAA TTC TGA CAG-3') and LSASIG1R (SEQ ID NO:125) (5'-CTG TCA GAA TTC TTT ATT ATC TTT CCA TTT ATA TGA AAT ATC AAT AAA TTA ACA AGG ATA AAG TAA AAT GAT ATG TAC AAA ATA TGT TTC ATA TTA ATA AGA CTT AAG GAT ATC-3') was digested with AflII and EcoRI and then ligated with an AflII/EcoRI-digested pLSA7.1 vector fragment. The LSA1-repeatless gene in the resultant plasmid, designated pLSA7.2, has a corrected C10LW promotor and includes the LSA-1 leader sequence.

Correction of the position 351 deletion. To correct the single nucleotide deletion at position 351, the PCR mutagenesis procedure of Mikaelian and Sergeant (1992) was used with the primer pairs LSA110 (SEQ ID NO:126) (5'-GCA CGA GAA GAA ACA CG-3')/LSA375R (SEQ ID NO:127) (5'-CGT TAT ATC TCA AGA TCT TCT TGT CTG-3'), LSAM (SEQ ID NO:128) (5'-CCT TAA AGA AAA TAA ATT AAA TAA GGA AGG GAA ATT AAT TGA ACA C-3')/LSA675R (SEQ ID NO:131) (5'-TTA TGT ATA TCC CTT CGT CC-3'), and LSA110/LSA675R and plasmid pLSA7.2 as template. The resulting ~430 base pair amplified fragment, which includes the unique HincII and StyI sites at positions 251 and 659, respectively, and contains the sequence TTAAATT at position 349 (modified from TTAATT) was then digested with HincII and StyI.

To correct the nucleotide substitution (T for A) at position 684, a PCR fragment was generated with primers LSAG101II (SEQ ID NO:130) (5'-AGA GAT TCC AAG GAA ATA TCT ATA ATA GAA AAA ACA AAT AGA GAA TCT ATT ACA ACA AAT GTT GAA GGA CG-3'), which contains the correction, and M13RP2 (SEQ ID NO:131) (5'-TGT GAG CGG ATA ACA ATT-3'), which primes after the 3' end of the coding region, and plasmid pLSA7.2 as template. The resulting ~700 base pair amplified fragment was digested with StyI and KpnI. This fragment and the HincII/StyI PCR fragment were included in a three-way ligation with a HincII/KpnI-digested pIBI24 vector fragment. The resulting plasmid was designated pIBI.LSA7.3 and contains a repeatless LSA construct extending from the internal HincII site at position 251 through the 3 end of the coding sequence. DNA sequence analysis of pIBI.LSA7.3 indicated that the deletion at position 351 was corrected but the position 684 substitution (T) had not been corrected to an A residue.

Reconstruction of full length LSA-1 gene and correction of the position 684 and 868 substitutions. In this step, the repeat region of LSA-1 was inserted into the incomplete repeatless LSA construct and the position 684 substitution was corrected. This fragment was then subcloned with a vector fragment containing the remaining 5' LSA-1 and promotor sequences to generate a complete LSA-1 construct, afterwhich the position 868 substitution was corrected.

A 4630 base pair BglII/StyI fragment, which contains the repeat region of LSA-1, was obtained from plasmid pLSA.EcoRI (Zhu and Hollingdale, 1991, referred to as "EcoRI clone;" provided by Dr. D. Lanar, WRAIR). This fragment was included with the 700 base pair StyI/KpnI PCR fragment derived with the primer pair LSAG101II/M13RP2 (described above, corrects the position 684 substitution) in a 3-way ligation with a BglII/KpnI-digested pIBI.LSA7.3 vector fragment to generate pLSA7.4. This plasmid contains an LSA-1 insert which extends from the internal HincII site through the 3' end of the coding sequence, contains the LSA-1 repeat region, and has corrected the position 684 substitution. This insert was removed by HindIII/Asp718 digestion (cuts at same sites as HincII/KpnI) and ligated with a HindIII/Asp718-digested pLSA7.2 vector fragment. The resulting plasmid, designated pLSA7.5, contains the complete LSA-1 coding sequence. However, the amino acid altering nucleotide substitution at position 868 (number relative to sequence in FIG. 7) remains.

To correct the position 868 substitution, PCR was performed with the primer pair LSAG10II/LSAEND1 (SEQ ID NO:132) (5'-GAT AAG GTA CCA TAA AAA TTA TAG TTT CAT AAA ATA TTT AG-3') and plasmid pLSA.EcoRI as template. The resulting amplified fragment extends from the internal StyI site through the 3' end of the coding sequence and contains a vaccinia early transcriptional termination sequence ($T_5AT$) immediately after the TAA translational termination codon, which is then followed by a KpnI site. After digestion with StyI and KpnI, this fragment was ligated with a StyI/KpnI-digested pLSA7.5 vector fragment to generate pLSA7.7INT2. The C10LW/LSA-1 fragment was removed from pLSA7.7INT2 by digestion with BamHI and KpnI. This ~5800 base pair fragment was ligated with a BamHI/KpnI-digested pSD550 vector fragment. The resultant plasmid, designated pLSAI4L.2, contains the C10LW/LSA-1 cassette (full length LSA-1 including repeats, all mutations corrected) in a vaccinia I4L donor plasmid.

Generation of unmutated LSA1-repeatless gene. The primer pair M13F (SEQ ID NO:133) (5'-GTA AAA CGA CGG CCA GT-3') and LSASTY1 (SEQ ID NO:134) (5'-TAT TTC CTT GGA ATC TCT ACT ATT CC-3') were used in PCR with pIBI.LSA7.3 as template to amplify a fragment of ~410 base pairs which extends from the HincII site at position 251 through the StyI site at position 659 of the LSA1-repeatless construct. This amplified fragment was digested with HincII and StyI and ligated with a HincII/StyI-digested pLSA7.5 vector fragment. In the resultant plasmid, pLSARPLS.INT1, the HincII/StyI fragment from LSA1-repeatless replaces the repeat region-containing HincII/StyI fragment of pLSA7.5.

This "full length" LSA1-repeatless gene still contains the position 868 substitution. This was corrected by generating a PCR fragment from pLSA.EcoRI template with the primer pair LSAG10II/LSAEND1 which extends from the internal StyI site at position 659 through the 3' end of the coding sequence. After digestion with StyI and KPnI, this fragment was ligated with a pLSARPLS.INT1 vector fragment obtained by StyI/KpnI digestion. In the resulting plasmid, designated pLSARPLS.INT2, the StyI/KpnI fragment containing the position 868 substitution has been replaced by the analogous unmutated fragment from pLSA.EcoRI. This plasmid thus contains an unmutated LSA1-repeatless gene under the control of the C10LW promotor.

To generate an I4L donor plasmid containing LSA1-repeatless, an 895 base pair BglII fragment from pLSAR-PLS.INT2 was isolated which extends from the internal LSA1-repeatless BglII site at position 443 to a BglII site after the 3' end of the coding sequence. This fragment was subcloned into a BglII-digested pLSA.I4L.2 vector fragment to generate pLSARPLS.I4L.1. In this plasmid, the BglII fragment of pLSA.I4L.2 containing the repeat region has been replaced by the analogous repeatless fragment. Thus, pLSARPLS.I4L.1 is an I4L donor plasmid containing the C10LW/LSA1-repeatless gene expression cassette. The nucleotide sequence of the LSA1-repeatless gene in pLSARPLS.I4L.1 is shown in FIG. 7.

Subcloning of the LSA1-repeatless gene into a Pfs25/I4L donor plasmid: Generation of pLSARPLS/Pfs25.1. A HindIII/BqlII fragment which contains the C10LW promotor and extends through the LSA-1 coding sequence to the BglII site at position 443 was obtained from pLSAI4L.2. A BqlII/Asp718 fragment which extends from the BglII site at position 443 through the 3' end of the LSA1-repeatless coding sequence was obtained from pLSARPLS.I4L.1. These two fragments were included in a three-way ligation with an Asp718/HindIII-digested pPfs25/LSA.2 vector fragment. The resulting plasmid, pLSARPLS/Pfs25.1, contains the C10LW/LSA1-repeatless and 42K/Pfs25 expression cassettes in a head-to-head orientation (transcription is in opposite directions) and targets these genes for insertion at the I4L site. This plasmid can be used to insert the LSA1-repeatless gene into vP1154E. Because 42K/Pfs25 is already present at the I4L site of vP1154E, the 42K/Pfs25 cassette in the pLSARPLS/Pfs25 donor plasmid will function as an extension of the flanking arm.

Derivation of pPfs25/LSA.2 and pPfs25ILSA.1. The plasmid pPfs25/LSA.2 was used in the derivation of pLSARPLS/Pfs25.1 and was itself derived by modification of plasmid pPfs25/LSA.1. The construction of these plasmids was as follows.

For the construction of pPfs25/LSA.1, a 5.8 Kb HindIII/KDnI fragment containing the C10LW/LSA-1 gene (includes the repeat region, the position 868 substitution is not corrected) was isolated from pLSA7.5. This fragment was included with a HindIII/BglII fragment containing the I3L/Pfs25 expression cassette from pPfs25.1 in a three-way ligation with a KpnI/BalII-digested pSD550 vector fragment. The resulting plasmid, pPfs25/LSA.1, contains the C10LW/LSA-1 (with the position 868 substitution) and I3L/Pfs25 expression cassettes in a head-to-head orientation (transcription is in opposite directions) inserted between the I4L flanking arms provided by pSD550.

The pPfs25/LSA.2 plasmid was derived from pPfs25/LSA.1 to correct the position 868 substitution. A HindIII/KpnI fragment which contains the unmutated C10LW/LSA-1 gene (includes the repeat region) was obtained from pLSA7.7INT2. This fragment was ligated to a HindIII/KpnI-digested pPfs25/LSA.1 vector fragment. The resulting plasmid, pPfs25/LSA.2, contains the C10LW/LSA-1 and I3L/Pfs25 expression cassettes in a head-to-head orientation (transcription is in opposite directions) and directs insertion to the I4L site.

Insertion of the LSA1-repeatless gene into the I4L site of vP1154E. The pLSARPLS/Pfs25.1 donor plasmid was used to insert the C10LW/LSA1-repeatless gene cassette into the I4L site of vP1154E by in vivo recombination. The resulting NYVAC recombinant was designated NYVAC-Pf7. Restriction analysis was performed on NYVAC-Pf7 genomic DNA to confirm the insertion of the LSA1-repeatless gene at the I4L site.

Figure 12:
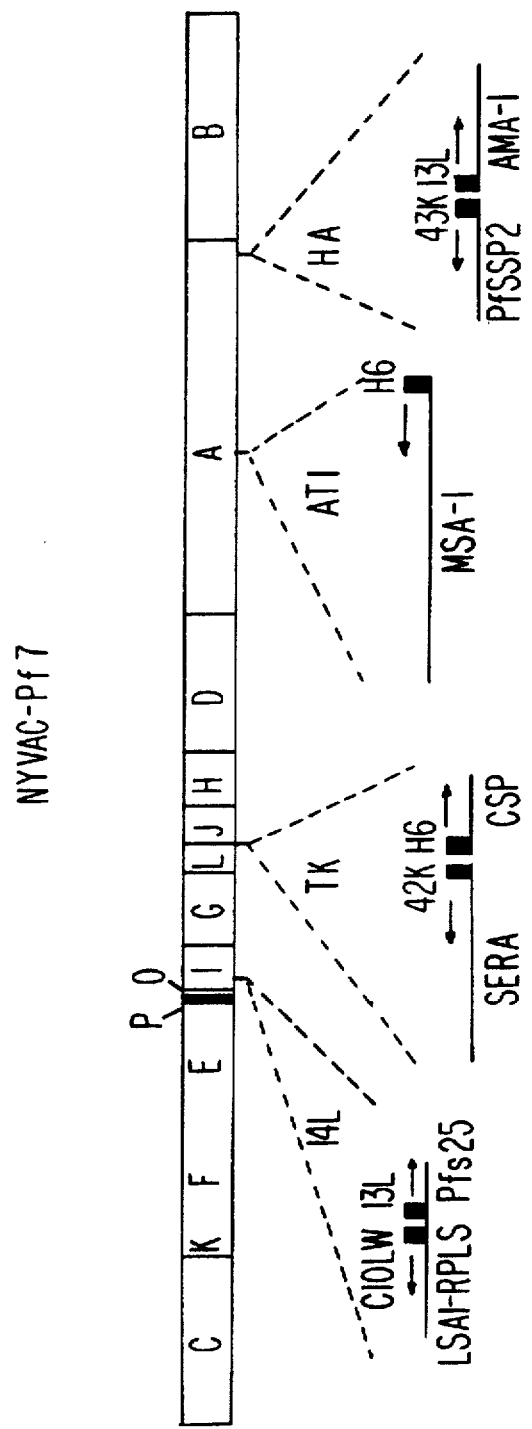
FIG. 12 shows a schematic representation of the construction of NYVAC-Pf7.

Evaluation of LSA1-repeatless, PfSSP2, Pfs25, AMA-1, CSP, SERA, and MSA-1 expression by NYVAC-Pf7. The rabbit anti-LSA-1 serum immunoprecipitates 72 Kd and 75 Kd secreted LSA1-repeatless peptides from NYVAC-Pf7-infected Hela cells. The expression of MSA-1, SERA, AMA-1, CSP, Pfs25, and PfSSP2 in NYVAC-Pf7-infected cells was detected by immunoprecipitation with rabbit anti-gp195 serum, rabbit anti-p126 serum, pooled human anti-malaria serum, mAb Pf2A10, mAb 4B7, and mouse anti-PfSSP2 serum, respectively. A schematic presentation of the genome of NYVAC Pf7 is shown in FIG. 12.

The *P. falciparum* proteins included in this multicomponent, multistage vaccine are the CSP and PfSSP2 sporozoite proteins, the LSA-1 liver stage protein, the MSA-1, SERA, and AMA-1 blood (and liver) stage proteins, and the Pfs25 sexual stage protein.

EXAMPLE 35

SURFACE EXPRESSION OF P. FALCIPARUM ANTIGENS BY NYVAC-Pf7 (vP1209)

To determine if the *P. falciparum* antigens expressed by NYVAC-Pf7 (vP1209) were expressed on the cell surface, infected cells were evaluated by flow cytometry after staining for surface fluorescence with specific antibodies. Expression of CSP, PfSSP2, and Pfs25 on the surface of HeLa cells infected with NYVAC-Pf7 (vP1209) was demonstrated. The quantity of CSP and PfSSP2 expressed on the cell surface by NYVAC-Pf7 is somewhat less than that expressed by the appropriate NYVAC single recombinants. Expression of Pfs25 by NYVAC-Pf7 is equivalent to that of NYVAC-Pfs25.

Because of the lack of monospecific reagents with which to detect AMA-1, applicants utilized pooled human antimalarial serum. Surface expression of AMA-1 and CSP were detected by this reagent, based on reactivity with HeLa cells infected with NYVAC-AMAL and NYVAC-CSP. Levels of expression of these two antigens were generally equivalent by these single recombinants. The pooled serum reagent reacted with NYVAC-Pf7-infected cells with an intensity roughly twice that of the single recombinants. From this result, without necessarily wishing to be bound by any one theory, AMA-1 is being expressed by NYVAC-Pf7, as the expression of both CSP and AMA-1 by this recombinant should be additive, resulting in a fluorescence intensity with this reagent that is higher than the control single recombinants.

Although NYVAC-Pf7 expressed low levels of MSA-1 on the cell surface, the NYVAC-MSA1 single recombinant is negative for surface expression with the rabbit anti-gp195 serum. These results were replicated with two mAbs, one of which recognizes the N-terminus and the other the C-terminus of MSA-1. The expression of MSA-1 with other malaria antigens by NYVAC-Pf7 may alter either the conformation of the protein on the cell surface or transport to the cell surface. NYVAC-Pf7-expressed MSA-1 is recognized by immunoprecipitation. Based on these results, applicants have classified the cell surface expression of NSA-1 by NYVAC-Pf7 as ±.

Surface expression of LSA1-repeatless and SERA was not evaluated as previous studies with other recombinants expressing these proteins have indicated that they are not surface associated, but secreted.

EXAMPLE 36

PHENOTYPIC HOMOGENEITY OF NYVAC-Pf7 (vP1209)

In order to determine that NYVAC-Pf7 (vP1209) is genetically homogenous and that all plaques in the population were expressing the *P. falciparum* gene products, a plaque immunoscreen was performed using monospecific sera. Applicants evaluated expression of five of the *P. falciparum* components of NYVAC-Pf7 (vP1209) with this assay: CSP with mAb Pf2A10, PfSSP2 with mAb 88:10:161. MSA-1 with mAb 3D3, SERA with mAb 23D5, and Pfs25 with mAb 4B7. LSA1-repeatless or AMA-1 expression were not evaluated because the rabbit anti-LSA-1 serum does not recognize LSA1-repeatless in this assay and there is currently a lack of monospecific reagent for AMA-1. Two lots of NYVAC-Pf7 (vP1209) were evaluated. The results indicated that the viral populations in both NYVAC-Pf7 (vP1209) stocks were homogenous for expression of the five *P. falciparum* proteins. For each stock, 100% of the evaluated plaques were positive for expression of CSP, PfSSP2, MSP-1, SERA, and Pfs25.

EXAMPLE 37

PHENOTYPIC STABILITY OF NYVAC-Pf7 (vP1209) AFTER PASSAGE

A blind passaging experiment was performed to evaluate the stability of the *P. falciparum* inserts in NYVAC-Pf7 (vP1209). NYVAC-Pf7 (vP1209) was passaged five times on CEF monolayers at low moi (approximately 0.01 pfu/cell) or high moi (approximately 0.1 pfu/cell). After the fifth passage, the homogeneity of the resulting virus populations was assessed by plaque immunoscreen. The results indicated that after five blind passages at low or high multiplicities, the resulting NYVAC-Pf7 (vP1209) populations are homogeneous for expression of the five tested *P. falciparum* genes (CSP, PfSSP2, MSP-1, SERA, Pfs25). Analysis by immunoprecipitation indicated that there was no alteration in the size of the expressed *P. falciparum* proteins after the five blind passages. These results demonstrated the phenotypic stability of NYVAC-Pf7 (vP1209).

EXAMPLE 38

SAFETY AND IMMUNOGENICITY OF NYVAC-Pf7 IN RHESUS MONKEYS

NYVAC-Pf7 (vP1209) was produced under GMP conditions by Connaught Laboratories, Swiftwater, Pa. Two dosages were prepared: $10^8$ pfu/dose and $10^7$ pfu/dose. Groups of three rhesus monkeys (*Macaca mulatta*) were inoculated by the intramuscular route with this material in a safety/immunogenicity study conducted at the Walter Reed Army Institute of Research. Monkeys received $10^8$ pfu NYVAC-Pf7 (vP1209), $10^7$ pfu NYVAC-Pf7 (vP1209), $10^8$ pfu NYVAC, or saline at week 0 and week 4. No adverse events were observed in any animals after either inoculation. Thus, two inoculations of NYVAC-Pf7 (vP1209) are safe when administered by the intramuscular route in rhesus monkeys.

Preliminary studies were performed to assess the immunogenicity of NYVAC-Pf7 (vP1209) in these animals. Sera from immunized monkeys was evaluated by ELISA with recombinant proteins as capture antigens to determine antibody responses to several of the *P. falciparum* components of the vaccine. Antibody responses to the repeat region of CSP were demonstrated in all monkeys inoculated with the two doses of NYVAC-Pf7 (vP1209). The antibody titers were boosted by the second inoculation. One animal in each of the two dosage groups of NYVAC-Pf7 exhibited antibody responses to MSA-1 by ELISA. One control animal also showed a weak positive response. A booster effect was observed in positive monkeys after the second inoculation. There were weak or no responses to SERA in the animals. However, the SERA fragment used as capture antigen represented only a subfragment of the protein, and ELISA is but one way to measure antibodies to a particular protein. Strong responses to Pfs25 were demonstrated in all NYVAC-Pf7 (vP1209) immunized monkeys. These responses were boosted by the second inoculation.

The elicitation of sporozoite-specific antibodies by immunization with NYVAC-Pf7 (vP1209) was also assessed by immunofluorescence assay (IFA). Results indicated that all animals inoculated with NYVAC-Pf7 developed antibodies which recognize this stage of the parasite life cycle.

EXAMPLE 39

SAFETY AND IMMUNOGENICITY OF NYVAC-Pf7 (vP1209) IN RABBITS, MICE, AND GUINEA PIGS

A series of studies was performed in laboratory animals to evaluate the safety and immunogenicity of NYVAC-Pf7. Four rabbits were inoculated three times with $10^8$ or $10^7$ pfu of NYVAC-Pf7 (vP1209) by the intramuscular route. Six additional rabbits received two inoculations by the intramuscular route with either $10^8$ or $10^7$ pfu of NYVAC-Pf7 (vP1209) prepared under GMP conditions. Twenty mice each of the $CAF_1/J$ and B10.BR strains received three inoculations of $10^7$ pfu NYVAC-Pf7 (vP1209) by either the intramuscular or intradermal routes. Ten outbred Swiss Webster mice received three inoculations of $10^7$ pfu NYVAC-Pf7 (vP1209) by the intramuscular route. Four guinea pigs were inoculated three times with $10^8$ or $10^7$ pfu of NYVAC-Pf7 (vP1209) by the intramuscular route. Of the 64 animals inoculated with NYVAC-Pf7 (vP1209), no adverse events related to the immunizations were noted.

EXAMPLE 40

GENERATION OF NYVAC-LSA1-REPEATLESS

Insertion of the PfSSP2 gene into the HA site of NYVAC. The pLSARPLS.I4L.1 donor plasmid (see Example 34) was used to insert the LSA1-repeatless gene, under the control of the C10LW promoter, into the I4L site of NYVAC by in vivo recombination. The resulting NYVAC recombinant was designated vP1197. Restriction analysis of vP1197 genomic DNA confirmed the insertion of the LSA1-repeatless expression cassette at the I4L site.

Evaluation of LSA1-repeatless expression by vP1197.

The expression of two secreted LSA1-repeatless peptides of 75 and 72 kDa was detected in vP1197-infected HeLa cells by immunoprecipitation analysis with rabbit anti-LSA-1 serum.

EXAMPLE 41

GENERATION OF NYVAC-PfSSP2

Subcloning of the PfSSP2 gene into an HA donor plasmid. A fragment containing the 42K promoter/PfSSP2 gene expression cassette was isolated from plasmid pVAC-SSP2 (see Example 33) by digestion with BamHI. This fragment was ligated with a BamHI-digested pSD544 vector fragment to generate pSSP2.HA. This HA donor plasmid contains the 42K/PfSSP2 cassette with transcription oriented left to right in relation to the NYVAC flanking arms.

Insertion of the PfSSP2 gene into the HA site of NYVAC. The pSSP2.HA donor plasmid was used to insert the PfSSP2 gene, under the control of the 42K promoter, into the HA site of NYVAC by in vivo recombination. The resulting NYVAC recombinant was designated vP1189. Restriction analysis of vP1189 genomic DNA confirmed the insertion of the PfSSP2 expression cassette at the HA site.

Evaluation of PfSSP2 expression by vP1189. The expression of cell-associated and secreted PfSSP2 peptides of 107 and 91 kDa, respectively, was detected in vP1189-infected HeLa cells by immunoprecipitation analysis with mouse anti-PfSSP2 serum.

EXAMPLE 42

GENERATION OF NYVAC-SERA

Subcloning of the SERA gene into a TK donor plasmid.

A fragment containing the 42K promoter/SERA gene expression cassette was isolated from plasmid p126.C3 (see Example 28) by digestion with BamHI and XhoI. This fragment was ligated with a BamHI/XhoI-digested pSD542 vector fragment to generate p126.TK. This TK donor plasmid contains the 42K/SERA cassette with transcription oriented right to left in relation to the NYVAC flanking arms.

Insertion of the SERA gene into the TK site of NYVAC. The p126.TK donor plasmid was used to insert the SERA gene, under the control of the 42K promoter, into the TK site of NYVAC by in vivo recombination. The resulting NYVAC recombinant was designated vP1187. Restriction analysis of vP1187 genomic DNA confirmed the insertion of the SERA expression cassette at the TK site.

Evaluation of SERA expression by vP1187. The expression of cell-associated and secreted SERA peptides of 135 and 137 kDa, respectively, was detected in vP1187-infected HeLa cells by immunoprecipitation analysis with rabbit anti-p126 serum.

EXAMPLE 43

GENERATION OF NYVAC-CSP

Insertion of the CSP gene into the TK site of NYVAC.

The p542MLF-CS donor plasmid (see Example 30) was used to insert the CSP gene, under the control of the H6 promoter, into the TK site of NYVAC by in vivo recombination. The resulting NYVAC recombinant was designated vP1190C. Restriction analysis of vP1190C genomic DNA confirmed the insertion of the CSP expression cassette at the TK site.

Evaluation of CSP expression by vP1190C. The expression of cell-associated CSP peptides of 60 and 56 kDa was detected in vP1190C-infected HeLa cells by immunoprecipitation analysis with mAb Pf2A10.

EXAMPLE 44

GENERATION OF NYVAC-p83/gp42, EXPRESSING THE N-TERMINAL p83 AND C-TERMINAL gp42 PROCESSING FRAGMENTS OF MSA-1

Subcloning of the p83 and gp42 gene constructs into an ATI donor plasmid.

Insertion of the p83 gene into the ATI donor plasmid DSD541. The MSA1 processed N-terminal fragment is a 83 kd protein. Its N-terminal amino acid is probably the valine residue (position 20) obtained after cleavage of the leader peptide. Its C-terminal amino acid has never been experimentally determined, but by computer analysis (IBI Pustell sequence Analysis Program; IBI, New Haven, Conn.) can be mapped at the amino acid 752 (Gly). By using PCR and specific oligonucleotides, a DNA fragment coding for amino acids 1 to 752 was generated and cloned into the vaccinia donor plasmid COPAK H6-1.

Oligonucleotides C008 (SEQ ID NO:135) and C009 (SEQ ID NO:136) were used to amplify by PCR a 439 bp MSA1 fragment (position 1812 to 2251).

```
C008:  AACTGGCCTCGAAGCTG
       |
       1812

C009:  G TGT TAA AGG GTT AGT CCT TGGTTCCAGCTGACG
       |                       |    StyI   SalI
       2240                    2251
```

The PCR fragment was digested with XbaI and SalI and ligated at XbaI/SalI pIBI24 derived plasmid. The resulting plasmid was called 24–83. The nucleotidic sequence of the 24-83 inserted fragment was verified. 24–83 was digested with StyI, filled in with DNA polymerase I Klenow fragment in presence of dNTP, digested with XhoI and subsequently ligated with the XhoI digested PCR fragment generated with oligonucleotides C001 and C002. The resulting plasmid was called 24-(83+42). The nucleotidic sequence flanking the restored StyI site was determined:

```
CAA TCA GGA ACC AAG GCA ATA TCT GTC ACA  (SEQ ID
        Gly  StyI  Ala                      NO:137)
        752        1333
```

The 1590 bp XbaI/SphI fragment of 24-(83+42) was inserted into the 4696 bp XbaI/SphI fragment of 24-XVII plasmid. The resulting plasmid was called 24-XXI. The 3480 bp NruI/XhoI fragment of 24-XXI was inserted into the NruI/XhoI vaccinia donor plasmid COPAK H6-1. The resulting plasmid was called pCOPAK-XXI. Plasmid PCOPAK-XXI which contains the H6 promoted coding sequence for the MSA-1 p83 N-terminal processing fragment linked by a StyI restriction site to the coding sequence for the MSA-1 gp42 C-terminal processing fragment, was partially digested with StyI followed by XhoI to remove the gp42 coding sequence. The remaining vector/p83 gene fragment was then ligated with the annealed oligonucleotide pair JAT65 (SEQ ID NO:138) (5'-CAA GTA ATT TTT ATC)/ JAT66 (SEQ ID NO:139) (5'-TCG AGA TAA AAA TTA-3'), which introduces a translational stop codon and vaccinia early transcriptional termination signal at the 3' end of the p83 coding sequence. The resulting plasmid was designated p83.1. An NruI/XhoI fragment was obtained from p83.1 that contained the 3' one-third of the H6 promoter and the p83 coding sequence. This fragment was ligated with an NruI/XhoI-digested pSD541 vector fragment, which contained the 5' two-thirds of the H6 promoter, to generate p83.ATI-2. In this plasmid, transcription of p83 is oriented right to left in relation to the NYVAC flanking arms.

Insertion of the gp42 gene into p83.ATI-2. A fragment containing the gp42 coding sequence linked to the 42K promoter was generated by PCR with the primer pair JAT74 (SEQ ID NO:140) (5'-TAT GGG ATC CTC AAA ATT GAA AAT ATA TAA TTA CAA TAT AAA ATG AAG ATC ATA TTC TTT CTA TGT TC-3')/JAT75 (SEQ ID NO:141) (5'-TGT GGG ATC CTC GAG ATA AAA ATT AAA TGA AAC TGT A-'3) and pCOPAK XIX plasmid (Application Ser. No. 07/724,109. CMS Ref. 454310-2330, example 4) as template. This fragment was digested with BamHI and ligated with BamHI-digested pIBI25 vector to generate p42.1. The 42K/gp42 expression cassette was obtained as a BamHI fragment from p42.1 and ligated with BlII-digested p83.ATI-2. The resulting plasmid, designated p83/42.ATI-1, is an ATI site insertion vector that contains the H6/p83 and 42K/gp42 expression cassettes in a head-to-head orientation with transcription of p83 oriented right to left and gp42 oriented left to right in relation to the NYVAC flanking arms.

Insertion of the p83 and gp42 genes into the ATI site of NYVAC. The p83/42.ATI-1 donor plasmid was used to insert the p83 and gp42 genes, under the control of the H6 and 42K promoters, respectively, into the ATI site of NYVAC by in vivo recombination. The resulting NYVAC recombinant was designated vP1172. Restriction analysis of vP1172 genomic DNA confirmed the insertion of the p83 and gp42 expression cassettes at the ATI site.

Evaluation of p83 and gp42 expression by vP1172.

The expression of p83 and gp42 peptides of 97–110 kDa and 45 kDa, respectively, was detected in vP1172-infected HeLa cells by immunoprecipitation analysis with rabbit anti-gp195 serum.

EXAMPLE 45

GENERATION OF COPAK-PfSSP2

Subclonina of the PfSSP2 gene into a COPAK donor plasmid. A fragment containing the 42K promoter/PfSSP2 gene expression cassette was isolated from plasmid pVAC-SSP2 (see Example 33) by digestion with BamHI. This fragment was ligated with a BamHI-digested pSD553 (COPAK) vector fragment to generate pCOPAK.SSP2. This COPAK donor plasmid directs the insertion of the 42K/PfSSP2 cassette, and the vaccinia K1L host range gene, at the ATI site of NYVAC.

Insertion of the PfSSP2 gene (and K1L) into the ATI site of NYVAC. The pCOPAK.SSP2 donor plasmid was used to insert the PfSSP2 gene under the control of the 42K promoter, and the vaccinia K1L gene, into the ATI site of NYVAC by in vivo recombination. The resulting COPAK recombinant was designated vP1155. Restriction analysis of vP1155 genomic DNA confirmed the insertion of the PfSSP2 expression cassette and K1L at the ATI site.

Evaluation of PfSSP2 expression by vP1155. The expression of cell-associated and secreted PfSSP2 peptides of 107 and 91 kDa, respectively, was detected in vP1155-infected HeLa cells by immunoprecipitation analysis with mouse anti-PfSSP2 serum.

EXAMPLE 46

IMMUNOGENICITY OF COPAK-PfSSP2 (vP1155)

C57BL/6 mice were immunized by the intravenous route with a single dose of $1\times10^7$ pfu of vP1155. After three weeks, spleen cells from immunized mice were stimulated in vitro for 6 days with syngeneic cells either infected with vP1155 or pulsed with one of two synthetic peptides corresponding to PfSSP2 CTL epitopes. The spleen cell cultures were then evaluated for cytotoxicity by standard $^{51}$Cr-release assay either untreated or after depletion of CD4+ or CD8+ T cells. Target cells consisted of EL4 cells infected with vP1155 or pulsed with the homologous synthetic peptide. The results indicated that mice immunized with a single dose of vP1155 develop significant PfSSP2-specific lytic responses mediated by classical CD8+ CTLs.

Humoral responses elicited by vP1155 were evaluated in BALB/c and C57BL/6 mice immunized by the intradermal or intraperitoneal routes. After one dose of $10^7$ pfu, anti-sporozoite antibody titers as measured by IFA ranged from 1:160–1:640. After two doses, IFA titers ranged from 1:640–1:5120. Thus, immunization of these mice with vP1155 elicited strong antibody responses directed against the sporozoite which were boosted on subsequent inoculation.

EXAMPLE 47

IMMUNOGENICITY OF NYVAC-Pfs25 (vP1085)

The NYVAC-Pfs25 recombinant vP1085 was described above in Examples 14–17. As previous studies have demonstrated that Pfs25-specific antibodies can block the transmission of sexual forms of the parasite to mosquitoes in a membrane feeding system (Kaslow et al., 1991), Applicants evaluated the ability of NYVAC-Pfs25 (vP1085) to elicit transmission blocking antibodies. Groups of 10 $CAF_1$ mice were immunized with $10^7$ PFU of NYVAC or vP1085 by the ID, IM, or SQ route on day 0 and boosted with the same dose at weeks 3 and 6. Pooled serum collected at week 8 was evaluated. Transmission blocking activity was scored as the ability of serum, when mixed with infected blood, to prevent the development of oocysts in the midgut after mosquitoes are membrane fed. Under conditions where transmission rates are low (i.e., ingestion of infected blood results in the development of a few oocysts per mosquito—mean 1.4–2.1 per gut), serum from mice immunized by the ID route with vP1085 shows very strong transmission blocking activity (see Table 1), and compared favorably with Wyeth- and WR-Pfs25 recombinants that have been previously demonstrated to induce transmission blocking antibodies.

TABLE 1

| serum sample | | mean oocyst no. | mosq infected/ | % transmission blocking |
|---|---|---|---|---|
| species | immunization | (range) | mosq dissected | activity |
| mouse[a] | vP1085, ID[b] | .005 (0–1) | 1/21 | 95.2 |
| mouse | Wyeth, Scr | 1.4 (0–6) | 16/23 | 30.4 |
| mouse | Wy-25, Scr | 0.19 (0–2) | 3/21 | 85.7 |
| mouse | WR, Scr | 2.1 (0–9) | 16/21 | 23.8 |
| mouse | WR-25, Scr | 0.75 (0–4) | 9/24 | 62.5 |

[a]Groups of 10 $CAF_1$ mice were immunized with $10^7$ PFU of the appropriate virus on day 0 and boosted with the same dose at weeks 3 and 6. Pooled serum collected at week 8 was evaluated.
[b]Animals were immunized with the appropriate virus by intradermal (ID) route or tail scratch (Scr). Wyeth and WR serum samples were provided by Dr. D. Kaslow, NIAID, NIH.

When the vP1085-immunized mouse serum was analyzed under conditions of high transmission (mean 15–26 per gut) and compared with the Wyeth and WR recombinants, there was no transmission blocking activity and no decrease in oocyst counts. Sera from mice immunized with the Wyeth- and WR-Pfs25 recombinants exhibit low levels of transmission blocking activity under these conditions (<16%) but they do significantly reduce the oocyst counts. Serum from guinea pigs immunized with v1085 block tran smission by 25% under conditions of high transmission.

These results indicate that mice develop transmission blocking antibodies when immunized with vP1085. This activity is very strong wh en transmission is relatively low (oocyst burdens of 1–9 per mosquito) and compared favorably with the activity developed when Pfs25 is expressed by other vaccinia strains. In the wild, infected mo squitoes usually carry a parasite burden of 1–2 oocysts per mosquito. Thus, under conditions approximating those found in nature, specific antib odie s elicited by vP1085 exhibit strong transmission blocking activity.

EXAMPLE 48

GENERATION OF WR-HR-SERA

Subcloning of the SERA gene into a WR-HR donor plasmid. The 42K promoter/SERA gene expression cassette was isolated as a BamHI/XhoI fragment from plasmid p126.C3. This fragment was ligated with a BamBI/XhoI-digested pSD157K1LINS vector fragment to generate pKILSERA. The transcriptional orientation of the SERA gene in pK1LSERA is right to left relative to the vaccinia flanking arms.

Insertion of the SERA gene into the K1L site of vaccinia WR. The pKILSERA donor plasmid was used to insert the 42K/SERA expression cassette, and the K1L gene, into the K1L site of vaccinia WR by in vivo recombination. The resulting WR-HR recombinant was designated vP1252. Restriction analysis of vP1252 genomic DNA confirmed the insertion of the SERA expression cassette at the K1L site.

Evaluation of SERA expression by vP1252. The expression of SERA peptides of 135 and 137 kDa was detected in vP1252-infected HeLa cells by immunoprecipitation analysis with rabbit anti-p126 serum.

EXAMPLE 49

GENERATION OF WR-HR-ANAL

Subcloning of the AMA-1 gene into a WR-HR donor plasmid. The I3L promoter/AMA-1 gene expression cassette was isolated as a PstI/BamHI fragment from plasmid pC6L.AMA1. This fragment was ligated with a PstI/BamHI-digested pSD157K1LINS vector fragment to generate pK1LAMA. The transcriptional orientation of the AMA-1 gene in pK1LAMA is right to left relative to the vaccinia flanking arms.

Insertion of the AMA-1 gene into the K1L site of vaccinia WR. The pK1LAMA donor plasmid was used to insert the I3L/AMA-1 expression cassette, and the K1L gene, into the K1L site of vaccinia WR by in vivo recombination. The resulting WR-HR recombinant was designated vP1257. Restriction analysis of vP1257 genomic DNA confirmed the insertion of the AMA-1 expression cassette at the K1L site.

Evaluation of AMA-1 expression by vP1257. The expression of AMA-1 peptides of 83 and 90 kDa was detected in vP1257-infected HeLa cells by immunoprecipitation analysis with a human anti-malarial serum pool from immune African donors.

EXAMPLE 50

GENERATION OF WR-HR-LSA1-REPEATLESS

Subcloning of the LSA1-repeatless gene into a WR-HR donor plasmid. The C10LW promoter/LSA1-repeatless gene expression cassette was isolated as a PspAI/BamHI fragment from plasmid pLSARPLS.I4L.1. This fragment was ligated with a PspAI/BamHI-digested pSD157KILINS vector fragment to generate pK1LLSA. The transcriptional orientation of the LSA1-repeatless gene in pK1LLSA is right to left relative to the vaccinia flanking arms.

Insertion of the LSA1-repeatless gene into the K1L site of vaccinia WR. The pK1LLSA donor plasmid was used to insert the C10LW/LSA1-repeatless expression cassette, and the K1L gene, into the K1L site of vaccinia WR by in vivo recombination. The resulting WR-HR recombinant was designated vP1253. Restriction analysis of vP1253 genomic DNA confirmed the insertion of the LSA1-repeatless expression cassette at the K1L site.

Evaluation of LSA1-repeatless expression by vP1253. The expression of LSA1-repeatless peptides of 75 and 72 kDa was detected in vP1253-infected HeLa cells by immunoprecipitation analysis with rabbit anti-LSA-1 serum.

EXAMPLE 51

GENERATION OF WR-HR-CSP

Subcloning of the CSP gene into a WR-HR donor plasmid. The H6 promoter/CSP gene expression cassette was isolated as a Ps AI/BamHI fragment from plasmid p542-MLFCS. This fragment was ligated with a PspAI/BamHI-digested pSD157K1LINS vector fragment to generate PKILCSP. The transcriptional orientation of the CSP gene in pK1LCSP is right to left relative to the vaccinia flanking arms.

Insertion of the CSP gene into the K1L site of vaccinia WR. The pK1LCSP donor plasmid was used to insert the H6/CSP expression cassette, and the K1L gene, into the K1L site of vaccinia WR by in vivo recombination. The resulting WR-HR recombinant was designated vP1255. Restriction analysis of vP1255 genomic DNA confirmed the insertion of the CSP expression cassette at the K1L site.

Evaluation of CSP expression by vP1255. The expression of CSP peptides of 60 and 56 kDa was detected in vP1255-infected HeLa cells by immunoprecipitation analysis with mAb Pf2A10.

EXAMPLE 52

GENERATION OF WR-HR-PfSSP2

Subcloning of the PfSSP2 gene into a WR-HR donor plasmid. The 42K promoter/PfSSP2 gene expression cassette was isolated as a PsPAI/BamHI fragment from plasmid pVAC-SSP2. This fragment was ligated with a PspAI/BamHI-digested pSD157K1LINS vector fragment to generate pK1LSSP. The transcriptional orientation of the PfSSP2 gene in pK1LSSP is right to left relative to the vaccinia flanking arms.

Insertion of the PfSSP2 gene into the K1L site of vaccinia WR. The pK1LSSP donor plasmid was used to insert the 42K/PfSSP2 expression cassette, and the K1L gene, into the K1L site of vaccinia WR by in vivo recombination. The resulting WR-HR recombinant was designated vP1254. Restriction analysis of vP1254 genomic DNA confirmed the insertion of the PfSSP2 expression cassette at the K1L site.

Evaluation of PfSSP2 expression by vP1254. The expression of PfSSP2 peptides of 107 and 91 kDa was detected in vP1254-infected HeLa cells by immunoprecipitation analysis with mAb 88:10:161.

EXAMPLE 53

GENERATION OF WR-HR-MSA1

Subcloning of the MSA-1 gene into a WR-HR donor plasmid. The H6 promoter/MSA-1 gene expression cassette was isolated as a PspAI/XhoI fragment from plasmid pC7H6MSA. This fragment was ligated with a PspAI/XhoI-digested pSD157K1LINS vector fragment to generate pK1LMSA. The transcriptional orientation of the MSA-1 gene in pK1LMSA is right to left relative to the vaccinia flanking arms.

Insertion of the MSA-1 gene into the K1L site of vaccinia WR. The pK1LMSA donor plasmid was used to insert the H6/MSA-1 expression cassette, and the K1L gene, into the K1L site of vaccinia WR by in vivo recombination. The resulting WR-HR recombinant was designated vP1256. Restriction analysis of vP1256 genomic DNA confirmed the insertion of the MSA-1 expression cassette at the K1L site.

Evaluation of MSA-1 expression by vP1256. The expression of MSA-1 peptides of approximately 220 and 230 kDa was detected in vP1256-infected HeLa cells by immunoprecipitation analysis with both rabbit anti-gp195 serum and mAb 3D3.

EXAMPLE 54

GENERATION OF ALVAC-LSA1-REPEATLESS

Subcloning of the LSA1-repeatless gene into a C5 donor plasmid. A fragment containing the C10LW promoter/LSA1-repeatless gene expression cassette was isolated from plasmid pLSARPLS.INT2 (see Example 34) by digestion with BamHI and KpnI. This fragment was ligated with a BamHI/KpnI-digested pVQC5LSP6 vector fragment to generate pLSARPLSC5.1.

Insertion of the LSA1-repeatless gene into the C5 sites of ALVAC. The pLSARPLSC5.1 donor plasmid was used to insert the LSA1-repeatless gene, under the control of the C10LW promoter, into the C5 sites of ALVAC by in vivo recombination. The resulting ALVAC recombinant was designated vCP266. Restriction analysis of vCP266 genomic DNA confirmed the insertion of the LSA1-repeatless expression cassette at the C5 sites.

Evaluation of LSA1-repeatless expression by vCP266. The expression of two secreted LSA1-repeatless peptides of 75 and 72 kDa was detected in vCP266-infected HeLa cells by immunoprecipitation analysis with rabbit anti-LSA-1 serum.

EXAMPLE 55

IMMUNOGENICITY OF ALVAC-LSA1-REPEATLESS (VCP266)

Studies performed with peripheral blood lymphocytes from a Ghanian individual with many years of exposure to malaria demonstrated that cells infected with vCP266 can restimulate LSA1-specific cytotoxic lymphocytes in vitro.

EXAMPLE 56

GENERATION OF ALVAC-PfSSP2

Subcloning of the PfSSP2 gene into a C5 donor plasmid. A fragment containing the 42K promoter/PfSSP2 gene expression cassette was isolated from plasmid pVAC-SSP2 by digestion with BamHI. This fragment was ligated with a BamHI-digested pVQC5LSP6 vector fragment to generate pSSP2.C5. This C5 donor plasmid contains the 42K/PfSSP2 cassette with transcription oriented left to right in relation to the ALVAC flanking arms.

Insertion of the PfSSP2 gene into the C5 sites of ALVAC. The pSSP2.C5 donor plasmid was used to insert the PfSSP2 gene, under the control of the 42K promoter, into the C5 sites of ALVAC by in vivo recombination. The resulting ALVAC recombinant was designated vCP238. Restriction analysis of vCP238 genomic DNA confirmed the insertion of the PfSSP2 expression cassette at the C5 sites.

Evaluation of PfSSP2 expression by vCP238. The expression of cell-associated and secreted PfSSP2 peptides of 107 and 91 kDa, respectively, was detected in vCP238-infected HeLa cells by immunoprecipitation analysis with mouse anti-PfSSP2 serum.

EXAMPLE 57

GENERATION OF ALVAC-MSA1

Subcloning of the MSA-1 gene into a C7 donor plasmid. A fragment containing the 3' one-third of the H6 promoter linked to the MSA-1 gene was isolated from plasmid p24.H6.195 (see Example 29) by digestion with NruI and XhoI. This fragment was ligated with an NruI/XhoI-digested pC7 vector fragment which contained the pC7 backbone and the 5' two-thirds of the H6 promoter (inserted at the Sma site of pC7L). In the resulting donor plasmid, designated pC7H6.MSA, the complete H6 promoter is linked to the MSA-1 coding sequence, with transcription oriented left to right in relation to the flanking arms.

Insertion of the MSA-1 gene into the C7 site of ALVAC. The pC7H6.MSA donor plasmid was used to insert the MSA-1 gene, under the control of the H6 promoter, into the C7 site of ALVAC by in vivo recombination. The resulting ALVAC recombinant was designated vCP289. Restriction analysis of vCP289 genomic DNA confirmed the insertion of the MSA-1 expression cassette at the C7 site.

Evaluation of MSA-1 expression by vCP289. The expression of cell associated and secreted MSA-1 peptides of approximately 220 and 230 kDa, respectively, was detected in vCP289-infected HeLa cells by immunoprecipitation analysis with both rabbit anti-gp195 serum and mAb 3D3.

EXAMPLE 58

GENERATION OF ALVAC-p83/gp42, EXPRESSING THE N-TERMINAL p83 AND C-TERMINAL gp42 PROCESSING FRAGMENTS OF MSA-1

Subcloning of the P83 and gp42 gene constructs into a C3 donor plasmid. A fragment containing both the H6/p83 and 42K/gp42 expression cassettes was isolated from plasmid p83/42.ATI-1 by digestion with XhoI. This fragment was ligated with a XhoI-digested pVQC3PL vector fragment to generate p83/42.C3. This C3 insertion vector contains the H6/p83 and 42K/gp42 expression cassettes in a head-to-head orientation with transcription of p83 oriented right to left and gp42 oriented left to right in relation to the ALVAC flanking arms.

Insertion of the p83 and gp42 genes into the C3 sites of ALVAC. The p83/42.C3 donor plasmid was used to insert the p83 and gp42 genes, under the control of the H6 and 42K promoters, respectively, into the C3 sites of ALVAC by in vivo recombination. The resulting ALVAC recombinant was designated vCP252. Restriction analysis of vCP252 genomic DNA confirmed the insertion of the p83 and gp42 expression cassettes at the C3 sites.

Evaluation of p83 and gp42 expression by vCP252. The expression of p83 and gp42 peptides of 97–110 kDa and 45 kDa, respectively, was detected in vCP252-infected HeLa cells by immunoprecipitation analysis with rabbit anti-gp195 serum.

EXAMPLE 59

GENERATION OF AN ALVAC DONOR PLASMID FOR INSERTION OF THE MSA-1 p83 AND gp42 GENE CONSTRUCTS AT THE C7 SITE

A fragment containing both the H6/p83 and 42K/gp42 expression cassettes was isolated from plasmid p83/42.C3 by digestion with PspAI and BamHI. This fragment was ligated with a PspAI/BamHI-digested pC7+vector fragment to generate pC7.83/42. The pC7+vector was derived from the pC7 plasmid by the expansion of the polylinker region to include the following restriction sites; SmaI (PspAI), NruI, EcoRI, SalI, BamHI, XhoI, Asp718, SphI. The pC7.83/42 plasmid is a C3 insertion vector contains the H6/p83 and 42K/gp42 expression cassettes in a head-to-head orientation with transcription of p83 oriented right to left and gp42 oriented left to right in relation to the ALVAC flanking arms.

EXAMPLE 60

INSERTION OF THE AMA-1 AND CSP GENES INTO ALVAC TO GENERATE ALVAC-Pf2 (vCP223)

Subcloning of the AMA-1 and CSP genes into a C6 donor plasmid.

Insertion of the AMA-1 gene into the C6 donor plasmid pC6L. The I3L promoter/AMA-1 gene expression cassette was isolated from plasmid pHA.AMA-1 after digestion with HindIII, fill-in with the Klenow fragment of DNA polymerase I to create blunt ends, and digestion with SmaI. This fragment was ligated with a SmaI-digested pC6L vector fragment to generate pC6.AMA-2.

Insertion of the CSP gene into pC6.AMA-2.

The H6 promoter/CSP gene expression cassette was obtained by digestion of plasmid pCOPCS-5H-MLFCS with HindIII, fill-in with the Klenow fragment of DNA polymerase I to create blunt ends, and digestion with SmaI. This fragment was ligated with a XhoI-digested, Klenow-treated pC6.AMA-2 vector fragment. The resulting donor plasmid, designated pC6AMA/CS-2, contains the I3L/AMA-1 and H6/CSP expression cassettes (promoters positioned "head-to-head," with opposite transcriptional orientations) and directs insertion to the ALVAC C6 site.

Insertion of the AMA-1 and CSP genes into the C6 site of ALVAC. The pC6AMA/CS-2 donor plasmid was used to insert the AMA-1 and CSP genes, under the control of the I3L and H6 promoters, respectively, into the C6 site of ALVAC (CPpp) by in vivo recombination. The resulting ALVAC recombinant was designated vCP223. Restriction analysis of vCP223 genomic DNA confirmed the insertion of the AMA-1 and CSP expression cassettes at the C6 site.

Evaluation of AMA-1 and CSP expression by vCP223. The expression of cell associated and secreted AMA-1 peptides of 83 and 90 kDa, respectively, has been detected in vCP223-infected HeLa cells by immunoprecipitation analysis with a human anti-malarial serum pool from immune African donors. Expression of cell-associated CSP peptides of 60 and 56 kDa was detected in vCP223-infected HeLa cells with mAb Pf2A10.

EXAMPLE 61

INSERTION OF THE LSA1-REPEATLESS, Pfs25, AND PfSSP2 GENES INTO vCP223 TO GENERATE ALVAC-Pf5 (vCP259)

Subcloning of the Pfs25, LSA-1, and PfSSP2 genes into a C5 donor plasmid.

Insertion of the Pfs25 gene into the C5 donor plasmid pNC5LSP-5. A fragment containing the I3L promoter/Pfs25 gene expression cassette was isolated from plasmid pPfs25.3 by digestion with XhoI and Asp718. This fragment was ligated with a XhoI/Asp718-digested pNC5LSP-5 vector fragment to generate pC5.Pfs25. This C5 donor plasmid contains the I3L/Pfs25 cassette with transcription oriented right to left in relation to the ALVAC flanking arms.

Insertion of the LSA-1 gene into pC5.Pfs25.

A fragment containing the C10LW promoter/LSA-1 gene expression cassette was isolated from plasmid pLSA7.5 by digestion with BamHI and Asp718. This fragment was ligated with a BamHI/Asp718-digested pC5.Pfs25 vector fragment. The resulting donor plasmid, pC5.LSA/25-1, contains the C10LW/LSA-1 and I3L/Pfs25 gene expression cassettes in a tail-to-tail orientation, with the 3' end of LSA-1 adjacent to the 3' end of the Pfs25 gene.

Insertion of the PfSSP2 gene into pC5.LSA/25-1. A fragment containing the 42K/PfSSP2 gene expression cassette was isolated by digestion of plasmid pCOPAK.SSP2 with BamHI and treatment with Klenow fragment to generate blunt ends. This fragment was ligated with a SmaI-digested pC5.LSA/25-1 vector fragment to generate pC5.LSA/25/SSP-1. This donor plasmid contains, from left to right in relation to the ALVAC C5 flanking arms, the C10LW/LSA-1 cassette in a tail-to-tail orientation with the I3L/Pfs25 cassette which is in a head-to-head orientation with the 42K/PfSSP2 cassette.

Replacement of LSA-1 with the LSA1-repeatless gene in pC5.LSA/25/SSP-1. While the generation of the C5 donor plasmid was in progress we determined that the sequences encoding the extensive central repeat region of the LSA-1 gene were not genetically stable in our poxvirus vectors. We therefore sought to replace the full length gene in pC5.LSA/25/SSP-1 with an LSA1-repeatless gene from which the sequences encoding the repeat region were removed. This was accomplished by isolating a fragment containing the C10LW promoter/LSA1-repeatless gene cassette from plasmid pLSARPLS.I4L.1 after digestion with BamHI and Asp718. This fragment was then ligated with a BamHI/Asp718-digested pC5.LSA/25/SSP-1 vector fragment. The resulting plasmid was designated pC5triple. This C5 donor plasmid has the same orientation of genes as its predecessor, pC5.LSA/25/SSP-1, except that the LSA1-repeatless gene replaces the LSA-1 gene.

Insertion of the LSA1-repeatless, Pfs25, and PfSSP2 genes into the C5 sites of vCP223. The pC5triple donor plasmid was used to insert the LSA1-repeatless, Pfs25 and PfSSP2 genes, under the control of the C10LW, I3L and 42K promoters, respectively, into the C5 sites of vCP223 by in vivo recombination. The resulting ALVAC recombinant was designated vCP259. Restriction analysis of vCP259 genomic DNA confirmed the insertion of the LSA1-repeatless, Pfs25 and PfSSP2 expression cassettes at the C5 sites.

Evaluation of LSA1-repeatless, Pfs25, PfSSP2, AMA-1, and CSP expression by vCP259. Evaluation of expression of malarial antigens in vCP259-infected HeLa cells was performed by immunoprecipitation analysis with specific serological reagents. AMA-1 and CSP peptides were detected with the human anti-malarial pool and mAb Pf2A10, respectively. The rabbit anti-LSA-1 serum detected two secreted LSA1-repeatless peptides of 75 and 72 kDa. The Pfs25-specific mAb 4B7 detected a series of cell associated Pfs25 peptides of 33, 27, and 25 kDa and a secreted Pfs25 peptide of 27 kDa. Cell-associated and secreted PfSSP2 peptides of 107 and 91 kDa were detected with mouse anti-PfSSP2 serum.

EXAMPLE 62

INSERTION OF THE SERA GENE INTO vCP259 TO GENERATE ALVAC-Pf6 (vCP276)

Subcloning of the SERA gene into a C3 donor plasmid.

The insertion of the 42K promoter/SERA gene expression cassette into an ALVAC C3 site donor plasmid to generate p126.C3 has been previously described (see Example 28).

Insertion of the SERA gene into the C3 sites of vCP259. The 126.C3 donor plasmid was used to insert the SERA gene, under the control of the 42K promoter, into the C3 sites of vCP259 by in vivo recombination. The resulting ALVAC recombinant was designated vCP276. Restriction analysis of vCP276 genomic DNA confirmed the insertion of the SERA expression cassette at the C3 sites.

Evaluation of SERA. LSA1-repeatless, Pfs25, PfSSP2, AMA-1, and CSP expression by vCP276. Evaluation of expression of malarial antigens in vCP276-infected HeLa cells was performed by immunoprecipitation analysis with specific serological reagents. The rabbit anti-p126 serum detects cell-associated and secreted SERA peptides of 135 and 137 kDa, respectively. Expression of LSA1-repeatless, Pfs25,PfSSP2, AMA-1 and CSP was detected with rabbit anti-LSA-1 serum, mAb 4B7, mouse anti-PfSSP2 serum, the human anti-malarial pool and mAb Pf2A10, respectively.

EXAMPLE 63

INSERTION OF THE MSA-1 GENE INTO vCP276 TO GENERATE ALVAC-Pf7 (vCP312)

Insertion of the MSA-1 gene into the C7 site of vCP276. The pC7H6. MSA donor plasmid was used to insert the MSA-1 gene, under the control of the H6 promoter, into the C7 site of vCP276 by in vivo recombination. The resulting ALVAC recombinant was designated ALVAC-Pf7 (vCP312). Restriction analysis of ALVAC-Pf7 (vCP312) genomic DNA confirmed the insertion of the MSA-1 expression cassette at the C7 site.

Evaluation of MSA-1. SERA. LSA1-repeatless, Pfs25, PfSSP2, AMA-1, and CSP expression by vCP312. Analysis of malarial antigens in vCP312-infected HeLa cells by immunoprecipitation with specific serological reagents confirms expression.

Having thus described in detail preferred embodiments of the present invention, it is to be understood that the invention defined by the appended claims is not to be limited by particular details set forth in the above description as many apparent variations thereof are possible without departing from the spirit or scope of the present invention.

REFERENCES

1. Ardeshir, F., Flint, J., Richman, S., and Reese, R., EMBO J. 6, 493–499 (1987).
2. Aviv, H., and Leder, P., Proc. Natl. Acad. Sci. U.S.A. 69, 1408–1412 (1972).
3. Ballou, W. R., Hoffman, S. L., Sherwood, J. A., Hollingdale, M. R., Neva, F. A., Wasserman, G. F., Reeve, P., Diggs, C. L., and Chulay, J. D., Lancet 1, 1277–1281 (1987).
4. Banyal, H., and Inselburg, J., Am. J. Trop. Med. Hyg. 34, 1055–1064 (1985).
5. Bertholet, C., Drillien, R., and Wittek, R., Proc. Natl. Acad. Sci. USA 82, 2096–2100 (1985).
6. Bhatia, A., Delplace, P., Fortier, B., Dubremetz, J-F., and Vernes, A., Am. J. Trop. Med. Hyg. 36, 15–19 (1987).
7. Bianco, A., Favaloro, J., Burkot, T., Culvenor, J., Crewther, P., Brown, G., Anders, R., Coppel, R., and Kemp, D., Proc. Natl. Acad. Sci. U.S.A. 83, 8713–8717 (1986).
8. Blisnick, T., Lema, F., Mazie, J., and Pereira da Silva, L., Exper. Parasitol. 67, 247–256 (1988).
9. Buller, R. M. L., Chakrabarti, S., Cooper, J. A., Twardzik, D. R., and Moss, B., J.Virol. 62, 866–874 (1988).
10. Buller, R. M. L., G. L. Smith, Cremer, K., Notkins, A. L., and Moss, B., Nature 317, 813–815 (1985).
11. Bzik, D., Li, W., Horii, T., and Inselburg, J., Molec. Biochem. Parasitol. 30, 279–288 (1988).
12. Cadoz, M., A. Strady, B. Meignier, J. Taylor, J. Tartaglia, E. Paoletti and S. Plotkin, The Lancet, 339, 1429 (1992).
13. Carter, R., Kumar, N., Quakyi, I., Good, M., Mendis, K., Graves, P., and Miller, L., Prog. Allergy 41, 1930–214 (1988).
14. Caspers, P., Gentz, R., Matile, H., Pink, J. R., Sinigaglia, F., Mol. Biochem. Parasitol. 35, 185–190 (1989).
15. Chang, S. P., Kramer, K. J., Yamaga, K. M., Kato, A., Case, S. E., and Siddiqui, W. A., Exp. Parasitol. 67, 1–11 (1988).
16. Cheng, K.-C., Smith, G. L., Moss, B., Zavala, F., Nussenzweig, R., and Nussenzweig, V. In Vaccines 86 eds.
Chanock, R. M., Lerner, R. A., Brown, F., and Ginsberg, H. (Cold Spring Harbor Press, Cold Spring Harbor, N.Y.) pp. 165–168 (1986).
17. Cheung, A., Leban, J., Shaw, A. R., Merkli, B., Stocker, J., and Chizzolini, C., Proc. Natl. Acad. Sci. U.S.A. 83, 8328–8332 (1986).
18. Child, S. J., Palumbo, G. J., Buller, R. M. L., and Hruby, D. E. Virology 174, 625–629 (1990).
19. Chulay, J., Lyon, J., Haynes, J., Meierovics, A., Atkinson, C., and Aikawa, M., J. Immunol. 139, 2768–2774 (1987).
20. Clewell, D. B., J. Bacteriol. 110, 667–676 (1972).
21. Clewell, D. B. and Helinski, D. R., Proc. Natl. Acad. Sci. USA 62, 1159–1166 (1969).
22. Clyde, D. F., Am. J. Trop. Med. Hyg. 24, 397–401 (1975).
23. Colinas, R. J., R. C. Condit and E. Paoletti, Virus Research 18, 49–70 (1990).
24. Coppel, R., Crewther, P., Culvenor, J., Perrin, L., Brown, G., Kemp, D., and Anders, R., Mol. Biol. Med. 5, 155–166 (1988).
25. Crisanti, A., Muller, H.-M., Hilbich, C., Sinigaglia, F., Matile, H., McKay, M., Scaife, J., Beyreuther, K., and Bujard, H., Science 240, 1324–1326 (1988).
26. Dame, J. B., Williams, J. L., McCutchan, T. F., Weber, J. L., Wirtz, R. A., Hockmeyer, W. T., Maloy, W. L., Haynes, J. D., Schneider, I., Roberts, D., Sanders, G. S., Reddy, E. P., Diggs, C. L., Miller, L. H. Science 225, 593–599 (1984).
27. Deans, J. A., Knight, A. M., Jean, W. C., Waters, A. P., Cohen, S., and Mitchell, G. H., Para. Immunol. 10, 535–552 (1988).
28. Debrabant, A., and Delplace, P., Molec. Biochem. Parasitol. 33, 151–158 (1989).
29. Delplace, P., Fortier, B., Tronchin, G., Dubremetz, J. F., and Vernes, A., Molec. Biochem. Parasitol. 23, 193–201 (1987).
30. Delplace, P., Bhatia, A., Cagnard, M., Camus, D., Colombet, G., Debrabant, A., Dubremetz, J.-F., Dubreuil, N., Prensier, G., Fortier, B., Haq, A., Weber, J., and Vernes, A., Biol. Cell 64, 215–221 (1988).
31. Delplace, P., Dubremetz, J.-F., Fortier, B., and Vernes, A., Molec. Biochem. Parasitol. 17, 239–251 (1985).
32. Dubois, P., Dedet, J.-P., Fandeur, T., Roussilhon, C., Jendoubi, M., Pauillac, S., Mercereau-Puijalon, O., and Pereira da Silva, L., Proc. Natl. Acad. Sci. U.S.A. 81, 229–232 (1984).
33. Eakin, A., Higaki, J., McKerrow, J., and Craik, C., Nature 342, 132 (1989).
34. Engelke, D. R., Hoener, P. A., and Collins, F. S., Proc. Natl. Acad. Sci. U.S.A. 85, 544–548 (1988).

35. Flexner, C., Hugen, A., and Moss, B., Nature 330, 259–262 (1987).
36. Fries et al., 32nd Interscience Conference on Antimicrobial Agents and Chemotherapy, Anaheim, Calif. (October 1992).
37. Frohman, M., Dush, M., and Martin, G., Proc. Natl. Acad. Sci. U.S.A. 85, 8998–9002 (1988).
38. Fruh, K., Doumbo, O., Muller, H.-M., Koita, O., McBride, J., Crisanti, A., Toure, Y., and Bujard, H., Infec. Immun. 59, 1319–1324 (1991).
39. Gentz, R., Certa, U., Takacs, B., Matile, H., Dobeli, H., Pink, R., Mackay, M., Bone, N., and Scaife, J. G., EMBO J. 7, 225–230 (1988).
40. Gillard, S., D. Spehner, R. Drillien and A. Kirn Proc. Natl. Acad. Sci. U.S.A. 83, 5573–5577 (1986).
41. Goebel, S., Johnson, G., Perkus, M., Davis, S., Winslow, J., and Paoletti, E., Virol. 179, 247–266 (1990a).
42. Goebel, S. J., G. P. Johnson, M. E. Perkus, S. W. Davis, J. P. Winslow and E. Paoletti, Virology 179, 517–563 (1990b).
43. Good, M. F., Miller, L. H., Kumar, S., Quakyi, I. A., Keister, D., Adams, J. H., Moss, B., Berzofsky, J. A., and Carter, R. Science 242, 574–577 (1988).
44. Good M. F., Pombo, D., Quakyi, I.A., Riley, E. M., Houghton, R. A., Menon, A., Alling, D. W., Berzofsky, J. A., and Miller, L. H. Proc. Natl. Acad. Sci. U.S.A. 85, 1199–1203 (1987).
45. Guerin-Marchand, C., Druilhe, P., Galey, B., Londono, A., Patarapotikul, J., Beaudoin, R. L., Dubeaux, C., Tartar, A., Mercereau-Puijalon, O., and Langsley, G., Nature 329, 164–167 (1987).
46. Guo, P., Goebel, S., Perkus, M. E., Taylor, J., Norton, E., Allen, G., Languet, B., Desmettre, P., and Paoletti, E., J. Virol. 64, 2399–2406 (1990).
47. Guo, P., Goebel, S., Davis, S., Perkus, M. E., Languet, B., Desmettre, P., Allen, G., and Paoletti, E., J. Virol. 63, 4189–4198 (1989).
48. Guo, H.-G., diMarzo Veronese, F., Tschachler, E., Pal, R., Kalyanaraman, V. S., Gallo, R. C., and Reitz, Jr., M. S., Virology 174, 217–224 (1990).
49. Haldar, K., Ferguson, M. A., and Cross, G. A., J. Biol. Chem. 260, 4969–4974 (1985).
50. Hall, R., Hyde, J. E., Goman, M., Simmons, D. L., Hope, I. A., Mackay, M., Scaife, J., Merkli, B., Richle, R., and Stocker, J., Nature 311, 379–382 (1984).
51. Hattori, M., and Sakaki, Y., Anal. Biochem. 152, 232–237 (1986).
52. Herrington, D. A., Clyde, D. F., Losonsky, G., Cortesia, M., Murphy, F. R., Davis, J., Baqar, A., Felix, A. M., Heimer, E. P., Gillessen, D., Nardin, E., Nussenzweig, R. S., Nussenzweig, V., Hollingdale, M. R., and Levine, M. M. Nature 328, 257–259 (1987).
53. Higgins, D., McConnell, D., Sharp, P., Nature 340, 604 (1989). 54. Hill, A.V.S., Elvin, J., Willis, A.C., Aidoo, M., Allsopp, C. E. M., Gotch, F. M., Gao, X. M., Takiguchi, M., Greenwood, B. M., Townsend, A. R. M., McMichael, A. J., and Whittle, H. C., Nature 360, 434–439 (1992).
55. Hoffman, S. L., Oster, C. N., Plowe, C. V., Woollett, G. R., Chulay, J. D., Wirtz, R. A., Hollingdale, M. R., and Mugambi, M. Science 237, 639–642 (1987).
56. Holder, A. A., Prog. Allergy 41, 72–97 (1988).
57. Holder, A. A., Freeman, R. R., and Nichols, S. C., Parasite Immunol. 10, 607–617 (1988).
58. Holder, A. A., and Freeman, R. R., J. Exp. Med. 156, 1528–1538 (1982).
59. Hollingdale, M. R., Aikawa, M., Atkinson, C. T., Ballou, W. R., Chen, G., Li, J., Meis, J. F. G. M., Sina, B., Wright, C., and Zhu, J., Immunol. Lett. 25, 71–76 (1990).
60. Horii, T., Bzik, D., and Inselburg, J., Molec. Biochem. Parasitol. 30, 9–18 (1988).
61. Howard, R. J., Lyon, J. A., Diggs, C. L., Haynes, J. D., Leech, J. H., and Barnwell, J. W., Mol. Biochem. Parasitol. 11, 349–362 (1984).
62. Inselburg, J., Bzik, D., Li, W.-B., Green, K., Kansopon, J., Hahm, B., Bathurst, I., Barr, P., and Rossan, R., Infec. Immun. 59, 1247–1250 (1991).
63. Jendoubi, M., and Pereira da Silva, L., Am. J. Trop. Med. Hyg. 37, 9–16 (1987).
64. Kaslow, D. C., Isaacs, S. N., Quakyi, I. A., Gwadz, R. W., Moss, B., and Keister, D. B., Science 252, 1310–1313 (1991).
65. Kaslow, D. C., Quakyi, I. A., and Keister, D. B. Mol. Biochem. Parasitol. 32, 101–104 (1989).
66. Kaslow, D. C., Quakyi, I. A., Syin, C., Raum, M. G., Keister, D. B., Coligan, J. E., McCutchan, T. F., and Miller, L. M. Nature 333, 74–76 (1988).
67. Khusmith, S., Charoenvit, Y., Kumar, S., Sedegah, M., Beaudoin, R. L., and Hoffman, S. L., Science 252, 715–718 (1991).
68. Kingston, R., In Current Protocols in Molecular Biology, eds. Ausubel, F., Brent, R., Kingston, R., Moore, D., Seidman, J., Smith, J., and Struhl, K., (John Wiley and Sons, New York) p. 4.5.1. (1987).
69. Klickstein, L., and Neve, R., In Molecular Biology, eds. Ausubel, F., Brent, R., Kingston, R., Moore, D., Seidman, J., Smith, J., and Struhl, K., (John Wiley and Sons, New York) pp. 5.5.1.–5.5.10. (1987).
70. Knapp, B., Hundt, E., Nau, U., and Kupper, H., Molec. Biochem. Parasitol. 32, 73–84 (1989).
71. Konishi, E., Pincus, S., Paoletti, E., Laegreid, W. W., Shope, R. E., and Mason, P. W., Virology 190, 454–458 (1992).
72. Kotwal, G. J. and B. Moss, J. Virol. 63, 600–606 (1989).
73. Kumar, N., Zhao, Y., Graves, P., Folgar, J., Maloy, L., and Zheng, H., Infect. Immun. 58, 1408–1414 (1990).
74. Kumar, N., Syin, C., Carter, R., Quakyi, I., and Miller, L., Proc. Natl. Acad. Sci. U.S.A. 85, 6277–6281 (1988a).
75. Kumar, S., Miller, L. H., Quakyi, I. A., Keister, D. B., Houghton, R. A., Maloy, W. L., Moss, B., Berzosky, J. A., Good, M. F. Nature 34, 258–260 (1988b).
76. Kunkel, T. A., Roberts, J. D., and Zakour, R. A., Method in Enzym. 154, 367–382 (1987).
77. Laemmli, U. K., Nature 227, 680–685 (1970).
78. Li, W., Bzik, D., Horii, T., and Inselburg, J., Molec. Biochem. Parasitol. 33, 13–26 (1989).
79. Lockyer, M. J., and Holder, A. A. In Vaccination strategies of tropical diseases, ed. Liew, F. Y. (CRC Press, Boca Raton, Fla.) pp. 124–148 (1989).
80. Lyon, J. A., Haynes, J. D., Diggs, C. L., Chulay, J. D., and Pratt-Rossiter, J. M., J. Immunol. 136, 2252–2258 (1986).
81. Lyon, J. A., Haynes, J. D., Diggs, C. L., Chulay, J. D., Haidaris, C. G., and Pratt-Rossiter, J., J. Immunol. 138, 895–901 (1987).
82. Lyon J., Thomas, A., Hall, T., and Chulay, J., Molec. Biochem. Parasitol. 36, 77–86 (1989).
83. Mandecki, W., Proc. Natl. Acad. Sci. U.S.A. 83, 7177–7182 (1986).
84. Maniatis, T., Fritsch, E. F., and Sambrook, J. In Molecular cloning: a laboratory manual, (Cold Spring Harbor Laboratory, Cold Spring Harbor, N.Y.) (1982).
85. Mason, P., Virology 169, 354–364 (1989).
86. Mattei, D., Scherf, A., Bensaude, O., and Pereira da Silva, L., Eur. J. Immunol. 19, 1823–1828 (1989).
87. Mikaelian, I., and Sargeant, A., Nucl. Acids Res. 20, 376. (1992).

88. Miller, L., Howard, R. J., Carter, R., Good, M. F., Nussenzweig, V., and Nussenzweig, R. S., Science 234, 1349–1356 (1986).
89. Moelans, I. I. M. D., Meis, J. F. G. M., Kocken, C., Konings, R. N. H., and Schoenmakers, J. G. G. Mol. Biochem. Parasitol. 45, 193–204. (1991a).
90. Moelans, I. I. M. D., Klaasen, C. H. W., Kaslow, D. C., Konigs, R. N. H., and Schoenmakers, J. G. G. Mol. Biochem. Parasitol. 46, 311–314 (1991b).
91. Mottram, J., Coombs, G., North, M., Nature 342, 132 (1989).
92. Muller, H.-M., Fruh, K., von Brunn, A., Esposito, F., Lombardi, S., Crisanti, A., and Bujard, H., Infec. Immun. 57, 3765–3769 (1989).
93. Newport, G., Culpepper, J., and Agabian, N., Parasitol. Today 4, 306–312 (1988).
94. Nussenzweig, R. S., and Nussenzweig, V., Philos. Trans. R. Soc. London Ser. B 307, 117–128 (1984).
95. Nussenzweig, V., and Nussenzweig, R. S. Cell 42, 401–403 (1985).
96. Nussenzweig, V., and Nussenzweig, R. S., Advances Immunol. 45, 283–334 (1989).
97. Panicali, D. and E. Paoletti, Proc. Natl. Acad. Sci. U.S.A. 79, 4927–4931 (1982).
98. Panicali, D., Davis, S. W., Mercer, S. R., and Paoletti, E., J. Virol. 37, 1000–1010 (1981).
99. Patarroyo, M. E., Amador, R., Clavijo, P., Moreno, A., Guzman, F., Romero, P., Tascon, R., Franco, A., Murillo, L. A., Ponton, G., and Trujillo, G., Nature 332, 158–161 (1988).
100. Patarroyo, M. E., Romero, P., Torres, M. L., Clavijo, P., Andreu, D., Lozada, D., Sanchez, L., del Portillo, P., Pinilla, C., Moreno, A., Alegria, A., and Houghten, R., In Vaccines 87 (Chanock, R. M., Lerner, R. A., Brown, F., and Ginsberg, H., eds.) pp. 117–124 (Cold Spring Harbor Press, Cold Spring Harbor, N.Y.) (1987a).
101. Patarroyo, M. E., Romero, P., Torres, M. L., Clavijo, P., Moreno, A., Martinez, A., Rodriguez, R., Guzman, F., and Cabezas, E., Nature 328, 629–632 (1987b).
102. Perkus, M. E., Goebel, S. J., Davis, S. W., Johnson, G. P., Limbach, K., Norton, E. K., and Paoletti, E., Virology 179, 276–286 (1990).
103. Perkus, M. E., Limbach, K., and Paoletti, E., J. Virol. 63, 3829–3836 (1989).
104. Perkus, M., Goebel, S., Davis, S., Johnson, G., Norton, E., and Paoletti, E., Virol. 180, 406–410 (1991).
105. Perkus, M. E., Piccini, A., Lipinskas, B. R., and Paoletti, E., Science 229, 981–984 (1985).
106. Perrin, L. H., Dayal, R., and Rieder, H., Trans. R. Soc. Trop. Med. Hyg. 75, 163–165 (1981).
107. Perrin, L., Merkli, B., Loche, M., Chizzolini, C., Smart, J., and Richle, R., J. Exp. Med. 160, 441–451 (1984).
108. Perrin, L. H., and Dayal, R., Immunol. Rev. 61, 245–269 (1982).
109. Peterson, M. G., Coppel, R. L., Moloney, M. B., Kemp, D. J., Mol. Cell. Biol. 8, 2664–2667 (1988).
110. Peterson, M. G., Marshall, V. M., Smythe, J. A., Crewther, P. E., Lew, A., Siva, A., Anders, R. F., and Kemp, D. J., Mol. Cell. Bio. 9, 3151–3154 (1988).
111. Piccini, A., Perkus, M. E. and Paoletti, E., In Methods in Enzymology, Vol. 153, eds. Wu, R., and Grossman, L., (Academic Press) pp. 545–563 (1987).
112. Reese, R. T., Motyl, M. R., and Hofer-Warbinek, R., Am. J. Trop. Med. Hyg. 30, 1168–1178 (1981).
113. Renia, L., Mattei, D., Goma, J., Pied, S., Dubois, P., Miltgen, F., Nussler, A., Matile, H., Menegaux, F., Gentilini, M., and Mazier, D., Eur. J. Immunol. 20, 1445–1449 (1990).
114. Rieckmann, K. H., Trans. Roy. Soc. Trop. Med. Hyg. 68, 258–259 (1974).
115. Robson, K. J. H., Hall, J. R. S., Jennings, M. W., Harris, T. J. R., Marsh, K., Newbold, C. I., Tate, V. E., and Weatherall, D. J., Nature 335, 79–82 (1988).
116. Rogers, W. O., Malik, A., Mellouk, S., Nakamura, K., Rogers, M., Szarfman, A., Gordon, D. M., Nussler, A. K., Aikawa, M., and Hoffman, S. L., Proc. Natl. Acad. Sci. U.S.A. 89, 9176–9180 (1992).
117. Rosel, J., Earl, P., Weir, J., and Moss, B., J. Virol. 60, 436–449 (1986).
118. Rzepczyk, C. M., Ramasamy, R., Mutch, D. A., Ho, P. C.-L., Battistutta, D., Anderson, K. L., Parkinson, D., Doran, T. J., and Honeyman, M., Eur. J. Immunol. 19, 1797–1802 (1989).
119. Saiki, R., Gelfand, D., Stoffel, S., Scharf, S., Higuchi, R., Horn, G., Mullis, K., and Erlich, H., Science 239, 487–491 (1988).
120. Sambrook, J., Fritsch, E. F., and Maniatis, T., In Molecular cloning: A laboratory manual, 2nd edition, (Cold Spring Harbor Press, New York) (1989).
121. Sanger, F., Nickeln, S. Coulson, A. R., Proc. Natl. Acad. Sci. 74, 5463–5467 (1977).
122. Schmitt, J. F., and Stunnenberg, H. G., J. Virol. 62, 1889–1897 (1988).
123. Shapira, S. K., Chou, J., Richaud, F. V. and Casadaban, M. J., Gene 25, 71–82 (1983).
124. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
125. Siddiqui, W. A., Tam, L. Q., Kramer, K. J., Hui, G.S., Case, S. E., Yamaga, K. M., Chang, S. P., Chan, E. B., and Kan, S. C., Proc. Natl. Acad. Sci. U.S.A. 84, 3014–3018 (1987).
126. Siddiqui, W. A., Tam, L. Q., Kan, S. C., Kramer, K. J., Case, S. E., Palmer, K. L., Yamaga, K. M., and Hui, G. S., Imfec. Immun. 52, 314–318 (1986).
127. Simitsek, P. D., Ramirez, E., and Perrin, L. H., Eur. J. Immunol. 20, 1755–1759 (1990).
128. Singigaglia, F., Guttinger, M., Kilgus, J., Doran, D. W., Matile, H., Etlinger, H., Trzeciak, A., Gillessen, D., and Pink, J. R. L., Nature 336, 778 (1988).
129. Sinigaglia, F., Takacs, B., Jacot, H., Matile, H., Pink, J. R. L., Crisanti, A., and Bujard, H., J. Immunol. 140, 3568–3572 (1988).
130. Stahl, H., Bianco, A., Crewther, P., Anders, R., Kyne, A., Coppel, R., Mitchell, G., Kemp, D., and Brown, G., Mol. Biol. Med. 3, 351–368 (1986).
131. Stephenson, J., and ter Meulen, V., Proc. Natl. Acad. Sci. U.S.A. 76, 6601–6605 (1979).
132. Szarfman, A., Lyon, J., Walliker, D., Quakyi, I., Howard, R., Sun, S., Ballou, W. R., Esser, K., London, W. Wirtz, R., and Carter, R., Parasite Immunol. 10, 339–351 (1988).
133. Tabor, S. and C. C. Richardson, Proc. Natl. Acad. Sci. U.S.A. 84, 4767–4771 (1987).
134. Tanabe, K., Mackay, M., Goman, M., and Scaife, J. G., J. Mol. Biol. 195, 273–287 (1987).
135. Targett, G. A. T., In Report of a meeting on transmission-blocking immunity in malaria. UNDP/World Bank/WHO Special Programme for Research and Training in Tropical Diseases, Geneva, Switzerland (1990).
136. Tartaglia, J., Pincus, S., and Paoletti, E., Crit. Rev. Immunol. 10, 13–30 (1990).
137. Tartaglia, J., M. E. Perkus, J. Taylor, E. K. Norton, J. C. Audonnet, W. I. Cox, S. W. Davis, J. VanderHoeven, B.

Meignier, M. Riviere, B. Languet, and E. Paoletti, Virology 188, 217–232 (1992).
138. Tartaglia, J., J. Taylor, W.I. Cox, J.-C. Audonnet, M. E. Perkus, A. Radaelli, C. de Giuli Morghen, B. Meignier, M. Riviere, K. Weinhold & E. Paoletti, In *AIDS Research Reviews*, W. Koff, F. Wong-Staal & R.C. Kenedy, Eds., Vol. 3, Marcel Dekker, N.Y. (In press)(1993a).
139. Tartaglia, J., Jarrett, O., Desmettre, P., Paoletti, E. (1993b) J. Virol., in press.
140. Taylor, J., Edbauer, C., Rey-Senelonge, A., Bouquet, J. F., Norton, E., Goebel, S., Desmettre, P., and Paoletti, E., J. Virol. 64, 1441–1450 (1990).
141. Taylor, J., S. Pincus, J. Tartaglia, C. Richardson, G. Alkhatib, D. Briedis, M. Appel, E. Norton and E. Paoletti, J. Virology 65, 4263–4274 (1991).
142. Taylor, J., Weinberg, R., Languet, B., Desmettre, P., and Paoletti, E., Vaccine 6, 497–503 (1988a).
143. Taylor, J., Weinberg, R., Kawaoka, L., Webster, R. G., and Paoletti, E., Vaccine 6, 504–506 (1988b).
144. Taylor, G., E. J. Stott, G. Wertz and A. Ball, J. Gen. Virol. 72, 125–130 (1991a).
145. Taylor, J., C. Trimarchi, R. Weinberg, B. Languet, F. Guillemin, P. Desmettre and E. Paoletti, Vaccine 9, 190–193 (1991b).
146. Taylor, J., R. Weinberg, J. Tartaglia, C. Richardson, G. Alkhatib, D. Briedis, M. Appel, E. Norton & E. Paoletti, Virology 187, 321–328 (1992).
147. Thomas, A. W., Waters, A. P., and Carter, D., Molec. Biochem. Parasitol. 42, 285–288 (1990).
148. Vermeulen, A. N., Ponnudurai, T., Beckers, P. J. A., Verhave, J. P., Smits, M. A., and Meuwissen, J. H. E. T. J. Exp. Med. 162, 1460–1476 (1985).
149. Vos, J. C. and Stunnenberg, H. G., EMBO J. 7, 3487–3492 (1988).
150. Wachsman, M., Luo, J. H., Aurelian, L., Perkus, M. E., and Paoletti, E., J. Gen. Virol. 70, 2513–2520 (1989).
151. Waters, A. P., Thomas, A. W., Deans, J. A., Mitchell, G. H., Hudson, D. E., Miller, L. H., McCutchan, T. F., and Cohen, S., J. Bio. Chem. 265, 17974–17979 (1990).
152. Watson, C., and Jackson, J., In DNA Cloning, Volume I: a practical approach, ed. Glover, D. M., (IRL Press, Oxford) pp. 79–88 (1985).
153. Weber, J., Lyon, J., Wolff, R., Hall, T., Lowell, G., and Chulay, J., J. Biol. Chem. 263, 11421–11425 (1988).
154. Weber, J., Lyon, J., and Camus, D., In Molecular Strategies of Parasitic Invasion (Alan R. Liss, Inc.) pp. 379–388 (1987).
155. Yang, Y.-F., Tan-ariya, P., Sharma, Y., and Kilejian, A. Molec. Biochem. Parasitol. 26, 61–68 (1987).
156. Yuen, L., and Moss, B., Proc. Natl. Acad. Sci. U.S.A. 84, 6417–6421 (1987).
157. Zhu, J., and Hollingdale, M. R., Mol. Biochem. Parasitol. 48, 223–226 (1991).

What is claimed is:

1. A recombinant poxvirus containing therein DNA from *Plasmodium falciparum* coding for at least one Plasmodium antigen in a nonessential region of the poxvirus genome wherein the poxvirus expresses the at least one antigen and the poxvirus is selected from the group consisting of:

(i) recombinant vaccinia virus wherein regions C7–K1L, J2R, B13R+B14R, A56R and I4L have been deleted therefrom, or wherein the open reading frames for the thymidine kinase gene, the hemorrhagic region, the A type inclusion body region, the hemagglutinin gene, the host range gene region, and the large subunit, ribonucleotide reductase have been deleted therefrom;

(ii) NYVAC vaccinia virus; and (iii) ALVAC canarypox virus.

2. A recombinant poxvirus as in claim 1 wherein said DNA codes for a Plasmodium antigen from each of sporozoite, liver, blood and sexual stages of the Plasmodium life cycle.

3. A recombinant poxvirus as in claim 1 wherein said Plasmodium antigen is selected from the group consisting of SERA, ABRA, Pfhsp70, AMA-1, Pfs25, Pfs16, CSP, PfSSP2, LSA-1, LSA-1-repeatless, MSA-1 N-terminal p83, MSA-1 C-terminal gp42 and MSA-1 and combinations thereof.

4. The recombinant poxvirus of claim 1 wherein the DNA codes for CSP, PfSSP2, LSA-1-repeatless, MSA-1, SERA, AMA-1 and Pfs25.

5. A recombinant poxvirus as in claim 1 wherein the poxvirus is the vaccinia virus.

6. A recombinant poxvirus as in claim 1 wherein the poxvirus is the canarypox virus.

7. A recombinant poxvirus as claimed in claim 1 which is vP1039, vP1040, vP1023, vP1018, vP1052, vP1085, H3xx1, H3xx2, H3xx3, H3xx4, vP1006, vP967, vP924, vP1108, vCP182, vCP179, vCP185, vCP196, vCP198, vP924, vP967, vP1108, vP1127, vP1154E, vP1209, vP1197, vP1189, vP1187, vP1190C, vP11172, vP1155, vCP266, vCP238, vCP289, vCP252, vCP223, vCP259, vCP276, or vCP312.

8. An immunological composition for inducing an immunological response in a host animal inoculated with said composition, said composition comprising a carrier and a recombinant poxvirus as claimed in claim 1.

9. A composition as in claim 8 wherein said Plasmodium antigen is selected from the group consisting of SERA, ABRA, Pfhsp70, AMA-1, Pfs25, Pfs16, CSP, PfSSP2, LSA-1, MSA-1, LSA-1-repeatless, MSA-1 N-terminal p83, MSA-1 C-terminal gp42, and combinations thereof.

10. A composition as in claim 8 wherein the poxvirus is the vaccinia virus.

11. The composition of claim 10 wherein the Plasmodium antigen is selected from the group consisting of SERA, ABRA, Pfhsp70, AMA-1, Pfs25, CSP, PfSSP2, LSA-1, MSA-1, LSA-1-repeatless, MSA-1 N-terminal p83, MSA-1 C-terminal gp42 and combinations thereof.

12. The composition of claim 10 wherein the DNA codes for CSP, PfSSP2, LSA-1-repeatless, MSA-1, SERA, AMA-1 and Pfs25.

13. A composition as in claim 8 wherein the poxvirus is the canarypox virus.

14. A composition as claimed in claim 8 wherein the poxvirus is vP1039, vP1040, vP1023, vP1018, vP1052, vP1085, H3xx1, H3xx2, H3xx3, H3xx4, vP1007, vP967, vP924, vP1108, vCP182, vCP179, vCP185, vCP196, vCP198, vP924, vP967, vP1108, vP1127, vP1154E, vP1209, vP1197, vP1189, vP1187, vP1190C, vP1172, vP1155, vCP266, vCP238, vCP289, vCP252, vCP223, vCP259, vCP276 or vCP312.

15. A method for producing at least one *Plasmodium falciparum* antigen, said method comprising infecting a cell in vitro with a recombinant poxvirus as claimed in claim 1.

16. The method of claim 15 wherein the antigens are CSP, PfSSP2, LSA-1-repeatless, MSA-1, SERA, AMA-1 and Pfs25.

17. The method of claim 15 wherein the poxvirus is a vaccinia virus.

18. The method of claim 15 wherein the poxvirus is the canarypox virus.

19. The method of claim 15 wherein the poxvirus is vP1039, vP1040, vP1023, vP1018, vP1052, vP1085, H3xx1, H3xx2, H3xx3, H3xx4, vP1007, vP967, vP924, vP1108, vCP182, vCP179, vCP185, vCP196, vCP198, vP924, vP967, vP1108, vP1127, vP1154E, vP1209, vP1197, vP1189, vP1187, vP1190C, vP1172, vP1155, vCP266, vCP238, vCP289, vCP252, vCP223, vCP259, vCP276, or vCP312.

* * * * *